(12) United States Patent
Chilkoti et al.

(10) Patent No.: US 11,965,164 B2
(45) Date of Patent: Apr. 23, 2024

(54) AMPHIPHILIC POLYNUCLEOTIDES

(71) Applicant: Duke University, Durham, NC (US)

(72) Inventors: Ashutosh Chilkoti, Durham, NC (US); Stefan Zauscher, Durham, NC (US); Lei Tang, Durham, NC (US); Sonal Deshpande, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 18/051,487

(22) Filed: Oct. 31, 2022

(65) Prior Publication Data
US 2023/0183699 A1    Jun. 15, 2023

Related U.S. Application Data

(62) Division of application No. 16/927,982, filed on Jul. 13, 2020, now Pat. No. 11,512,314.

(60) Provisional application No. 62/873,306, filed on Jul. 12, 2019.

(51) Int. Cl.
| C12N 15/113 | (2010.01) |
| A61K 31/7105 | (2006.01) |
| C12N 15/115 | (2010.01) |
| C12Q 1/68 | (2018.01) |

(52) U.S. Cl.
CPC ........ *C12N 15/113* (2013.01); *A61K 31/7105* (2013.01); *C12N 15/115* (2013.01); *C12N 2310/16* (2013.01)

(58) Field of Classification Search
None
See application file for complete search history.

(56) References Cited

U.S. PATENT DOCUMENTS

| | | |
|---|---|---|
| 4,415,732 A | 11/1983 | Caruthers et al. |
| 4,458,066 A | 7/1984 | Caruthers et al. |
| 4,500,707 A | 2/1985 | Caruthers et al. |
| 4,554,101 A | 11/1985 | Hopp |
| 4,668,777 A | 5/1987 | Caruthers et al. |
| 4,973,679 A | 11/1990 | Caruthers et al. |
| 4,976,734 A | 12/1990 | Urry et al. |
| 5,153,319 A | 10/1992 | Caruthers et al. |
| 5,250,516 A | 10/1993 | Urry |
| 5,278,302 A | 1/1994 | Caruthers et al. |
| 5,336,256 A | 8/1994 | Urry |
| 5,453,496 A | 9/1995 | Caruthers et al. |
| 5,534,408 A | 7/1996 | Green et al. |
| 5,578,577 A | 11/1996 | Ching et al. |
| 5,580,859 A | 12/1996 | Felgner et al. |
| 5,602,244 A | 2/1997 | Caruthers et al. |
| 5,676,646 A | 10/1997 | Hofmann et al. |
| 5,679,647 A | 10/1997 | Carson et al. |
| 5,702,359 A | 12/1997 | Hofmann et al. |
| 5,703,055 A | 12/1997 | Felgner et al. |
| 5,935,776 A | 8/1999 | Green et al. |
| 6,068,650 A | 5/2000 | Hofmann et al. |
| 6,096,020 A | 8/2000 | Hofmann |
| 6,120,493 A | 9/2000 | Hofmann |
| 6,150,148 A | 11/2000 | Nanda et al. |
| 6,181,964 B1 | 1/2001 | Hofmann et al. |
| 6,192,270 B1 | 2/2001 | Hofmann et al. |
| 6,207,749 B1 | 3/2001 | Mayes et al. |
| 6,208,893 B1 | 3/2001 | Hofmann |
| 6,216,034 B1 | 4/2001 | Hofmann et al. |
| 6,233,482 B1 | 5/2001 | Hofmann et al. |
| 6,241,701 B1 | 6/2001 | Hofmann |
| 6,245,515 B1 | 6/2001 | Vogelstein et al. |
| 6,296,831 B1 | 10/2001 | Weller et al. |
| 6,302,874 B1 | 10/2001 | Zhang et al. |
| 6,413,587 B1 | 7/2002 | Hawker et al. |
| 6,512,060 B1 | 1/2003 | Matyjaszewski et al. |
| 6,541,580 B1 | 4/2003 | Matyjaszewski et al. |
| 6,623,950 B1 | 9/2003 | Osten et al. |
| 6,649,138 B2 | 11/2003 | Adams et al. |
| 6,660,247 B1 | 12/2003 | Gutowska et al. |
| 6,841,617 B2 | 1/2005 | Jeong et al. |
| 6,852,834 B2 | 2/2005 | Chilkoti |
| 6,869,588 B2 | 3/2005 | Weller et al. |
| 7,033,571 B2 | 4/2006 | Gutowska et al. |
| 7,087,244 B2 | 8/2006 | Jeong et al. |
| 7,300,922 B2 | 11/2007 | Sullenger et al. |
| 7,429,458 B2 | 9/2008 | Chilkoti |
| 7,531,524 B2 | 5/2009 | Rusconi |
| 7,664,545 B2 | 2/2010 | Westersten et al. |
| 7,674,882 B2 | 3/2010 | Kaplan et al. |
| 8,129,330 B2 | 3/2012 | Martinez et al. |

(Continued)

FOREIGN PATENT DOCUMENTS

| AU | 2007265628 B2 | 12/2012 |
| CA | 2327325 A1 | 11/1999 |

(Continued)

OTHER PUBLICATIONS

U.S. Appl. No. 13/245,459, filed Sep. 26, 2011, U.S. Pat. No. 8,470,967, Jun. 25, 2013.
U.S. Appl. No. 13/904,836, filed May 29, 2013, U.S. Pat. No. 8,912,310, Dec. 16, 2014.
U.S. Appl. No. 14/572,391, filed Dec. 16, 2014, U.S. Pat. No. 9,771,396, Jun. 25, 2013.
U.S. Appl. No. 15/679,751, filed Aug. 17, 2017, 2018/0037609, Feb. 8, 2018.
U.S. Appl. No. 62/138,847, filed Mar. 26, 2015.

(Continued)

*Primary Examiner* — Sean McGarry
(74) *Attorney, Agent, or Firm* — Michael Best & Friedrich LLP

(57) ABSTRACT

Compositions and methods disclosed herein can help provide improved delivery of non-natural therapeutic nucleotides for the treatment of diseases such as cancer. An example composition includes an assembly of amphiphilic polynucleotides, where each amphiphilic polynucleotide includes an aptamer portion, a first nucleotide portion, and a second nucleotide portion.

5 Claims, 46 Drawing Sheets
Specification includes a Sequence Listing.

(56) References Cited

U.S. PATENT DOCUMENTS

| | | |
|---|---|---|
| 8,283,125 B2 | 10/2012 | Cebolla Ramirez et al. |
| 8,470,967 B2 | 6/2013 | Chilkoti et al. |
| 8,497,356 B2 | 7/2013 | Chilkoti et al. |
| 8,506,963 B2 | 8/2013 | Li et al. |
| 8,586,347 B2 | 11/2013 | Lochhead et al. |
| 8,841,414 B1 | 9/2014 | Raucher et al. |
| 8,912,310 B2 | 12/2014 | Chilkoti et al. |
| 8,937,153 B2 | 1/2015 | Abrahmsén et al. |
| 9,127,047 B2 | 9/2015 | Chilkoti |
| 9,132,178 B2 | 9/2015 | Philip |
| 9,138,743 B2 | 9/2015 | Yager et al. |
| 9,482,664 B2 | 11/2016 | Chilkoti et al. |
| 9,592,303 B2 | 3/2017 | Chilkoti et al. |
| 9,771,396 B2 | 9/2017 | Chilkoti et al. |
| 9,804,170 B2 | 10/2017 | Krishna et al. |
| 9,890,420 B2 | 2/2018 | Chilkoti et al. |
| 10,064,954 B2 | 9/2018 | Wu |
| 10,131,690 B2 | 11/2018 | Bonny et al. |
| 10,302,636 B2 | 5/2019 | Chilkoti et al. |
| 10,364,451 B2 | 7/2019 | Chilkoti et al. |
| 10,385,115 B2 | 8/2019 | Chilkoti et al. |
| 10,434,182 B2 | 10/2019 | Weng et al. |
| 2001/0034050 A1 | 10/2001 | Chilkoti |
| 2002/0052443 A1 | 5/2002 | Greenwald et al. |
| 2002/0146794 A1 | 10/2002 | Tomycz |
| 2003/0008308 A1 | 1/2003 | Enzelberger et al. |
| 2003/0138829 A1 | 7/2003 | Unger et al. |
| 2003/0175290 A1 | 9/2003 | Renner et al. |
| 2003/0185741 A1 | 10/2003 | Matyjaszewski et al. |
| 2003/0225251 A1 | 12/2003 | Sallberg et al. |
| 2003/0233675 A1 | 12/2003 | Cao et al. |
| 2004/0053976 A1 | 3/2004 | Martinez et al. |
| 2004/0101852 A1 | 5/2004 | Bennett et al. |
| 2004/0192072 A1 | 9/2004 | Snow et al. |
| 2005/0186214 A1 | 8/2005 | Liu et al. |
| 2005/0255554 A1 | 11/2005 | Chilkoti |
| 2005/0288229 A1 | 12/2005 | Sindrey et al. |
| 2006/0025524 A1 | 2/2006 | Schneider et al. |
| 2006/0034796 A1 | 2/2006 | Ashwell et al. |
| 2006/0051798 A1 | 3/2006 | Mirkin et al. |
| 2007/0087114 A1 | 4/2007 | Chilkoti et al. |
| 2007/0117173 A1 | 5/2007 | Levison et al. |
| 2008/0181861 A1 | 7/2008 | Jiang et al. |
| 2009/0098652 A1 | 4/2009 | Stupp et al. |
| 2009/0215194 A1 | 8/2009 | Magni et al. |
| 2009/0247424 A1 | 10/2009 | Chilkoti et al. |
| 2010/0015070 A1 | 1/2010 | Bollschweiler et al. |
| 2010/0022455 A1 | 1/2010 | Chilkoti |
| 2010/0048473 A1 | 2/2010 | Chaikof et al. |
| 2010/0120018 A1 | 5/2010 | Quake et al. |
| 2010/0241054 A1 | 9/2010 | Dacey et al. |
| 2010/0311059 A1 | 12/2010 | Didion et al. |
| 2010/0311669 A1 | 12/2010 | Greene et al. |
| 2010/0325765 P1 | 12/2010 | Pait et al. |
| 2011/0082283 A1 | 4/2011 | Dagher et al. |
| 2011/0119778 A1 | 5/2011 | Liss |
| 2011/0165557 A1 | 7/2011 | Ah et al. |
| 2011/0207673 A1 | 8/2011 | Chilkoti et al. |
| 2011/0248698 A1 | 10/2011 | Kikuchi et al. |
| 2011/0294189 A1 | 12/2011 | Chilkoti et al. |
| 2011/0303303 A1 | 12/2011 | Proper et al. |
| 2011/0305718 A1 | 12/2011 | Mugica et al. |
| 2012/0172298 A1 | 7/2012 | Andersen et al. |
| 2012/0208742 A1 | 8/2012 | Primiano et al. |
| 2013/0039927 A1 | 2/2013 | Dewhurst et al. |
| 2013/0079277 A1 | 3/2013 | Chilkoti |
| 2013/0079280 A1 | 3/2013 | Baca et al. |
| 2013/0096058 A1 | 4/2013 | Baca et al. |
| 2013/0102993 A1 | 4/2013 | Kim et al. |
| 2013/0130384 A1 | 5/2013 | Okamoto et al. |
| 2013/0157889 A1 | 6/2013 | Chilkoti et al. |
| 2013/0165389 A1 | 6/2013 | Schellenberger et al. |
| 2013/0172274 A1 | 7/2013 | Chilkoti |
| 2013/0197359 A1 | 8/2013 | Park et al. |
| 2013/0315823 A1 | 11/2013 | Trieu |
| 2013/0330335 A1 | 12/2013 | Bremel et al. |
| 2014/0024600 A1 | 1/2014 | Chilkoti et al. |
| 2014/0163201 A1 | 6/2014 | Winter et al. |
| 2014/0275227 A1 | 9/2014 | Hoge et al. |
| 2014/0294932 A1 | 10/2014 | Kim et al. |
| 2015/0094270 A1 | 4/2015 | Harris et al. |
| 2015/0099707 A1 | 4/2015 | Pastan et al. |
| 2015/0112022 A1 | 4/2015 | Chilkoti et al. |
| 2016/0017278 A1 | 1/2016 | Montclare et al. |
| 2016/0114053 A1 | 4/2016 | Chilkoti |
| 2016/0120952 A1 | 5/2016 | Chilkoti |
| 2016/0200787 A1 | 7/2016 | Matern et al. |
| 2016/0209356 A1 | 7/2016 | Herget et al. |
| 2016/0220727 A1 | 8/2016 | Lu et al. |
| 2016/0250165 A1 | 9/2016 | Sullenger et al. |
| 2016/0271262 A1 | 9/2016 | Lopez et al. |
| 2016/0303091 A1 | 10/2016 | Wang |
| 2016/0348147 A1 | 12/2016 | Lopez et al. |
| 2016/0355802 A1 | 12/2016 | Isaacs et al. |
| 2017/0088670 A1 | 3/2017 | Rowan et al. |
| 2017/0102357 A1 | 4/2017 | Liang et al. |
| 2017/0166621 A1 | 6/2017 | Boettcher et al. |
| 2017/0170142 A1 | 6/2017 | Edelstein et al. |
| 2017/0189545 A1 | 7/2017 | Lee et al. |
| 2017/0233714 A1 | 8/2017 | Chilkoti et al. |
| 2017/0239363 A1 | 8/2017 | Chilkoti et al. |
| 2017/0369651 A1 | 12/2017 | Cheng et al. |
| 2018/0037609 A1 | 2/2018 | Chilkoti et al. |
| 2018/0135060 A1 | 5/2018 | Romero Ramos et al. |
| 2018/0161772 A1 | 6/2018 | Rammohan et al. |
| 2018/0171337 A1 | 6/2018 | O'Neill et al. |
| 2018/0200196 A1 | 7/2018 | Fahmy et al. |
| 2018/0217136 A1 | 8/2018 | Chilkoti et al. |
| 2018/0231469 A1 | 8/2018 | Gibbons et al. |
| 2018/0238864 A1 | 8/2018 | Burd et al. |
| 2018/0258157 A1 | 9/2018 | Chilkoti et al. |
| 2018/0326044 A1 | 11/2018 | Carter |
| 2018/0327752 A1 | 11/2018 | Pillay et al. |
| 2018/0369399 A1 | 12/2018 | Hershfield et al. |
| 2019/0015520 A1 | 1/2019 | Chilkoti et al. |
| 2019/0016763 A1 | 1/2019 | Kitazawa et al. |
| 2019/0204309 A1 | 7/2019 | Gibbs |
| 2019/0285623 A1 | 9/2019 | Chilkoti et al. |
| 2019/0292549 A1 | 9/2019 | Zhang et al. |
| 2019/0345228 A1 | 11/2019 | Chilkoti et al. |
| 2020/0078313 A1 | 3/2020 | Roy et al. |
| 2020/0121809 A1 | 4/2020 | Hope et al. |
| 2020/0148724 A1 | 5/2020 | Chilkoti et al. |
| 2020/0163878 A1 | 5/2020 | Baumhof et al. |
| 2020/0181555 A1 | 6/2020 | Hinojosa et al. |
| 2021/0128734 A1 | 5/2021 | Chilkoti et al. |
| 2021/0154143 A1 | 5/2021 | Chilkoti et al. |

FOREIGN PATENT DOCUMENTS

| | | |
|---|---|---|
| CA | 2423488 A1 | 4/2002 |
| CN | 104725628 B | 4/2018 |
| CN | 112961065 A | 6/2021 |
| EP | 1670315 B1 | 4/2017 |
| EP | 2664340 B1 | 2/2020 |
| JP | 2014-156428 A | 8/2014 |
| JP | 2014-534265 A | 12/2014 |
| WO | WO1991/019813 A1 | 12/1991 |
| WO | WO2003/040165 A2 | 10/2002 |
| WO | WO2004/096124 A2 | 11/2004 |
| WO | WO2006/004778 A2 | 1/2006 |
| WO | WO2006/110292 A2 | 10/2006 |
| WO | WO2007/073486 A2 | 6/2007 |
| WO | WO2007/108013 A2 | 9/2007 |
| WO | WO2007/134245 A2 | 11/2007 |
| WO | WO2008/012543 A1 | 1/2008 |
| WO | WO2008/030968 A2 | 3/2008 |
| WO | WO2009/067584 A1 | 5/2009 |
| WO | WO2010/054699 A1 | 5/2010 |
| WO | WO2010/057154 A1 | 5/2010 |
| WO | WO2010/096422 A1 | 8/2010 |
| WO | WO2011/025572 A1 | 3/2011 |
| WO | WO2011/123813 A2 | 10/2011 |
| WO | WO2012/162426 A1 | 11/2012 |

(56) References Cited

FOREIGN PATENT DOCUMENTS

| WO | WO2013/049234 A2 | 4/2013 |
|---|---|---|
| WO | WO2013/065009 A1 | 5/2013 |
| WO | WO2013/106715 A1 | 7/2013 |
| WO | WO2014/037373 A1 | 3/2014 |
| WO | WO2014/194244 A1 | 12/2014 |
| WO | WO2015/011231 A1 | 1/2015 |
| WO | WO2015/130846 A2 | 9/2015 |
| WO | WO2016/065273 A1 | 4/2016 |
| WO | WO2016/065300 A1 | 4/2016 |
| WO | WO2016/090103 A1 | 6/2016 |
| WO | WO2016/154530 A1 | 9/2016 |
| WO | WO2017/015132 A1 | 1/2017 |
| WO | WO2017/024182 A1 | 2/2017 |
| WO | WO2017/112825 A2 | 6/2017 |
| WO | WO2017/112826 A2 | 6/2017 |
| WO | WO2017/192449 A1 | 11/2017 |
| WO | WO2018/115401 A1 | 6/2018 |
| WO | WO2018/144854 A1 | 8/2018 |
| WO | WO2019/103744 A1 | 5/2019 |
| WO | WO2019/147954 A1 | 8/2019 |
| WO | WO2019/213150 A1 | 11/2019 |
| WO | 2020/037100 A1 | 2/2020 |
| WO | WO2020/037214 A1 | 2/2020 |
| WO | 2020/051223 A1 | 3/2020 |
| WO | WO2020/160472 A1 | 8/2020 |
| WO | 2021/178898 A1 | 9/2021 |
| WO | 2022/016089 A2 | 1/2022 |
| WO | 2022/178438 A1 | 8/2022 |

OTHER PUBLICATIONS

PCT/US2016/024202, Mar. 25, 2016, WO2016/154530, Sep. 26, 2016.
U.S. Appl. No. 15/561,799, filed Sep. 26, 2017, U.S. Pat. No. 10/385,115, Aug. 20, 2019.
U.S. Appl. No. 16/525,374, filed Jul. 29, 2019, 2019/0345228, Nov. 14, 2019.
U.S. Appl. No. 62/399,123, filed Sep. 23, 2016.
PCT/US2017/052887, Sep. 22, 2017, WO2018/057847, Mar. 29, 2019.
U.S. Appl. No. 16/335,734, filed Mar. 22, 2019, 2020/0017557, Jan. 16, 2020.
U.S. Appl. No. 17/477,192, filed Sep. 16, 2021.
U.S. Appl. No. 13/942,037, filed Jul. 15, 2015, 2014/0024600, Jan. 23, 2014.
U.S. Appl. No. 16/058,924, filed Aug. 8, 2018, 2019/0023743, Jan. 24, 2019.
U.S. Appl. No. 62/270,401, filed Dec. 21, 2015.
U.S. Appl. No. 62/310,534, filed Mar. 18, 2016.
U.S. Appl. No. 62/329,800, filed Apr. 29, 2016.
U.S. Appl. No. 62/407,403, filed Oct. 12, 2016.
PCT/US2016/068141, Dec. 21, 2016, WO2017/112825, Jun. 29, 2017.
PCT/US2016/068142, Dec. 21, 2016, WO2017/112826, Jun. 29, 2017.
U.S. Appl. No. 15/387,536, filed Dec. 21, 2016, U.S. Pat. No. 10,364,451, Jul. 30, 2019.
U.S. Appl. No. 15/387,540, filed Dec. 21, 2016, U.S. Pat. No. 10,392,611, Aug. 27, 2019.
U.S. Appl. No. 16/064,424, filed Jun. 20, 2018, 2019/0015520, Jan. 17, 2019.
U.S. Appl. No. 16/064,425, filed Sep. 12, 2016, 2018/0369399, Dec. 27, 2018.
U.S. Appl. No. 62/506,593, filed May 15, 2017.
U.S. Appl. No. 62/534,442, filed Jul. 19, 2017.
U.S. Appl. No. 62/544,720, filed Aug. 11, 2017.
U.S. Appl. No. 62/545,313, filed Aug. 14, 2017.
PCT/US20168/032785, May 15, 2018, WO2018/213320, Nov. 22, 2018.
U.S. Appl. No. 16/614,282, filed Nov. 15, 2019, 2021/0154143, May 27, 2021.
U.S. Appl. No. 62/200,726, filed Aug. 4, 2015.
PCT/US2016/045655, Aug. 4, 2016, WO2017/024182, Feb. 9, 2017.
U.S. Appl. No. 15/749,797, filed Feb. 2, 2018, 2018/0228908, Aug. 16, 2018.
U.S. Appl. No. 62/394,662, filed Sep. 14, 2016.
PCT/US2017/051661, Sep. 14, 2017, WO2018/053201, Mar. 22, 2018.
U.S. Appl. No. 16/332,865, filed Mar. 13, 2019, U.S. Pat. No. 11/135,301, May 10, 2021.
U.S. Appl. No. 62/445,504, filed Jan. 12, 2017.
U.S. Appl. No. 62/479,977, filed Mar. 31, 2017.
PCT/US2018/013611, Jan. 12, 2018, WO2018/132732, Jul. 19, 2018.
U.S. Appl. No. 16/477,229, filed Jul. 11, 2019, 2019/0328662, Oct. 31, 2019.
U.S. Appl. No. 62/527,836, filed Jun. 30, 2017.
U.S. Appl. No. 62/534,019, filed Jul. 18, 2017.
PCT/US2018/040409, Jun. 29, 2018, WO2019/006374, Jan. 3, 2019.
U.S. Appl. No. 16/625,899, filed Dec. 23, 2019, 2020/0148724, May 14, 2020.
U.S. Appl. No. 62/343,926, filed Jun. 1, 2016.
U.S. Appl. No. 62/414,877, filed Oct. 31, 2016.
PCT/US2017/035530, Jun. 1, 2017, WO2017/210476, Dec. 7, 2018.
U.S. Appl. No. 16/305,696, filed Nov. 29, 2018, 2020/0378916, Dec. 3, 2020.
U.S. Appl. No. 62/728,582, filed Sep. 7, 2018.
PCT/US2019/050077, Sep. 6, 2019, WO2020/051541, Mar. 12, 2020.
U.S. Appl. No. 17/272,887, filed Mar. 2, 2021, 2021/0316007, Oct. 14, 201.
U.S. Appl. No. 62/767,736, filed Nov. 15, 2018.
PCT/US2019/061144, Nov. 13, 2019, WO2020/102324, May 22, 2020.
U.S. Appl. No. 17/294,368, filed May 14, 2021, 2022/0008567, Jan. 13, 2022.
U.S. Appl. No. 62/622,249, filed Jan. 26, 2018.
PCT/US2019/015176, Jan. 25, 2019, WO2019/147954, Aug. 1, 2019.
U.S. Appl. No. 16/964,832, filed Jul. 24, 2020, 2021/0060171, Mar. 4, 2021.
U.S. Appl. No. 62/647,199, filed Mar. 23, 2018.
PCT/US2019/023583, Mar. 22, 2019, WO2019/183476, Sep. 26, 2019.
U.S. Appl. No. 62/664,512, filed Apr. 30, 2018.
PCT/US2019/030022, Apr. 30, 2019, WO2019/213150, Nov. 7, 2019.
U.S. Appl. No. 17/051,202, filed Oct. 28, 2020.
U.S. Appl. No. 62/713,752, filed Aug. 2, 2018.
PCT/US2019/044911, Aug. 2, 2019, WO2020/028806, Feb. 6, 2020.
U.S. Appl. No. 17/265,165, filed Feb. 1, 2021, 2021/0309722, Oct. 7, 2021.
U.S. Appl. No. 62/985,174, filed Mar. 4, 2020.
PCT/US2021/020589, Mar. 3, 2021, WO2021/178481, Sep. 10, 2021.
U.S. Appl. No. 17/908,415, filed Aug. 31, 2022.
U.S. Appl. No. 62/985,179, filed Mar. 4, 2020.
PCT/US2021/020591, Mar. 3, 2021, WO2021/178483, Sep. 10, 2021.
U.S. Appl. No. 17/908,427, filed Aug. 31, 2022.
U.S. Appl. No. 62/898,353, filed Sep. 12, 2019.
U.S. Appl. No. 17/015,315, filed Sep. 9, 2020, 2021/0046188, Feb. 18, 2021.
U.S. Appl. No. 62/975,479, filed Feb. 12, 2020.
PCT/US2021/017809, Feb. 12, 2021, WO2021/163445, Aug. 19, 2021.
U.S. Appl. No. 17/798,868, filed Aug. 10, 2022.
U.S. Appl. No. 63/035,173, filed Jun. 5, 2020.
PCT/US2021/035823, Jun. 4, 2021, WO2021/247952, Dec. 9, 2021.

(56) References Cited

OTHER PUBLICATIONS

U.S. Appl. No. 18/007,879, filed Dec. 2, 2022.
U.S. Appl. No. 63/068,432, filed Aug. 21, 2020.
U.S. Appl. No. 63/116,511, filed Nov. 20, 2020.
PCT/US2021/046833, Aug. 20, 2021.
U.S. Appl. No. 63/236,064, filed Aug. 23, 2021.
PCT/US2022/041251, Aug. 23, 2022.
U.S. Appl. No. 63/169,541, filed Apr. 1, 2021.
PCT/US2022/023158, Apr. 1, 2022.
U.S. Appl. No. 63/151,878, filed Feb. 22, 2021.
U.S. Appl. No. 63/274,839, filed Nov. 2, 2021.
PCT/US2022/017349, Feb. 22, 2022.
U.S. Appl. No. 63/271,595, filed Oct. 25, 2021.
PCT/US2022/078659, Oct. 25, 2022.
U.S. Appl. No. 63/250,813, filed Sep. 30, 2021.
U.S. Appl. No. 17/957,373, Sep. 30, 2022.
U.S. Appl. No. 63/325,708, filed Mar. 31, 2022.
Erbacher et al., "Transfection and Physical Properties of Various Saccharide, Poly(ethylene glycol), and Antibody-Derivatized Polyethylenimines (PEI)," The Journal of Gene Medicine, 1999, 1: 210-222.
Alves et al., "Influence of doxorubicin on model cell membrane properties: insight from in vitro and in silico studies," Sci Rep, 2017, 7(1): 6343.
International Search Report and Written Opinion for Application No. PCT/US2022/078659 dated Feb. 1, 2023 (17 pages).
U.S. Appl. No. 16/964,832 dated Apr. 17, 2023 (17 pages).
International Search Report and Written Opinion for Application No. PCT/US2022/041241 dated Oct. 25, 2022 (10 pages).
Ozer et al., "Injectable non-immunogenic PEG-like conjugate that forms a subcutaneous depot and enables sustained delivery of a peptide drug," Research Square, 2021, 38 pages.
Hu et al., "Site-specific in situ growth of a cyclized protein-polymer conjugate with improved stability and tumor retention," Biomaterials, 2015, 47:13-19.
Liu et al., "Stable Evans Blue Derived Exendin-4 Peptide for Type 2 Diabetes Treatment," Bioconjugate Chem, 2016, 27: 54058.
United States Patent Office Notice of Allowance for U.S. Appl. No. 17/015,315 dated Apr. 26, 2023 (7 pages).
United States Patent Office Action for U.S. Appl. No. 17/051,202 dated Jun. 21, 2023 (10 pages).
AACR, "AACR Cancer Progress Report 2016," Clin Cancer Res, Oct. 2016, vol. 22, Issue 19, 143 pages.
Aaron et al., "Elastin as a Random-Network Elastomer—a Mechanical and Optical Analysis of Single Elastin Fibers," Biopolymers, 1981, 20(6):1247-1260.
Abbaspourrad et al., "Controlling release from pH-responsive microcapsules," Langmuir, 2013, 29: 12697-12702.
Abbaspourrad et al., "Polymer microcapsules with programmable active release," J Am Chem Soc, 2013, 135: 7744-7750.
Abbruzzese et al., "A phase I clinical, plasma, and cellular pharmacology study of gemcitabine," J. Clin. Oncol. 1991, 3, 491-498.
Adams et al., "Safety and utilization of blood components as therapeutic delivery systems," Curr Pharm Biotechnol, 2003, 4(5): 275-82.
Adams et al., "Sustained release of antibiotics from injectable and thermally responsive polypeptide depots," J Biomed Mater Res B Appl Biomater, Jul. 2009, vol. 90B, Issue 1, pp. 67-74.
Adamska et al., "Pancreatic ductal adenocarcinoma: Current and evolving therapies," J Mol Sci, Jun. 2017, vol. 18, Issue 7, pp. 1338-1380.
Adiseshaiah et al., "Nanomedicine strategies to overcome the pathophysiological barriers of pancreatic cancer," Nat Rev Clin Oncol, Dec. 2016, vol. 13, Issue 12, pp. 750-765.
Agarwal et al., "One-step microfluidic generation of pre-hatching embryo-like core-shell microcapsules for miniaturized 3D culture of pluripotent stem cells," Lab Chip, 2013, 13: 4525- 4533.
Ahmed et al., "Preliminary Identification of Potential Vaccine Targets for the COVID-19 Coronavirus (SARS-CoV-2) Based on SARS-CoV Immunological Studies, " Viruses, 2020, 12:254, 15 pages.
Aladini et al., "Chemical Synthesis and Characterization of Elastin-Like Polypeptides (ELPs) With Variable Guest Residues," J Pept Sci, May 2016, vol. 22, Issue 5, pp. 334-342.
Alarcon et al., "Exendin 4 controls insulin production in rat islet beta cells predominantly by potentiation of glucose-stimulated proinsulin biosynthesis at the translational level," Diabetologia, 2006, 49(12):2920-2929.
Albanese et al., "The effect of nanoparticle size, shape, and surface chemistry on biological systems," Annu. Rev. Biomed. Eng., Aug. 2012, vol. 14, pp. 1-16.
Alconcel et al., "FDA-approved poly(ethylene glycol)-protein conjugate drugs," Polym. Chem., vol. 2, Apr. 2011, Issue 7, pp. 1442-1448.
Alghoul et al., "The effect of hyaluronan hydrogel on fat graft survival," Aesthet Surg J, 2012, 32: 622-633.
Allen et al., "Liposomal drug delivery systems: from concept to clinical applications," Adv Drug Deliv Rev, Elsevier, Jan. 2013, 65(1):36-48.
Alley et al., "Feasibility of drug screening with panels of human tumor cell lines using a microculture tetrazolium assay," Cancer Res., 1988, 48, 589-601.
Aluri et al., "Elastin-like peptide amphiphiles Form nanofibers with tunable length," Biomacromolecules, Sep. 2012, vol. 13, Issue 9, pp. 2645-2654.
Amanat et al., "A serological assay to detect SARS-CoV-2 seroconversion in humans," Nat Med, 2020, 26(7): 1033-1036.
American Diabetes Association, Standards of medical care in diabetes—2018. Diabetes Care, Jan. 2018, vol. 41, Supplement 1, pp. S1-S159.
American Hospital Association, "AHA Hospital Statistics," 2020 edition. Available at: <https://www.aha.org/statistics/fast-facts-us-hospitals>.
American Society of Plastic Surgeons, "2017 Plastic Surgery Statistics Report," Oct. 2018, 25 pages.
Amiram et al., "A depot-forming glucagon-like peptide-1 fusion protein reduces blood glucose for five days with a single injection," J. Control. Release, Nov. 2013, vol. 172, Issue, pp. 144-151.
Amiram et al., "Evolution of translation machinery in recoded bacteria enables multi-site incorporation of nonstandard amino acids," Nat Biotechnol, 2015, 33: 1272-1279.
Amiram et al., "Injectable protease-operated depots of glucagon-like peptide-1 provide extended and tunable glucose control," Proc. Natl. Acad. Sci., Feb. 2013, vol. 110, Issue 8, pp. 2792-2797.
Andersen et al., "Extending Half-life by Indirect Targeting of the Neonatal Fc Receptor (FcRn) Using a Minimal Albumin Binding Domain," Journal of Biological Chemistry, Feb. 2011, vol. 286, Issue 7, pp. 5234-5241.
Anselmo et al., "Nanoparticles in the clinic, " Bioeng Transl Med, Jun. 2016, 1(1):10-29.
Antos et al., "Lipid Modification of Proteins through Sortase-Catalyzed Transpeptidation," J. Am. Chem. Soc., Dec. 2008, vol. 130, Issue 48, pp. 16338-16343.
Antos et al., "Site-Specific N- and C-Terminal Labeling of a Single Polypeptide Using Sortases of Different Specificity," J. Am. Chem. Soc., Aug. 2009, vol. 131, Issue 31, pp. 10800-10801.
Appleyard et al., "Multiplexed protein quantification with barcoded hydrogel microparticles," Anal Chem, 2011, 83: 193-199.
Arami et al., "In vivo delivery, pharmacokinetics, biodistribution and toxicity of iron oxide nanoparticles," Chem Soc Rev, Dec. 2015, 44(23):8576-8607.
Arias et al., "Superior preclinical efficacy of gemcitabine developed as chitosan nanoparticulate system," Biomacromolecules, Jan. 2011, vol. 12, Issue 1, pp. 97-104.
Armbruster et al., "Limit of blank, limit of detection and limit of quantitation," Clin Biochem Rev, 2008, 29 Suppl 1: S49-52.
Armstrong et al., "Antibody against poly(ethylene glycol) adversely affects PEG-asparaginase therapy in acute lymphoblastic leukemia patients," Cancer, Jul. 2007, vol. 110, Issue 1, pp. 103-111.

(56) References Cited

OTHER PUBLICATIONS

Armstrong et al., "The Hydrodynamic Radii of Macromolecules and Their Effect on Red Blood Cell Aggregation," Biophys. J., 2004, 87, 4259-4270.
Arner et al., "FGF21 attenuates lipolysis in human adipocytes—a possible link to improved insulin sensitivity," FEBS Lett, May 2008, vol. 582, Issue 12, pp. 1725-1730.
Arnida et al., "Geometry and surface characteristics of gold nanoparticles influence their biodistribution and uptake by macrophages," Eur J Pharm Biopharm, Apr. 2011, vol. 77, Issue 3, pp. 417-423.
Arshavsky-Graham et al., "Lab-on-a-Chip Devices for Point-of-Care Medical Diagnostics," Advances in Biochemical Engineering/Biotechnology, 2020, 19 pages.
Asai et al., "Protein polymer hydrogels by in situ, rapid and reversible self-gelation," Biomaterials, Jul. 2012, vol. 33, Issue 21, pp. 5451-5458.
Astete et al., "Synthesis and characterization of PLGA nanoparticles," Journal of Biomaterials Science, Polymer Edition 2006, 17(3):247-289.
Atun et al., "Expanding global access to radiotherapy," Lancet Oncol, Sep. 2015, vol. 16, Issue 10, pp. 1153-1186.
Atyeo et al., "Distinct Early Serological Signatures Track with SARS-COV-2 Survival," Immunity, 2020, 53: 524-532.
Averick et al., "ATRP under biologically relevant conditions: grafting from a protein," ACS Macro. Lett., Jan. 2012, vol. 1, Issue 1, pp. 6-10.
Averick et al., "Protein-polymer hybrids: conducting ARGET ATRP from a genetically encoded cleavable ATRP initiator," Eur. Polym. J., Oct. 2013, vol. 49, Issue 10, pp. 2919-2924.
Awai et al., "Studies of the metabolism of I-131-labeled human transferrin," J. Lab. Clin. Med. 61, 1963, 363-396.
Awasthi et al., "Comparative benefits of Nab-paclitaxel over gemcitabine or polysorbate-based docetaxel in experimental pancreatic cancer," Carcinogenesis, Oct. 2013, vol. 34, Issue 10, pp. 2361-2369.
Awasthi et al., "Evaluation of combination treatment benefits of nab-paclitaxel in experimental pancreatic cancer," Journal of Clinical Oncology, 2012, 30, 170.
Axup et al., "Synthesis of site-specific antibody-drug conjugates using unnatural amino acids," Proc Natl Acad Sci USA, Feb. 2012, vol. 109, Issue 40, pp. 16101-16106.
Azhdarinia et al., "Regional radiochemotherapy using in situ hydrogel," Pharm Res., 2005, 22, 776-783.
Babu, "The contribution of intrinsically disordered regions to protein function, cellular complexity, and human disease," Biochem Soc Trans, Oct. 2016, 44(5):1185-1200.
Bache et al., "Investigating the accuracy of microstereotactic-body-radiotherapy utilizing anatomically accurate 3D printed rodent-morphic dosimeters," Medical Physics, Feb. 2015, vol. 42, Issue 2, pp. 846-855.
Badi, "Non-linear PEG-based thermoresponsive polymer systems," Progress in Polymer Science, Mar. 2017, vol. 66, pp. 54-79.
Bae et al., "Targeted drug delivery to tumors: myths, reality and possibility," J Control Release, Elsevier, Aug. 2011, 153(3):198-205.
Baggio et al., "A recombinant human glucagon-like peptide (GLP)-1-albumin protein (Albugon) mimics peptidergic activation of GLP-1 receptor-dependent pathways coupled with satiety, gastrointestinal motility, and glucose homeostasis," Diabetes 53, 2004, 2492-2500.
Baggio et al., "Biology of Incretins: GLP-1 and GIP," Gastroenterology, May 2007, vol. 132, Issue 6, pp. 2131-2157.
Bailey et al., "Genomic analyses identify molecular subtypes of pancreatic cancer," Nature, Mar. 2016, vol. 531, Issue 7592, pp. 47-52.
Bain et al., "Formation of monolayer films by the spontaneous assembly of organic thiols from solution onto gold," Journal of the American Chemical Society, 1989, 111: 321-335.
Balaji, "Subdermal fat grafting for Parry-Romberg syndrome," Ann Maxillofac Surg, 2014, 4: 55-59.
Balu et al., "An16-resilin: an advanced multi-stimuli-responsive resilin-mimetic protein polymer," Acta Biomater, Nov. 2014, 10:4768-4777.
Bamford et al., "The COSMIC (Catalogue of Somatic Mutations in Cancer) database and website," British Journal of Cancer, 2004, 91, 355-358.
Banani et al., "Biomolecular condensates: organizers of cellular biochemistry," Nat Rev Mol Cell Biol, May 2017, 18(5):285-298.
Banerjee et al., "Nanoparticles in cancer chemotherapy," Prog Mol Biol Transl Sci, Elsevier, Nov. 2011, 104:489-507.
Banga et al., "Parenteral controlled delivery and parmacokinetics of therapeutic peptides and proteins," (CRC Press, Boca Raton, FL, 2005).
Banjade et al., "Phase transitions of multivalent proteins can promote clustering of membrane receptors," Elife, Oct. 2014, 3:e04123.
Bansal et al., "PEGylation improves pharmacokinetic profile, liver uptake and efficacy of Interferon gamma in liver fibrosis," J. Control. Release, Sep. 2011, vol. 154, Issue 3, pp. 233-240.
Banskota et al., "Genetically encoded stealth nanoparticles of a zwitterionic polypeptide- paclitaxel conjugate have wider therapeutic window than Abraxane in multiple tumor models," Nano Lett, Mar. 2020, 20(4):2396-2409.
Banyard et al., "Preparation, Characterization, and Clinical Implications of Human Decellularized Adipose Tissue Extracellular Matrix (hDAM): A Comprehensive Review," Aesthet Surg J, 2016, 36: 349-357.
Baraf et al., "Infusion-related reactions with pegloticase, a recombinant uricase for the treatment of chronic gout refractory to conventional therapy," J Clin Rheumatol, 2014, 20: 427-432.
Barbuti et al., "Paclitaxel through the ages of anticancer therapy: Exploring its role in chemoresistance and radiation therapy," Cancers, Dec. 2015, vol. 7, Issue 4, pp. 2360-2371.
Barnett et al., "Normal tissue reactions to radiotherapy: towards tailoring treatment dose by genotype," Nat Rev Cancer, Feb. 2009, vol. 9, Issue 2, pp. 134-142.
Barton et al., "Estimating the demand for radiotherapy form the evidence: A review of changes from 2003 to 2012," Radiother Oncol, Jul. 2014, vol. 112, Issue 1, pp. 140-144.
Baskar et al., "Cancer and Radiation Therapy: Current Advances and Future Directions," Int. J. Med. Sci., Feb. 2012, vol. 9, Issue 3, pp. 193-199.
Bates et al., "Block copolymer thermodynamics: theory and experiment," Annu Rev. Phys. Chem., 1990, 41:525-57.
Bedford et al., "WW domain-mediated interactions reveal a spliceosome-associated protein that binds a third class of proline-rich motif: The proline glycine and methionine-rich motif," PNAS, 1998, 95: 10602-10607.
Beenken et al., "The FGF family: biology, pathophysiology and therapy," Nat Rev Drug Discov, Mar. 2009, vol. 8, Issue 3, pp. 235-253.
Begg et al., "Strategies to improve radiotherapy with targeted drugs," Nat Rev Cancer, Apr. 2011, vol. 11, Issue 4, pp. 239-253.
Bellucci et al., "A noncanonical function of sortase enables site-specific conjugation of small molecules to lysine residues in proteins," Angew. Chem. Int. Ed. 54, Jan. 2015, vol. 54, Issue 2, pp. 441-445.
Bellucci et al., "Three-in-One Chromatography-Free Purification, Tag Removal, and Site- Specific Modification of Recombinant Fusion Proteins Using Sortase A and Elastin-like Polypeptides," Angewandte Chemie International Edition, Mar. 2013, vol. 52, Issue 13, pp. 3703-3708.
Bender et al., "Synthesis, Crystallization, and Biological Evaluation of an Orally Active Prodrug of Gemcitabine," J. Med. Chem., Nov. 2009, vol. 52, Issue 22, pp. 6958-6961.
Benn et al., "Physiology of Hyperuricemia and Urate-Lowering Treatments," Front Med (Lausanne), 2018, 5: 160, 28 pages.
Bennett et al., "Association of Fat Grafting With Patient-Reported Outcomes in Postmastectomy Breast Reconstruction," JAMA Surg, 2017, 152: 944-950.
Berisio et al., "Imino Acids and Collagen Triple Helix Stability: Characterization of Collagen-like Polypeptides Containing Hyp-Hyp-Gly Seqeucne Repeats," JACS, 2004, 126: 11402-11403.

(56) References Cited

OTHER PUBLICATIONS

Bernacki et al., "Length-dependent aggregation of uninterrupted polyalanine peptides," Biochemistry, Sep. 2011, vol. 50, Issue 43, pp. 9200-9211.
Berndt et al., "Synthetic lipidation of peptides and amino acids: Monolayer structure and properties," J. Am. Chem. Soc., 1995, 117, 9515-9522.
Berry et al., "Development and characterisation of neutralising monoclonal antibody to the SARS-coronavirus," J Virol Methods, 2004, 120: 87-96.
Bessa et al., "Thermoresponsive self-assembled elastin-based nanoparticles for delivery of BMPs," Journal of Controlled Release, Mar. 2010, vol. 142, Issue 3, pp. 312-318.
Best, "Computational and theoretical advances in studies of intrinsically disordered proteins," Curr Opin Struct Biol, Feb. 2017, 42:147-154.
Bhattacharyya et al., "A paclitaxel-loaded recombinant polypeptide nanoparticle outperforms Abraxane in multiple murine cancer models," Nat. Commun., Aug. 2015, Issue 6, Article 7939, 30 pages.
Bhattacharyya et al., "Encapsulating a Hydrophilic Chemotherapeutic into Rod-Like Nanoparticles of a Genetically Encoded Asymmetric Triblock Polypeptide Improves its Efficacy," Advanced functional materials, Mar. 2017, vol. 27, Issue 12, Article 1605421, 9 pages.
Bidwell et al., "Development of elastin-like polypeptide for thermally targeted delivery of doxorubicin," Biochemical Pharmacology, Mar. 2007, vol. 73, Issue 5, pp. 620-631.
Binz et al., "Engineering novel binding proteins from nonimmunoglobulin domains," Nat Biotechnol, 2005, 23(10):1257-68.
Blanco et al., "Principles of nanoparticle design for overcoming biological barriers to drug delivery," Nat Biotechnol, Sep. 2015, 33(9): 941-51.
Blasko et al., "Brachytherapy for carcinoma of the prostate: Techniques, patient selection, and clinical outcomes," Seminars in Radiation Oncology, 2002, 12, 81-94.
Blasko et al., "The role of external beam radiotherapy with I-125/Pd-103 brachytherapy for prostate carcinoma," Radiother Oncol, 2000, 57, 273-278.
Blasko et al., "Transperineal percutaneous iodine-125 implantation for prostatic carcinoma using transrectal ultrasound and template guidance," Endocurietherapy/Hyperthermia Oncology, 1987, 3, 131-139.
Bley et al., "Microtubule stabilising agents and ionising radiation: Multiple exploitable mechanisms for combined treatment," Eur J Cancer, Jan. 2013, vol. 49, Issue 1, pp. 245-253.
Bobo et al., "Nanoparticle-based medicines: a review of FDA-approved materials and clinical trials to date." Pharmaceutical research, Oct. 2016, vol. 33, Issue 10, pp. 2373-2387.
Bocci et al., "The pharmacological bases of the antiangiogenic activity of paclitaxel," Angiogenesis, Jul. 2013, vol. 16, Issue 3, pp. 481-492.
Bochicchio et al., "Investigating by CD the molecular mechanism of elasticity of elastomeric proteins, " Chirality, Sep. 2008, vol. 20, Issue 9, pp. 985-994.
Boekhorst et al., "Genome-wide detection and analysis of cell wall-bound proteins with LPxTG- like sorting motifs," J. Bacteriol. 187, 2005, 4928-4934.
Boeynaems et al., "Protein Phase Separation: A New Phase in Cell Biology," Trends Cell Biol, Jun. 2018, 28(6):420-435.
Boeynaems et al., "Spontaneous driving forces give rise to protein-RNA condensates with coexisting phases and complex material properties," Proc Natl Acad Sci U S A, 2019, 116: 7889-7898.
Boldt, "Use of albumin: an update," Br J. Anaesth., Mar. 2010, vol. 104, Issue 3, pp. 276-284.
Bond, "Exenatide (Byetta) as a novel treatment option for type 2 diabetes mellitus," Proc. (Bayl. Univ. Med. Cent.), Jul. 2006, vol. 19, Issue 3, pp. 281-284.
Bontempo et al., "Streptavidin as a macroinitiator for polymerization: in situ protein-polymer conjugate formation," J. Am. Chem. Soc., 2005, 6508-6509.
Bowditch et al., "Identification of a novel integrin binding site in fibronectin. Differential utilization by ß3 integrins," Journal of Biological Chemistry, 1994, 269(14): 10856-10863.
Borst et al., "The Therapeutic Antibody LM609 Selectively Inhibits Ligand Binding to Human aVB3 Integrin via Steric Hindrance," Structure, Nov. 2017, 25(11):1732-1739.e5.
Boyer et al., "Well-Defined Protein-Polymer Conjugates via in Situ RAFT Polymerization," J. Am. Chem. Soc., Jun. 2007, vol. 129, Issue 22, pp. 7145-7154.
Branco et al., "Self-assembling materials for therapeutic delivery," Acta Biomaterialia, Mar. 2009, vol. 5, Issue 3, pp. 817-831.
Brangwynne et al., "Polymer physics of intracellular phase transitions," Nature Physics, Nov. 2015, 11(11):899-904.
Brannon-Peppas et al., "Nanoparticle and targeted systems for cancer therapy," Advanced Drug Delivery Reviews, Elsevier, Sep. 2012, 64(11):206-212.
Broome et al., "Expanding the utility of beta-galactosidase complementation: piece by piece," Mol Pharm, ACS Publications, Feb. 2010, 7(1):60-74.
Broyer et al., "Emerging synthetic approaches for protein-polymer conjugations," Chem. Commun., Feb. 2011, vol. 47, Issue 8, pp. 2212-2226.
Brusa et al., "Antitumor activity and pharmacokinetics of liposomes containing lipophilic gemcitabine prodrugs, " Anticancer Res., Jan. 2007, vol. 27, Issue 1A, pp. 195-199.
Bryant et al., "Serology for SARS-COV-2: Apprehensions, opportunities, and the path forward," Sci Immunol, 2020, 5: eabc6347, 4 pages.
Brzezinski et al., "Autologous Fat Grafting to the Breast Using REVOLVE System to Reduce Clinical Costs," Ann Plast Surg, 2016, 77: 286-289.
Burchard, "Light Scattering Techniques," Physical techniques for the study of food biopolymers, 1994, 151-213.
Burke et al., "Multimodal nanoparticle imaging agents: design and applications," Philos Trans A Math Phys Eng Sci, Nov. 2017, 375:20170261.
Burnouf, "Modern plasma fractionation," Transfus. Med. Rev., Apr. 2007, vol. 21, Issue 2, pp. 101-117.
Buteau et al., "Glucagon-like peptide-1 prevents beta cell glucolipotoxicity," Diabetologia, 2004, 47(5):806-815.
Butler et al., "ß-Cell Deficit and Increased B-Cell Apoptosis in Humans With Type 2 Diabetes," Diabetes, 2003, 52(1):102-110.
Cabral et al., "Accumulation of sub-100 nm polymeric micelles in poorly permeable tumours depends on size," Nature Nanotechnology, Oct. 2011, vol. 6, Issue 12, pp. 815-823.
Cabrera et al., "Automated, High-Throughput Assays for Evaluation of Human Pancreatic Islet Function," Cell Transplant, First published Nov. 2007, vol. 16, Issue 10, pp. 1039-1048.
Cabrera et al., "Glutamate Is a Positive Autocrine Signal for Glucagon Release," Cell Metab, Jun. 2008, vol. 7, Issue 6, pp. 545-554.
Cai et al., "Long-acting preparations of exenatide," Drug Des. Devel. Ther., Sep. 2013, vol. 7, pp. 963-970.
Calabrese et al., "Frequency, distribution and immunologic nature of infusion reactions in subjects receiving pegloticase for chronic refractory gout," Arthritis Res Ther, 2017, 19: 191, 7 pages.
Caliceti et al., "Pharmacokinetic and biodistribution properties of poly(ethylene glycol)-protein conjugates," Adv. Drug Deliv. Rev, 2003, 55, 1261-1277.
Callahan et al., "Triple stimulus-responsive polypeptide nanoparticles that enhance intratumoral spatial distribution," Nano Letters, Mar. 2012, vol. 12, Issue 4, pp. 2165-2170.
Camilloni et al., "Determination of secondary structure populations in disordered states of proteins using nuclear magnetic resonance chemical shifts," Biochemistry, Feb. 2012, vol. 51, Issue 11, pp. 2224-2231.
Campbell et al., "Pegylated peptides V. Carboxy-terminal PEGlyted analogs of growth hormone- releasing factor (GRF) display enhanced duration of biological activity in vivo," J. Peptide Res., 1997, 49:527-537.
Cao et al., "Monitoring the effects of anti-angiogenesis on the radiation sensitivity of pancreatic cancer xenografts using dynamic

(56) References Cited

OTHER PUBLICATIONS contrast-enhanced computed tomography," Int J Radiation Oncol Biol Phys, Feb. 2014, vol. 88, Issue 2, pp. 412-418.
Cardenes et al., "Locally advanced pancreatic cancer: Current therapeutic approach," The Oncologist, Jun. 2006, vol. 11, Issue 6, pp. 612-623.
Carreiras et al., "Expression and localization of alpha v integrins and their ligand vitronectin in normal ovarian epithelium and in ovarian carcinoma," Gynecol Oncol, 1996, 62(2):260-7.
Carrico et al., "Introducing genetically encoded aldehydes into proteins," Nat Chem Biol, Jun. 2007, vol. 3, Issue 6, pp. 321-322.
Cataldo et al., "Radiation-induced crosslinking of collagen gelatin into a stable hydrogel," Journal of Radioanalytical and Nuclear Chemistry, Sep. 2008, vol. 275, Issue 1, pp. 125-131.
Caves et al., "Thermal inactivation of uricase (urate oxidase): mechanism and effects of additives," Biochemistry, 2013, 52: 497-507.
Centers for Disease Control and Prevention, "National Diabetes Statistics Report, 2017," Atlanta, GA: Centers for Disease Control and Prevention, US Department of Health and Human Services; 2017. Reviewed: Feb. 24, 2018.
Ceska et al., "A new and rapid method for the clinical determination of α-amylase activities in human serum and urine. Optimal conditions," Clinica Chimica Acta, 1969, 26, 437-444.
Cha et al., "Microfluidics-assisted fabrication of gelatin-silica core-shell microgels for injectable tissue constructs," Biomacromolecules, 2014, 15: 283-290.
Chae et al., "Pharmacokinetic and pharmacodynamic evaluation of site-specific PEGylated glucagon-like peptide-1 analogs as flexible postprandial-glucose controllers," J Pharm Sci, 2009, 98(4): 1556-1567.
Chakrabartty et al., "Stability of a-Helices," Adv Protein Chem, 1995, 46, 141-176.
Champion et al., "Particle shape: a new design parameter for micro- and nanoscale drug delivery carriers," J Control Release, Elsevier, Aug. 2007, 121(1-2):3-9.
Champion et al., "Role of particle size in phagocytosis of polymeric microspheres," Pharm Res, Srpinger, Mar. 2008, 25(8):1815-21.
Champion et al., "Role of target geometry in phagocytosis," Proc Natl Acad Sci U S A, The National Academy of Sciences of the USA, Mar. 2006, 103(13):4930-4.
Champion et al., "Shape induced inhibition of phagocytosis of polymer particles," Pharm Res, Springer, Jan. 2009, 26(1):244-9.
Chan et al., "A randomized, repeat-dose, pharmacodynamic and safety study of an antidote- controlled factor IXa inhibitor," J Thromb Haemost, 2008, 6(5): 789-796.
Chan et al., "Phase 1b randomized study of antidote-controlled modulation of factor IXa activity in patients with stable coronary artery disease," Circulation, 2008, 117(22): 2865-2874.
Chang et al., "Thermoprecipitation of Glutathione S-Transferase by Glutathione-Poly(N- isopropylacrylamide) Prepared by RAFT Polymerization," Macromolecular Rapid Communications, Oct. 2010, 31: 1691-1695.
Chang et al., "Tumor-stroma interaction in orthotopic primary pancreatic cancer xenografts during hedgehog pathway inhibition," Int. J. Cancer, Jul. 2013, vol. 133, Issue 1, pp. 225-235.
Chapin et al., "Rapid microRNA profiling on encoded gel microparticles," Angew Chem Int Ed Engl, 2011, 50: 2289-2293.
Chappell et al., "Computational design of small transcription activating RNAs for versatile and dynamic gene regulation," Nat Commun, 2017, 8(1): 1051.
Chappell et al., "Creating small transcription activating RNAs," Nat Chem Biol, 2015, 11(3): 214- 220.
Chase et al., "Single-Stranded DNA Binding Proteins Required for DNA Replication," Ann. Rev. Biochem., 1986, 55: 103-136.
Chatterjee et al., "Type 2 diabetes," The Lancet, Jun. 2017, vol. 389, Issue 10085, pp. 2239-2251.
Chaudhury et al., "The major histocompatibility complex-related Fc receptor for IgG (FcRn) binds albumin and prolongs its lifespan," J Exp Med, 2003, 197(3): p. 315-22.

Chen et al., "Anisotropic hydrogels fabricated with directional freezing and radiation-induced polymerization and crosslinking method," Materials Letters, Dec. 2012, vol. 89, pp. 104-107.
Chen et al., "Anti-hypervariable region antibody induced by a defined peptide: An approach for studying the structural correlates of idiotypes," PNAS, 1984, 81:1784-1788.
Chen et al., "Bioinspired Modular Synthesis of Elastin-Mimic Polymers To Probe the Mechanism of Elastin Elasticity," J. Am. Chem. Soc., Mar. 2010, vol. 132, Issue 13, pp. 4577-4579.
Chen et al., "Real-world patterns of pegloticase use for treatment of gout: descriptive multidatabase cohort study," BMJ Open, 2020, 10: e041167, 6 pages.
Chen et al., "Rheology of Soft Materials," Annual Review of Condensed Matter Physics, May 2010, vol. 1, pp. 301-322.
Chen et al., "Site-specific labeling of cell surface proteins with biophysical probes using biotin ligase," Nat Methods, 2005, 2(2):99-104.
Chen et al., "The influence of polymer topology on pharmacokinetics: differences between cyclic and linear PEGylated poly(acrylic acid) comb polymers," J Control Release, 2009, 140: 203-209.
Chen et al., "The use of self-adjuvanting nanofiber vaccines to elicit high-affinity B cell responses to peptide antigens without inflammation," Biomaterials, Nov. 2013, vol. 34, Issue 34, pp. 8776-8785.
Chen, "Small-molecule delivery by nanoparticles for anticancer therapy," Trends Mol Med, Cell Press, Dec. 2010, 16(12):594-602.
Chilkoti et al., "Design of thermally responsive, recombinant polypeptide carriers for targeted drug delivery," Advance Drug Delivery Reviews, 2002, 54:1093-1111.
Chilkoti et al., "Stimulus responsive elastin biopolymers: applications in medicine and biotechnology," Curr Opin Chem Biol, Dec. 2006, vol. 10, Issue 6, pp. 652-657.
Chilkoti et al., "Targeted drug delivery by thermally responsive polymers," Advanced Drug Delivery Reviews, 2002, 54:613-630.
Chin et al., "Addition of p-azido-I-phenylalanine to the genetic code of *Escherichia coli*," Journal of the American Chemical Society, 2002, 124: 9026-9027.
Chithrani et al., "Determining the size and shape dependence of gold nanoparticle uptake into mammalian cells," Nano Lett, Apr. 2006, vol. 6, Issue 4, pp. 662-668.
Chithrani et al., "Elucidating the mechanism of cellular uptake and removal of protein-coated gold nanoparticles of different sizes and shapes," Nano letters, ACS Publications, Jun. 2007, 7(6):1542-1550.
Chitkara et al., "Self-Assembling, Amphiphilic Polymer-Gemcitabine Conjugate Shows Enhanced Antitumor Efficacy Against Human Pancreatic Adenocarcinoma," Bioconjug. Chem., Jun. 2013, vol. 24, Issue 7, pp. 1161-1173.
Cho et al., "Effects of hofmeister anions on the phase transition temperature of elastin-like polypeptides," J. Phys. Chem. B., Nov. 2008, vol. 112, Issue 44, pp. 13765-13771.
Cho et al., "Hydrogen bonding of B-turn structure is stabilized in D(2)O," J Am Chem Soc, Oct. 2009, vol. 131, Issue 42, pp. 15188-15193.
Cho et al., "Therapeutic nanoparticles for drug delivery in cancer," Clin. Cancer Res., Mar. 2008, vol. 14, Issue 5, pp. 1310-1316.
Chockalingam et al., "Design and application of stimulus-responsive peptide systems," Protein Engineering, Design & Selection, Apr. 2007, 20(4):155-161.
Choi et al., "Multiplexed detection of mRNA using porosity-tuned hydrogel microparticles, " Anal Chem, 2012, 84: 9370-9378.
Choi et al., "Recent advances in engineering microparticles and their nascent utilization in biomedical delivery and diagnostic applications," Lab Chip, 2017, 17: 591-613.
Choi et al., "Renal Clearance of Nanoparticles," Nature biotechnology, Oct. 2007, vol. 25, Issue 10, pp. 1165-1170.
Chow et al., "Peptide-based biopolymers in biomedicine and biotechnology," Mater. Sci. Eng. R Reports, Jan. 2008, vol. 62, Issue 4, pp. 125-155.
Chow et al., "Ultra-High Expression of a Thermally Responsive Recombinant Fusion Protein in *E. coli*," Biotechnology Progress, Sep. 2006, vol. 22, Issue 3, pp. 638-646.
Choy et al., "Investigation of taxol as a potential radiation sensitizer," Cancer, 1993, 71, 3774-3778.

(56) References Cited

OTHER PUBLICATIONS

Christensen et al., "Fusion order controls expression level and activity of elastin-like polypeptide fusion proteins," Protein Science, Jul. 2009, vol. 18, Issue 7, pp. 1377-1387.
Christensen et al., "Predicting Transition Temperatures of Elastin-Like Polypeptide Fusion Proteins," Biomacromolecules, Mar. 2013, vol. 14, Issue 5, pp. 1514-1519.
Chu et al., "Controllable monodisperse multiple emulsions," Angew Chem Int Ed Engl, 2007, 46: 8970-8974.
Chu et al., "Molecular Diagnosis of a Novel Coronavirus (2019-nCOV) Causing an Outbreak of Pneumonia," Clin Chem, 2020, 66(4): 549-555.
Cid-Arregui et al., "Perspectives in the treatment of pancreatic adenocarcinoma," World Journal of Gastroenterology, Aug. 2015, vol. 21, Issue 31, pp. 9297-9316.
Ciezki et al., "Brachytherapy or surgery? A composite view," Oncology, Oct. 2009, vol. 23, Issue 11, pp. 960-964.
Cima, "AVMA Guidelines for the Euthanasia of Animal: 2013 Edition," Journal of the American Veterinary Medical Association, Jan. 2013, vol. 242, 102 pages.
Cirulis et al., "Viscoelastic properties and gelation of an elastin-like polypeptide," Journal of Rheology, Sep. 2009, vol. 53, Issue 5, pp. 1215-1228.
Clarke et al., "Tropoelastin massively associates during coacervation to form quantized protein spheres," Biochemistry, Jul. 2006, vol. 45, Issue 33, pp. 9989-9996.
Clavéet al., "Amylase, lipase, pancreatic isoamylase, and phospholipase A in diagnosis of acute pancreatitis," Clinical Chemistry, 1995, 41, 1129-1134.
Cohen et al., "First clinical application of an actively reversible direct factor IXa inhibitor as an anticoagulation strategy in patients undergoing percutaneous coronary intervention," Circulation, 2010, 122(6): 614-622.
Coin et al., "Solid-phase peptide synthesis: from standard procedures to the synthesis of difficult sequences," Nat. Protoc., Dec. 2007, vol. 2, Issue 12, 3247-3256.
Colomb et al., "Radiation-Convertible Polymers from Norbornenyl Derivatives. Crosslinking with Ionizing Radiation," Journal of Applied Polymer Science, 1970, 14, 1659-1670.
Cong et al., "Nucleocapsid Protein Recruitment to Replication-Transcription Complexes Plays a Crucial Role in Coronaviral Life Cycle," J Virol, 2020, 94: e01925-19, 21 pages.
Conner et al., "Regulated portals of entry into the cell," Nature, 2003, 422(6927):37-44.
Conrad et al., "ELPylated anti-human TNF therapeutic single-domain antibodies for prevention of lethal septic shock," Plant Biotechnology Journal, Jan. 2011, vol. 9, Issue 1, pp. 22-31.
Coskun et al., "Fibroblast Growth Factor 21 Corrects Obesity in Mice," Endocrinology, Dec. 2008, vol. 149, Issue 12, pp. 6018-6027.
Costa et al., "Active Targeting of Cancer Cells by Nanobody Decorated Polypeptide Micelle with Bio-orthogonally Conjugated Drug," Nano letters, Dec. 2018, 19(1):247-254.
Costa et al., "Photo-crosslinkable unnatural amino acids enable facile synthesis of thermoresponsive nano- to microgels of intrinsically disordered polypeptides," Adv Mater, 2018, 30(5): 1704878.
Craik et al., "The future of peptide-based drugs," Chemical biology & drug design 81, Dec. 2013, vol. 81, Issue 1, pp. 136-147.
Crowther, "The ELISA guidebook," Methods Mol Biol, 2000, 149(III-IV): 1-413.
Cui et al., "Amino acid sequence in constitutionally isomeric tetrapeptide amphiphiles dictates architecture of one-dimensional nanostructures," J. Am. Chem. Soc., Aug. 2014, vol. 136, Issue 35, 12461-12468.
Cui et al., "Self-assembly of peptide amphiphiles: from molecules to nanostructures to biomaterials," Biopolymers, Jan. 2010, vol. 94, Issue 1, pp. 1-18.
Da Pieve Chiara et al., "Modification of Thiol Functionalized Aptamers by Conjugation of Synthetic Polymers," Bioconjugate Chemistry, 2009, 1(1): 169-174.

Dai et al., "Versatile biomanufacturing through stimulus-responsive cell-material feedback," Nature chemical biology, Sep. 2019, 15(10):1017-1024.
Dale et al., "Direct covalent mercuration of nucleotides and polynucleotides," Biochemistry, 1975, 14(11): 2447-2457.
Dalhaimer et al., "Single Molecule Visualization of Stable, Stiffness-Tunable, Flow-Conforming Worm Micelles," Macromolecules, 2003, 36(18):6873-6877.
Dalla Poza et al., "Targeting gemcitabine containing liposomes to CD44 expressing pancreatic adenocarcinoma cells causes an increase in the antitumoral activity," Biochim. Biophys. Acta, May 2013, vol. 1828, Issue 5, pp. 1396-1404.
Darling et al., "Viscoelastic properties of zonal articular chondrocytes measured by atomic force microscopy," Osteoarthritis Cartilage, 2006, 14: 571-579.
Darzynkiewicz et al., "DNA content measurement for DNA ploidy and cell cycle analysis," Current Protocols in Cytometry, 2001, 7.5.1 - 7.5.24.
Das et al., "Conformations of intrinsically disordered proteins are influenced by linear sequence distributions of oppositely charged residues," Proc Natl Acad Sci U S A, National Academy of Sciences, Aug. 2013, 110(33):13392-13397.
Dasgupta et al., "Isopeptide Ligation Catalyzed by Quintessential Sortase A: Mechanistic Cues From Cyclic and Branched Oligomers of Indolicidin," The Journal of Biological Chemistry, May 2011, vol. 286, No. 27, p. 23996-24006, Supplemental Information.
Davis et al., "Antibodies and the RNA World: A Role for Low-molecular-weight Effectors in Biochemical Evolution," RNA World, 1993, Chapter 8, p. 185-204.
Day et al., "A new glucagon and GLP-1 co-agonist eliminates obesity in rodents," Nat Chem Biol, Oct. 2009, 5:749.
De et al., "Temperature-Regulated Activity of Responsive Polymer-Protein Conjugates Prepared by Grafting-from via RAFT Polymerization," J. Am. Chem. Soc. Jul. 2008, 130, 11288-11289.
De Leon-Rodriguez et al., "Multifunctional thermoresponsive designer peptide hydrogels," Acta Biomaterialia, 2017, 47: 40-49.
De Simone et al., "Accurate random coil chemical shifts from an analysis of loop regions in native states of proteins," J Am Chem Soc, Nov. 2009, 131, 16332-16333.
Deer et al., "Phenotype and genotype of pancreatic cancer cell lines," Pancreas, May 2010, 39, 425-435.
Dejana et al., "The role of adherens junctions and VE-cadherin in the control of vascular permeability," J Cell Sci, Jul. 2008, 121, 2115-2122.
Delaglio et al., "NMRPipe: A multidimensional spectral processing system based on UNIX pipes," Journal of Biomolecular NMR 6, 1995, 277-293.
Delisser et al., "Vascular endothelial platelet endothelial cell adhesion molecule 1(PECAM-1) regulates advanced metastatic progression," PNAS, Oct. 2010, 107, 18616-18621.
Dennis et al., "Albumin binding as a general strategy for improving the pharmacokinetics of proteins," J Biol Chem, 2002, 277(38): p. 35035-43.
Dennis et al., "Co-Translational Myristoylation Alters the Quaternary Structure of HIV-1 Nef in Solution," Proteins: Structure, Function, and Bioinformatics, 2005, 60:658-669.
Depp et al., "Native protein-initiated ATRP: A viable and potentially superior alternative to PEGylation for stabilizing biologics," Acta Biomater. Feb. 2009, 5, 560-569.
Deshayes et al., "Radium 223 dichloride for prostate cancer treatment," Drug Des Devel Ther, Sep. 2017, 11, 2643-2651.
DeYoung et al., "Encapsulation of exenatide in poly-(D,L-lactide-co-glycolide) microspheres produced an investigational long-acting once-weekly formulation for type 2 diabetes," Diabetes Technol Ther, Nov. 2011, 13, 1145-1154.
Diana et al., "Prognostic role and correlation of CA9, CD31, CD68 and CD20 with the desmoplastic stroma in pancreatic ductal adenocarcinoma," Oncotarget, Nov. 2016, 7, 72819-72832.
Diehl et al., "A Good Practice Guide to the Administration of Substances and Removal of Blood Including Routes and Volumes," J Appl Toxicol, 2001, 21, 15-23.

(56) References Cited

OTHER PUBLICATIONS

Dignon et al., "Relation between single-molecule properties and phase behavior of intrinsically disordered proteins," Proc Natl Acad Sci U S A, Oct. 2018, 115(40): 9929-9934.
Dignon et al., "Sequence determinants of protein phase behavior from a coarse-grained model," PLOS Comput Biol, Jan. 2018, 14(1):e1005941.
Dincer et al., "Multiplexed Point-of-Care Testing—xPOCT," Trends Biotechnol, 2017, 35(8): 728-742.
Ding et al., "Mechanism for the alpha-helix to beta-hairpin transition," Proteins, 2003, 53, 220-228.
Ding et al., "BKlotho Is Required for Fibroblast Growth Factor 21 Effects on Growth and Metabolism," Cell Metab, Sep. 2012, 16(3):387-393.
Dong et al., "An interactive web-based dashboard to track COVID-19 in real time," Lancet Infect Dis, 2020, 20: 533-534.
Donnelly et al., "DNA Vaccines," Ann. Rev. Immunol., 1997, 15, 617-648.
Dreher et al., "Evaluation of an elastin-like polypeptide-doxorubicin conjugate for cancer therapy," J. of Controlled Release, 2003, 91:31-43.
Dreher et al., "Temperature triggered self-assembly of polypeptides into multivalent spherical micelles," J. Am. Chem. Soc. Jan. 2008, 130, 687-694.
Dreher et al., "Thermal cycling enhances the accumulation of a temperature-sensitive biopolymer in solid tumors," Cancer Res, May 2007, 67, 4418-4424.
Dreher, M. R. Ph.D. Thesis, Duke University, Durham, NC, Apr. 2006.
Dreis et al., "Preparation, Characterisation and Maintenance of Drug Efficacy of Doxorubicin- Loaded Human Serum Albumin (HSA) Nanoparticles," Int. J. Pharm., Aug. 2007, 341, 207-214.
Drucker "Mechanisms of Action and Therapeutic Application of Glucagon-like Peptide-1," Cell Metab, Apr. 2018, 27(4):740-756.
Drucker et al., "The incretin system: glucagon-like peptide-1 receptor agonists and dipeptidyl peptidase-4 inhibitors in type 2 diabetes," Lancet 368, Nov. 2006, 1696-1705.
Drucker, "Glucagon-like peptides," Diabetes 47, 1998, 159-169.
Drucker, "Incretin action in the pancreas: potential promise, possible perils, and pathological pitfalls," Diabetes, Oct. 2013, 62, 3316-3323.
Du et al., "Endoscope-assisted brachytherapy for pancreatic cancer: From tumor killing to pain relief and drainage," Journal of interventional gastroenterology, Jan. 2011, 1, 23-27.
Du et al., "Tailor-made dual pH-sensitive polymer-doxorubicin nanoparticles for efficient anticancer drug delivery," J. Am. Chem. Soc., Oct. 2011, 133, 17560-17563.
Duan et al., "Fibronectin type III domain based monobody with high activity, " Biochemistry, Oct. 2007 46(44):12656-12664.
Duan et al., "Improving the thermostability and catalytic efficiency of Bacillus deramificans pullulanase by site-directed mutagenesis," Appl Environ Microbiol, American Society for Microbiology, Jul. 2013, 79(13):4072-4077.
Dubey et al., "Development and evaluation of folate functionalized albumin nanoparticles for targeted delivery of gemcitabine," Int J Pharm., Aug. 2015, 492(1-2):80-91.
Ducreux et al., "Radiation plus docetaxel and cisplatin in locally advanced pancreatic carcinoma: A non-comparative randomized phase II trial," Digestive and Liver Disease, Oct. 2014, 46, 950-955.
Duke University, "Gemcitabine/Nab-Paclitaxel With HIGRT in Resectable Pancreatic Cancer," Clinical Trial NCT02318095 <https://clinicaltrials.gov/ct2/show/NCT02318095> Webpage accessed Jan. 11, 2017.
Duncan, "The dawning era of polymer therapeutics," Nature Reviews Drug Discovery, 2003, 2, 347-360.
Duncan, R. "Polymer conjugates as anticancer nanomedicines," Nat. Rev. Cancer, Sep. 2006, 6, 688-701.
Duronio et al., "Protein N-myristoylation in *Escherichia coli*: Reconstitution of a eukaryotic protein modification in bacteria," Proc. Natl. Acad. Sci. USA, 1990, vol. 87, pp. 1506-1510.

Dutta et al., "The Nucleocapsid Protein of SARS-COV-2: a Target for Vaccine Development," J Virol, 2020, 94(13): e00647-20, 2 pages.
Dyke et al., "First-in-human experience of an antidote-controlled anticoagulant using RNA aptamer technology: a phase 1a pharmacodynamic evaluation of a drug-antidote pair for the controlled regulation of factor IXa activity," Circulation, 2006, 114(23): 2490-2497.
Dyrberg et al., "Peptide as Atigens," J. Exp. Med., 1986, 164:1344-1349.
Dzuricky et al., "Avidity and Cell Uptake of Integrin Targeting Polypeptide Micelles is Strongly Shape Dependent," Nano letters, Sep. 2019, 19(9):6124-6132.
Dzuricky et al., "The Convergence of Artificial Protein Polymers and Intrinsically Disordered Proteins," Biochemistry, May 2018, 57(17):2405-2414.
Egan et al., "The Insulinotropic Effect of Acute Exendin-4 Administered to Humans: Comparison of Nondiabetic State to Type 2 Diabetes," The Journal of Clinical Endocrinology & Metabolism, 2002, 87, 1282-1290.
Ehlerding et al., "Biodegradable and Renal Clearable Inorganic Nanoparticles," Adv Sci (Weinh), Feb. 2016, 3(2):1500223.
Eichhorn et al., "Interactions of metal ions with polynucleotides and related compounds. XII. The relative effect of various metal ions on DNA helicity," J. Am. Chem. Soc, 1968, 90: 7323-7328.
Eisenhaber et al., "Prediction of lipid posttranslational modifications and localization signals from protein sequences: Big-n, NMT and PTS1," Nucleic Acids Res., 2003, 31, 3631-3634.
Eisenhauer et al., "New response evaluation criteria in solid tumours: Revised RECIST guideline (version 1.1)," Eur J Cancer, Jan. 2009, 45(2):228-247.
Ekladious et al., "Polymer-drug conjugate therapeutics: advances, insights and prospects," Nature Reviews Drug Discovery, 2019, 18: 273-294.
El-Assaad et al., "Saturated Fatty Acids Synergize with Elevated Glucose to Cause Pancreatic B-Cell Death," Endocrinology, 2003, 144(9):4154-4163.
Elbaum-Garfinkle et al., "The disordered P granule protein LAF-1 drives phase separation into droplets with tunable viscosity and dynamics," Proc Natl Acad Sci U S A, Jun. 2015, 112(23):7189-7194.
Ellis, "Macromolecular crowding: obvious but underappreciated," Trends Biochem. Sci., 2001, 26 (10), 597-604.
Elsabahy et al., "Design of polymeric nanoparticles for biomedical delivery applications," Chem Soc Rev, Royal Society of Chemistry, Apr. 2012, 41(7):2545-61.
Elvin et al., "Synthesis and properties of crosslinked recombinant pro-resilin," Nature, 2005, 437(7061):999-1002.
Elzoghby et al., "Implications of Protein- and Peptide-Based Nanoparticles as Potential Vehicles for Anticancer Drugs," Advances in Protein Chemistry and Structural Biology, Academic Press, Elsevier, Mar. 2015, Chapter Six, vol. 98, pp. 169-221.
Engin et al., "Thermoradiotherapy in the management of superficial malignant tumors," Clinical Cancer Research, 1995, 1, 139-145.
Eom et al., "The No. of operations required for completing breast reconstruction," Plast Reconstr Surg Glob Open, 2012, 2: e242.
Erickson-Miller et al., "Differential toxicity of camptothecin, topotecan and 9-aminocamptothecin to human, canine, and murine myeloid progenitors (CFU-GM) in vitro," Cancer Chemother. Pharmacol., 1997, 39 (5), 467-472.
Etrych et al., "HPMA Copolymer Conjugates of Paclitaxe; and Docetaxel with pH-Controlled Drug Release," Molecular Pharmaceutics, Jun. 2010, 7(4):1015-1026.
Falk et al., "Hyperthermia in oncology," Int J Hyperthermia, 2001, 17, 1-18.
Farazi et al., "Structures of *Saccharomyces cerevisiae* N-myristoyltransferase with bound myristoylCoA and peptide provide insights about substrate recognition and catalysis," Biochemistry, 2001, 40, 6335-6343.
Farmer et al., "Conformational behavior of chemically reactive alanine-rich repetitive protein polymers," Biomacromolecules, 2005, 6, 1531-1539.

(56) References Cited

OTHER PUBLICATIONS

Farokhzad et al., "Targeted nanoparticle-aptamer bioconjugates for cancer chemotherapy in vivo," Proc Natl Acad Sci U S A, The National Academy of Sciences of the USA, Apr. 2006, 103(16):6315-20.
Fathallah et al., "Immunogenicity of Subcutaneously Administered Therapeutic Proteins—a Mechanistic Perspective," The AAPS Journal, 2013, 15(4): 897-900.
Feng et al., "Protein resistant surfaces: comparison of acrylate graft polymers bearing oligo-ethylene oxide and phosphorylcholine side chains," Biointerphases, Mar. 2006, 1 (1), 50.
Fernandez-Colino et al., "Amphiphilic Elastin-Like Block Co-Recombinamers Containing Leucine Zippers: Cooperative Interplay between Both Domains Results in Injectable and Stable Hydrogels," Biomacromolecules, Sep. 2015, 16, 3389-3398.
Finan et al., "A rationally designed monomeric peptide triagonist corrects obesity and diabetes in rodents," Nat Med, Jan. 2015, 21:27-36.
Finan et al., "Unimolecular Dual Incretins Maximize Metabolic Benefits in Rodents, Monkeys, and Humans," Sci Transl Med, Oct. 2013, 5(209):209ra151.
Fluegel et al., "Chain stiffness of elastin-like polypeptides, " Biomacromolecules, Oct. 2010, 11, 3216-3218.
Fosgerau et al., "Peptide therapeutics: current status and future directions," Drug Discovery Today, Jan. 2015, 20, 122-128.
Fox et al., "Soluble polymer carriers for the treatment of cancer: the importance of molecular architecture," Acc Chem Res, 2009, 42(8): 1141-1151.
Frandsen et al., "Recombinant protein-based polymers for advanced drug delivery," Chem Soc Rev, 2012, 41: 2696-2706.
Franzmann et al., "Phase separation of a yeast prion protein promotes cellular fitness," Science, Jan. 2018, 359(6371):eaao5654.
Free et al., "A Phase 1, multi-center, randomized, double-blind, placebo controlled study to evaluate the safety/tolerability, pharmacokinetic and hemodynamic response following single ascending subcutaneous doses of PB1046 (Vasomera) in subjects with essential hypertension," Circulation, Mar. 2018, 130:A19112.
Friedman et al., "Directed Evolution to Low Nanomolar Affinity of a Tumor-Targeting Epidermal Growth Factor Receptor-Binding Affibody Molecule," J. Mol. Biol., Mar. 2008, 376, 1388-1402.
Frilling et al., "Recommendations for management of patients with neuroendocrine liver metastases, " The lancet oncology, Jan. 2014, 15, e8-21.
Fu et al., "Nanoparticle Albumin - Bond (NAB) Technology is a Promising Method for Anti- Cancer Drug Delivery," Recent Patents on Anti-Cancer Drug Discovery, Nov. 2009. 4(3):262-272.
Fujiwara et al., "Modulating effect of the PI3-kinase inhibitor LY294002 on cisplatin in human pancreatic cancer cells," Journal of Experimental & Clinical Cancer Research, Nov. 2008, 27, 76.
Furgeson et al., "Structural optimization of a "smart" doxorubicin-polypeptide conjugate for thermally targeted delivery to solid tumors," Journal of Controlled Release, Jan. 2006, 110:362-369.
Furumoto et al., "Effect of coupling of albumin onto surface of PEG liposome on its In vivo disposition," International Journal of Pharmaceutics, Mar. 2007, 329(1-2): p. 110-116.
Gaberc-Porekar et al., "Obstacles and pitfalls in the PEGylation of therapeutic proteins," Curr. Opin. Drug Discov. Devel. 11, Mar. 2008, 242-250.
Gabizon et al., "Prolonged circulation time and enhanced accumulation in malignant exudates of doxorubicin encapsulated in polyethylene-glycol coated liposomes," Cancer Res., Feb. 1994, 54, 987-992.
Gabriel et al., "Fat grafting and breast reconstruction: tips for ensuring predictability," Gland Surg, 2015, 4: 232-243.
Gaich et al., "The Effects of LY2405319, an FGF21 Analog, in Obese Human Subjects with Type 2 Diabetes," Cell Metab, Sep. 2013, 18(3):333-340.
Ganesan et al., "Lipid Nanoparticles: Different Preparation Techniques, Characterization, Hurdles, and Strategies for the Production of Solid Lipid Nanoparticles and Nanostructured Lipid Carriers for Oral Drug Delivery," Sustain. Chem. Pharm., 2017, 6: 37-56.
Ganson et al., "Control of hyperuricemia in subjects with refractory gout, and induction of antibody against poly(ethylene glycol) (PEG), in a phase I trial of subcutaneous PEGylated urate oxidase," Arthritis Res. Ther. 8, Feb. 2006, R12-R22.
Ganson et al., "Pre-existing anti-polyethylene glycol antibody linked to first-exposure allergic reactions to pegnivacogin, a PEGylated RNA aptamer," J Allergy Clin Immunol, May 2016, 137(5): 1610-1613, e1617.
Gao et al., "In situ growth of a PEG-like polymer from the C terminus of an intein fusion protein improves pharmacokinetics and tumor accumulation" PNAS Early Edition, Jul. 2010, vol. 107, 1-6.
Gao et al., "In situ growth of a PEG-like polymer from the C terminus of an intein fusion protein improves pharmacokinetics and tumor accumulation," Proc. Natl. Acad. Sci., Sep. 2010, 107(38):16432-16437.
Gao et al., "In situ growth of a stoichiometric PEG-like conjugate at a protein's N-terminus with significantly improved pharmacokinetics," Proc. Natl. Acad. Sci., Sep. 2009, 15231-15236.
Gao, "Site-specific and in situ growth of stealth polymer conjugates of proteins with significally improved pharmacology," Journal of Controlled Release, Nov. 2013, 172(1):e116-e117.
Garanger et al., "Structural Evolution of a Stimulus-Responsive Diblock Polypeptide Micelle by Temperature Tunable Compaction of its Core," Macromolecules, Sep. 2015, 48, 6617-6627.
Garay et al., "Antibodies against polyethylene glycol in healthy subjects and in patients treated with PEG-conjugated agents," Expert Opinion. Drug Deliv. 9, Nov. 2012, 1319-1323.
Garay et al., "Therapeutic perspectives on uricases for gout," Joint Bone Spine, 2012, 79: 237-242.
Garcia Quiroz et al., "Syntax of Phase Transition Peptide Polymers with LCST and UCST Behavior," Jan. 1, 2013, Retrieved from the Internet: URL:https://dukespace.lib.duke.edu/dspace/bitstream/handle/10161/7256/GarciaQuirozduke00 66D 11972.pdf?sequence=I &isAllowed=y.
Gauthier et al., "Peptide/protein-polymer conjugates: synthetic strategies and design concepts," Chem. Commun., Jul. 2008, 2591-2611.
Ge et al., "Self-Cleavable Stimulus Responsive Tags for Protein Purification without Chromatography" J. Am. Chem. Soc., 2005, 127: 11228-11229.
Genbank Accession NM_001182082.1 (Mar. 2017).
Geng et al., Shape effects of filaments versus spherical particles in flow and drug delivery, Nat Nanotechnol, Nature Research, Apr. 2007, 2(4):249-55.
Ghoorchian et al., "Molecular architecture influences the thermally induced aggregation behavior of elastin-like polypeptides," Biomacromolecules, Oct. 2011, 12, 4022-4029.
Gianni et al., "Nonlinear pharmacokinetics and metabolism of paclitaxel and its pharmacokinetic/pharmacodynamic relationships in humans," J. Clin. Oncol., 1995, 13 (1), 180-190.
Giberti et al., "Radical retropubic prostatectomy versus brachytherapy for low-risk prostatic cancer: a prospective study," World J Urol, Oct. 2009, 27, 607-612.
Gibson et al., "Enzymatic assembly of DNA molecules up to several hundred kilobases," Nat Methods, May 2009, 6, 343-345.
Gilbreth et al., "Structural insights for engineering binding proteins based on non-antibody scaffolds," Curr Opin Struct Biol, Elsevier, Jun. 2012, 22(4):413-20.
Gillies et al., "Dendrimers and dendritic polymers in drug delivery," Drug Discovery Today, 2005, 10(1):35-43.
Gilroy et al., "Fusion of fibroblast growth factor 21 to a thermally responsive biopolymer forms an injectable depot with sustained anti-diabetic action," J Control Release, May 2018, 277:154-164.
Gilroy et al., "Sustained release of a GLP-1 and FGF21 dual agonist from an injectable depot protects mice from obesity and hyperglycemia," Science Advances, 2020, 6(35): eaaz9890, 12 pages.
Glassman et al., "Toughening of Thermoresponsive Arrested Networks of Elastin-Like Polypeptides To Engineer Cytocompatible Tissue Scaffolds, " Biomacromolecules, Feb. 2016, 17, 415-426.
Gluck et al., "Single Vector System for Efficient N-myristoylation of Recombinant Proteins in E. coli," Plos One, Apr. 2010, 5(4) e100881.

(56) References Cited

OTHER PUBLICATIONS

Göke et al., "Exendin-4 is a high potency agonis and truncated exendin-(9-39)-amide an antagonist at the glucagon-like peptide 1-(7-36)-amide receptor of insulin-secreting b-cells," J. Biol. Chem. 268, 1993, 19650-19655.
Gold et al., "Aptamers and the RNA World, Past and Present," Cold Spring Harbor Perspect. Biol., 2012, 4: a003582, 9 pages.
Goldsmith et al., "Enzyme engineering: reaching the maximal catalytic efficiency peak, " Curr Opin Struct Biol, Dec. 2017, 47:140-150.
Gordon et al., "Protein N-myristoylation," J. Biol. Chem., 1991, 266, 8647-8650.
Gosline et al., "Elastic proteins: biological roles and mechanical properties," Philos Trans R Soc Lond B Biol Sci, 2002, 357, 121-132.
Gottlieb et al., "NMR chemical shifts of common laboratory solvents as trace impurities," J. Org. Chem., 1997, 62, 7512-7515.
Goutelle et al., "The Hill equation: a review of its capabilities in pharmacological modelling. Fundam," Clin. Pharmacol. 22, Dec. 2008, 633-648.
Graff et al., "Theoretical analysis of antibody targeting of tumor spheroids: importance of dosage for penetration, and affinity for retention," Cancer Research, 2003, 63(6):1288-1296.
Gratton et al., "The effect of particle design on cellular internalization pathways," Proc Natl Acad Sci U S A, The National Academy of Sciences of the USA, Aug. 2008, 105(33):11613-8.
Greco et al., "The search for synergy: a critical review from a response surface perspective," Pharmacological Reviews, 1995, 24, 331-385.
Green et al., "Abraxane®, a novel Cremophor®-free, albumin-bound particle form of paclitaxel for the treatment of advanced non-small-cell lung cancer," Annals of Oncology, Aug. 2006, 17, 1263-1268.
Green et al., "Novel dipeptidyl peptidase IV resistant analogues of glucagon-like peptide-1(7- 36) amide have preserved biological activities in vitro conferring improved glucose-lowering action in vivo" J. of Mol. Endocrin., 2003, 31(3): 529-540.
Greenfield, "Using circular dichroism spectra to estimate protein secondary structure," Nat. Protoc., Dec. 2006, 1(6):2876-90.
Griffin et al., "Accelerated wound healing by injectable microporous gel scaffolds assembled from annealed building blocks," Nat Mater, 2015, 14: 737-744.
Grimm et al., "Advances in Brachytherapy," Reviews in Urology, 2004, 6, S37-S48.
Grover et al., "Protein-Polymer Conjugates: Synthetic Approaches by Controlled Radical Polymerizations & Interesting Applications", Curr Opin Chem Bioi., Dec. 2010; 14(6): 818- 827.
Gu et al., "Enzymatic Synthesis of Nucleobase-Modified Single-Stranded DNA Offers Turnable Resistance to Nuclease Degradation," Biomacromolecules, Jul. 2018, 19, 3525-3535.
Gu et al., "Photocontrolled micellar aggregation of amphiphilic DNA-azobenzene conjugates," Colloids Surfaces B: Biointerfaces, Nov. 2015, 135, 126-132.
Gu et al., "Precise engineering of targeted nanoparticles by using self-assembled biointegrated block copolymers," Proc Natl Acad Sci U S A, The National Academy of Sciences of the USA, Feb. 2008, 105(7):2586-91.
Güngör et al., "Pancreatic cancer," British Journal of Pharmacology, Jan. 2014, 171, 849-858.
Guo et al., "Nanoparticles escaping RES and endosome: challenges for siRNA delivery for cancer therapy," J. Nanomaterials, Aug. 2011, 2011: 1-12.
Gustafsson, "Nonlinear structured-illumination microscopy: widefield fluorescence imaging with theoretically unlimited resolution," Proc Natl Acad Sci U S A, 2005, 102, 13081-13086.
Gustafsson, "Surpassing the lateral resolution limit by a factor of two using structured illumination microscopy," Short Communication. Journal of Microscopy, 2000, 198, 82-87.
Guzman et al., "Leiodermatolide, a novel marine natural product, has potent cytotoxic and antimitotic activity against cancer cells, appears to affect microtubule dynamics, and exhibits antitumor activity," Int. J. Cancer, Nov. 2016, 139, 2116-2126.
Gylbert, "Applanation tonometry for the evaluation of breast compressibility," Scand J Plast Reconstr Surg Hand Surg, 1989, 23: 223-229.
Ha et al., "Immunoglobulin Fc Heterodimer Platform Technology: From Design to Applications in Therapeutic Antibodies and Proteins," Front Immunol, Oct. 2016, 7(394) (in English).
Haider et al., "Genetically engineered polymers: Status and prospects for controlled release," J. Control. Release, 2004, 95, 1-26.
Halozyme Therapeutics, "PEGPH20 Plus Nab-Paclitaxel Plus Gemcitabine Compared With Nab-Paclitaxel Plus Gemcitabine in Subjects With Stage IV Untreated Pancreatic Cancer (HALO-109-202)," Clinical Trial NCT01839487 <https://clinicaltrials.gov/ct2/show/study/NCT01839487> Accessed May 29, 2018.
Hamada et al., "Novel therapeutic strategies targeting tumor-stromal interactions in pancreatic cancer," Frontiers in Physiology, Nov. 2013, vol. 4, Article 331, 7 pages.
Hamidi et al., "Pharmacokinetic Consequences of Pegylation," Drug Deliv., Dec. 2006, 13, 399-409.
Hamley, "Self-assembly of amphiphilic peptides," Soft Matter, Feb. 2011, 7, 4122.
Hampp et al., "Use of Antidiabetic Drugs in the U.S., 2003-2012," Diabetes Care, May 2014, 37: 1367-1374.
Han et al., "Survival of patients with advanced pancreatic cancer after iodine 125 seeds implantation brachytherapy: A meta-analysis," Medicine, Feb. 2017, 96, e5719.
Harmon et al., "A Model for Hysteresis Observed in Phase Transitions of Thermally Responsive Intrinsically Disordered Protein Polymers," Biophysical Journal, Feb. 2017, 112(3):207a.
Harries et al., "Nanoparticle Albumin-Bound Paclitaxel for Metastatic Breast Cancer," J. Clin. Oncol., 2005, 23(31):7768-7771.
Harris et al., "Effect of pegylation on pharmaceuticals," Nature Reviews Drug Discovery, 2003, 2: 214-221.
Harris et al., "Pegylation," Clinical Pharmacokinetics, 2001, 40(7):539-551.
Hart et al., "Attenuation of FGF signalling in mouse B-cells leads to diabetes," Nature, 2000, 408:864.
Hartgerink et al., "Self-assembly and mineralization of peptide-amphiphile nanofibers," Science, 2001, 294, 1684-8.
Hassouneh et al., "Elastin-like Polypeptide Diblock Copolymers Self-Assemble into Weak Micelles," Macromolecules, Jun. 2015, 48, 4183-4195.
Hassouneh et al., "Elastin-Like Polypeptides as a Purification Tag for Recombinant Proteins," Curr Protoc Protein Sci., Aug. 2010, Chapter 6. Unit 6.11. 10.1002/0471140864.ps0611s61.
Hassouneh et al., "Fusions of elastin-like polypeptides to pharmaceutical proteins," Methods Enzymol., Jan. 2012, 502, 215-37.
Hassouneh et al., "Unexpected Multivalent Display of Proteins by Temperature Triggered Self- assembly of Elastin-like Polypeptide Block Copolymers," Biomacromolecules, Apr. 2012, vol. 13, Issue 4, pp. 1598-1605.
Hathout et al., "Analysis of seed loss and pulmonary seed migration in patients treated with virtual needle guidance and robotic seed delivery," American journal of clinical oncology, Oct. 2011, 34, 449-453.
He et al., "Comparative genomics of elastin: Sequence analysis of a highly repetitive protein," Matrix Biology, Sep. 2007, 26:524-540.
He et al., "Improving protein resistance of α-Al2O3 membranes by modification with POEGMA brushes," Applied Surface Science, Nov. 2011, 258(3):1038-1044.
Heagerty et al., Biometrics, "Time-dependent ROC curves for censored survival data and a diagnostic marker," Jun. 2000, 56(2):337-44.
Heal et al., "N-Myristoyl transferase-mediated protein labelling in vivo," Org. Biomol. Chem., Aug. 2008, 6(13):2308-2315.
Heal et al., "Site-specific N-terminal labelling of proteins in vitro and in vivo using N-myristoyl transferase and bioorthogonal ligation chemistry," Chem. Commun., Jan. 2008, 3, 480-482.
Heggestad et al., "In Pursuit of Zero 2.0: Recent Developments in Nonfouling Polymer Brushes for Immunoassays," Adv Mater, 2020, 32: e1903285.

(56) References Cited

OTHER PUBLICATIONS

Heredia et al., "In Situ Preparation of Protein-"Smart" Polymer Conjugates with Retention of Bioactivity," J. Am. Chem. Soc. Jan. 2006, 127, 16955-16960.
Hermanson et al., "Peginesatide for the treatment of anemia due to chronic kidney disease—an unfulfilled promise," Expert Opin Drug Saf, 2016, 15(10): 1421-1426.
Herrero-Vanrell et al., "Self-assembled particles of an elastin-like polymer as vehicles for controlled drug release," J Control Release, 2005, 102, 113-122.
Hershfield et al., "Induced and pre-existing anti-polyethylene glycol antibody in a trial of every 3- week dosing of pegloticase for refractory gout, including in organ transplant recipients," Arthritis Res. Ther. 16, Mar. 2014, R63.
Hershfield et al., "Treating gout with pegloticase, a PEGylated urate oxidase, provides insight into the importance of uric acid as an antioxidant in vivo," Proc Natl Acad Sci U S A, 2010, 107(32): 14351-14356.
Hess et al., "Graphene Transistors for Multifunctional Polymer Brushes for Biosensing Applications," Applied Materials & Interfaces, 2014, 6: 9705-9710.
Heus, "RNA aptamers," Nat Struct Biol, 1997, 4(8): 597-600.
Hidalgo, "Pancreatic Cancer," N Engl J Med, Apr. 2010, 362, 1605-1617.
Hingorani et al., "Phase Ib Study of PEGylated Recombinant Human Hyaluronidase and Gemcitabine in Patients with Advanced Pancreatic Cancer," Clinical Cancer Research, Jun. 2016, 22, 2848-2854.
Ho et al., "Chemoenzymatic Labeling of Proteins for Imaging in Bacterial Cells," J. Am. Chem. Soc., Nov. 2016, 138(46):15098-15101.
Ho et al., "Internal radiation therapy for patients with primary or metastatic hepatic cancer: a review," Cancer, 1998, 83, 1894-1907.
Hober et al., "Protein A chromatography for antibody purification," Journal of Chromatography B 848, Mar. 2007, pp. 40-47.
Hochkoeppler, "Expanding the landscape of recombinant protein production in *Escherichia coli*," Biotechnol. Lett., Dec. 2013, 35, 1971-1981.
Hofmann et al., "A kinetic study on the enzymatic hydrolysis of fluoresceindiacetate and fluorescein-di-ß-D-galactopyranoside," Analytical biochemistry, 1983, 131(1): 180-186.
Holehouse et al., "CIDER: Classification of Intrinsically Disordered Ensemble Regions," Biophysical Journal, Feb. 2015, vol. 108, Issue 2, Supplement 1, p. 228a.
Holehouse et al., "Functional Implications of Intracellular Phase Transitions," Biochemistry, May 2018, 57(17):2415-2423.
Holm et al., "Transperineal $^{125}$iodine seed implantation in prostatic cancer guided by transrectal ultrasonography," The Journal of urology, 2002, 167, 985-988.
Hopp et al., "The effects of affinity and valency of an albumin-binding domain (ABD) on the half- life of a single-chain diabody-ABD fusion protein," Protein Engineering Design and Selection, Sep. 2010, 23(11): p. 827-834.
Hortobágyi, "Anthracyclines in the Treatment of Cancer," Drugs, 1997, vol. 54, No. 4, pp. 1-7.
Howell et al., "The MIRD Perspective 1999," J Nucl Med, 1999, 40, 3S-10S.
Hruby et al., "New bioerodable thermoresponsive polymers for possible radiotherapeutic applications," Journal of Controlled Release, May 2007, 119, 25-33.
Hruby et al., "Thermoresponsive polymeric radionuclide delivery system—an injectable brachytherapy," Eur J Pharm Sci., Feb. 2011, 42, 484-488.
Hrycushko et al., "Direct intratumoral infusion of liposome encapsulated rhenium radionuclides for cancer therapy: effects of non-uniform intratumoral dose distribution," Med Phys, Mar. 2011, 38, 1339-1347.
Hsu et al., "Fat grafting's past, present, and future: why adipose tissue is emerging as a critical link to the advancement of regenerative medicine," Aesthet Surg J, 2015, 32: 892-899.
Hu et al., "Design of tumor-homing and pH-responsive polypeptide-doxorubicin nanoparticles with enhanced anticancer efficacy and reduced side effects," Chemical Communications, Jun. 2015, 51, 11405-11408.
Hu et al., "Nanografting De Novo Proteins onto Gold Surfaces," Langmuir, 2005, vol. 21:9103- 9109.
Huang et al., "Clinical features of patients infected with 2019 novel coronavirus in Wuhan," China. Lancet, 2020, 395: 497-506.
Huang et al., "Photodynamic Therapy Synergizes with Irinotecan to Overcome Compensatory Mechanisms and Improve Treatment Outcomes in Pancreatic Cancer," Cancer Research, Mar. 2016, 76, 1066-1077.
Huber et al., "Designer amphiphilic proteins as building blocks for the intracellular formation of organelle-like compartments," Nat Mater, Jan. 2015, 14(1):125-132.
Hucknall et al., "Simple Fabrication of Antibody Microarrays on Nonfouling Polymer Brushes with Femtomolar Sensitivity for Protein Analytes in Serum and Blood," Adv Mater, 2009, 21(19): 1968-1971.
Hucknall et al., "Simple Fabrication of Antibody Microarrays on Nonfouling Polymer Brushes with Femtomolar Sensitivity for Protein Analytes in Serum and Blood," Adv Mater, 2009, 21: 1968-1971.
Huotari et al., "Endosome maturation," EMBO J, Aug. 2011, 30 (17), 3481-3500.
Hutter et al., "Calibration of atomic-force microscope tips," Review of Scientific Instruments, 1993, 64: 1868-1873.
Hwang et al., "Caprolactonic poloxamer analog: PEG-PCL-PEG," Biomacromolecules, 2005, 6, 885-890.
Hwang et al., "Differentially degradable janus particles for controlled release applications," Macromol Rapid Commun, 2012, 33: 1178-1183.
Hwang et al., "Gene therapy for primary and metastatic pancreatic cancer with intraperitoneal retroviral vector bearing the wild-type p53 gene," Surgery, 1998, 124, 143-151.
Hwang et al., "Inhibition of gene expression in human cells through small molecule-RNA interactions," Proc. Natl. Acad. Sci. USA, 1999, 96(23): 12997-13002.
Hwang et al., "Synthesis and Characterization of Polystyrene Brushes for Organic Thin Film Transistors," Journal of Nanoscience and Nanotechnology, 2012, 12: 4137-4141.
Ibrahim et al., "Phase I and pharmacokinetic study of ABI-007, a Cremophor-free, protein-stabilized, nanoparticle formulation of paclitaxel," Clin. Cancer Res., 2002, 8 (5), 1038-1044.
Ilangovan et al., "Structure of sortase, the transpeptidase that anchors proteins to the cell wall of *Staphylococcus aureus*," Proc. Natl. Acad. Sci. 98, 2001, 6056-6061.
Inostroza-Brito et al., "Co-assembly, spatiotemporal control and morphogenesis of a hybrid protein-peptide system," Nat. Chem., Nov. 2015, 7, 1-8.
Ishida et al., "Accelerated blood clearance (ABC) phenomenon upon repeated injection of PEGylated liposomes, " International Journal of Pharmaceutics, May 2008, 354(1-2):56-62.
Ito et al., "Impaired negative feedback suppression of bile acid synthesis in mice lacking ßKlotho," J Clin Invest, 2005, 115(8):2202-2208.
Ito et al., "In vivo antitumor effect of the mTOR inhibitor CCI-779 and gemcitabine in xenograft models of human pancreatic cancer," International Journal of Cancer, May 2006, 118, 2337-2343.
Jacob et al., "Human phagocytes employ the myeloperoxidase-hydrogen peroxide system to synthesize dityrosine, trityrosine, pulcherosine, and isodityrosine by a tyrosyl radical-dependent pathway," J. Biol. Chem., 1996, 271, 19950-19956.
Jain, "Barriers to Drug-Delivery in Solid Tumors," Sci Am, 1994, 271, 58-65.
Jakubowski et al., "Activators regenerated by electron transfer for atom-transfer radical polymerization of (meth)acrylates and related block copolymers," Angew. Chem. Int. Ed., Jun. 2006, 4482-4486.
Janes et al., "Chitosan nanoparticles as delivery systems for doxorubicin," J. Control Release, 2001, 73, 255-267.
Jang et al., "Engineering Globular Protein Vesicles through Tunable Self-Assembly of Recombinant Fusion Proteins," Small, 2017, 13(36): 1700399.

(56) References Cited

OTHER PUBLICATIONS

Jenkins et al., In vivo monitoring of tumor relapse and metastasis using bioluminescent PC-3M-luc-C6 cells in murine models of human prostate cancer. Clinical & Experimental Metastasis, 2003, 20, 745-756.
Ji et al., "RGD-conjugated albumin nanoparticles as a novel delivery vehicle in pancreatic cancer therapy," Cancer Biology & Therapy, Feb. 2012, 13, 206-215.
Jia et al., "Preparation, physicochemical characterization and cytotoxicity in vitro of gemcitabine-loaded PEG-PDLLA nanovesicles," World J. Gastroenterol., Feb. 2010, 16(8):1008-1013.
Jiang et al., "Nanoparticle-mediated cellular response is size-dependent," Nat Nanotechnol, Nature Research, Mar. 2008, 3(3):145-50.
Jiang et al., "Neutralizing Antibodies against SARS-CoV-2 and Other Human Coronaviruses," Trends Immunol, 2020, 41(5): 355-359.
Jiang et al., "The internal structure of self-assembled peptide amphiphiles nanofibers," Soft Matter, Feb. 2007, 3, 454.
Jin et al., "Protein-resistant polyurethane prepared by surface-initiated atom transfer radical graft polymerization (ATRgP) of water-soluble polymers: effects of main chain and side chain lengths of grafts," Colloids and surfaces. B, Biointerfaces, Apr. 2009, 70 (1), 53-9.
Joh et al., "Architectural Modification of Conformal PEG-Bottlebrush Coatings Minimizes Anti-PEG Antigenicity While Preserving Stealth Properties," Advanced Healthcare Materials, 2019, 8(8): 1801177, 27 pages.
Joh et al., "Inkjet-printed point-of-care immunoassay on a nanoscale polymer brush enables subpicomolar detection of analytes in blood," Proc Natl Acad Sci U S A, 2017, 114: E7054-E7062.
Johansson et al., "Structure, Specificity, and Mode of Interaction for Bacterial Albumin-binding Modules," J. Biol. Chem. 2002, 277 (10), 8114-8120.
Johansson et al., "The GA module, a mobile albumin-binding bacterial domain, adopts a three-helix-bundle structure," FEBS Lett, 1995, 374(2): 257-261.
Johnson et al., "Fibroblast Growth Factor 21 Reduces the Severity of Cerulein-Induced Pancreatitis in Mice," Gastroenterology, Nov. 2009, 137(5):1795-1804.
Jokerst et al., "Nanoparticle PEGylation for imaging and therapy," Nanomedicine (Lond), Future Medicine, Jun. 2011, 6(4):715-28.
Jonsson et al., "Engineering of a femtomolar affinity binding protein to human serum albumin," Protein Engineering Design and Selection, Aug. 2008, 21(8): 515-527.
Junutula et al., "Site-specific conjugation of a cytotoxic drug to an antibody improves the therapeutic index," Nat Biotechnol, Aug. 2008, 26(8):925-932.
Jurney et al., "Unique size and shape-dependent uptake behaviors of non-spherical nanoparticles by endothelial cells due to a shearing flow," J Control Release, Jan. 2017, 245:170-176.
Kaighn et al., "Establishment and characterization of a human prostatic carcinoma cell line (PC-3)," Investigative urology, 1979, 17, 16-23.
Kaitin et al., "Pharmaceutical innovation in the 21st century: new drug approvals in the first decade, 2000-2009," Clin Pharmacol Ther, Feb. 2011, 89, 183-188.
Kamaly et al., "Targeted polymeric therapeutic nanoparticles: design, development and clinical translation," Chem Soc Rev, Royal Society of Chemistry, Apr. 2012, 41(7):2971-3010.
Kamisawa et al., "Pancreatic cancer," Lancet, Jul. 2016, 388, 73-85.
Kang et al., "Crystal structure of SARS-CoV-2 nucleocapsid protein RNA binding domain reveals potential unique drug targeting sites," Acta Pharm Sin B, 2020, 10(7): 1228-1238.
Kanoski et al., "The role of nausea in food intake and body weight suppression by peripheral GLP-1 receptor agonists, exendin-4 and liraglutide," Neuropharmacology 62, Apr. 2012, 1916-1927.
Kanyama et al., "Usefulness of Repeated Direct Intratumoral Gene Transfer Using Hemagglutinating Virus of Japan-Liposome Method for Cytosine Deaminase Suicide Gene Therapy," Cancer Research, 2001, 61, 14-18.
Karagoz et al., "Polymerization-Induced Self-Assembly (PISA)—control over the morphology of nanoparticles for drug delivery applications," Polym. Chem., Jan. 2014, 5(2):350-355.
Karamanolis et al., "Increased expression of VEGF and CD31 in postradiation rectal tissue: implications for radiation proctitis," Mediators Inflamm, May 2013, 515048.
Karperien, A. FracLac for Image J, version 2.5 <http://rsb.info.nih.gov/ij/plugins/fraclac/FLHelp/Introduction.htm> 1999-2012.
Kaspar et al., "Future directions for peptide therapeutics development," Drug Discovery Today, Sep. 2013, 18, 807-817.
Katakura, "Nuclear Data Sheets for A = 125," Nuclear Data Sheets, Mar. 2011, 112, 495-705.
Kataoka et al., "Block copolymer micelles for drug delivery: Design, characterization and biological significance," Advanced Drug Delivery Reviews, 2001, 47:113-131.
Kato et al., "Acidic extracellular microenvironment and cancer," Cancer Cell Int, Sep. 2013, 13, 89, 8 pages.
Katti et al., "Amino acid repeat patterns in protein sequences: Their diversity and structural- functional implications," Protein Science, 2000, 9: 1203-1209.
Keefe et al., "Aptamers as therapeutics," Nature Reviews Drug Discovery, 2010, 9: 537-550.
Keefe et al., "Poly(zwitterionic) protein conjugates offer increased stability without sacrificing binding affinity or bioactivity," Nat Chem, Jan. 2012, 4(1):59-63.
Keller et al., "Empirical Statistical Model To Estimate the Accuracy of Peptide Identifications Made by MS/MS and Database Search," Anal. Chem. 2002, 74, 5383-5392.
Kelly et al., "How to study proteins by circular dichroism," Biochim. Byophys. Acta—Proteins Proteomics, 2005, 1751(2):119-39.
Kelly et al., "Shape-specific, monodisperse nano-molding of protein particles," J Am Chem Soc, ACS Publications, Apr. 2008, 130(16):5438-9.
Kesharwani et al., "Dendrimer as nanocarrier for drug delivery," Progress in Polymer Science, Feb. 2014, 39(2):268-307.
Keten et al., "Nanoconfinement controls stiffness, strength and mechanical toughness of ß-sheet crystals in silk," Nat Mater, Mar. 2010, 9, 359-367.
Khademhosseini et al., "Micromolding of photocrosslinkable hyaluronic acid for cell encapsulation and entrapment," J Biomed Mater Res A, 2006, 79: 522-532.
Khailany et al., "Genomic characterization of a novel SARS-CoV-2," Gene Rep, 2020, 9: 100682, 6 pages.
Khandare et al., "Polymer-drug conjugates: Progress in polymeric drugs," Prog. Polym. Sci., 2005, vol. 31, pp. 359-397.
Khanna et al., "The dog as a cancer model," Nat. Biotechnol., Sep. 2006, 24, 1065-1066.
Kharitonenkov et al., "FGF-21 as a novel metabolic regulator," J Clin Invest, 2005, 115(6):1627-1635.
Kharitonenkov et al., "FGF21 Revolutions: Recent Advances Illuminating FGF21 Biology and Medicinal Properties," Trends Endocrinol Metab, Nov. 2015, 26(11):608-617.
Kharitonenkov et al., "Fibroblast growth factor 21 night watch: advances and uncertainties in the field," J Intern Med, Nov. 2016, 281(3):233-246.
Kharitonenkov et al., "Inventing new medicines: The FGF21 story," Mol Metab, Jun. 2014, 3(3):221-229.
Khazov et al., "Nuclear Data Sheets for A = 131," Nuclear Data Sheets, 2006, 107, 2715-2930.
Khoo et al., "Activation of mitogen-activating protein kinase by glucose is not required for insulin secretion," Proc Natl Acad Sci USA, 1997, 94(11):5599-5604.
Khoo et al., "Regulation of Insulin Gene Transcription by ERK1 and ERK2 in Pancreatic ß Cells," J Biol Chem, 2003, 278(35):32969-32977.
Kim et al., "Effects of Once-Weekly Dosing of a Long-Acting Release Formulation of Exenatide on Glucose Control and Body Weight in Subjects With Type 2 Diabetes," Diabetes Care, Jun. 2007, 30, 1487-93.

(56) References Cited

OTHER PUBLICATIONS

Kim et al., "Generation of core-shell microcapsules with three-dimensional focusing device for efficient formation of cell spheroid," Lab Chip, 2011, 11: 246-252.
Kim et al., "Recombinant elastin-mimetic biomaterials: Emerging applications in medicine," Adv Drug Deliv Rev, Dec. 2010, 62, 1468-1478.
Kim et al., "Site-Specific PEGylated Exendin-4 Modified with a High Molecular Weight Trimeric PEG Reduces Steric Hindrance and Increases Type 2 Antidiabetic Therapeutic Effects," Bioconjugate Chem., Nov. 2012, 23, 2214-2220.
Kim et al., "Ultrasensitive Carbon nanotube-based biosensors using antibody-binding fragments," Analytical Biochemistry, Jul. 2008, 381, 193-198.
Knop et al., "Poly(ethylene glycol) in Drug Delivery: Pros and Cons as Well as Potential Alternatives," Angewandte Chemie International Edition, Aug. 2010, 49(36):6288-6308.
Knudsen, "Glucagon-like Peptide-1: The Basis of a New Class of Treatment for Type 2 Diabetes" J. Med. Chem, 2004, 47: 4128-4134.
Kobashigawa et al., "Attachment Of An NMR-Invisible Solubility Enhancement Tag Using A Sortase-Mediated Protein Ligation Method," J Biomol NMR. Mar. 2009, vol. 43, No. 3; pp. 145-150.
Kobayashi et al., "Summary of recombinant human serum albumin development," Biologicals, Mar. 2006, 34(1): 55-59.
Koehler et al., "Albumin affinity tags increase peptide half-life In vivo," Bioorganic & Medicinal Chemistry Letters, 2002, 12(20): 2883-2886.
Kontos et al., "Drug development: longer-lived proteins," Chemical Society Reviews, Feb. 2012, 41(7):2686-2695.
Koong et al., "Phase II study to assess the efficacy of conventionally fractionated radiotherapy followed by a stereotactic radiosurgery boost in patients with locally advanced pancreatic cancer," Int J Radiation Oncol Biol Phys, 2005, 63, 320-323.
Korte et al., "Short activated partial thromboplastin times are related to increased thrombin generation and an increased risk for thromboembolism," Am J Clin Pathol, 2000, 113(1): 123- 127.
Kothare et al., "Pharmacokinetics, pharmacodynamics, tolerability, and safety of exenatide in Japanese patients with type 2 diabetes mellitus," J. Clin. Pharmacol. 48, Jan. 2009, 1389-1399.
Kowalczyk et al., "Elastin-like Polypeptides as a Promising Family of Genetically-Engineered Protein Based Polymers," World Journal of Microbiology and Biotechnology, Springer, Apr. 2014, 30(8):2141-2152.
Kozel et al., "Point-of-care testing for infectious diseases: past, present, and future," J Clin Microbiol, 2017, 55: 2313-2320.
Kozma et al., "Anti-PEG antibodies: Properties, formation, testing and role in adverse immune reactions to PEGylated nano-biopharmaceuticals," Adv Drug Deliv Rev, 2020, 154-155, 163-175.
Kramer et al., "Quantitative Side-Chain Modifications of Methionine-Containing Elastin-Like Polypeptides as a Versatile Tool to Tune Their Properties," ACS Macro Lett., Nov. 2015, 4(11):1283-1286.
Krammer et al., "Serology assays to manage COVID-19," Science, 2020, 368: 1060-1061.
Kraulis et al., "The serum albumin-binding domain of streptococcal protein G is a three-helical bundle: a heteronuclear NMR study," FEBS letters, 1996, 378(2): p. 190-194.
Krause et al., "Structure and function of claudins," Biochmica et Biophysica Acta, Mar. 2008, 1778, 631- 645.
Krempien et al., "Neoadjuvant chemoradiation in patients with pancreatic adenocarcinoma," HPB (Oxford), Feb. 2006, 8(1):22-28.
Kronowitz et al., "Delayed-Immediate Breast Reconstruction," Plastic and Reconstructive Surgery, 2004, 113: 1617- 1628.
Kruger et al., "Analysis of the Substrate Specificity of the Staphylococcus aureus Sortase Transpeptidase SrtAt," Biochemistry, 2004, 43, 1541-1551.
Kulkarni et al., "Bioorthogonal Chemoenzymatic Functionalization of Calmodulin for Bioconjugation Applications," Bioconjug. Chem., Oct. 2015, 26(10):2153-2160.
Kulkarni et al., "Design of lipid nanoparticles for in vitro and in vivo delivery of plasmid DNA," Nanomedicine, May 2017, 13(4):1377-1387.
Kulkarni et al., "Selective functionalization of the protein N terminus with N-myristoyl transferase for bioconjugation in cell lysate," ChemBioChem, Oct. 2013, 14, 1958-1962.
Kumar et al., "N-Terminal Region of the Catalytic Domain of Human N-Myristoyltransferase 1 Acts as an Inhibitory Module," PLoS One, May 2015, 10(5):e0127661.
Kuo et al., "Global epidemiology of gout: prevalence, incidence and risk factors, " Nature Reviews Rheumatology, 2015, 11: 649-662.
Kupelian et al., "Radical prostatectomy, external beam radiotherapy <72 Gy, external beam radiotherapy > or =72 Gy, permanent seed implantation, or combined seeds/external beam radiotherapy for stage T1-T2 prostate cancer," International journal of radiation oncology, biology, physics, 2004, 58, 25-33.
Kurosu et al., "Tissue-specific Expression of ßKlotho and Fibroblast Growth Factor (FGF) Receptor Isoforms Determines Metabolic Activity of FGF19 and FGF21," J Biol Chem, Sep. 2007, 282(37):26687-26695.
Kyte et al., "A Simple Method for Displaying the Hydropathic Character of a Protein," J. Mol. Biol., 1982, 157:105-132.
Labelle et al., "Vascular endothelial cadherin promotes breast cancer progression via transforming growth factor ß signaling," Cancer Res, Mar. 2008, 68, 1388-1397.
Lacroix et al., "Elucidating the folding problem of alpha-helices: local motifs, long-range electrostatics, ionic-strength dependence and prediction of NMR parameters," J Mol Biol, 1998, 284, 173-191.
Laing et al., "A dynamic COVID-19 immune signature includes associations with poor prognosis," Nat Med, 2020, 26:1623-1635.
Langer et al., "Designing materials for biology and medicine," Nature, 2004, 428, 487-92.
Laybutt et al., "Endoplasmic reticulum stress contributes to beta cell apoptosis in type 2 diabetes," Diabetologia, Apr. 2007, 50(4):752-763.
Le Droumaguet et al., "Recent advances in the design of bioconjugates from controlled/living radical polymerization," Polym. Chem. Jan. 2010, 1, 563-598.
Le Meins et al., "Hybrid polymer/lipid vesicles: State of the art and future perspectives," Mater. Today, Oct. 2013, 16, 397-402.
Leader et al., "Protein therapeutics: a summary and pharmacological classification," Nat. Rev. Drug Discov. 7, Jan. 2008, 21-39.
Lee et al., "Atomistic molecular dynamics simulations of peptide amphiphile self-assembly into cylindrical nanofibers," J. Am. Chem. Soc., Feb. 2011, 133, 3677-3683.
Lee et al., "Immunohistochemical analysis of claudin expression in pancreatic cystic tumors," Oncology Reports, Apr. 2011, 25(4): 971-978.
Lee et al., "In vivo bioluminescent imaging of irradiated orthotopic pancreatic cancer xenografts in nonobese diabetic-severe combined immunodeficient mice: a novel method for targeting and assaying efficacy of ionizing radiation," Transl. Oncol., Jun. 2010, 3, 153-159.
Lee et al., "Mechanical properties of cross-linked syntheti elastomeric polypentapeptides," Macromolecules, 2001, 34, 5968-5974.
Lee et al., "Nanoparticle-Delivered Chemotherapy: Old Drugs in New Packages." Oncology (Williston Park, NY) 31.3 (Mar. 2017): 198-208.
Lee et al., "Phase transition and elasticity of protein-based hydrogels," J. Biomater. Sci. Polymer Edn, 2001, 12, 229-242.
Lee et al., "Polymersomes for drug delivery: design, formation and characterization," J Control Release, Elsevier, Jul. 2012, 161(2):473-83.
Lee et al., "Structures of ß-klotho reveal a 'zip code'-like mechanism for endocrine FGF signaling," Nature, Jan. 2018, 553:501-505.
Lee et al., "Theranostic nanoparticles with controlled release of gemcitabine for targeted therapy and MRI of pancreatic cancer," ACS Nano, Mar. 2013, 7(3):2078-2089.
Leibowitz et al., "Glucose-Regulated Proinsulin Gene Expression Is Required for Adequate Insulin Production during Chronic Glucose Exposure," Endocrinology, 2002, 143(9):3214-3220.

(56) References Cited

OTHER PUBLICATIONS

Lele et al., "Synthesis of uniform protein-polymer conjugates," Biomacromolecules 6, 2005, 3380-3387.
Lennen et al., "Membrane Stresses Induced by Overproduction of Free Fatty Acids in Escherichia coli," Appl Environ Microb., Nov. 2011, 77(22):8114-28.
Leung et al., "Bio-Click Chemistry: Enzymatic Functionalization of PEGylated Capsules for Targeting Applications **," Angew. Chem. Int. Ed. Jul. 2012, 51, 7132-7136.
Levine et al., "Thioflavine T interaction with synthetic Alzheimer's disease beta-amyloid peptides: detection of amyloid aggregation in solution," Protein Sci., 1993, 2, 404-10.
Levy et al., "Novel Exenatide Analogs with Peptidic Albumin Binding Domains: Potent Anti-Diabetic Agents with Extended Duration of Action," PLoS ONE, Feb. 2014, 9(2): e87704, 9 pages.
Lewis et al., "Use of digitized video microscopy with a fluorogenic enzyme substrate to demonstrate cell-and compartment-specific gene expression in *Salmonella enteritidis* and *Bacillus subtilis*," Molecular microbiology, 1994, 13:655-662.
Li et al., "Elastin is an essential determinant of arterial morphogenesis," Nature, 1998, 393, 276-280.
Li et al., "Ferric Chloride-induced Murine Thrombosis Models," J. Vis. Exp., 2016, 115: e54479, 12 pages.
Li et al., "FGF21 Is Not a Major Mediator for Bone Homeostasis or Metabolic Actions of PPARa and PPARy Agonists," J Bone Miner Res, Apr. 2017, 32(4):834-845.
Li et al., "Molecular description of the LCST behavior of an elastin-like polypeptide," Biomacromolecules, Aug. 2014, 15, 3522-3530.
Li et al., "Nanoparticles Evading The Reticuloendothelial System: Role of The Supported Bilayer," Biochim. Biophys. Acta, Oct. 2009, 1788 (10), 2259-2266.
Li et al., "Pancreatic cancer," Lancet, 2004, 363, 1049-1057.
Li et al., "Phase transitions in the assembly of multivalent signalling proteins," Nature, Nature Research, Mar. 2012, 483(7389):336-340.
Li et al., "Prediction of solvent-induced morphological changes of polyelectrolyte diblock copolymer micelles," Soft Matter, Nov. 2015, 11(42): 8236-45.
Li et al., "Protein adsorption on oligo(ethylene glycol)-terminated alkanethiolate self-assembled monolayers: The molecular basis for nonfouling behavior," The journal of physical chemistry. B, 2005, 109 (7), 2934-41.
Li et al., "Temperature-Triggered Phase Separation of a Hydrophilic Resilin-Like Polypeptide," Macramol. Rapid Commun., Jan. 2015, 36(1):90-95.
Li et al., "Tunable Assembly of Protein-Microdomains in Living Vertebrate Embryos," Advanced Biosystems, Oct. 2018, 2(10):1800112.
Liao et al., "Removal of N-terminal methionine from recombinant proteins by engineered *E. coli* methionine aminopeptidase," Prot. Sci. 13, 2004, 1802-1810.
Lieberman et al., "Comparison of Commercially Available and Laboratory-Developed Assays for In Vitro Detection of SARS-COV-2 in Clinical Laboratories," J Clin Microbiol, 2020, 58(8):e00821-20.
Liechty et al., "Polymers for Drug Delivery Systems," Annual review of chemical and biomolecular engineering, Aug. 2010, 1:149-173.
Lillie et al., "The viscoelastic basis for the tensile strength of elastin," Int J Biol Macromol, 2002, 30, 119-127.
Lim et al., "Improved Non-Chromatographic Purification of a Recombinant Protein by Cationic Elastin-like Polypeptides" Biomacromolecules, May 2007, 8(5): 1417-1424.
Lim et al., "In situ cross-linking of elastin-like polypeptide block copolymers for tissue repair," Biomacromolecules, Feb. 2008, 9, 222-230.
Lim et al., "In vivo post-translational modifications of recombinant mussel adhesive protein in insect cells," Biotechnol. Prog., September-Oct. 2011, 27(5):1390-1396.

Lin et al., "Adiponectin Mediates the Metabolic Effects of FGF21 on Glucose Homeostasis and Insulin Sensitivity in Mice," Cell Metab, May 2013, 17(5):779-789.
Lin et al., "Formation and Maturation of Phase-Separated Liquid Droplets by RNA-Binding Proteins," Mol Cell, Oct. 2015, 60(2):208-219.
Lin et al., "Functional expression of a biologically active fragment of soluble gp130 as an ELP- fusion protein in transgenic plants: purification via inverse transition cycling," Biochem J, Sep. 2006, 398(3):577-583.
Lin et al., "Intrinsically disordered sequences enable modulation of protein phase separation through distributed tyrosine motifs," J Biol Chem, Nov. 2017, 292(46):19110-19120.
Lin et al., "Phase Separation and Single-Chain Compactness of Charged Disordered Proteins Are Strongly Correlated," Biophys J, May 2017, 112(10):2043-2046.
Lin et al., "Sequence-Specific Polyampholyte Phase Separation in Membraneless Organelles," Phys Rev Lett, Oct. 2016, 117(17):178101.
Lin et al., "Statistical properties of the traditional algorithm-based designs for phase I cancer clinical trials," Biostatistics, 2001, 2(2):203-215.
Lin et al., "Utility of immunohistochemistry in the pancreatobiliary tract," Arch Pathol Lab Med, Jan. 2015, 139, 24-38.
Lincoff et al., "Effect of the REG1 anticoagulation system versus bivalirudin on outcomes after percutaneous coronary intervention (REGULATE-PCI): a randomised clinical trial," Lancet, 2016, 387(10016): 349-356.
Linder et al., "Lipid Modifications of G Protein Subunits," J. Biol. Chem., 1991, 266(7):4654-4659.
Ling et al., "Protein thioester synthesis enabled by sortase," J. Am Chem Soc, Jul. 2012, 134(26): 10749-10752.
Liong et al., "Multifunctional inorganic nanoparticles for imaging, targeting, and drug delivery," ACS Nano, ACS Publications, May 2008, 2(5):889-96.
Lippard et al., "Platinum complexes: probes of polynucleotide structure and antitumor drugs," Acc. Chem. Res., 1978, 11(5): 211-217.
Lipsitch et al., "Antibody testing will enhance the power and accuracy of COVID-19-prevention trials," Nat Med, 2020, 26: 818-819.
Lipsky et al., "Pegloticase immunogenicity: the relationship between efficacy and antibody development in patients treated for refractory chronic gout," Arthritis Res Ther, 2014, 16: R60.
Lisboa Bastos et al., "Diagnostic accuracy of serological tests for covid-19: systematic review and meta-analysis," BMJ, 2020, 370: m2516.
Litiere et al., "RECIST—learning from the past to build the future," Nat Rev Clin Oncol, Mar. 2017, 14, 187-192.
Liu et al., "Brachytherapy using injectable seeds that are self-assembled from genetically encoded polypeptides in situ," Cancer Res, Nov. 2012, 72, 5956-5965.
Liu et al., "High neutralizing antibody titer in intensive care unit patients with COVID-19," Emerg Microbes Infect, 2020, 9: 1664-1670.
Liu et al., "Hydrophobic modifications of cationic polymers for gene delivery," Prog. In Polym. Sci., Sep. 2010, 35, 1144-1162.
Liu et al., "In Situ Formation of Protein-Polymer Conjugates through Reversible Addition Fragmentation Chain Transfer Polymerization **," Angew. Chem. Int. Ed. Apr. 2007, 46, 3099-3103.
Liu et al., "Injectable intratumoral depot of thermally responsive polypeptide-radionuclide conjugates delays tumor progression in a mouse model," J. Control Release, May 2010, 144(1):2-9.
Liu et al., "Integrin avB3-Targeted Cancer Therapy," Drug Dev Res, Wiley, Sep. 2008, 69(6):329-339.
Liu et al., "Semi-permeable coatings fabricated from comb-polymers efficiently protect proteins in vivo," Nature Communications, 2014, 5: 5526.
Liu et al., "The experiences of health-care providers during the COVID-19 crisis in China: a qualitative study," Lancet Glob Health, 2020, 8: e790-e798.
Liu et al., "Tracking the in vivo fate of recombinant polypeptides by isotopic labeling," Journal of Controlled Release, Sep. 2006, 114, 184-192.

(56) References Cited

OTHER PUBLICATIONS

Liu et al., "Tumor accumulation, degradation and pharmacokinetics of elastin-like polypeptides in nude mice," Journal of Controlled Release, Nov. 2006, 116, 170-178.
Liu, L. et al., "Monodisperse core-shell chitosan microcapsules for pH-responsive burst release of hydrophobic drugs," Soft Matter, 2011, 7: 4821-4827.
Livingstone, "Theoretical property predictions. Curr Top Med Chem FIELD Full Journal Title: Current topics in medicinal chemistry," Curr. Top. Med. Chem. 2003, 3, 1171-1192.
Loh et al., "Utilising inorganic nanocarriers for gene delivery," Biomater Sci, Jan. 2016, 4(1):70-86.
Lopresti et al., "Polymersomes: nature inspired nanometer sized compartments," Journal of Materials Chemistry, RSC Publishing, Jun. 2009, 19(22):3576-3590.
Lovshin et al., "Incretin-based therapies for type 2 diabetes mellitus," Nat. Rev. Endocrinol. 5, Jun. 2009, 262-269.
Lu et al., "Genomic characterisation and epidemiology of 2019 novel coronavirus: implications for virus origins and receptor binding," Lancet, 2020, 395: 565-574.
Ludden, "Nonlinear pharmacokinetics: clinical Implications," Clin. Pharmacokinet., 1991, 20 (6), 429-446.
Luginbuhl et al., "One-week glucose control via zero-order release kinetics from an injectable depot of glucagon-like peptide-1 fused to a thermosensitive biopolymer," Nat. Biomed. Eng. 1, Jun. 2017, Article No. 0078.
Luginbuhl et al., "Recombinant Synthesis of Hybrid Lipid-Peptide Polymer Fusions that Self-Assemble and Encapsulate Hydrophobic Drugs," Angew Chem Int Ed Engl., Nov. 2017, 56(45):13979-13984.
Lukyanov et al., "Micelles From Lipid Derivatives of Water-Soluble Polymers as Delivery Systems for Poorly Soluble Drugs," Adv. Drug Deliver. Rev., 2004, 56(9):1273-1289.
Lukyanov et al., "Tumor-targeted liposomes: doxorubicin-loaded long-circulating liposomes modified with anti-cancer antibody," J Control Release, 2004, 100(1):135-44.
Lund et al., "Phase II study of gemcitabine (2',2'-difluorodeoxycytidine) in previously treated ovarian cancer patients," J. Natl. Cancer. Inst. 1994, 86(20):1530-1533.
Luo et al., "Noncovalent Modulation of the Inverse Temperature Transition and Self-Assembly of Elastin-b-Collagen-like Peptide Bioconjugates," J Am Chem Soc, Dec. 2015, 137, 15362-15365.
Lutz et al., "About the Phase Transitions in Aqueous Solutions of Thermoresponsive Copolymers and Hydrogels Based on 2-(2-methoxyethoxy)ethyl Methacrylate and Oligo(ethylene glycol) Methacrylate, " Macromolecules, Mar. 2007, 40, 2503-2508.
Lutz et al., "Preparation of Ideal PEG Analogues with a Tunable Thermosensitivity by Controlled Radical Copolymerization of 2-(2-Methoxyethoxy)ethyl Methacrylate and Oligo(ethylene glycol) Methacrylate," Macromolecules, Jan. 2006, 39, 893-896.
Lyons et al., "Comparisons of Recombinant Resilin-like Proteins: Repetitive Domains Are Sufficient to Confer Resilin-like Properties," Biomacromolecules, ACS Publications, Oct. 2009, 10(11):3009-3014.
Lyons et al., "Design and facile production of recombinant resilin-like polypeptides: Gene construction and a rapid protein purification method," Protein Engineering Design & Selection, Oxford university Press, Jan. 2007, 20(1):25-32.
Ma et al., "Core-shell hydrogel microcapsules for improved islets encapsulation," Adv Healthc Mater, 2013, 2: 667-672.
Ma et al., "Non-fouling" oligo(ethylene glycol)-functionalized polymer brushes synthesized by surface-initiated atom transfer radical polymerization, Advanced Materials 2004, 16 (4), 338.
Ma et al., "Protein-resistant polymer coatings on silicon oxide by surface-initiated atom transfer radical polymerization," Langmuir: the ACS journal of surfaces and colloids, Mar. 2006, 22 (8), 3751-6.
Ma et al., "Surface-Initiated Atom Transfer Radical Polymerization of Oligo(ethylene glycol) Methyl Methacrylate from a Mixed Self-Assembled Monolayer on Gold," Advanced Functional Materials, Mar. 2006, 16 (5), 640-648.

MacEwan et al., "Applications of elastin-like polypeptides in drug delivery," Journal of Controlled Release, Sep. 2014, 190: p. 314-330.
MacEwan et al., "Controlled apoptosis by a thermally toggled nanoscale amplifier of cellular uptake," Nano Letters, Apr. 2014, 14, 2058-2064.
MacEwan et al., "Digital switching of local arginine density in a genetically encoded self-assembled polypeptide nanoparticle controls cellular uptake," Nano Lett., Jun. 2012, 12, 3322-3328.
MacEwan et al., "Elastin-like polypeptides: Biomedical applications of tunable biopolymers," Biopolymers, Jan. 2010, 94, 60-77.
MacEwan et al., "Non-chromatographic Purification of Recombinant Elastin-like Polypeptides and their Fusions with Peptides and Proteins from *Escherichia coli*," Jun. 2014, 88, p. e51583.
MacEwan et al., "Phase Behavior and Self-Assembly of Perfectly Sequence-Defined and Monodisperse Multiblock Copolypeptides," Biomacromolecules, Jan. 2017, 18(2):599-609.
Mack et al., "Antiobesity action of peripheral exenatide (exendin-4) in rodents: effects on food intake, body weight, metabolic status and side-effect measures," Int. J. Obes. 30, Sep. 2006, 1332-1340.
MacKay et al., "Self-assembling chimeric polypeptide-doxorubicin conjugate nanoparticles the abolish tumors after single injection," Nat Mater, Dec. 2009, 8(12):993-999.
Maeda et al., "Tumor vascular permeability and the EPR effect in macromolecular therapeutics: a review," J. Control. Release, Mar. 2000, 65(1-2)271-284.
Maeda et al., "Tumoritropic and lymphotropic principles of macromolecular drugs," Critical reviews in therapeutic drug carrier systems, 1989, 6(3): 193-210.
Maeda, "The enhanced permeability and retention (EPR) effect in tumor vasculature: the key role of tumor-selective macromolecular drug targeting," Advances in Enzyme Regulation, 2001, 41(1):189-207.
Magnusson et al., "In Situ Growth of Side-Chain PEG Polymers from Functionalized Human Growth Hormone-A New Technique for Preparation of Enhanced Protein-Polymer Conjugates," Bioconjugate Chem. 21, Mar. 2010, 671-678.
Magnusson et al., "Ion-Sensitive "Isothermal" Responsive Polymers Prepared in Water," Journal of the American Chemical Society, Aug. 2008, 130, 10852-10853.
Maier et al., "From selection hits to clinical leads: progress in aptamer discovery," Mol. Ther. Methods Clin. Dev., 2016, 3: 16014, 10 pages.
Maitra et al., "Pancreatic Cancer," Annu Rev Pathol Mech Dis, Feb. 2008, 3, 157-188.
Malam et al., "Liposomes and nanoparticles: nanosized vehicles for drug delivery in cancer," Trends Pharmacol Sci, Cell Press, Nov. 2009, 30(11):592-9.
Malik et al., "Recent advances in protein and peptide drug delivery systems, " Curr. Drug Deliv. 2, Apr. 2007, 141-151.
Manders et al., "Dynamics of three-dimensional replication patterns during the S-phase, analysed by double labelling of DNA and confocal microscopy," Journal of cell science, 1992, 103(Pt 3):857-862.
Mann et al., "Proteomic analysis of post-translational modifications," Nat. Biotechnol., 2003, 21, 255-61.
Manzoor et al., "Overcoming limitations in nanoparticle drug delivery: triggered, intravascular release to improve drug penetration into tumors," Cancer Res, Nov. 2012, 72, 5566-5575.
Mao et al., "DNA repair by nonhomologous end joining and homologous recombination during cell cycle in human cells," Cell cycle, Sep. 2008, 7, 2902-2906.
Mao et al., "Net charge per residue modulates conformational ensembles of intrinsically disordered proteins," Proc Natl Acad Sci U S A, 2010, 107(18):8183-8188.
Mao et al., "Sortase-mediated protein ligation: a new method for protein engineering," J. Am. Chem. Soc., 2004, 126(9):2670-2671.
Maraffini et al., "Sortases and the art of anchoring proteins to the envelopes of Gram-positive bacteria," Microbiol Mol Biol Rev, Mar. 2006, 70(1):192-221.
Mariam et al., "Albumin corona on nanoparticles - a strategic approach in drug delivery," Drug Deliv., Oct. 2016, 23 (8), 2668-2676.

(56) References Cited

OTHER PUBLICATIONS

Marr et al., "Effect of Temperature on the Composition of Fatty Acids in *Escherichia coli*," J Bacteriol., 1962, 84(6):1260-7.

Marten et al., "A randomized multicentre phase II trial comparing adjuvant therapy in patients with interferon alpha-2b and 5-FU alone or in combination with either external radiation treatment and cisplatin (CapRI) or radiation alone regarding event-free survival - CapRI-2," BMC Cancer, Feb. 2009, 9, 1-8.

Maskarinec et al., "Protein engineering approaches to biomaterials design," Curr. Opin. Biotechnol., 2005, 16, 422-426.

Masood, "Polymeric nanoparticles for targeted drug delivery system for cancer therapy," Mater Sci Eng C Mater Biol Appl, Mar. 2016, 60:569-578.

Massey et al., "Self-Assembly of a Novel Organometallic-Inorganic Block Copolymer in Solution and the Solid State: Nonintrusive Observation of Novel Wormlike Poly(ferrocenyldimethylsilane)-b-Poly(dimethylsiloxane) Micelles," J. Am. Chem. Soc. 1998, 120(37):9533-9540.

Mastria et al., "Doxorubicin-conjugated polypeptide nanoparticles inhibit metastasis in two murine models of carcinoma," J Control Release, Jun. 2015, 208:52-8.

Mastria et al., "Nanoparticle formulation improves doxorubicin efficacy by enhancing host antitumor immunity," J Control Release, Jan. 2018, 269:364-373.

Matsumura et al., "A new concept for macromolecular therapeutics in cancer chemotherapy: mechanism of tumoritropic accumulation of proteins and the antitumor agent smancs," Cancer Res. 1986, 46, 6387-6392.

Matsumura, "Cancer stromal targeting (CAST) therapy," Advanced Drug Delivery Reviews, Jun. 2012, 64, 710-719.

Matsunaga et al., "Molding cell beads for rapid construction of macroscopic 3D tissue architecture," Adv Mater, 2011, 23: H90-94.

Matthews et al., "Pharmacodynamics, Pharmacokinetics, Safety, and Tolerability of Albiglutide, a Long-Acting Glucagon-Like Peptide-1 Mimetic, in Patients with Type 2 Diabetes," J Clin Endocrinol Metab, Dec. 2008, 93(12):4810-4817.

Matyjaszewski et al., "Atom transfer radical polymerization," Chem. Rev. 101, Sep. 2001, 2921-2990.

Matyjaszewski et al., "Macromolecular engineering by atom transfer radical polymerization," J. Am. Chem. Soc. 136, 2014, 6513-6533.

Maurer-Stroh et al., "N-terminal N-myristoylation of proteins: prediction of substrate proteins from amino acid sequence" J Mol Biol., 2002, 317(4):541-557.

Maurer-Stroh et al., "N-terminal N-myristoylation of proteins: Refinement of the sequence motif and its taxon-specific differences," J Mol Biol., 2002, 317(4):523-540.

Mayo et al., "Cell Adhesion Promoting Peptide GVKGDKGNPGWPGAP from the Collagen Type IV Triple Helix: Cis/Trans Proline-Induced Multiple 1H NMR Conformations and Evidence for a KG/PG Multiple Turn Repeat Motif in the All-Trans proline State," Biochemistry, 1991, 30: 8251-8267.

McAndrews et al., "Heterogeneous antibodies against SARS-CoV-2 spike receptor binding domain and nucleocapsid with implications for COVID-19 immunity," JCI Insight, 2020, 5(18):e142386, 14 pages.

McConkey et al., "Molecular Characterization of Pancreatic Cancer Cell Lines," Pancreatic Cancer, Jan. 2010, 457-469.

McDaniel et al., "A unified model for de novo design of elastin-like polypeptides with tunable inverse transition temperatures," Biomacromolecules, Aug. 2013, 14(8):2866-2872.

McDaniel et al., "Actively targeting solid tumours with thermoresponsive drug delivery systems that respond to mild hyperthermia," Int J Hyperthermia, Aug. 2013, 29, 501-510.

McDaniel et al., "Doxorubicin-conjugated chimeric polypeptide nanoparticles that respond to mild hyperthermia," Control. Release, May 2012, 159 (3), 362-367.

McDaniel et al., "Drug delivery to solid tumors by elastin-like polypeptides," Adc. Drug Deliver. Rev., Dec. 2010, 62(15):1456-1467.

McDaniel et al., "Noncanonical Self-Assembly of Highly Asymmetric Genetically Encoded Polypeptide Amphiphiles into Cylindrical Micelles," Nano Lett., Sep. 2014, 14(11):6590-6598.

McDaniel et al., "Rational design of "heat seeking" drug loaded polypeptide nanoparticles that thermally target solid tumors," Nano Letters, Apr. 2014, 14, 2890-2895.

McDaniel et al., "Recursive Directional Ligation by Plasmid Reconstruction Allows Rapid and Seamless Cloning of Oligomeric Genes," Biomacromolecules, Feb. 2010, 11(4):944-952.

McDaniel et al., "Self-assembly of thermally responsive nanoparticles of a genetically encoded peptide polymer by drug conjugation," Chem. Int. Ed. Feb. 2013, 52, 1683-1687.

McDaniel, "Assembly of Highly Asymmetric Genetically-Encoded Amphiphiles for Thermally Targeted Delivery of Therapeutics," Dissertation, 2013, 295 pages, Published Mar. 1, 2014.

McElvaney et al., "A linear prognostic score based on the ratio of interleukin-6 to interleukin-10 predicts outcomes in COVID-19," EBioMedicine, 2020, 61: 103026, 8 pages.

McHale et al., "Synthesis and in vitro evaluation of enzymatically cross-linked elastin-like polypeptide gels for cartilaginous tissue repair," Tissue Eng., 2005, 11, 1768-1779.

McIlhinney et al., "Characterization of a polyhistidine-tagged form of human myristoyl-CoA: protein N-myristoyltransferase produced in *Escherichia coli*," European Journal of Biochemistry, 1994, 222(1):137-146.

McKenzie et al., "Multivalent Binding of a Ligand-Coated Particle: Role of Shape, Size, and Ligand Heterogeneity," Biophys J, Apr. 2018, 114(8):1830-1846.

McManus et al., "Gene silencing in mammals by small interfering RNAs," Nat Rev Genet, 2002, 3(10): 737-747.

Meier et al., "Determination of Optimal Sample Size for Quantification of ß-Cell Area, Amyloid Area and ß-Cell Apoptosis in Isolated Islets," J Histochem Cytochem, Aug. 2015, 63(8):663-673.

Mejía-Salazar et al., "Microfluidic Point-of-Care Devices: New Trends and Future Prospects for eHealth Diagnostics," Sensors, 2020, 20: 1951, 19 pages.

Mejuch et al., "Synthesis of lipidated proteins," Bioconjug. Chem. 27, Jul. 2016, 1771-1783.

Meng et al., "Stimuli-responsive polymersomes for programmed drug delivery," Biomacromolecules, ACS Publications, Feb. 2009, 10(2):197-209.

Merkel et al., "Using mechanobiological mimicry of red blood cells to extend circulation times of hydrogel microparticles," Proc Natl Acad Sci U S A, The National Academy of Sciences of the USA, Jan. 2011, 108(2):586-91.

Mero et al., "Transglutaminase-mediated PEGylation of proteins: direct identification of the sites protein modification by mass spectrometry using a novel monodisperse PEG," Bioconjug Chem, Feb. 2009, 20(2):384-389.

Merriam Webster Dictionary, "Plurality," <https://www.merriam-webster.com/dictionary/plurality> webpage accessed Jun. 25, 2020.

Merrick et al., "Seed fixity in the prostate/periprostatic region following brachytherapy," International journal of radiation oncology, biology, physics, 2000, 46, 215-220.

Meyer et al., "Drug targeting using thermally responsive polymers and local hyperthermia," Journal of Controlled Release, 2001, 74, 213-224.

Meyer et al., "Genetically Encoded Synthesis of Protein-Based Polymers with Precisely Specified Molecular Weight and Sequence by Recursive Directional Ligation: Examples from the Elastin-like Polypeptide System," Biomacromolecules, 2002, 3:357-367.

Meyer et al., "Purification of recombinant proteins by fusion with thermally-responsive polypeptide," Nat. Biotechnol., 1999, 17(11):1112-1115.

Meyer et al., "Quantification of the effects of chain length and concentration on the thermal behavior of elastin-like polypeptides," Biomacromolecules, 2004, 5(3):846-51.

Meyer et al., "Targeting a Genetically Engineered Elastin-Like Polypeptide to Solid Tumors by Local Hyperthermia," Cancer Res., 2001, 61(4):1548-1554.

Miao et al., "Sequence and domain arrangements influence mechanical properties of elastin-like polymeric elastomers," Biopolymers, Jun. 2013, 99, 392-407.

(56) References Cited

OTHER PUBLICATIONS

Miao et al., "Structural determinants of cross-linking and hydrophobic domains for self-assembly of elastin-like polypeptides," Biochemistry, 2005, 44, 14367-14375.
Michl et al., "Current concepts and novel targets in advanced pancreatic cancer," Gut, Jan. 2013, 62, 317-326.
Micsonai et al. "Accurate secondary structure prediction and fold recognition for circular dichroism spectroscopy," Proc Natl Acad Sci U S A, Jun. 2015, 112, E3095-3103.
Milenic et al., "Antibody-targeted radiation cancer therapy," Nature Reviews Drug Discovery, 2004, 3, 488-498.
Miller et al., "Disease and healthcare burden of COVID-19 in the United States, " Nat Med, 2020, 26: 1212-1217.
Miller et al., "Solubilized, Spaced Polyalanines: A Context-Free System for Determining Amino Acid a-Helix Propensities," Journal of the American Chemical Society, 2002, 124, 945-962.
Minteer et al., "Fat Grafting for Pedal Fat Pad Atrophy in a 2-Year, Prospective, Randomized, Crossover, Single-Center Clinical Trial," Plast Reconstr Surg, 2018, 142: 862e-871e.
Mitragotri et al., "Physical approaches to biomaterial design," J. Nat Mater, Nature Publishing Group, Jan. 2009, 8(1):15-23.
Miyata et al., "Polymeric micelles for nano-scale drug delivery," Reaction & Functional Polymers, Mar. 2011, 71, 227-234.
Mjelle et al., "Cell cycle regulation of human DNA repair and chromatin remodeling genes," DNA Repair, Jun. 2015, 30, 53-67.
Modery et al., "Heteromultivalent liposomal nanoconstructs for enhanced targeting and shear- stable binding to active platelets for site-selective vascular drug delivery," Biomaterials, Elsevier, Dec. 2011, 32(35):9504-9514.
Molliex et al., "Phase separation by low complexity domains promotes stress granule assembly and drives pathological fibrillization," Cell, Sep. 2015, 163(1):123-133.
Moosmann et al., "Alpha complementation of LacZ in mammalian cells," Nucleic Acids Res, 1996, 24(6):1171-1172.
Moreno et al., "Anti-PEG Antibodies Inhibit the Anticoagulant Activity of PEGylated Aptamers," Cell Chem Biol, 2019, 26(5): 634-644.e3.
Morgan et al., "The combination of epidermal growth factor receptor inhibitors with gemcitabine and radiation in pancreatic cancer," Clin Cancer Res, Aug. 2008, 14, 5142-5149.
Mosbach et al., "Formation of proinsulin by immobilized Bacillus subtilis," Nature, 1983, 302, 543-545.
Mozhdehi et al., "Genetically Encoded Cholesterol-Modified Polypeptides," Journal of the American Chemical Society, Jan. 2019, 141(2):945-951.
Mozhdehi et al., "Genetically encoded lipid-polypeptide hybrid biomaterials that exhibit temperature-triggered hierarchical self-assembly," Nature chemistry, May 2018, 10(5):496-505.
Mu et al., "FGF21 Analogs of Sustained Action Enabled by Orthogonal Biosynthesis Demonstrate Enhanced Antidiabetic Pharmacology in Rodents," Diabetes, Feb. 2012, 61(2):505-512.
Muiznieks et al., "Modulated growth, stability and interactions of liquid-like coacervate assemblies of elastin," Matrix Biology 36, Jun. 2014, pp. 39-50.
Muiznieks et al., "Proline periodicity modulates the self-assembly properties of elastin-like polypeptides," J Biol Chem, The American Society for Biochemistry and Molecular Biology, Inc, Dec. 2010, 285(51):39779-39789.
Muiznieks et al., "Structural changes and facilitated association of tropoelastin," Archives of Biochemistry and Biophysics, 2003, 410, 317-323.
Muñoz et al., "Elucidating the folding problem of helical peptides using empirical parameters," Nature Structural Biology, 1994, 1, 399-409.
Muñoz et al., "Elucidating the Folding Problem of Helical Peptides using Empirical Parameters. IIt. Helix Macrodipole Effects and Rational Modification of the Helical Content of Natural Peptides," Journal of Molecular Biology, 1995, 245, 275-296.
Muñoz et al., "Elucidating the folding problem of helical peptides using empirical parameters. III. Temperature and pH dependence," J Mol Biol, 1995, 245, 297-308.
Muralidharan et al., "Protein Ligation: an Enabling Technology for the Biophysical Analysis of Proteins," Nature Methods, Jun. 2006, vol. 3, No. 6, pp. 429-438.
Muro, "Challenges in design and characterization of ligand-targeted drug delivery systems," J Control Release, Elsevier, Dec. 2012, 164(2):125-37.
Murphy et al., "A dosimetric model of duodenal toxicity after stereotactic body radiotherapy for pancreatic cancer," Int J Radiation Oncology Biol Phys, Dec. 2010, 78, 1420-1426.
Na et al., "Thermoresponsive pore structure of biopolymer microspheres for a smart drug carrier," Langmuir, Jun. 2010, 26, 11165-11169.
Nagarsekar et al., "Genetically Engineered Polymers for Drug Delivery," Journal of Drug Targeting, 1999, 7(1):11-32.
Nahire et al., "Multifunctional Polymersomes for Cytosolic Delivery of Gemcitabine and Doxorubicin to Cancer Cells," Biomaterials, Aug. 2014, 35(24):6482-6497.
Nairn et al., "A Synthetic Resilin Is Largely Unstructured," Biophysical Journal, Oct. 2008, vol. 95 3358-3365.
Nakaoka et al., "Prolongation of the serum half-life period of superoxide dismutase by poly(ethylene glycol) modification," Journal of Controlled Release, 1997, 46(3):253-261.
Nalla et al., "Comparative Performance of SARS-COV-2 Detection Assays Using Seven Different Primer-Probe Sets and One Assay Kit," J Clin Microbiol, 2020, 58: e00557-20, 6 pages.
Nanoprecision Medical, "Pipeline, Type II Diabetes," <http://www.nanoprecisionmedical.com/pipeline/diabetes> webpage available as early as Aug. 2018.
Napier et al., "Nanoparticle drug delivery platform," Journal of Macromolecular Science, Part C: Polymer Reviews, Taylor & Francis Group, LLC, Aug. 2007, 47(3):321-327.
National Institute of Mental Health, "Methods and Welfare Considerations in Behavioral Research with Animals: Report of a National Institutes of Health Workshop," NIH Publication No. 02-54083, Washington, DC: U.S. Government Printing Office. (Mar. 2002).
Nauck "Glucagon-like Peptide 1 (GLP-1) in the Treatment of Diabetes," Horm Metab Res, 2004, 36(11/12):852-858 (in English).
Nayeem et al., "Engineering enzymes for improved catalytic efficiency: a computational study of site mutagenesis in epothilone-B hydroxylase," Protein Eng Des Sel, Oxford Academy, Apr. 2009, 22(4):257-266.
Neidigh et al., "Exendin-4 and glucagon-like-peptide-q: NMR structural comparisons in the solution and micelle-associated states," Biochemistry 40, 2001, 13188-13200.
Nettles et al., "Applications of elastin-like polypeptides in tissue engineering," Adv Drug Deliv Rev, Dec. 2010, 62, 1479-1485.
Nettles et al., "In situ crosslinking elastin-like polypeptide gels for application to articular cartilage repair in a goat osteochondral defect model," Tissue Eng Part A, Jul. 2008, 14, 1133-1140.
Newcomb et al., "Advances in cryogenic transmission electron microscopy for the characterization of dynamic self-assembling nanostructures, " Current Opinion in Colloid and Interface Science, Dec. 2012, 17, 350-359.
Newton et al., "Commissioning a small-field biological irradiator using point, 2D, and 3D dosimetry techniques," Medical Physics, Dec. 2011, 38, 6754-6762.
Ni et al., "Engineering of inorganic nanoparticles as magnetic resonance imaging contrast agents," Chem Soc Rev, Nov. 2017, 46(23):7438-7468.
Nichols et al., "Claudin 4 protein expression in primary and metastatic pancreatic cancer," Am J Clin Pathol, 2004, 121, 226-230.
Nicolas et al., "Fluorescently tagged polymer bioconjugates from protein derived macroinitiators," Chem. Commun. Jan. 2007, 45, 4697-4699.
Nie, "Understanding and overcoming major barriers in cancer nanomedicine," Nanomedicine (Lond) Jun. 2010, 5 (4), 523-528.
Nielsen, "Incretin mimetics and DPP-IV inhibitors for the treatment of type 2 diabetes, " Drug Discov. Today 10, 2005, 703-710.

(56) References Cited

OTHER PUBLICATIONS

Nies et al., "Fibroblast Growth Factor Signaling in Metabolic Regulation," Front Endocrinol, Jan. 2016, 6(193) (in English).
Nikolic et al., "Structural basis for the recognition of LDL-receptor family members by VSV glycoprotein," Nature Communications, 2018, 9: 1029, 12 pages.
Nilvebrant et al., "The albumin-binding domain as a scaffold for protein engineering," Computational and Structural Biotechnology Journal, Mar. 2013, 6: e201303009, 8 pages.
Nimjee et al., "Aptamers as Therapeutics," Annu Rev Pharmacol Toxicol, 2017, 57: 61-79.
Niu et al., "The role of adhesion molecules, avB3, avB5 and their ligands in the tumor cell and endothelial cell adhesion," Eur J Cancer Prev, Wolters Kluwer, Dec. 2007, 16(6):517-27.
Norman et al., "Ultrasensitive high-resolution profiling of early seroconversion in patients with COVID-19," Nat Biomed Eng, 2020, 11 pages.
Nott et al., "Phase transition of a disordered nuage protein generates environmentally responsive membraneless organelles," Mol Cell, Mar. 2015, 57(5):936-947.
Nucci et al., "The therapeutic value of poly(ethylene glycol)-modified proteins," Adv. Drug Deliv. Rev., 1991, 6(2):133-151.
Nuhn et al., "Secondary structure formation and LCST behavior of short elastin-like peptides," Biomacromolecules, Sep. 2008, 9, 2755-2763.
Nunn et al., "Crystal Structure of Tobacco Etch Virus Protease Shows the Protein C Terminus Bound within the Active Site," Journal of Molecular Biology, 2005, 350: 145-155.
Nyborg et al., "A Therapeutic Uricase with Reduced Immunogenicity Risk and Improved Development Properties," PLOS One, 2016, 11(12): e0167935, 23 pages.
O'Day et al., "Therapeutic Protein-polymer Conjugates: Advancing beyond PEGylation," J. Am. Chem. Soc., Sep. 2014, vol. 136, pp. 14323-14332.
Ogawara et al., "Pre-coating with serum albumin reduces receptor-mediated hepatic disposition of polystyrene nanosphere: implications for rational design of nanoparticles," Journal of Controlled Release, 2004, 100(3): 451-455.
Oh et al., "The development of microgels/nanogels for drug delivery applications," Progress in Polymer Science, 2008, 33(4): 448-477.
Okba et al., "Severe Acute Respiratory Syndrome Coronavirus 2-Specific Antibody Responses in Coronavirus Disease Patients," Emerg Infect Dis, 2020, 26: 1478-1488.
Olafsen et al., "Covalent disulfide-linked anti-CEA diabody allows site-specific conjugation and radiolabeling for tumor targeting applications," Protein Engineering, Design & Selection, 2004, 17(1):21-27.
Ortega et al., "Hydrodynamic properties of rodlike and dislike particles in dilute solution," The Journal of Chemical Physics, 2003, 119(18):9914-9919.
Ortony et al., "Internal dynamics of a supramolecular nanofibre," Nat. Mater., Aug. 2014, 13, 1-5.
Ozer et al., "Effect of Molecular Architecture on Cell Interactions and Stealth Properties of PEG, " Biomacromolecules, 2017, 18: 2699-2710.
Ozer et al., "PEG-like brush polymer conjugate of RNA aptamer that shows reversible anticoagulant activity and minimal immune response," Advanced Materials, 2022, 34(10): 210852.
Ozer et al., "Site-Specific and Stoichiometric Stealth Polymer Conjugates of Therapeutic Peptides and Proteins," Bioconjug Chem, Mar. 2017, 28(3):713-723.
Pace et al., "How to measure and predict the molar absorption coefficient of a protein" Protein Science 1995, 4: 2411-2423.
Pagani et al., "International guidelines for management of metastatic breast cancer: can metastatic breast cancer be cured?," Journal of the National Cancer Institute, Apr. 2010, 102, 456-463.
Pak et al., "Sequence Determinants of Intracellular Phase Separation by Complex Coacervation of a Disordered Protein," Mol Cell, Jul. 2016, 63(1):72-85.
Palmerston Mendes et al., "Dendrimers as Nanocarriers for Nucleic Acid and Drug Delivery in Cancer Therapy," Molecules, Aug. 2017, 22(9):1401.
Palta et al., "Interim Acute Toxicity Analysis and Surgical Outcomes of Neoadjuvant Gemcitabine/nab-Paclitaxel and Hypofractionated Image Guided Intensity Modulated Radiation Therapy in Resectable and Borderline Resectable Pancreatic Cancer (ANCHOR) Study," International Journal of Radiation Oncology • Biology • Physics, Oct. 2016, 96, S204-S205.
Palva et al., "Secretion of interferon by Bacillus subtilis," Gene, 1983, 22, 229-235.
Pan et al., "A Pig Model for the Histological Analysis of Adipocytes after Co - injections of Autologous Fat with Fillers," International Journal of Surgery & Surgical Techniques, 2016, 2: 7 pages.
Panda et al., "Stop-flow lithography to generate cell-laden microgel particles," Lab Chip, 2008, 8: 1056-1061.
Pang et al., "A Modular Method for the High-Yield Synthesis of Site-Specific Protein-Polymer Therapeutics," Angew Chem Int Ed Engl, Jul. 2016, 55, 10296-10300.
Paolino et al., "Folate-targeted supramolecular vesicular aggregates as a new frontier for effective anticancer treatment in in vivo model," Eur. J. Pharm. Biopharm., Jun. 2012, 82(1):94-102.
Paolino et al., "Gemcitabine-loaded PEGylated unilamellar liposomes vs GEMZAR: biodistribution, pharmacokinetic features and in vivo antitumor activity," J. Control. Release Jun. 2010, 144(2):144-150.
Paoloni et al., "Translation of new cancer treatments from pet dogs to humans," Nat. Rev. Cancer Feb. 2008, 8 (2), 147-156.
Papa et al., "PEGylated Liposomal Gemcitabine: Insights Into a Potential Breast Cancer Therapeutic," Cell Oncol. (Dordr), Oct. 2013, 36(6):449-457.
Paramonov et al., "Self-assembly of peptide-amphiphile nanofibers: The roles of hydrogen bonding and amphiphilic packing, " J. Am. Chem. Soc., May 2006, 128, 7291-7298.
Pardridge, "The blood-brain barrier: bottleneck in brain drug development, " NeuroRx, 2005, 2(1):3-14.
Park et al., "Exendin-4 and exercise improve hepatic glucose homeostasis by promoting insulin signaling in diabetic rats," Metabolism, Janury 2010, 59, 123-133.
Park et al., "Formulation optimization and in vivo proof-of-concept study of thermosensitive liposomes balanced by phospholipid, elastin-like polypeptide, and cholesterol," PLOS One, Jul. 2014, 9: e103116, 13 pages.
Park et al., "Polymer Brush As a Facile Dielectric Surface Treatment for High-Performance, Stable, Soluble Acene-Based Transistors," Chemistry of Materials, 2010, 22: 5377-5382.
Park et al., "Protein stitchery: Design of a protein for selective binding to a specific DNA sequence," PNAS, 1992, vol. 89:9094-9096.
Parker et al., "Antibody mimics based on human fibronectin type three domain engineered for thermostability and high-affinity binding to vascular endothelial growth factor receptor two," Protein Eng Des Sel, 2005, 18(9):435-44.
Parkes et al. "Discovery and development of exenatide: the first antidiabetic agent to leverage the multiple benefits of the incretin hormone, GLP-1," Expert Opinion. Drug Deliv., Feb. 2013, 8(2):219-244.
Parveen et al., "Nanomedicine," Clinical Pharmacokinetics, Oct. 2006, 45(10):965-988.
Pastuszka et al., "A tunable and reversible platform for the intracellular formation of genetically engineered protein microdomains," Biomacromolecules, ACS Publications, Oct. 2012, 13(11):3439-3444.
Patil et al., "Cellular delivery of doxorubicin via pH-controlled hydrazone linkage using multifunctional nano vehicle based on poly(beta-I-malic acid)," Int J Mol Sci, Sep. 2012, 13, 11681-11693.
Paulsen et al., "Optofluidic fabrication for 3D-shaped particles," Nat Commun, 2015, 6: 6976.
Pecoraro et al., "A systematic evaluation of immunoassay point-of-care testing to define impact on patients' outcomes," Ann Clin Biochem, 2017, 54(4): 420-431.
Peeler et al., "Genetically encoded initiator for polymer growth from proteins," J. Am. Chem. Soc. 132, Oct. 2010, 13575-13577.

(56) References Cited

OTHER PUBLICATIONS

Peng et al., "Length-dependent prediction of protein intrinsic disorder," BMC Bioinformatics, Springer Nature, Apr. 2006, 7:208.
Peters, "Serum albumin," Adv. Protein Chem. 37, 1985, 161-245.
Petitdemange et al., "Tuning Thermoresponsive Properties of Cationic Elastin-like Polypeptides by Varying Counterions and Side-Chains," Bioconjug. Chem., May 2017, 28(5):1403-1412.
Petros et al., "Strategies in the design of nanoparticles for therapeutic applications," Nat Rev Drug Discov, Nature Research, Aug. 2010, 9(8):615-27.
Phan et al., "Temperature-responsive self-assembly of charged and uncharged hydroxyethylcellulose-graft-poly(N-isopropylacrylamide) copolymer in aqueous solution," Colloid Polym. Sci., Apr. 2011, 289 (9), 993-1003.
Pinkas et al., "Tunable, post-translational hydroxylation of collagen domains in Escherichia coli," ACS Chem. Biol., Apr. 2011, 6(4):320-324.
Pisal et al., "Delivery of therapeutic proteins," Journal of Pharmaceutical Sciences, 2010, 99(6):2557-2575.
Pliarchopoulou et al., "Pancreatic cancer: Current and future treatment strategies," Cancer Treatment Reviews, Aug. 2009, 35, 431-436.
Poitout et al., "Glucolipotoxicity: Fuel Excess and B-Cell Dysfunction," Endocr Rev, May 2008, 29(3):351-366.
Pometun et al., "Quantitative observation of backbone disorder in native elastin," J Biol Chem, 2004, 279, 7982-7987.
Ponti et al., "Biomarkers associated with COVID-19 disease progression," Crit Rev Clin Lab Sci, 2020, 57, 11 pages.
Popp et al., "Site-specific labeling via sortase-mediated transpeptidation," Curr. Protoc. Protein Sci. 56, Apr. 2009, 15.13.1-15.13.9.
Popp et al., "Sortase-Catalyzed Transformations That Improve The Properties Of Cytokines," PNAS, Feb. 2011, vol. 108, No. 8, pp. 3169-3174.
Posthuma-Trumpie et al., "Lateral flow (immuno)assay: its strengths, weaknesses, opportunities and threats. A literature survey," Anal Bioanal Chem, 2009, 393: 569-582.
Potters et al., "12-year outcomes following permanent prostate brachytherapy in patients with clinically localized prostate cancer," The Journal of urology, 2005, 173, 1562-1566.
Potters et al., "Monotherapy for stage T1-T2 prostate cancer: radical prostatectomy, external beam radiotherapy, or permanent seed implantation," Radiotherapy and oncology: journal of the European Society for Therapeutic Radiology and Oncology, 2004, 71, 29-33.
Potters et al., "Potency after permanent prostate brachytherapy for localized prostate cancer," International journal of radiation oncology, biology, physics, 2001, 50(5): 1235-1242.
Potthoff et al., "Endocrine fibroblast growth factors 15/19 and 21: from feast to famine," Genes Dev, Feb. 2012, 26(4):312-324.
Povsic et al., "A Phase 2, randomized, partially blinded, active-controlled study assessing the efficacy and safety of variable anticoagulation reversal using the REG1 system in patients with acute coronary syndromes: results of the RADAR trial," Eur Heart J, 2013, 34(31): 2481-2489.
Povsic et al., "Pre-existing anti-PEG antibodies are associated with severe immediate allergic reactions to pegnivacogin, a PEGylated aptamer," J Allergy Clin Immunol, 2016, 138(6): 1712-1715.
Prestwich et al., "Beta dose point kernels for radionuclides of potential use in radioimmunotherapy," J Nucl Med, 1989, 30, 1036-1046.
Privratsky et al., "PECAM-1: regulator of endothelial junctional integrity," Cell Tissue Res, Mar. 2014, 355, 607-619.
Prostate Seed Center, "Brachytherapy seed pre-plan rendering," <http://www.prostateseedcenter.com/dynamics-of-brachytherapy> webpage available as early as Aug. 30, 2012.
Provenzano et al., "Enzymatic targeting of the stroma ablates physical barriers to treatment of pancreatic ductal adenocarcinoma," Cancer cell, Mar. 2012, 21, 418-429.
Provenzano et al., "Hyaluronan, fluid pressure, and stromal resistance in pancreas cancer," Br J Cancer, Jan. 2013, 108, 1-8.

Pulaski et al., "Mouse 4T1 breast tumor model," Curr. Protoc. Immunol., 2001, Chapter 20, Unit 20.2.
Purtell et al., "Isoelectric point of albumin: effect on renal handling of albumin," Kidney Int, 1979, 16(3): 366-376.
Qamar et al., "FUS Phase Separation Is Modulated by a Molecular Chaperone and Methylation of Arginine Cation-pi Interactions," Cell, Apr. 2018, 173(3):720-734.e15.
Qi et al., "A brush-polymer conjugate of exendin-4 reduces blood glucose for up to five days and eliminates poly(ethylene glycol) antigenicity," Nat Biomed Eng, Nov. 2016, 1:0002.
Qi et al., Dataset for A brush-polymer conjugate of exendin-4 reduces blood glucose for up to five days and eliminates poly(ethylene glycol) antigenicity. Figshare, Nov. 2016, <http://dx.doi.org/10.6084/m9.figshare.3976761>.
Qi et al., "Growing polymers from peptides and proteins: a biomedical perspective," Polym. Chem., Jan. 2014, 5(2):266-276.
Qi et al., "Protein-polymer conjugation-moving beyond PEGylation," Curr. Opin. Chem. Biol. 28, Oct. 2015, 181-193.
Qi et al., "Sortase-catalyzed initiator attachment enables high yield growth of a stealth polymer from the C terminus of a protein," Macromol. Rapid Commun., Aug. 2013, 34(15):1256-1260.
Qiu et al., "Development of Orthotopic Pancreatic Tumor Mouse Models," Methods Mol Biol, Jan. 2013, 980: 215-223.
Qiu et al., "Polymer Architecture and Drug Delivery," Pharmaceutical Research, Feb. 2006, 23(1):1-30.
Quarmby et al., "Irradiation induces upregulation of CD31 in human endothelial cells," Arterioscler Thromb Vasc Biol, 1999, 19, 588-597.
Quarmby et al., "Radiation-induced normal tissue injury: role of adhesion molecules in leukocyte-endothelial cell interactions," Int J Cancer, 1999, 82, 385-395.
Quiroz et al., "Intrinsically disordered proteins access a range of hysteretic phase separation behaviors," Scientific advances, Oct. 2019, 5(10):eaax5177.
Quiroz et al., "Sequence heuristics to encode phase behaviour in intrinsically disordered protein polymers," Nat. Mater., Nov. 2015, 14(11):1164-1171.
Rabotyagova et al., "Protein-based block copolymers," Biomacromolecules, Feb. 2011, 12(2): 269-289.
Radivojac et al., "Intrinsic Disorder and Functional Proteomics," Biophysical Journal, Mar. 2007, vol. 92, Issue 5, pp. 1439-1456.
Radzicka et al., "Comparing the Polrities of the Amino Acids: Side-Chain Distribution Coefficients between the Vapor Phase, Cyclohexane, 1-Octanol, and Neutral Aqueous Solution," Biochemistry, 1988, 27: 1664-1670.
Ragupathi et al., "Abstract A73: Antitumor activity of MVT-5873, a monoclonal antibody targeting sialyl Lewisa, alone and in combination with gemcitabine/nab-paclitaxel in a BxPC3 human pancreatic cancer xenograft model," Cancer Research, Dec. 2016, 76.
Rankine et al., "Investigating end-to-end accuracy of image guided radiation treatment delivery using a micro-irradiator," Physics in Medicine and Biology, Nov. 2013, 58(21): 7791-7801.
Rao et al., "Synthetic nanoparticles camouflaged with biometric erythrocyte membranes for reduced reticuloendothelial system uptake," Nanotechnology, Jan. 2016, 27 (8), 85106, 9 pages.
Rapaka et al., "Coacervation of Sequential Polypeptide Models of Tropoelastin," Int J Peptide Protein Res, 1978, 11: 97-108.
Rasmussen et al., "A Novel Porcine Model for Future Studies of Cell-enriched Fat Grafting," Plast Reconstr Surg Glob Open, 2018, 6: e1735.
Ratner et al., "Radiation-grafted hydrogels for biomaterial applications as studied by the ESCA technique," Journal of Applied Polymer Science, 1978, 22, 643-664.
Ratner, "A pore way to heal and regenerate: 21st century thinking on biocompatibility," Regen Biomater, Feb. 2016, 3(2):107-110.
Rauscher et al. "Proline and Glycine Control Protein Self-Organization into Elastomeric or Amyloid Fibrils," Structure, Nov. 2006, 14(11):1667-1676.
Ravichandran et al., "Antibody signature induced by SARS-CoV-2 spike protein immunogens in rabbits," Sci Transl Med, 2020, 10.1126/scitranslmed.abc3539, 9 pages.

(56) References Cited

OTHER PUBLICATIONS

Ravikumar et al., "Mimicking adhesive functionalities of blood platelets using ligand-decorated liposomes," Bioconjugate chemistry, ACS Publications, May 2012, 23(6):1266-1275.
Ray et al., "Aptamer-mediated delivery of chemotherapy to pancreatic cancer cells." Nucleic acid therapeutics, Oct. 2012, 22(5): 295-305.
Regier et al., American Heart Association 2014 Scientific Sessions, May 2015, vol. 7, pp. 299-303.
Reguera et al., "Thermal Behavior and Kinetic Analysis of the Chain Unfolding and Refolding and of the Concomitant Nonpolar Solvation and Desolvation of Two Elastin-like Polymers," Macromolecules, 2003, 36, 8470-8476.
Ren et al., "Mesenchymal stem cell-mediated immunosuppression occurs via concerted action of chemokines and nitric oxide," Cell Stem Cell, Feb. 2008, 2(2): p. 141-150.
Ren et al., "Stimulus-Responsive Polymer Prodrugs," Progress in Chemistry, 2013, 25(5): 10 pages.
Resh, "Covalent Lipid Modifications of Proteins," Curr Biol., May 2013, 23(10): R431-R435.
Ribeiro et al., "Influence of the amino-acid sequence on the inverse temperature transition of elastin-like polypeptides," Biophysical Journal, Jul. 2009, 97(1):312-320.
Richards et al., "Engineered fibronectin type III domain with a RGDWE sequence binds with enhanced affinity and specificity to human avB3 integrin," J Mol Biol, 2003, 326(5):1475-1488.
Richards et al., "Man's best friend: what can pet dogs teach us about non-Hodgkin lymphoma?" Inmunol Rev., Jan. 2015, 263 (1): 173-191.
Richter et al., "Mechanistic determinants of biotherapeutics absorption following SC administration," Aaps J, 2012, 14(3): 559-570.
Riddles et al., "Ellman's reagent: 5,5'-dithiobis(2-nitrobenzoic acid)—a reexamination, " Anal Biochem. 1979, 94(1):75-81.
Riedel et al., "Engineered glucagon-like peptide-1-producing hepatocytes lower plasma glucose levels in mice," Am J Physiol Endocrinol Metab, Apr. 2009, 296(4):E936-E944.
Rinaldi et al., "Antisense oligonucleotides: the next frontier for treatment of neurological disorders," Nat Rev Neurol, 2018, 14(1): 9-21.
Rincon et al., "Biocompatibility of elastin-like polymer poly(VPAVG) microparticles: in vitro and in vivo studies," Journal of Biomedical Materials Research, 2005, 78A, 343-351.
Rios-Doria et al., "Doxil synergizes with cancer immunotherapies to enhance antitumor responses in syngeneic mouse models," Neoplasia, Aug. 2015, 17(8):661-670.
Ritcher et al., "Antibodies against polyethylene glycol produced in animals by immunization with monomethoxy polyethylene glycol modified proteins," Int. Arch. Allergy Appl. Immunol. 70, 1983, 124-131.
Ritcher et al., "Polyethylene glycol reactive antibodies in man: titer distribution in allergic patients treated with monomethoxy polyethylene glycol modified allergens or placebo, and in healthy blood donors," Int. Arch. Allergy Appl. Immunol. 74, 1984, 36-39.
Rivory et al., "Effects of lipophilicity and protein binding on the hepatocellular uptake and hepatic disposition of two anthracyclines, doxorubicin and iododoxorubicin," Cancer Chemother Pharmacol, 1996, 38(5):439-445.
Roberts et al., "Elastin-like polypeptides as models of intrinsically disordered proteins," FEBS Lett., Sep. 2015, 589, 2477-2486.
Roberts et al., "Injectable tissue integrating networks from recombinant polypeptides with tunable order," Nature Materials, 2018, 17(12): 1154-1163.
Robinet et al. "Elastin-derived peptides enhance angiogenesis by promoting endothelial cell migration and tubulogenesis through upregulation of MT1-MMP," J. Cell Science, 2005, 118:343-356.
Roca et al., "Autologous Fat Grafting for Treatment of Breast Implant Capsular Contracture: A Study in Pigs," Aesthet Surg J, 2014, 34: 769-775.
Rodriguez-Cabello et al., "Elastin-like polypeptides in drug delivery," Adv Drug Deliv Rev, 2016, 97: 85-100.
Rodriguez-Diaz et al., "Alpha cells secrete acetylcholine as a non-neuronal paracrine signal priming beta cell function in humans," Nat Med, Jun. 2011, 17:888-892.
Rogers et al., "Isolation of potent SARS-CoV-2 neutralizing antibodies and protection from disease in a small animal model," Science, 2020, 369: 956-963.
Rolland et al., "Direct fabrication and harvesting of monodisperse, shape-specific nanobiomaterials," J Am Chem Soc, 2005, 127(28):10096-100.
Romer et al., "The elaborate structure of spider silk: structure and function of a natural high performance fiber," Prion, Nov. 2008, 2(4):154-161.
Roopenian et al., "FcRn: the neonatal Fc receptor comes of age," Nat. Rev. Immunol., Sep. 2007, vol. 7, No. 9, 715-725.
Rosadas et al., "Testing for responses to the wrong SARS-CoV-2 antigen," Lancet, 2020, 396:e23.
Rosenberg et al., "Present and future innovations in radiation oncology," Surg Oncol Clin N Am, Jul. 2013, 22(3):599-618.
Rosenholm et al., "Towards multifunctional, targeted drug delivery systems using mesoporous silica nanoparticles - opportunities & challenges," Nanoscale, Royal Society of Chemistry, Oct. 2010, 2(10):1870-83.
Rösler et al., "Advanced drug delivery devices via self-assembly of amphiphilic block copolymers," Advanced Drug Delivery Reviews, 2001, 53:95-108.
Rothe et al., "Transmission of 2019-nCOV Infection from an Asymptomatic Contact in Germany," N Engl J Med, 2020, 382: 10, 2 pages.
Rozak et al., "G148-GA3: a streptococcal virulence module with atypical thermodynamics of folding optimally binds human serum albumin at physiological temperatures," Biochim Biophys Acta, 2005, 1753(2): p. 226-33.
Ruiz van Haperen et al., "Regulation of phosphorylation of deoxycytidine and 2',2'-difluorodeoxycytidine (gemcitabine); effects of cytidine 5'-triphosphate and uridine 5'-triphosphate in relation to chemosensitivity for 2',2'-difluorodeoxycytidine," Biochem. Pharmacol. 1996, 51(7):911-908.
Rusconi et al., "Antidote-mediated control of an anticoagulant aptamer in vivo," Nat Biotechnol, 2004, 22(11): 1423-1428.
Rusconi et al., "RNA aptamers as reversible antagonists of coagulation factor Ixa," Nature, 2002, 19(6902): 90-94.
Russo et al., "The role of neoadjuvant therapy in pancreatic cancer: a review," Future Oncol, Mar. 2016, 12(5):669-685.
Ryerson et al., "Annual report to the nation on the status of cancer, 1975-2012, featuring the Increasing incidence of liver cancer," Cancer, May 2016, 122(9): 1312-1337.
Ryu et al., "Elastin-like polypeptide for improved drug delivery for anticancer therapy: preclinical studies and future applications," Expert Opinion on Drug Delivery, Informa Healthcare, Oct. 2014, 12(4):653-667.
Saba et al., "A Comparative Oncology Study of Iniparib Defines Its Pharmacokinetic Profile and Biological Activity in a Naturally-Occurring Canine Cancer Model," PLOS One, Feb. 2016, 11(2): 1-11.
Safran et al., "Gemcitabine, paclitaxel, and radiation for locally advanced pancreatic cancer: A phase I trial," Int J Radiation Oncology Biol Phys, 2002, 54, 137-141.
Sagle et al., "Investigating the hydrogen-bonding model of urea denaturation," J Am Chem Soc, Jun. 2009, 131(26): 9304-9310.
Saifer et al., "Selectivity of binding of PEGs and PEG-like oligomers to anti-PEG antibodies induced by methoxyPEG-proteins," Molecular Immunology, Feb. 2014, 57(2):236-246.
Sandberg et al., "The Structure of the Elastic Fiber: An Overview," The Journal of Investigative Dermatology, 1982, 79(S1): 128s-132s.
Sandler et al., "Gemcitabine: Single-Agent and Combination Therapy in Non-Small Cell Lung Cancer," Oncologist 1999, 4(3)241-251.
Sanna et al., "Targeted therapy using nanotechnology: focus on cancer," Int J Nanomedicine, Jan. 2014, 9:467-83.
Schaal et al., "Biopolymer ß-brachytherapy delivered with concomitant paclitaxel outperforms traditional x-ray radiation to include complete regression in multiple pancreatic tumor xenograft models through synergistic modulation of the tumor microenvironment," Poster #5831, 2018.

(56) References Cited

OTHER PUBLICATIONS

Schaal et al., "Injectable polypeptide micelles that form radiation crosslinked hydrogels in situ for intratumoral radiotherapy," Journal of Controlled Release, Apr. 2016, 228, 58-66.

Schellenberg et al., "Gemcitabine chemotherapy and single-fraction stereotactic body radiotherapy for locally advanced pancreatic cancer," Int J Radiation Oncol Biol Phys, Nov. 2008, 72(3): 678-686.

Schellenberg et al., "Single-fraction stereotactic body radiation therapy and sequential gemcitabine for the treatment of locally advanced pancreatic cancer," Int J Radiation Oncology Biol Phys, Sep. 2011, 81(1): 181-188.

Schellenberger et al., "A recombinant polypeptide extends the in vivo half-life of peptides and proteins in a tunable manner," Nat. Biotechnol., Dec. 2009, 27(12):1186-1188.

Schlaff et al., "Bringing the heavy: carbon ion therapy in the radiobiological clinical context," Radiation Oncology, Mar. 2014, 9, Article 88, 1-18.

Schneider et al., "NIH Image to ImageJ: 25 years of image analysis," Nature Methods, Jul. 2012, 9(7): 671-675.

Schnell et al., "Expression of integrin avB3 in gliomas correlates with tumor grade and is not restricted to tumor vasculature," Brain Pathol, International Society of Neuropathology, Aug. 2008, 18(3):378-86.

Schwendeman et al., "Injectable controlled release depots for large molecules," J Control Release, Sep. 2014, 190, 240-253.

Senin et al., "N-Myristoylation of recoverin enhances its efficiency as an inhibitor of rhodopsin kinase," Febs. Lett., 1995, 376, 87-90.

Senior et al., "Val-Gly-Val-Ala-Pro-Gly, a Repeating Peptide in Elastin, Is Chemotactic for Fibroblasts and Monocytes," The Journal of Cell Biology, 1984, 99: 870-874.

Seow et al., "Longitudinal evaluation and decline of antibody responses in SARS-CoV-2 infection," medRxiv, 2020, 24 pages.

Serrano et al., "An infrared spectroscopic study of the conformational transition of elastin-like polypeptides," Biophys. J., Oct. 2007, 93(7):2429-2435.

Shadwick, "Mechanical design in arteries," J Exp Biol, 1999, 202, 3305-3313.

Shang et al., "pH-Dependent Protein Conformational Changes in Albumin: Gold Nanoparticle Bioconjugates: A Spectroscopic Study," Langmuir, Feb. 2007, 23 (5), 2714-2721.

Shao et al., "Super-resolution 3D microscopy of live whole cells using structured illumination," Nat Methods, Oct. 2011, 8(12): 1044-1046.

Sharma et al., "Dendrimer nanoarchitectures for cancer diagnosis and anticancer drug delivery," Drug Discov Today, Feb. 2017, 22(2):314-326.

Sharma et al., "PLGA-based nanoparticles: A new paradigm in biomedical applications," TrAC Trends in Analytical Chemistry, Jun. 2016, 80:30-40.

Sharma et al., "Polymer particle shape independently influences binding and internalization by macrophages," Journal of Controlled Release, Elsevier, Nov. 2010, 147(3):408-412.

Shen et al., "Conjugation site modulates the in vivo stability and thearpeutic activity of antibody- drug conjugates," Nat Biotechnol, Jan. 2012, 30(2):184-189.

Sheparovych et al., "Stimuli-Responsive Properties of Peptide-Based Copolymers Studied via Directional Growth of Self-Assembled Patterns on Solid Substrate," Biomacromolecules, Jul. 2009, 10:1955-1961.

Sherman et al., "Next-Generation PEGylation Enables Reduced Immunoreactivity of PEG- Protein Conjugates," Drug and Development & Delivery, Jun. 2012, vol. 12, No. 5, 36-42.

Sherman et al., "Role of the Methoxy Group in Immune Responses to mPEG-Protein Conjugates," Bioconjugate Chemistry, Mar. 2012, 23(3): 485-499.

Shi et al., "Cell adhesion on a POEGMA-modified topographical surface, " Langmuir: the ACS journal of surfaces and colloids, Dec. 2012, 28 (49), 17011-8.

Shi et al., "Triggered sorting and co-assembly of genetically engineered protein microdomains in the cytoplasm," Adv Mater, Wiley, Jan. 2014, 26(3):449-454.

Shimoboji et al., "Temperature-Induced Switching of Enzyme Activity with Smart Polymer- Enzyme Conjugates," Bioconjugate Chem. 2003, 14, 517-525.

Shin et al., "Liquid phase condensation in cell physiology and disease," Science, Sep. 2017, 357(6357):eaaf4382.

Shu et al., "GISAID: Global initiative on sharing all influenza data—from vision to reality," Euro Surveill 22, 2017, 22(13): 30494, 3 pages.

Shusharina et al., "Micelles of Diblock Copolymers with Charged and Neutral Blocks: Scaling and Mean-Field Lattice Approaches," Macromolecules, 2000, 33(10): 3892-3901.

Sickmeier et al., "DisProt: the Database of Disordered Proteins," Nucleic Acids Res, Oxford Academy, Jan. 2007, 35:D786-793.

Siegel et al., "Absorbed fractions for electrons and beta particles in spheres of various sizes," J Nucl Med, 1994, 35, 152-156.

Siegwart et al., "ATRP In The Design Of Functional Materials For Biomedical Applications," Prog Polymer Science, Jan. 2012, vol. 37, No. 1, pp. 18-37.

Silberstein et al., "The SNM Practice Guideline for Therapy of Thyroid Disease with $^{131}$1, 3.0," J Nucl Med, Jul. 2012, 53, 1-19.

Silva et al., "Selective differentiation of neural progenitor cells by high-epitope density nanofibers," Science, 2004, 303, 1352-5.

Simakova et al., "Aqueous ARGET ATRP," Macromolecules, Aug. 2012, 45(16):6371-6379.

Simnick et al., "In vivo tumor targeting by a NGR-decorated micelle of a recombinant diblock copolypeptide," J Control Release, Oct. 2011, 155(2): 144-151.

Simnick et al., "Morphing low-affinity ligands into high-avidity nanoparticles by thermally triggered self-assembly of a genetically encoded polymer," ACS Nano, Apr. 2010, 4(4):2217-2227.

Simon et al., "Engineered Ribonucleoprotein Granules Inhibit Translation in Protocells," Molecular cell, Jul. 2019, 75(1):66-75.

Simon et al., "Programming molecular self-assembly of intrinsically disordered proteins containing sequences of low complexity," Nat Chem, Jun. 2017, 9(6):509-515.

Simonacci et al., "Procedure, applications, and outcomes of autologous fat grafting," Ann Med Surg (Lond), 2017, 20: 49-60.

Singhal et al., "Fibroblast Growth Factor 21 (FGF21) Protects against High Fat Diet Induced Inflammation and Islet Hyperplasia in Pancreas," PLoS One, Feb. 2016, 11(2):e0148252.

Sisson et al., "Radiation safety in the treatment of patients with thyroid diseases by radioiodine 131I: practice recommendations of the American Thyroid Association, " Thyroid, Apr. 2011, 21(4):335-346.

Skerra, "Alternative non-antibody scaffolds for molecular recognition, " Curr Opin Biotechnol, Elsevier, Aug. 2007, 18(4):295-304.

Smith et al., "Coronaviruses lacking exoribonuclease activity are susceptible to lethal mutagenesis: evidence for proofreading and potential therapeutics," PLoS Pathog, 2013, 9:e1003565, 11 pages.

Smith et al., "The Role of Beta Cell Glucagon-like Peptide-1 Signaling in Glucose Regulation and Response to Diabetes Drugs," Cell Metab, Jun. 2014, 19(6):1050-1057.

Smits et al., "Elastin-Like Polypeptide Based Nanoparticled: Design Rationale Toward Nanomedicine," Macromolecular Bioscience, Macromolecular Journals, Jan. 2015, 15(1):36-51.

Sonawane et al., "Hydrazo linkages in pH responsive drug delivery systems," European Journal Pharmaceutical Sciences, Mar. 2017, 99, 45-65.

Song et al., "Budding-like division of all-aqueous emulsion droplets modulated by networks of protein nanofibrils," Nat Commun, 2018, 9: 2110.

Sorkin et al., "Signal transduction and endocytosis: close encounters of many kinds," Nat Rev Mol Cell Biol, 2002, 3(8):600-614.

Sousa et al., "Production of a polar fish antimicrobial peptide in *Escherichia coli* using an ELP-intein tag," J Biotechnol, Sep. 2016, 234:83-89.

Srinivas et al., "Aptamer-functionalized microgel particles for protein detection," Anal Chem, 2011, 83: 9138-9145.

Sriraman et al., "Barriers to drug delivery in solid tumors, " Tissue Barriers, Jul. 2014, 2(3): 2-10.

(56) References Cited

OTHER PUBLICATIONS

Stanislaus et al., "A Novel Fc-FGF21 With Improved Resistance to Proteolysis, Increased Affinity Toward B-Klotho, and Enhanced Efficacy in Mice and Cynomolgus Monkeys," Endocrinology, May 2017, 158(5):1314-1327.
Stefl et al., "RNA sequence-and shape-dependent recognition by proteins in the ribonucleoprotein particle" EMBO reports (2005) 6(1):33-38.
Steichen et al., "A Review of Current Nanoparticle and Targeting Moieties for the Delivery of Cancer Therapeutics," Eur J Pharm Sci, Elsevier, Feb. 2013, 48(3):416-27.
Stock et al., "Penile erectile function after permanent raioactive seed implantation for treatment of prostate cancer," The Journal of urology, 2001, 165, 436-439.
Stork et al., "A novel tri-functional antibody fusion protein with improved pharmacokinetic properties generated by fusing a bispecific single-chain diabody with an albumin-binding domain from streptococcal protein G," Protein Engineering Design and Selection, Nov. 2007, 20(11): p. 569-576.
Strohmaier et al., "Comparison of $^{60}$Co and $^{192}$Ir sources in HDR brachytherapy," J Contemp Brachyther, Dec. 2011, 3(4): 199-208.
Strong et al., "The Current State of Fat Grafting: A Review of Harvesting, Processing, and Injection Techniques," Plast Reconstr Surg, 2015, 136: 897-912.
Strulson et al., "RNA catalysis through compartmentalization," Nat Chem, Nature Publishing Group, Nov. 2012, 4(11):941-946.
Stutz et al., "Seed loss through the urinary tract after prostate brachytherapy: examining the role of cystoscopy and urine straining post implant," Medical physics, 2003, 30, 2695-2698.
Sugyo et al., "Evaluation of efficacy of radioimmunotherapy with 90Y-labeled fully human anti-transferring receptor monoclonal antibody in pancreatic cancer mouse models," PLoS One, Apr. 2015, 10, 1-17.
Suk et al., "PEGylation as a Strategy for Improving Nanoparticle-Based Drug and Gene Delivery ," Adv Drug Deliv Rev, Apr. 2016, 99(Pt A):28-51.
Sumerlin, "Proteins as Initiators of Controlled Radical Polymerization: Grafting-from via ATRP and Raft," ACS Macro Lett. Jan. 2012, 1(1): 141-145.
Sun et al., "Autofluorescence Imaging of Living Pancreatic Islets Reveals Fibroblast Growth Factor-21 (FGF21)-Induced Metabolism," Biophys J, Dec. 2012, 103(11):2379-2388.
Sun et al., "Contributions of the extracellular and cytoplasmic domains of platelet-endothelial cell adhesion molecule-1 (PECAM-1/CD31) in regulating cell-cell localization," J. Cell Sci., 2000, 113, 1459-1469.
Sun et al., "Efficacy and safety of the hypoxia-activated prodrug TH-302 in combination with gemcitabine and nab-paclitaxel in human tumor xenograft models of pancreatic cancer," Cancer Biology & Therapy, Feb. 2015, 16(3): 438-449.
Sun et al., "EUS-guided interstitial brachytherapy of the pancreas: a feasibility study," Gastrointestinal Endoscopy, 2005, 62, 775-779.
Sun et al., "On the Thermally Reversible Dynamic Hydration Behavior of Oligo(ethylene glycol) Methacrylate-Based Polymers in Water," Macromolecules, Jan. 2013, 46(1): 236-246.
Sunamura et al., "Gene Therapy for Pancreatic Cancer Targeting the Genomic Alterations of Tumor Suppressor Genes using Replication-selective Oncolytic Adenovirus," Human Cell, 2002, 15, 138-150.
Sundy et al., "Efficacy and tolerability of pegloticase for the treatment of chronic gout in patients refractory to conventional treatment: two randomized controlled trials," Jama, 2011, 306(7): 711-720.
Sundy et al., "Pharmacokinetics and pharmacodynamics of intravenous PEGylated recombinant mammalian urate oxidase in patients with refractory gout, " Arthritis Rheum, 2007, 56(3): 1021-1028.
Surwit et al., Diet-induced type II diabetes in C57BL/6J mice, Diabetes 37, 1988, 1163-1167.
Sussman et al., "Porous implants modulate healing and induce shifts in local macrophage polarization in the foreign body reaction, " Ann Biomed Eng, Jul. 2014, 42(7): 1508-1516.
Swee et al., "Sortase-mediated modification of aDEC205 affords optimization of antigen presentation and immunization against a set of viral epitopes," Proc Natl Acad Sci USA, Jan. 2013, 110(4):1428-1433.
Swers et al., Multivalent Scaffold Proteins as Superagonists of TRAIL Receptor 2-Induced Apoptosis, Mol Cancer Ther, Jul. 2013, 12(7): 1235-1244.
Swider et al., "Customizing Poly(lactic-Co-Glycolic Acid) Particles for Biomedical Applications," Acta Biomater, Jun. 2018, 73:38-51.
Takalkar et al., "Radium-223 dichloride bone-targeted alpha particle therapy for hormone-refractory breast cancer metastatic to bone," Exp Hematol Oncol, Sep. 2014, 8, Article No. 23.
Talelli et al., "Core-Crosslinked Polymeric Micelles: Principles, Preparation, Biomedical Applications and Clinical Translation," Nano Today, Feb. 2015, 10(1):93-117.
Tallarida, "Quantitative methods for assessing drug synergism," Genes & Cancer, Nov. 2011, 2(11): 1003-1008.
Talukdar et al., "A Long-Acting FGF21 Molecule, PF-05231023, Decreases Body Weight and Improves Lipid Profile in Non-human Primates and Type 2 Diabetic Subjects," Cell Metab, Mar. 2016, 23(3):427-440.
Tamburro et al., "Dissection of human tropoelastin: exon-by-exon chemical synthesis and related conformational studies," Biochemistry, 2003, 42, 13347-13362.
Tamburro et al., "Fractal aspects of elastin supramolecular organization, " J Biomol Struct Dyn, 1995, 12: 1161-1172.
Tamburro et al., "Localizing alpha-helices in human tropoelastin: assembly of the elastin "puzzle"," Biochemistry, Aug. 2006, 45(31): 9518-9530.
Tan et al., "Characterization of a new primary human pancreatic tumor line," Cancer investigation, 1986, 4, 15-23.
Tang et al., "Combinatorial codon scrambling enables scalable gene synthesis and amplification of repetitive proteins, " Nature Mater., Apr. 2016, 15(4): 419-424.
Tang et al., "Enzymatic Polymerization of High Molecular Weight DNA Amphiphiles That Self-Assemble into Star-Like Micelles," Advanced Materials, Feb. 2014, 26(19): 3050-3054.
Tang et al., "High-Molecular-Weight Polynucleotides by Transferase-Catalyzed Living Chain-Growth Polycondensation," Angew. Chem., Jun. 2017, 56(24): 6778-6782.
Tang et al., "Identification of PECAM-1 in solid tumor cells and its potential involvement in tumor cell adhesion to endothelium," J. Biol. Chem., 1993, 268, 22883-22894.
Tang et al., "Laboratory Diagnosis of COVID-19: Current Issues and Challenges," J Clin Microbiol, 2020, 58: e00512-20, 9 pages.
Tantakitti et al., "Energy landscapes and functions of supramolecular systems," Nat. Mater., Apr. 2016, 15(4): 469-476.
Tedja et al., "Effect of TiO2 nanoparticle surface functionalization on protein adsorption, cellular uptake and cytotoxicity: the attachment of PEG comb polymers using catalytic chain transfer and thiol-ene chemistry," Polymer Chemistry, Oct. 2012, 3 (10), 2743-2751.
Teicher, "In vivo/ex vivo and in situ assays used in cancer research: a brief review," Toxicol. Pathol., Jan. 2009, 37 (1), 114-122.
Thakor et al., "Clinically Approved Nanoparticle Imaging Agents," J Nucl Med, Oct. 2016, 57(12):1833-1837.
Theillet et al., "The alphabet of intrinsic disorder: I. Act like a Pro: On the abundance and roles of proline residues in intrinsically disordered proteins," Intrinsically Disord Proteins, Taylor & Francis, Apr. 2013, 1(1):e24360.
Therasse et al., "New guidelines to evaluate the response to treatment in solid tumors, " J Natl Cancer Inst, 2000, 92, 205-216.
Thorens et al., "Cloning and functional expression of the human islet GLP-1 receptor: demonstration that Exendin-4 Is an agonist and Exendin-(9-39) an antagonist of the receptor," Diabetes 42, 1993, 1678-1682.
Tomiyama et al., "Relevant use of Klotho in FGF19 subfamily signaling system in vivo," Proc Natl Acad Sci USA, Jan. 2010, 107(4):1666-71.
Tompa et al., "Fuzzy complexes: polymorphism and structural disorder in protein-protein interactions," Trends Biochem Sci, Jan. 2008, 33(1): 2-8.

(56) References Cited

OTHER PUBLICATIONS

Tong et al., "Protein Modification with Amphiphilic Block Copoly(2-oxazoline)s as a New Platform for Enhanced Cellular Delivery," Mol. Pharm., Aug. 2010, vol. 7, No. 4, pp. 984-992.
Ton-That et al., "Assembly of pili on the surface of Corynebacterium diptheriae," 2003, 50(4):1429-1438.
Ton-That et al., "Purification and characterization of sortase, the transpeptide that cleaves surface proteins of *Staphylococcus aureus* and the LPXTG motif," Proc Natl Acad Sci USA, 1999, 96(22):12424-12429.
Torchilin, "Recent advances with liposomes as pharmaceutical carriers," Nature Rev. Drug Discov. 2005, 4(2):145-160.
Toshima et al., "Three-dimensional architecture of elastin and collagen fiber networks in the human and rat lung," Arch Histol Cytol, 2004, 67: 31-40.
Towler et al., "Purification and Characterization of Yeast Myristoyl-Coa—Protein N-Myristoyltransferase," P Natl Acad Sci USA, 1987, 84(9):2708-12.
Trabbic-Carlson et al., "Effect of protein fusion on the transition temperature of an environmentally responsive elastin-like polypeptide: a role for surface hydrophobicity?," Protein Engineering Design and Selection, 2004, 17(1): 57-66.
Trabbic-Carlson et al., "Expression and purification of recombinant proteins from *Escherichia coli*: Comparison of an elastin-like polypeptide fusion with an oligohistidine fusion" Protein Science, 2004, 13: 3274-3284.
Trakul et al., "Stereotactic body radiotherapy in the treatment of pancreatic cancer," Semin Radiat Oncol, Apr. 2014, 24(2): 140-147.
Trieu et al., "P0157 Preclinical evaluation of NBN-paclitaxel in pancreatic cancer xenograft models," Eur J Cancer, May 2014, 50(4): e53.
Triola et al., "Chemical biology of lipidated proteins," ACS Chemical Biology, Jan. 2012, 7(1): 87-99.
Troyanskaya et al., "Nonparametric methods for identifying differentially expressed genes in microarray data," Bioinformatics, 2002, 18(11):1454-61.
Truong et al., "Polymeric filomicelles and nanoworms: two decades of synthesis and application," Polymer Chemistry, Jun. 2016, 7(26):4295-4312.
Truong et al., "The Importance of Nanoparticle Shape in Cancer Drug Delivery," Expert Opin Drug Deliv, Jan. 2015, 12(1):129-42.
Truong, et al., "The effect of hydration on molecular chain mobility and the viscoelastic behavior of resilin-mimetic protein-based hydrogels," Biomaterials, Elsevier, Nov. 2011, 32(33):8462-73.
Tsarevsky et al., "Deactivation efficiency and degree of control over polymerization in ATRP in protic solvents," Macromolecules 37, 2004, 9768-9778.
Tschöp et al., "Unimolecular Polypharmacy for Treatment of Diabetes and Obesity," Cell Metab, Jul. 2016, 24(1):51-62.
Tsuda et al., "Monodisperse cell-encapsulating peptide microgel beads for 3D cell culture," Langmuir, 2010, 26: 2645-2649.
Tsume et al., "The development of orally administrable gemcitabine prodrugs with D-enantiomer amino acids: Enhanced membrane permeability and enzymatic stability," Eur. J. Pharm. Biopharm., Apr. 2014, 86(3):514-523.
Tu et al., "Stages in tropoelastin coalescence during synthetic elastin hydrogel formation," Micron, Apr. 2010, 41(3): 268-272.
Tuerk et al., "Systematic evolution of ligands by exponential enrichment: RNA ligands to bacteriophage T4 DNA polymerase," Science, 1990, 249(4968): 505-510.
Turner et al., "Challenges and Opportunities for the Subcutaneous Delivery of Therapeutic Proteins," Journal of Pharmaceutical Sciences, 2018, 107(5): 1247-1260.
Turunen et al., "Paclitaxel Succinate Analogs: Anionic Introduction as a Strategy to Impart Blood Brain Barrier Permeability," Bioorg Med Chem Lett, Nov. 2008, 18(22):5971-5974.
Tward et al., "Survival of men with clinically localized prostate cancer treated with prostatectomy, brachytherapy, or no definitive treatment: impact of age at diagnosis," Cancer, Oct. 2006, 107(10): 2392-2400.

U.S. FDA—Classify your medical devices. Updated as of: Feb. 7, 2020. Available at: <https://www.fda.gov/medical-devices/overview-device-regulation/classify-your-medical-device>.
U.S. FDA—In Vitro Diagnostics. Updated as of: Oct. 25, 2019. Available at: <https://www.fda.gov/medical-devices/products-and-medical-procedures/vitro-diagnostics>.
Uchida et al., "Potential of adenovirus-mediated REIC/Dkk-3 gene therapy for use in the treatment of pancreatic cancer," Journal of Gastroenterology and Hepatology, Apr. 2014, 29(5): 973-983.
UniProtKB - P15214 (GST_PROMI) acessed online at <https://www.uniprot.org/uniprot/P152146/> on Jun. 8, 2021, 7 pages.
Urry et al., "Calculation of distorted circular dichroism curves for poly-L-glutamic acid suspensions," Arch Biochem Biophys, 1970, 137, 214-221.
Urry et al., "Coacervation of solubilized elastin effects a notable conformational change," Nature, 1969, 222, 795-796.
Urry et al., "Differential scatter of left and right circularly polarized light by optically active particulate systems," Proc Natl Acad Sci U S A, 1970, 65, 845-852.
Urry et al., "Distortions in circular dichroism patterns of particulate (or membranous) systems," Arch Biochem Biophys, 1968, 128, 802-807.
Urry et al., "Elastic protein-based polymers in soft tissue augmentation and generation," J. Biomater. Sci. Polym. Ed., 1998, 9, 1015-1048.
Urry et al., "Hydrophobicity Scale for Proteins Based on InverseTemperature Transitions," Biopolymers, 1992, 32:1243-1250.
Urry et al., "Physical chemistry of biological free energy transduction as demonstrated by elastic protein-based polymers," J. of Phys. Chem. B., 1997, 101, 11007-11028.
Urry et al., "Temperature dependence of length of elastin and its polypentapeptide," Biochem Biophys Res Commun, 1986, 141, 749-755.
Urry et al., "Temperature of polypeptide inverse temperature transition depends on mean residue hydrophobicity," J. Am. Chem. Soc., 1991, 113(11):4346-4348.
Urry, "Free energy transduction in polypeptides and proteins based on inverse temperature transitions," Prog Biophys Mol Biol, Jan. 1992, 57(1):23-57.
Urry, "Protein elasticity based on conformations of sequential polypeptides: The biological elastic fiber," J Protein Chemistry, 1984, 3, 403-436.
Utada et al., "Monodisperse double emulsions generated from a microcapillary device," Science, 2005, 308: 537-541.
Uversky et al., "Intrinsically disordered proteins as crucial constituents of cellular aqueous two phase systems and coacervates," FEBS Lett, Jan. 2015, 589(1):15-22.
Uversky et al., "Understanding protein non-folding," Biochim Biophys Acta, Elsevier, Jun. 2010, 1804(6):1231-1264.
Uversky, "Protein intrinsic disorder-based liquid-liquid phase transitions in biological systems: Complex coacervates and membraneless organelles," Adv Colloid Interface Sci, 2017, 239: 97-114.
Valkenburg et al., "Targeting the tumour stroma to improve cancer therapy," Nature Reviews Clinical Oncology, Jun. 2018, 15, 366-381.
Van der Lee et al., "Classification of intrinsically disordered regions and proteins," Chem Rev, Jul. 2014, 114(13): 6589-6631.
Van Roey et al., "Short linear motifs: ubiquitous and functionally diverse protein interaction modules directing cell regulation," Chem Rev, Jully 2014, 114(13): 6733-6778.
Van Roy, "Beyond E-cadherin: roles of other cadherin superfamily members in cancer," Nat Rev Cancer, Feb. 2014, 14(2): 121-134.
Vaninov, "In the eye of the COVID-19 cytokine storm," Nat Rev Immunol, 2020, 20: 277, 1 page.
Vasey et al., "Phase I clinical and Pharmacokinetic study of PK1 (N-(2- Hydroxypropyl)methacrylamide Copolymer Doxorubicin): First member of a New Class of Chemotherapeutic Agents-Drugs-Polymer Conjugates" Clinical Cancer Research, 1999, 5:83-94.
Vashist et al., "Emerging Technologies for Next-Generation Point-of-Care Testing," Trends Biotechnol, 2015, 33(11): 692-705.

(56) References Cited

OTHER PUBLICATIONS

Vazquez-Lombardi et al., "Challenges and Opportunities for Non-Antibody Scaffold Drugs," Drug Discov Today, Oct. 2015, 20(10):1271-83.
Vega et al., "Targeting Doxorubicin to Epidermal Growth Factor Receptors by Site-Specific Conjugation of C225 to Poly(L-Glutamic Acid) through a Polyethylene Glycol Spacer," Pharmaceutical Research, 2003, 20(5):826-832.
Venkataraman et al., "The Effects of Polymeric Nanostructure Shape on Drug Delivery," Adv Drug Deliv Rev, Elsevier, Nov. 2011, 63(14-15):1228-46.
Verhoef et al., "Potential induction of anti-PEG antibodies and complement activation toward PEGylated therapeutics," Drug Discov Today, 2014, 19(12): 1945-1952.
Verma et al., "Effect of surface properties on nanoparticle-cell interactions," Small, Wiley, Jan. 2010, 6(1):12-21.
Veronese et al., "PEGylation, successful approach to drug delivery," Drug Discovery Today, 2005, 10(21):1451-1458.
Veronese, "Peptide and protein PEGylation: a review of problems and solutions," Biomaterials 22, 2001, 405-417.
Vicini et al., "An interinstitutional and interspecialty comparison of treatment outcome data for patients with prostate carcinoma based on predefined prognostic categories and minimum follow-up," Cancer, 2002, 95, 2126-2135.
Viegas et al., "Polyoxazoline: Chemistry, properties and applications," Bioconjugate Chem., May 2011, 22(5): 976-986.
Vlieghe et al., "Synthetic therapeutic peptides: science and market," Drug Discovery Today, Jan. 2010, 15(1-2): 40-56.
Voelker et al., "Alteration of the specificity and regulation of fatty acid synthesis of Escherichia coli by expression of a plant medium-chain acyl-acyl carrier protein thioesterase," J Bacteriol., 1994, 176(23):7320-7.
Volkova et al., "Anthracycline Cardiotoxicity: Prevalence, Pathogenesis and Treatment," Curr. Cardiol. Rev., Nov. 2011, vol. 7, No. 4, pp. 214-220.
Volodkin et al., "One-Step Formulation of Protein Microparticles with Tailored Properties: Hard Templating at Soft Conditions," Advanced Functional Materials, 2012, 22: 1914-1922.
Von Roemeling et al., "Breaking Down the Barriers to Precision Cancer Nanomedicine," Trends Biotechnol, Feb. 2017, 35(2):159-171.
Vonarbourg et al., "Evaluation of pegylated lipid nanocapsules versus complement system activation and macrophage uptake," J Biomed Mater Res A, Wiley, Sep. 2006, 78(3):620-8.
Vrhovski et al., "Biochemistry of tropoelastin," Eur J Biochem, 1998, 258, 1-18.
Vrhovski et al., "Coacervation Characteristics of Recombinant Human Tropoelastin," European Journal of Biochemistry, 1997, 250(1):92-98.
Vrignaud et al., "Strategies for the nanoencapsulation of hydrophilic molecules in polymer-based nanoparticles," Biomaterials, Nov. 2011, 32(33):8593-8604.
Vugmeyster et al., "Pharmacokinetics and toxicology of therapeutic proteins: Advances and challenges," World J Biol Chem, 2012, 3(4): 73-92.
Walczak, "Death Receptor-Ligand Systems in Cancer, Cell Death, and Inflammation," Cold Spring Harb. Perspect. Biol., May 2013, 5(5): a008698.
Wali et al., "Measuring Death of Pancreatic Beta Cells in Response to Stress and Cytotoxic T Cells," Methods in Molecular Biology, Mar. 2015, 1292:165-176.
Walsh et al., "Post-translational modifications in the context of therapeutic proteins," Nat. Biotechnol., Oct. 2006, 24(10): 1241-1252.
Walsh et al., "Posttranslationale Proteinmodifikation: die Chemie der Proteomdiversifizierung," Angew Chem, 2005, 117, 7508-7539.
Walsh et al., "Protein posttranslational modifications: The chemistry of proteome diversifications," Angew. Chem. Int. Ed., 2005, 44, 7342-7372.
Wang et al., "A Molecular Grammar Governing the Driving Forces for Phase Separation of Prion-like RNA Binding Proteins," Cell, Jul. 2018, 174(3): 688-699.e616.
Wang et al., "Enhanced Tumor Delivery of Gemcitabine via PEG-DSPE/TPGS Mixed Micelles," Mol. Pharm., Apr. 2014, 11(4): 1140-1150.
Wang et al., "Extending Half Life of H-Ferritin Nanoparticle by Fusing Albumin Binding Domain for Doxorubicin Encapsulation," Biomacromolecules, Mar. 2018, 19(3):773-781.
Wang et al., "Functional polymeric microparticles engineered from controllable microfluidic emulsions," Acc Chem Res, 2014, 47: 373-384.
Wang et al., "More effective nanomedicines through particle design," Small, Wiley, Jul. 2011, 7(14):1919-31.
Wang et al., "Nanoparticle delivery of cancer drugs," Annu Rev Med, Annual Reviews, Feb. 2012, 63:185-98.
Wang et al., "Pigs Can Be Used as a Large Animal Model for Autologous Fat Grafting," Ophthalmic Plast Reconstr Surg, 2016, 32: 73-74.
Wang et al., "Quantitative Mapping of the Spatial Distribution of Nanoparticles in Endo-Lysosomes by Local pH," Nano Lett., Feb. 2017, 17(2): 1226-1232.
Wang et al., "Size and dynamics of caveolae studied using nanoparticles in living endothelial cells," ACS nano, Dec. 2009, 3(12): p. 4110-4116.
Wang et al., "Stimuli-responsive Dendrimers in Drug Delivery," Biomater Sci, Mar. 2016, 4(3):375-90.
Wang et al., "The Weak Link: Optimization of the Ligand-Nanoparticle Interface To Enhance Cancer Cell Targeting by Polymer Micelles," Nano Lett Oct. 2017, 17(10):5995-6005.
Waterboer et al., "Suppression of non-specific binding in serological Luminex assays," J Immunol Methods, 2006, 309: 200-204.
Waterman et al., "Edema associated with I-125 or Pd-103 prostate brachytherapy and its impact on post-implant dosimetry: an analysis based on serial CT acquisition," International journal of radiation oncology, biology, physics, 1998, 41, 1069-1077.
Wechsel et al., "Renal Cell Carcinoma: Immunohistological Investigation of Expression of the Integrin avß3," Anticancer research, 1999, 19(2C):1529-1532.
Wei et al., "Anticancer drug nanomicelles formed by self-assembling amphiphilic dendrimer to combat cancer drug resistance," Proceedings of the National Academy of Sciences of the United States of America, Mar. 2015, 112(10): 2978-2983.
Wei et al., "Fibroblast growth factor 21 promotes bone loss by potentiating the effects of peroxisome proliferator-activated receptor γ," Proc Natl Acad Sci USA, Feb. 2012, 109(8):3143-3148.
Weinhandl et al., "Relative safety of peginesatide and epoetin alfa," Pharmacoepidemiology and Drug Safety, 2014, 23(10): 1003-1011.
Weis et al., "αV Integrins in Angiogenesis and Cancer," Cold Spring Harb Perspect Med, Cold Spring Harbor Laboratory Press, Sep. 2011, 1(1):a006478.
Weitzhandler et al., "Micellar Self-Assembly of Recombinant Resilin-/Elastin-Like Block Copolypeptides," Biomacromolecules, Aug. 2017, 18(8):2419-2426.
Wendt et al., "DNA-mediated Folding and Assembly of MyoD-E47 Heterodimers," Journal of Biol. Chem., 1998, 273(10):5735-5743.
Wente et al., "Fibroblast Growth Factor-21 Improves Pancreatic ß-Cell Function and Survival by Activation of Extracellular Signal-Regulated Kinase 1/2 and Akt Signaling Pathways," Diabetes, Sep. 2006, 55(9):2470-2478.
Werle et al., "Strategies to improve plasma half life time of peptide and protein drugs, " Amino Acids 30, Jun. 2006, 30(4):351-367.
Werstuck et al., "Controlling gene expression in living cells through small molecule-RNA interactions," Science, 1998, 282(5387): 296-298.
Whitman et al., "Evaluation of SARS-CoV-2 serology assays reveals a range of test performance," Nat Biotechnol, 2020, 38: 1174-1183.
Wienkers et al., "Predicting in vivo drug interactions from in vitro drug discovery data," Nat. Rev. Drug. Discov. 2005, 4(10):825-833.
Wiersinga et al., "Pathophysiology, Transmission, Diagnosis, and Treatment of Coronavirus Disease 2019 (COVID-19): A Review," JAMA, 2020, 324(8): 782-793.

(56) References Cited

OTHER PUBLICATIONS

Wilkins et al., "Hydrodynamic Radii of Native and Denatured Proteins Measured by Pulse Field Gradient NMR Techniques," Biochemistry, 1999, 38(50):16424-16431.
Williams et al., "Targeted radionuclide therapy," Medical Physics, Jul. 2008, 35(7): 3062-3068.
Williamson et al., "Efficient N-terminal labeling of proteins by use of sortase," Angew Chem Int ed Engl, Sep. 2012, 51(37):9377-9380.
Wimley et al., "Experimentally determined hydrophobicity scale for proteins at membrane interfaces," Nature Structural & Molecular Biology, 1996, 3(10):842-848.
Winter et al., "The important role of serology for COVID-19 control," Lancet Infect Dis, 2020, 20:758-759.
Winzell et al., "The high-fat diet-fed mouse: a model for studying mechanisms and treatment of impaired glucose tolerance and type 2 diabetes," Diabetes 53, 2004, S215-S219.
Wold, "In vivo chemical modification of proteins," Annu. Rev. Med., 1981, 50, 783-814.
Wölfel et al., "Virological assessment of hospitalized patients with COVID-2019," Nature, 2020, 581: 465-469.
Wood et al., "Experiences Using Chloramine-T and 1,3,4,6-Tetrachloro-3-Alpha,6-Alpha- Diphenylglycoluril (Iodogen) for Radioiodination of Materials for Radioimmunoassay," J Clin Chem Clin Bio, 1981, 19, 1051-1056.
Woodruff et al., "Modulation of the Coagulation Cascade Using Aptamers," Arterioscler Thromb Vasc Biol, 2015, 35(10): 2083-2091.
Wright et al., "Intrinsically disordered proteins in cellular signalling and regulation, " Nat Rev Mol Cell Biol, Jan. 2015, 16(1):18-29.
Wright et al., "Self-assembly of block copolymers derived from elastin-mimetic polypeptide sequences," Advanced Drug Delivery Reviews, 2002, 54, 1057-1073.
Wright et al., "Thermoplastic elastomer hydrogels via self-assembly of an elastin-mimetic triblock polypeptide," Advanced Functional Materials, 2002, 12, 149-154.
Wu et al., "An injectable adipose matrix for soft-tissue reconstruction," Plast Reconstr Surg, 2012, 129: 1247-1257.
Wu et al., "Site-specific chemical modification of recombinant proteins produced in mammalian cells by using the genetically encoded aldehyde tag," Proc Natl Acad Sci USA, Mar. 2009, 106(9):3000-3005.
Wu et al., "Sortase A-Catalyzed Transpeptidation of Glycosylphosphatidylinositol Derivatives for Chemoenzymatic Synthesis of GPI-Anchored Proteins," J. Am. Chem. Soc., Feb. 2010, 132(5): 1567-1571.
Wust et al., "Hyperthermia in combined treatment of cancer," The Lancet Oncology, 2002, 3, 487-497.
Xavier et al., "HPLC Method for the Dosage of Paclitaxel in Copaiba Oil: Development, Validation, Application to the Determination of the Solubility and Partition Coefficients," Chromatographia, Apr. 2016, 79(7-8): 405-412.
Xia et al., "Tunable self-assembly of genetically engineered silk—elastin-like protein polymers," Biomacromolecules, Nov. 2011, 12(11): 3844-3850.
Xie et al., "The Effect of Shape on Cellular Uptake of Gold Nanoparticles in the Forms of Stars, Rods, and Triangles," Sci Rep, Jun. 2017, 7(1):3827.
Xiong et al., "Engineering of amphiphilic block copolymers for polymeric micellar drug and gene delivery," J Control Release, Elsevier, Oct. 2011, 155(2):248-61.
Xu et al., "A quality by design (QbD) case study on liposomes containing hydrophilic API: II. Screening of critical variables, and establishment of design space at laboratory scale," Int. J. Pharm., Feb. 2012, 423(2):543-553.
Xu et al., "Downregulation of GLP-1 and GIP Receptor Expression by Hyperglycemia," Diabetes, Jun. 2007, 56(6):1551-58.
Xu et al., "Exendin-4 stimulates both beta-cell replication and neogenesis, resulting in increased beta-cell mass and improved glucose tolerance in diabetic rats," Diabetes 48, 1999, 2270-2276.
Xu et al., "Fibroblast Growth Factor 21 Reverses Hepatic Steatosis, Increases Energy Expenditure, and Improves Insulin Sensitivity in Diet-Induced Obese Mice," Diabetes, Jan. 2009, 58(1):250-259.
Xu et al., "Genetically engineered block copolymers: influence of the length and structure of the coiled-coil blocks on hydrogel self-assembly," Pharm Res, Mar. 2008, 25, 674-682.
Xu et al., "Inorganic nanoparticles as carriers for efficient cellular delivery," Chemical Engineering Science, Elsevier, Feb. 2006, 61(3):1027-1040.
Xu et al., "Role of pancreatic stellate cells in pancreatic cancer metastasis," Am J of Pathology, Nov. 2010, 177(5): 2585-2596.
Xu et al., "Self-assembly behavior of peptide amphiphiles (PAS) with different length of hydrophobic alkyl tails," Colloids Surfaces B Biointerfaces, Nov. 2010, 81(1): 329-335.
Yamamoto et al., "ATRP Synthesis of Thermally Responsive Molecular Brushes from Oligo(ethylene oxide) Methacrylates," Macromolecules, Dec. 2007, 40(26): 9348-9353.
Yamaoka et al., "Distribution and tissue uptake of poly(ethylene glycol) with different molecular weights after intravenous administration to mice," Journal of Pharmaceutical Sciences, 1994, 83(4): 601-606.
Yang et al., "Analysis of Pre-existing IgG and IgM Antibodies against Polyethylene Glycol (PEG) in the General Population," Analytical Chemistry, 2016, 88(23): 11804-11812.
Yang et al., "Anti-PEG immunity: emergence, characteristics, and unaddressed questions," Wiley Interdiscip Rev Nanomed Nanobiotechnol, 2015, 7(5): 655-677.
Yang et al., "Long Term Exendin-4 Treatment Reduces Food Intake and Body Weight and Alters Expression of Brain Homeostatic and Reward Markers," Endocrinology, Sep. 2014, 155(9): 3473-3483.
Yang et al., "Plasma IP-10 and MCP-3 levels are highly associated with disease severity and predict the progression of COVID-19," J Allergy Clin Immunol, 2020, 146: 119-127.
Yang et al., "Poly(carboxybetaine) nanomaterials enable long circulation and prevent polymer-specific antibody production," Nano Today, Feb. 2014, 9(1):10-16.
Yang et al., "Uricases as therapeutic agents to treat refractory gout: Current states and future directions," Drug Dev Res, 2012, 73(2): 66-72.
Yates et al., "Contemporary management of patients with high-risk non-muscle-invasive bladder cancer who fail intravesical BCG therapy," World journal of urology, May 2011, 29(4): 415-422.
Yeh et al., "Micromolding of shape-controlled, harvestable cell-laden hydrogels," Biomaterials, 2006, 27: 5391-5398.
Yeo et al., "Coacervation of tropoelastin," Adv Colloid Interface Sci, Sep. 2011, 167(1-2): 94-103.
Yizhi et al., "A brush-polymer/exendin-4 conjugate reduces blood glucose levels for up to five days and eliminates poly(ethylene glycol) antigenicity," Nature Biomedical Engineering, 2016, 1(1): 0002.
Yokoe et al., "Albumin-conjugated PEG liposome enhances tumor distribution of liposomal doxorubicin in rats," International Journal of Pharmaceutics, May 2008, 353(1-2): 28-34.
Yong et al., "Connecting clusters of COVID-19: an epidemiological and serological investigation," Lancet Infect Dis, 2020, 20: 809-815.
Yoo et al., "A systemic Small RNA Signaling System in Plants" The Plant Cell (2004) vol. 16, pp. 1979-2000.
Yoo et al., "Biodegradable Nanoparticles Containing Doxorubicin-Plga Conjugate for Sustained Release," Pharm. Res., 1999, 16(7):1114-1118.
Youn et al., "Evaluation of therapeutic potentials of site-specific PEGylated glucagon-like peptide-1 isomers as a type 2 anti-diabetic treatment: Insulinotropic activity, glucose-stabilizing capability, and proteolytic stability" Biochem. Pharmacol, 2007, 73: 84-93.
Youn et al., "High-yield production of biologically active mono-PEGylated salmon calcitonin by site-specific PEGylation," J. Control. Release, Feb. 2007, 117(3):371-379.
Yousefpour et al., "Co-opting biology to deliver drugs," Biotechnol Bioeng, Sep. 2014, 111(9): p. 1699-1716.
Yousefpour et al., "Genetically Encoding Albumin Binding into Chemotherapeutic-loaded Polypeptide Nanoparticles Enhances Their Antitumor Efficacy," Nano Lett., Dec. 2018, 18(12): 7784-7793.

(56) References Cited

OTHER PUBLICATIONS

Yu et al., "Effectiveness and security of CT-guided percutaneous implantation of (125)l seeds in pancreatic carcinoma," The British journal of radiology, Jul. 2014, 87(1039): 20130642, 7 pages.
Yusta et al., "GLP-1 receptor activation improves B cell function and survival following induction of endoplasmic reticulum stress," Cell Metab, Nov. 2006, 4(5):391-406.
Zhang et al., "A self-assembly pathway to aligned monodomain gels," Nat. Mater., Jul. 2010, 9(7): 594-601.
Zhang et al., "Anti-PEG antibodies in the clinic: Current issues and beyond PEGylation," J Control Release, 2016, 244(Pt B): 184-193.
Zhang et al., "Impact of Large Aggregated Uricases and PEG Diol on Accelerated Blood Clearance of PEGylated Canine Uricase," Plos One, 2012, 7(6): e39659.
Zhang et al., "In Depth Analysis on the Unusual Multistep Aggregation Process of Oligo(ethylene glycol) Methacrylate-Based Polymers in Water," Macromolecules, Jul. 2014, 47(14): 4728-4737.
Zhang et al., "Nanoparticles in medicine: therapeutic applications and developments," Clin. Pharmacol. Ther., May 2008, 83(5):761-769.
Zhang et al., "Novel agents for pancreatic ductal adenocarcinoma: emerging therapeutics and future directions," Jounral of Hematology & Oncology, Jan. 2018, 11:14, 17 pages.
Zhang et al., "Sensitive and Quantitative Detection of Anti-Poly(ethylene glycol) (PEG) Antibodies by Methoxy-PEG-Coated Surface Plasmon Resonance Sensors," Anal Chem, Aug. 2017, 89(16): 8217-8222.
Zhang et al., "Shape Effects of Nanoparticles Conjugated with Cell-Penetrating Peptides (HIV Tat PTD) on CHO Cell Uptake," Bioconjugate Chem, Sep. 2008, 19(9):1880-1887.
Zhao et al., "A new Bliss Independence model to analyze drug combination data," J Biomol Screen, Jun. 2014, 19(5): 817-821.
Zhao et al., "Antibody responses to SARS-CoV-2 in patients of novel coronavirus disease 2019," Clin Infect Dis, 2020, 22 pages.
Zhao et al., "Cellular uptake, intracellular trafficking, and cytotoxicity of nanomaterials," Small, Wiley, May 2011, 7(10):1322-37.
Zhao et al., "Fluorescence probe techniques used to study micelle formation in water-soluble block copolymers," Langmuir 1990, 6(2):514-516.
Zhao et al., "Tumor avß3 Integrin Is a Therapeutic Target for Breast Cancer Bone Metastases," Cancer Res, AACR Publications, Jun. 2007, 67(12):5821-30.
Zhou et al., "Aptamers as targeted therapeutics: current potential and challenges," Nat Rev Drug Discov, 2017, 16(3): 181-202.
Zimm, "Apparatus and Methods for Measurement and Interpretation of the Angular Variation of Light Scattering; Preliminary Results on Polystyrene Solutions," J. Chem. Phys. 1948, 16, 1099-1116.
Zini et al., "Contemporary management of adrenocortical carcinoma," European urology, Nov. 2011, 60(5): 1055-1065.
Zong et al., "Crystal structures of Staphylococcus aureus sortase A and its substrate complex," J. Biol. Chem. 279, 2004, 31383-31389.
Zununi Vahed et al., "Targeted cancer drug delivery with aptamer-functionalized polymeric nanoparticles," Journal of drug targeting, Mar. 2019, 27(3):292-299.
International Search Report and Written Opinion for Application No. PCT/US2008/084159 dated Feb. 27, 2009 (8 pages).
International Search Report and Written Opinion for Application No. PCT/US2016/024202 dated Aug. 26, 2016 (9 pages).
International Search Report and Written Opinion for Application No. PCT/US2016/045655 dated Dec. 2, 2016 (13 pages).
International Search Report and Written Opinion for Application No. PCT/US2016/068141 dated Jul. 19, 2017 (12 pages).
International Search Report and Written Opinion for Application No. PCT/US2016/068142 dated Jul. 19, 2017 (12 pages).
International Search Report and Written Opinion for Application No. PCT/US2018/032785 dated Sep. 25, 2018 (16 pages).
International Search Report and Written Opinion for Application No. PCT/US2017/035530 dated Aug. 23, 2017 (13 pages).
International Search Report and Written Opinion for Application No. PCT/US2017/052887 dated Jan. 26, 2018 (20 pages).
International Search Report and Written Opinion for Application No. PCT/US2017/051661 dated Jan. 2, 2018 (12 pages).
International Search Report and Written Opinion for Application No. PCT/US2018/013611 dated May 30, 2018 (18 pages).
International Search Report and Written Opinion for Application No. PCT/US2018/040409 dated Nov. 5, 2018 (16 pages).
International Search Report and Written Opinion for Application No. PCT/US2019/015176 dated Jun. 3, 2019 (12 pages).
International Search Report and Written Opinion for Application No. PCT/US2019/023583 dated Jul. 5, 2019 (10 pages).
International Search Report and Written Opinion for Application No. PCT/US2019/030022 dated Jul. 25, 2019 (8 pages).
International Search Report and Written Opinion for Application No. PCT/US2019/044911 dated Dec. 10, 2019 (11 pages).
International Search Report and Written Opinion for Application No. PCT/US2019/050077 dated Jan. 27, 2020 (19 pages).
International Search Report and Written Opinion for Application No. PCT/US2019/061144 dated May 21, 2020 (15 pages).
International Search Report and Written Opinion for Application No. PCT/US2021/020589 dated Jul. 15, 2021 (21 pages).
International Search Report and Written Opinion for Application No. PCT/US2021/017809 dated Jul. 22, 2021 (20 pages).
International Search Report and Written Opinion for Application No. PCT/US2021/020591 dated Oct. 7, 2021 (14 pages).
International Search Report and Written Opinion for Application No. PCT/US2021/046833 dated Nov. 8, 2021 (13 pages).
International Search Report and Written Opinion for Application No. PCT/US2021/035823 dated Dec. 8, 2021 (16 pages).
International Search Report and Written Opinion for Application No. PCT2022/023158 dated Jun. 21, 2022 (7 pages).
International Search Report and Written Opinion for Application No. PCT/US2022/017349 dated Jun. 3, 2022 (20 pages).
United States Patent Office Action for U.S. Appl. No. 13/904,836 dated Mar. 27, 2014 (10 pages).
United States Patent Office Notice of Allowance for U.S. Appl. No. 13/904,836 dated Jul. 30, 2014 (6 pages).
United States Patent Office Action for U.S. Appl. No. 13/942,037 dated Jan. 15, 2016 (19 pages).
United States Patent Office Action for U.S. Appl. No. 13/942,037 dated Jun. 4, 2015 (33 pages).
United States Patent Office Action for U.S. Appl. No. 13/942,037 dated Nov. 28, 2016 (22 pages).
United States Patent Office Action for U.S. Appl. No. 13/942,037 dated Feb. 9, 2018 (29 pages).
United States Patent Office Notice of Allowance for U.S. Appl. No. 13/245,459 dated Feb. 27, 2013 (13 pages).
United States Patent Office Action for U.S. Appl. No. 14/572,391 dated Oct. 26, 2016 (11 pages).
United States Patent Office Notice of Allowance for U.S. Appl. No. 14/572,391 dated Jun. 16, 2017 (10 pages).
United States Patent Office Action for U.S. Appl. No. 15/387,536 dated Sep. 27, 2018 (11 pages).
United States Patent Office Action for U.S. Appl. No. 15/387,540 dated Sep. 27, 2018 (12 pages).
United States Patent Office Action for U.S. Appl. No. 15/561,799 dated Dec. 27, 2018 (8 pages).
United States Patent Office Notice of Allowance for U.S. Appl. No. 15/387,536 dated Mar. 13, 2019 (13 pages).
United States Patent Office Notice of Allowance for U.S. Appl. No. 15/561,799 dated Apr. 2, 2019 (6 pages).
United States Patent Office Notice of Allowance for U.S. Appl. No. 15/387,540 dated Apr. 17, 2019 (9 pages).
United States Patent Office Action for U.S. Appl. No. 16/058,924 dated Nov. 26, 2019 (23 pages).
United States Patent Office Action for U.S. Appl. No. 16/064,424 dated Apr. 22, 2020 (18 pages).
United States Patent Office Action for U.S. Appl. No. 16/064,425 dated Apr. 22, 2020 (18 pages).
United States Patent Office Action for U.S. Appl. No. 16/058,924 dated Jul. 6, 2020 (51 pages).

(56) References Cited

OTHER PUBLICATIONS

United States Patent Office Action for U.S. Appl. No. 15/749,797 dated May 11, 2020 (14 pages).
United States Patent Office Action for U.S. Appl. No. 15/749,797 dated Oct. 20, 2020 (16 pages).
United States Patent Office Action for U.S. Appl. No. 16/335,734 dated Nov. 20, 2020 (15 pages).
United States Patent Office Action for U.S. Appl. No. 16/525,374 dated Dec. 7, 2020 (9 pages).
United States Patent Office Action for U.S. Appl. No. 16/305,696 dated Jan. 28, 2021 (15 pages).
United States Patent Office Notice of Allowance for U.S. Appl. No. 16/332,865 dated Apr. 2, 2021 (10 pages).
United States Patent Office Action for U.S. Appl. No. 16/477,229 dated Apr. 12, 2021 (14 pages).
United States Patent Office Action for U.S. Appl. No. 15/749,797 dated May 12, 2021 (19 pages).
United States Patent Office Notice of Allowance for U.S. Appl. No. 16/332,865 dated May 17, 2021 (5 pages).
United States Patent Office Notice of Allowance for U.S. Appl. No. 16/335,734 dated Jun. 16, 2021 (9 pages).
United States Patent Office Action for U.S. Appl. No. 16/305,696 dated Jun. 22, 2021 (20 pages).
United States Patent Office Action for U.S. Appl. No. 16/614,282 dated Oct. 21, 2021 (14 pages).
United States Patent Office Action for U.S. Appl. No. 15/749,797 dated Nov. 29, 2021 (10 pages).
United States Patent Office Action for U.S. Appl. No. 16/477,229 dated Oct. 26, 2021 (10 pages).
United States Patent Office Action for U.S. Appl. No. 17/265,165 dated Dec. 21, 2021 (11 pages).
United States Patent Office Action for U.S. Appl. No. 16/964,832 dated Jan. 19, 2022 (12 pages).
United States Patent Office Action for U.S. Appl. No. 16/625,899 dated Dec. 15, 2021 (12 pages).
United States Patent Office Action for U.S. Appl. No. 16/927,982 dated Jan. 6, 2022 (6 pages).
United States Patent Office Action for U.S. Appl. No. 16/477,229 dated Mar. 3, 2022 (10 pages).
United States Patent Office Notice of Allowance for U.S. Appl. No. 15/749,797 dated Mar. 16, 2022 (6 pages).
United States Patent Office Action for U.S. Appl. No. 16/614,282 dated Apr. 27, 2022 (15 pages).
United States Patent Office Notice of Allowance for U.S. Appl. No. 16/305,696 dated May 23, 2022 (10 pages).
United States Patent Office Notice of Allowance for U.S. Appl. No. 16/305,696 dated Jun. 10, 2022 (4 pages).
United States Patent Office Notice of Allowance for U.S. Appl. No. 15/749,797 dated Jun. 2, 2022 (6 pages).
United States Patent Office Action for U.S. Appl. No. 16/477,229 dated Jun. 13, 2022 (11 pages).
United States Patent Office Action for U.S. Appl. No. 16/964,832 dated Jul. 14, 2022 (6 pages).
United States Patent Office Notice of Allowance for U.S. Appl. No. 16/927,982 dated Jul. 15, 2022 (8 pages).
United States Patent Office Notice of Allowance for U.S. Appl. No. 16/614,282 dated Aug. 23, 2022 (7 pages).
United States Patent Office Action for U.S. Appl. No. 17/265,165 dated Sep. 2, 2022 (5 pages).
Cereghetti et al., "Reversible, functional amyloids: towards an understanding of their regulation in yeast and humans," Cell Cycle, 2018, 17(13): 1545-1558.
Uversky et al., "Life in Phases: Intra- and Inter- Molecular Phase Transitions in Protein Solutions," Biomolecules, 2019, 9(12): 842.
McPherson, "Product purification by reversible phase transition following *Escherichia coli* expression of genes encoding up to 251 repeats of the elastomeric pentapeptide GVGVP," Protein Expression and Purification, 1996, 7: 51-57.
Cascarina et al., "Generalizable Compositional Features Influencing the Proteostatic Fates of Polar Low-Complexity Domains," International Journal of Molecular Sciences, 2021, 22(16): 8944.
Krainer et al., "Reentrant liquid condensate phase of proteins is stabilized by hydrophobic and non-ionic interactions," Nature Communications, 2021, 12(1): 1085.
United States Patent Office Action for U.S. Appl. No. 17/477,192 dated Jan. 4, 2024 (11 pages).
United States Patent Office Action for U.S. Appl. No. 16/964,832 dated Jan. 19, 2024 (9 pages).
United States Patent Office Action for U.S. Appl. No. 17/051,202 dated Jan. 19, 2024 (5 pages).

| Sample | Z-Ave (r. nm) | PDI |
|---|---|---|
| A10pFU (1) | 71.68 | 0.288 |
| A10pFU (2) | 111.5 | 0.296 |
| A10pFU (3) | 67.18 | 0.289 |

FIG. 16B

| Sample | ZAve (d.nm) | PDI |
|---|---|---|
| A10pFU (1) | 71.68 | 0.288 |
| A10pFU (2) | 111.5 | 0.296 |
| A10pFU (3) | 67.18 | 0.289 |
| A10pFU (2), 1X PBS | 108.8 | 0.267 |
| RefoldedA10pFU (1) | 20.29 | 0.193 |
| RefoldedA10pFU (2) | 20.51 | 0.222 |
| RefoldedA10pFU (3) | 19.91 | 0.212 |

FIG. 19B 1. 100 bp ladder
2. dsDNA +Exonuclease I
3. well 2 sample + Lambda exo
4. well 3 sample + Exonuclease I
5. ssdna control

AMPHIPHILIC POLYNUCLEOTIDES

STATEMENT REGARDING FEDERALLY SPONSORED RESEARCH

This patent application is a divisional of U.S. patent application Ser. No. 16/927,932, filed Jul. 13, 2020, which application claims priority to U.S. Provisional Patent Application No. 62/873,306 filed on Jul. 12, 2019, the entire contents of each of which are hereby incorporated by reference.

STATEMENT REGARDING FEDERALLY SPONSORED RESEARCH

This invention was made with government support under grant numbers DMR-14-11126, DMR-1121107, CBET-1033621 awarded by the National Science Foundation, and grant number 1R01EB026590-02 awarded by the National Institutes of Health. The government has certain rights in the invention.

SEQUENCE LISTING

The sequence listing is filed with the application and is incorporated by reference herein. The sequence listing text file "028193-9330-US04_As_Filed_Sequence_Listing.xml" was created on Oct. 21, 2022, and is 10,459 bytes in size.

BACKGROUND

Amphiphilic molecules can provide useful self-assembled structures, which can be beneficial for drug delivery applications.

SUMMARY

In one aspect, disclosed are compositions that include an assembly of amphiphilic polynucleotides, each amphiphilic polynucleotide being single-stranded and comprising, in a 5' to 3' direction, an aptamer portion, a first nucleotide portion, and a second nucleotide portion.

In another aspect, disclosed are methods of making an amphiphilic polynucleotide. The method includes combining a terminal deoxynucleotidyl transferase (TdT), an aptamer initiator having a secondary structure, and a non-natural cytostatic deoxynucleoside triphosphate (dNTP) monomer in a buffer to provide a first reaction mixture; incubating the first reaction mixture; adding a non-natural hydrophobic dNTP monomer to the first reaction mixture to provide a second reaction mixture; and incubating the second reaction mixture to provide the disclosed amphiphilic polynucleotide.

In another aspect, disclosed are methods of treating a disease or disorder in a subject in need thereof. The method includes administering to the subject a therapeutically effective amount of the disclosed composition.

A10-polyFU-AttodU10 micelle and A10polyFU, 50 U/mL DNase I; (F) A10-polyFU-AttodU10 micelle and A10polyFU, 60 U/mL DNase I. Final concentrations of all samples are 0.8 µM.

Figure 16A:
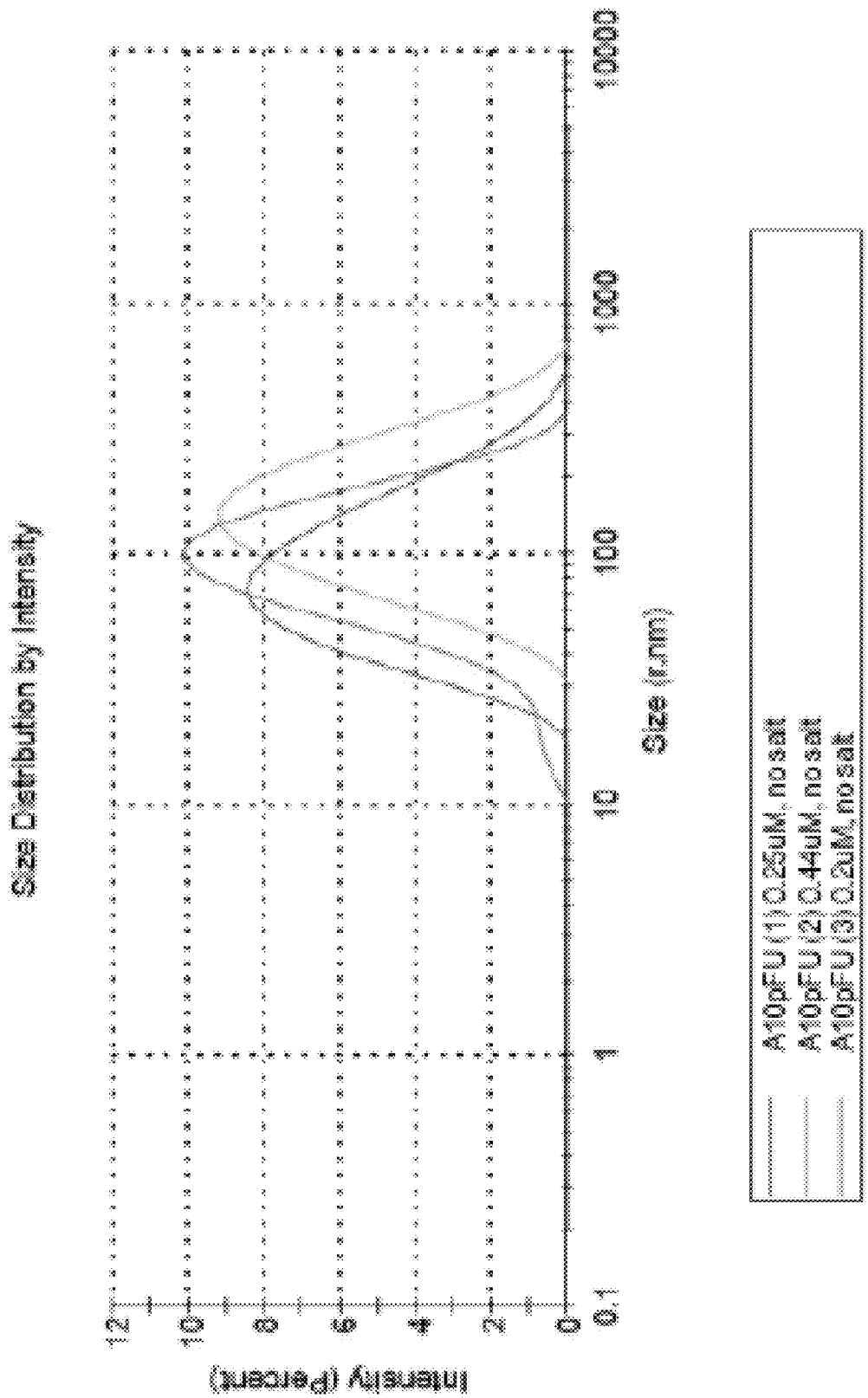

FIGS. 16A-16B are a dynamic light scattering (DLS) measurement showing (A) the size distribution profiles by intensity for three different batches of A10-polyFU in water, and the (B) Z-average radius and PDI of each sample.

Figure 17A:
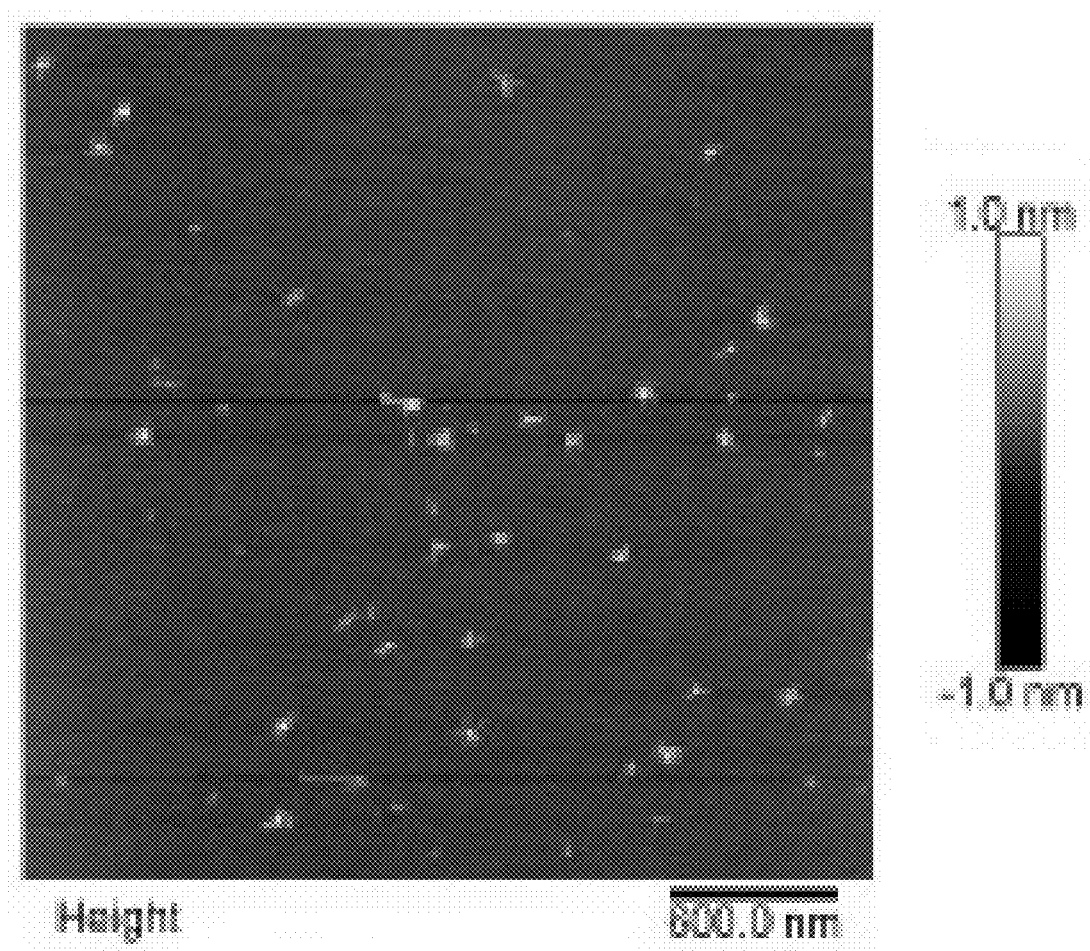
Figure 17B:
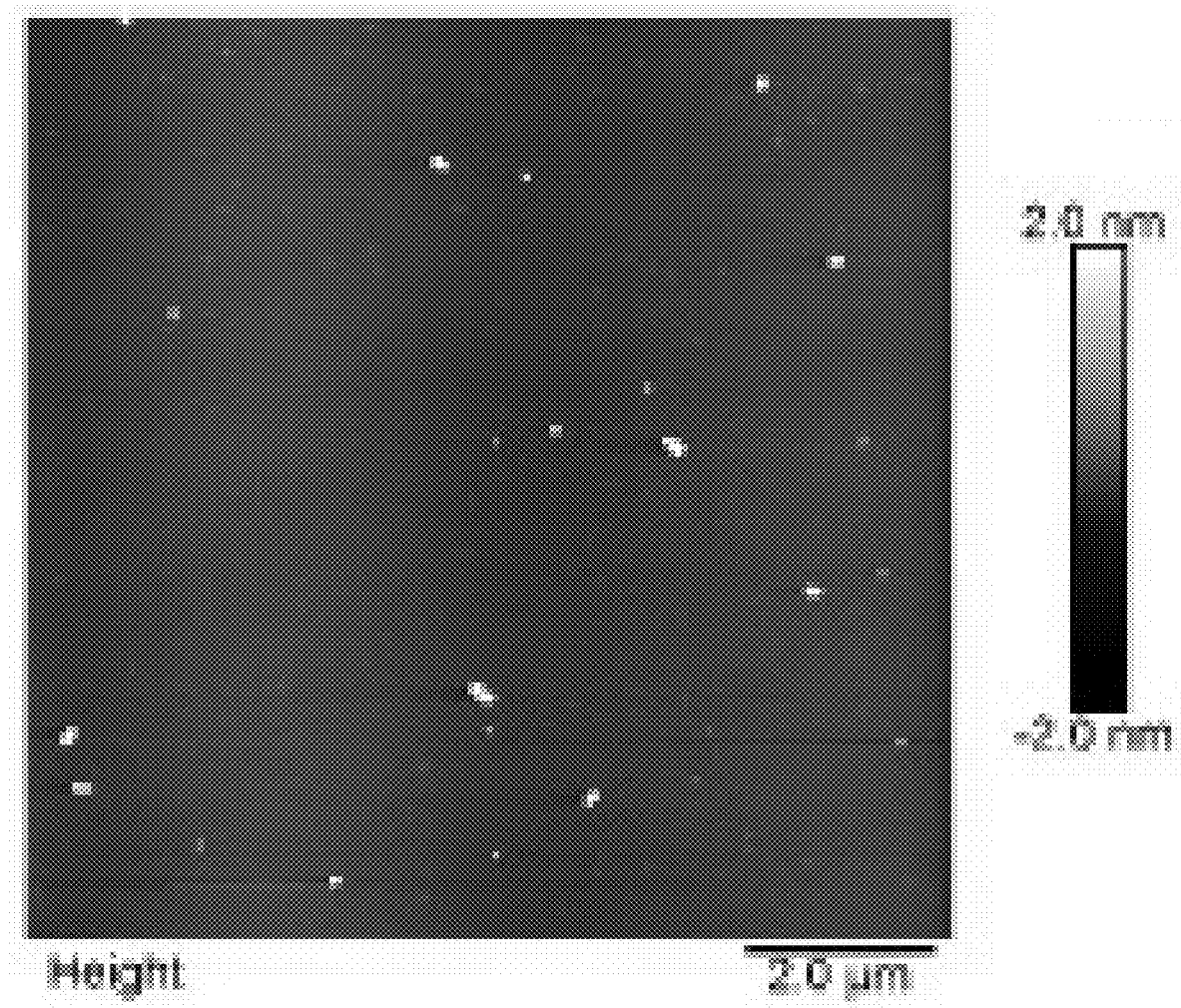

FIGS. 17A-17B are a set of AFM images for two different batches (A & B) of A10-polyFU ssDNA in water.

Figure 18A:
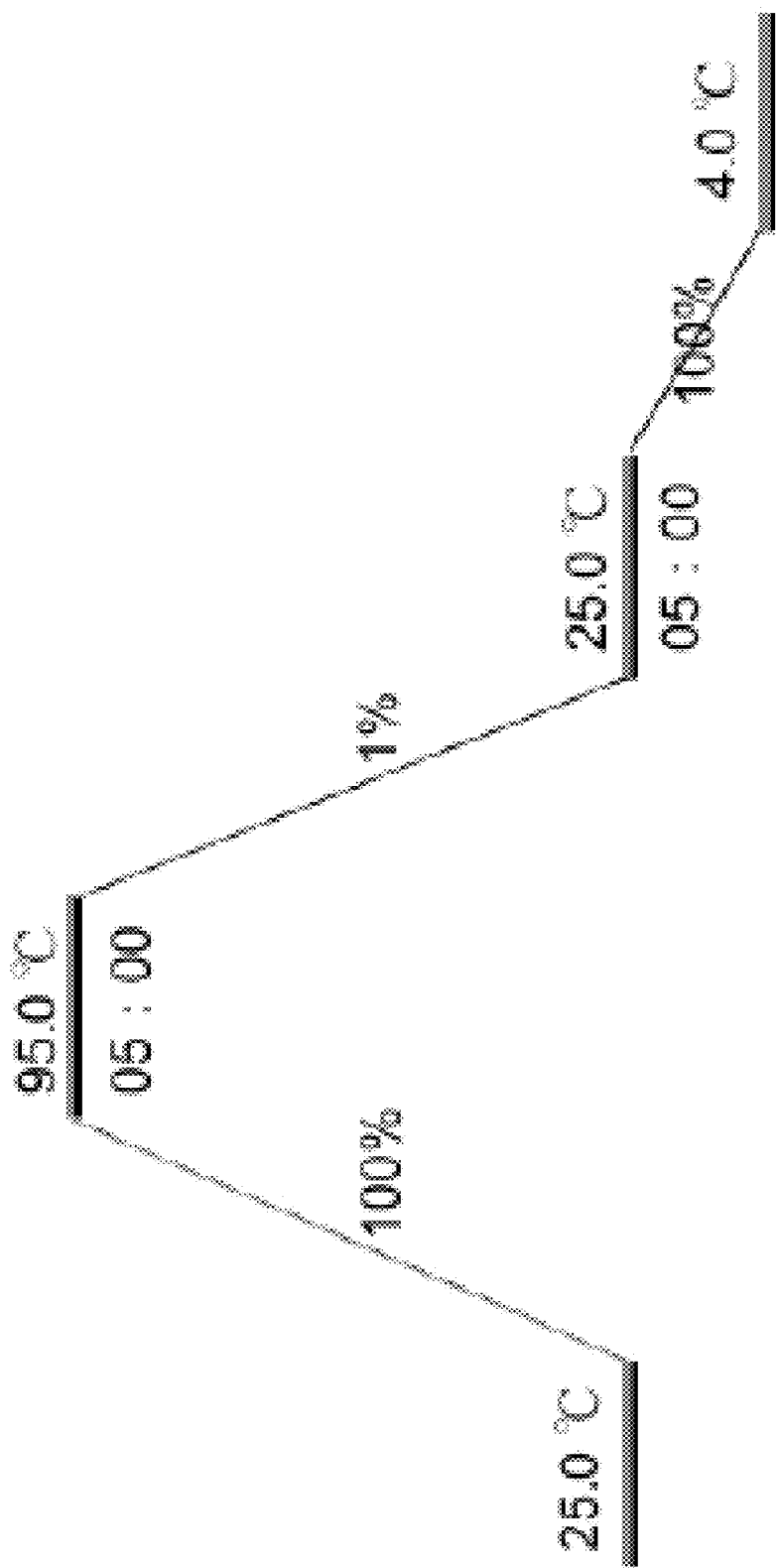
Figure 18B:
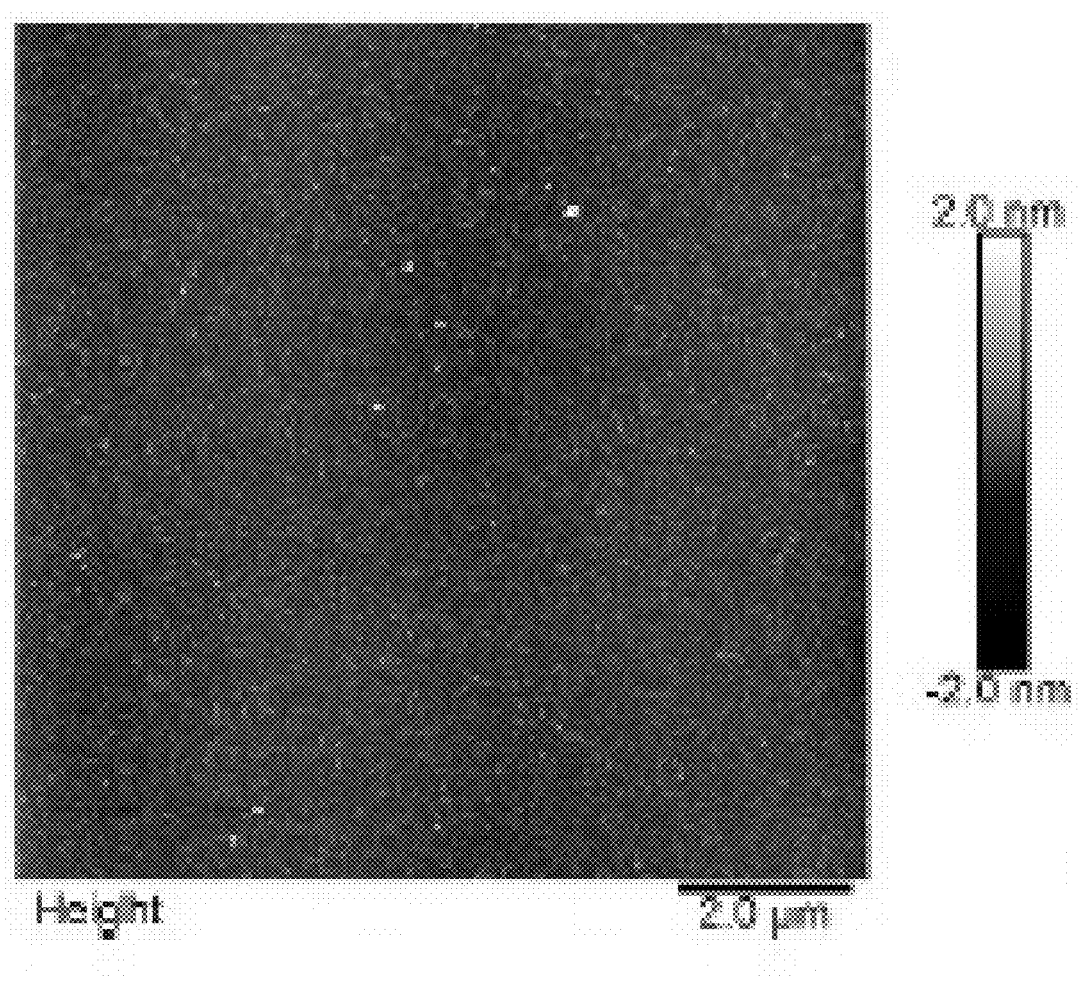

FIGS. 18A-18B are (A) a schematic illustration of the refolding process for aptamers using PCR. 1% and 100% are the rate of temperature changes; and (B) an AFM image for a batch of refolded A10-polyFU ssDNA in water.

Figure 19A:
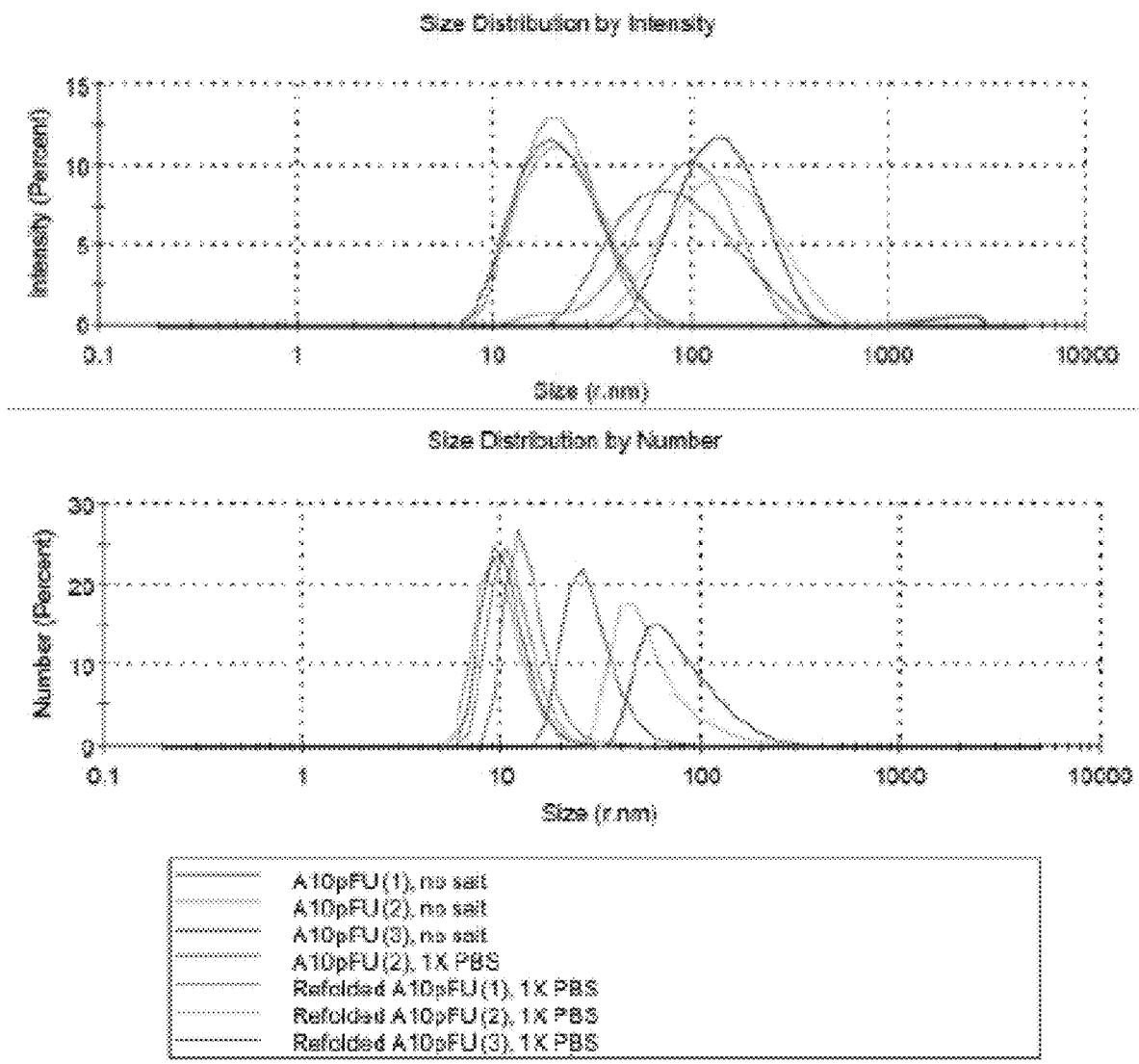

FIGS. 19A-19B are a DLS measurement showing (A) size distribution profiles by intensity and by number for three different batches of A10-polyFU and three different batches of refolded A10-polyFU; and the (B) Z-average radius and PDI of each sample.

Figure 20A:
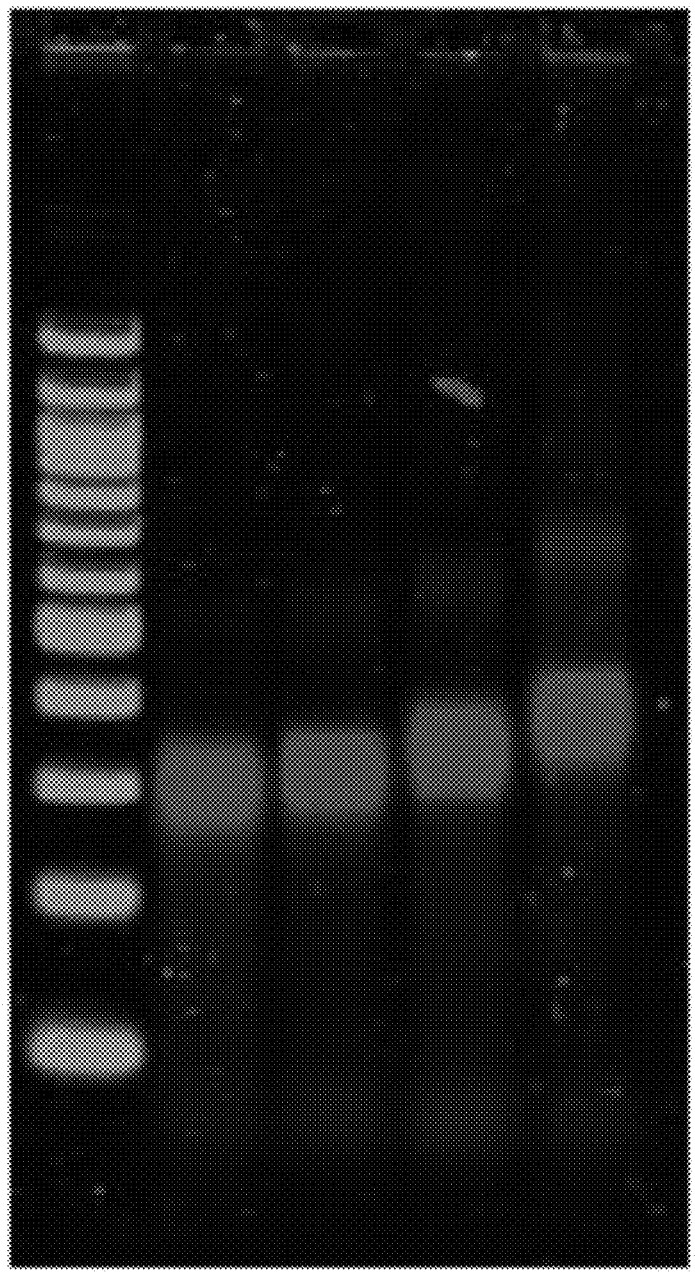
Figure 20B:
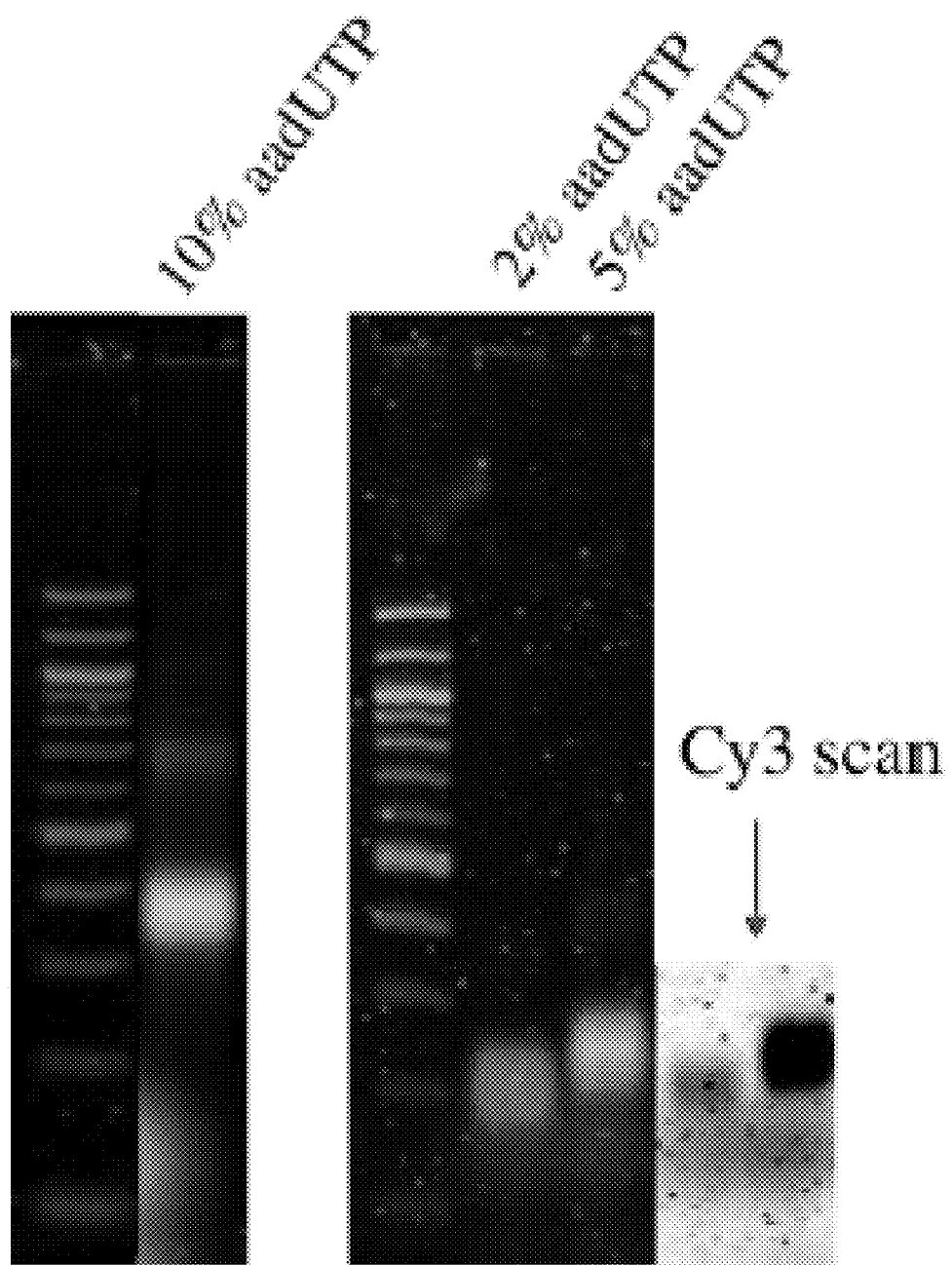

FIGS. 20A-20B are a set of agarose gel electrophoresis images showing: (A) From left to right: 100 bp ladder, Cy5T50-polyFU, Cy5T50-poly(FdU-co-aadU) (2% aadUTP), Cy5T50-poly(FdU-co-aadU) (5% aadUTP), Cy5T50-poly(FdU-co-aadU) (10% aadUTP); (B) Cy5 (red) and Cy3 (green) signals for Cy3-conjugated Cy5T50-poly (FdU-co-aadU) ssDNA containing different fractions of amine groups. The yellow color is produced by overlapping of red and green signal.

Figure 21A:
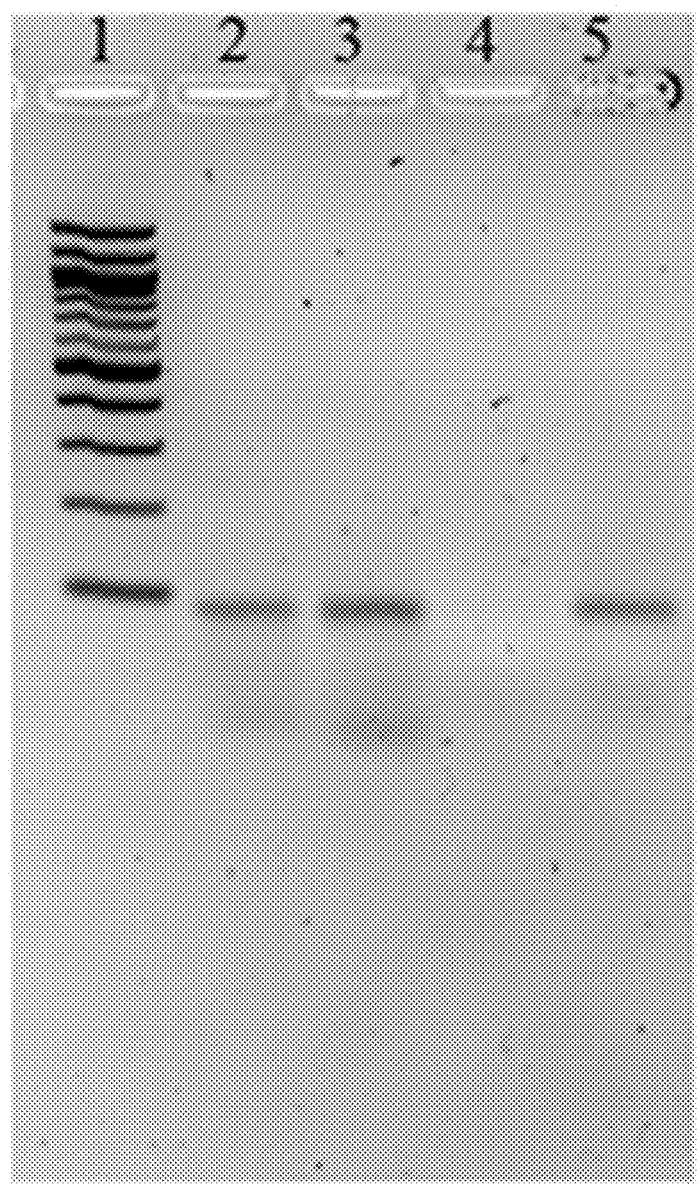
Figure 21B:
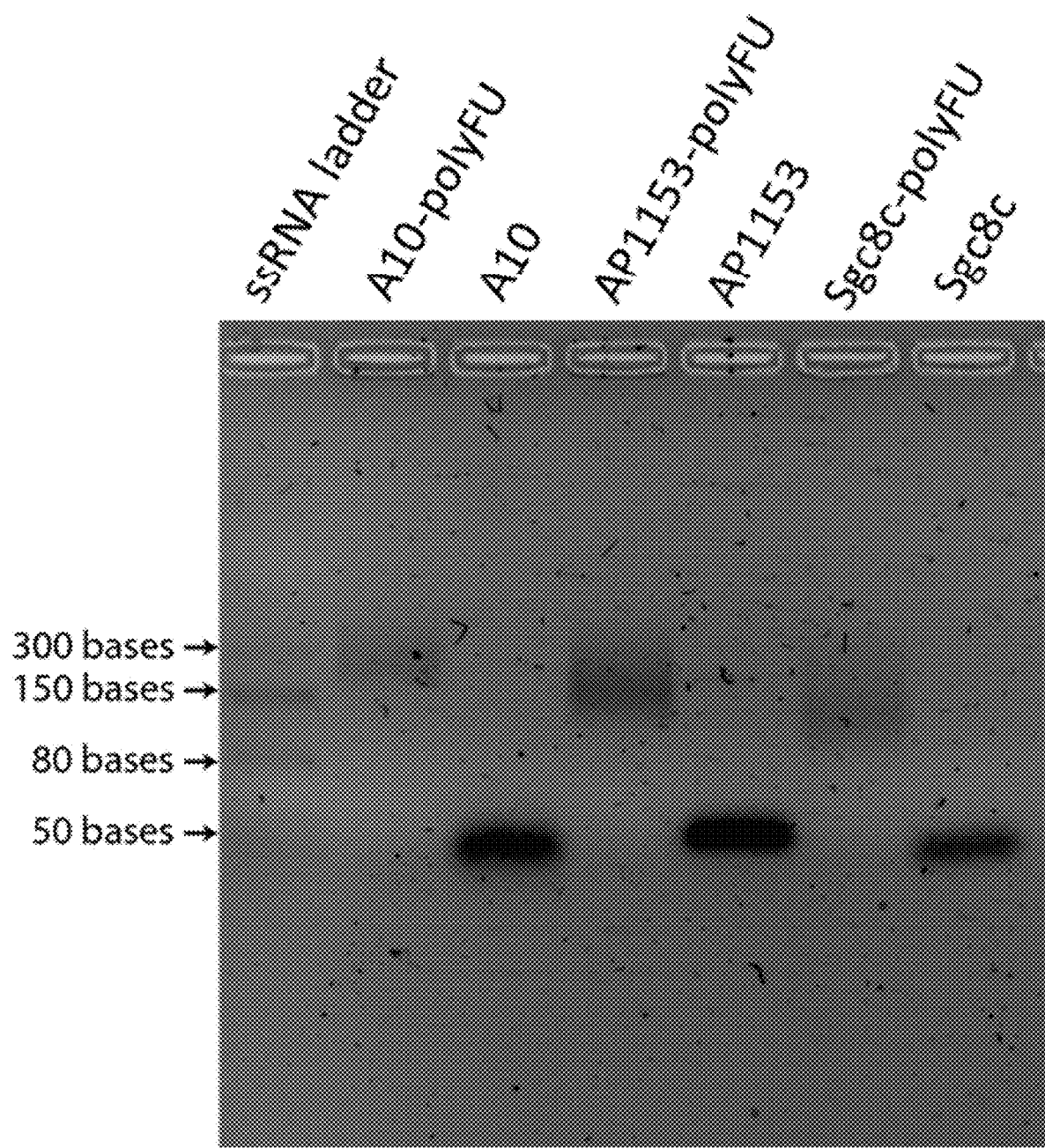

FIGS. 21A-21B are a set of agarose gel images: (A) an agarose gel image showing molecular weight and distribution of single stranded sgc8c-poly(FdUTP); and (B) agarose gel electrophoresis of aptamers A10, Ap1153, and sgc8c extended with FdUTP using TcEP.

DETAILED DESCRIPTION

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

The term "amphiphilic," as used herein, refers to a molecule (e.g., polynucleotide) having both hydrophilic and hydrophobic properties.

The term "alkynyl," as used herein, refers to straight or branched monovalent hydrocarbyl groups having from 2 to 30 carbon atoms, such as 2 to 20, or 2 to 10 carbon atoms and having at least 1 site of triple bond unsaturation. Examples of such alkynyl groups include, but are not limited to acetylenyl (—C≡CH), and propargyl (—CH$_2$C≡CH).

The term "amino," as used herein, refers to the functional group —NH$_2$.

The term "azide," as used herein, refers to the functional group —N$_3$.

The term "critical micelle concentration," as used herein, refers to the concentration of amphiphilic polynucleotides above which micelles are formed. Herein, this value was determined by AFM imaging analysis and/or fluorescence intensity analysis of micelle formation. Further details of determining CMC can be found in J. N. Phillips, Trans. Faraday 1955, 51, 561, which is incorporated by reference herein in its entirety.

The terms "effective amount" or "therapeutically effective amount," as used herein, refer to a sufficient amount of an agent or a composition or combination of compositions being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition as disclosed herein required to provide a clinically significant decrease in disease symptoms. An appropriate "effective" amount in any individual case may be determined using techniques, such as a dose escalation study. The dose could be administered in one or more administrations. However, the precise determination of what would be considered an effective dose may be based on factors individual to each patient, including, but not limited to, the patient's age, size, type or extent of disease, stage of the disease, route of administration, the type or extent of supplemental therapy used, ongoing disease process and type of treatment desired (e.g., aggressive vs. conventional treatment).

The term "non-natural nucleotide," as used herein, refers to nucleotides that are not present in a natural biological system. Similar to a naturally occurring nucleotide (e.g., ATP, UTP, etc.), a non-natural nucleotide includes a phosphate group(s), a sugar, and a base. However, a non-natural nucleotide can differ from a naturally occurring nucleotide by having its phosphate group(s), sugar, base or combination thereof modified. Examples of non-natural nucleotides include, but are not limited to, 5-fluoro-2'-deoxyuridne-5'triphosphate, arabinofuranosylcytosine triphosphate, Atto-dUTP, and BODIPY-dUTP.

The term "polynucleotide," as used herein, refers to 300 or more nucleotides covalently linked together. Polynucleotides may be single-stranded, double-stranded, or may contain portions of both double-stranded and single-stranded sequence. A polynucleotide can include natural or non-natural nucleotides, and can contain combinations of deoxyribo- and ribo-nucleotides, and combinations of bases including, for example, uracil, adenine, thymine, cytosine, guanine, inosine, xanthine hypoxanthine, isocytosine, and isoguanine.

A polynucleotide includes a 5' end and a 3' end. Polynucleotides are said to have "5' ends" and "3' ends" because nucleotides are reacted to make polynucleotides in a manner such that the 5' phosphate of one nucleotide pentose ring is attached to the 3' oxygen of its neighbor in one direction via a phosphodiester linkage. Thus, an end of a polynucleotide can be referred to as the "5' end" if its 5' phosphate is not linked to the 3' oxygen of a nucleotide pentose ring and as the "3' end" if its 3' oxygen is not linked to a 5' phosphate of a subsequent nucleotide pentose ring. In addition, a nucleotide portion or sequence, even if internal and linked within a larger polynucleotide, also may be said to have 5' and 3' ends. For example, the aptamer portion and the aptamer can have 5' and 3' ends.

The term "subject," "patient," or "organism," as used herein, includes humans and mammals (e.g., mice, rats, pigs, cats, dogs, and horses). Typical subjects of the present disclosure may include mammals, particularly primates, and especially humans. For veterinary applications, suitable subjects may include, for example, livestock such as cattle, sheep, goats, cows, swine, and the like; poultry such as chickens, ducks, geese, turkeys, and the like, as well as domesticated animals particularly pets such as dogs and cats. For diagnostic or research applications, suitable subjects may include mammals, such as rodents (e.g., mice, rats, hamsters), rabbits, primates, and swine such as inbred pigs and the like.

The term "treatment" or "treating," as used herein when referring to protection of a subject from a disease, means preventing, suppressing, repressing, ameliorating, or completely eliminating the disease. Preventing the disease involves administering a composition of the present disclosure to a subject prior to onset of the disease. Suppressing the disease involves administering a composition of the present disclosure to a subject after induction of the disease but before its clinical appearance. Repressing or ameliorating the disease involves administering a composition of the present disclosure to a subject after clinical appearance of the disease.

2. Amphiphilic Polynucleotides

Provided herein are compositions that include an assembly of amphiphilic polynucleotides. The amphiphilic polynucleotide can be single-stranded and includes at least three different portions. These three portions can also be referred to as three different nucleotide portions. The three portions include an aptamer portion, a first nucleotide portion, and a second nucleotide portion. The three portions can be included in the amphiphilic polynucleotide in a 5' to 3' direction. For example, the aptamer portion can be coupled to the first nucleotide portion, the first nucleotide portion can be coupled to the aptamer portion and the second nucleotide portion, and the second nucleotide portion can be coupled to the first nucleotide portion. In other words, the first nucleotide portion can be in between the aptamer portion and the second nucleotide portion, where the aptamer portion and the second nucleotide portion form individual ends of the amphiphilic polynucleotide.

The amount and composition of these three portions can instill an amphiphilicity characteristic to the amphiphilic polynucleotide. This amphiphilicity characteristic can allow the amphiphilic polynucleotide to self-assemble with other amphiphilic polynucleotides to form the assembly. For example, the first nucleotide portion and the second nucleotide portion can be included in the amphiphilic polynucleotide at a ratio that can promote self-assembly. In some embodiments, the first nucleotide portion and the second nucleotide portion are included at a ratio (number of nucleotides of the first nucleotide portion: number of nucleotides of the second nucleotide portion) of about 20:1 to about 60:1, such as about 25:1 to about 60:1, or about 30:1 to about 55:1. In addition, due to the ability of the amphiphilic polynucleotides to self-assemble, the amphiphilic polynucleotide can have a critical micelle concentration (CMC). In some embodiments, the amphiphilic polynucleotide has a CMC that is less than or equal to 0.1 µM, less than or equal to 0.09 µM, or less than or equal to 0.08 µM. In some embodiments, the amphiphilic polynucleotide has a CMC that is greater than or equal to 0.04 µM, greater than or equal to 0.05 µM, or greater than or equal to 0.06 µM.

The amphiphilic polynucleotide can include about 300 nucleotides to about 600 nucleotides, such as about 350 nucleotides to about 550 nucleotides, or about 400 nucleotides to about 525 nucleotides. In some embodiments, the amphiphilic polynucleotide includes about 500 nucleotides. In addition, the amphiphilic polynucleotide can be made from only nucleotides. Thus, in some embodiments, the amphiphilic polynucleotide is 100% nucleotide. In other embodiments the amphiphilic polynucleotide can include molecules other than nucleotides. For example, the amphiphilic polynucleotide can be modified with polymers such as polyethylene glycol (PEG), lipids, peptides, and/or proteins.

The amphiphilic polynucleotide can self-assemble into a variety of different particulate structures and sizes. For example, the assembly can be a nanoparticle. The nanoparticle can have a varying average hydrodynamic radius depending on the structure and portions of the amphiphilic polynucleotide. The hydrodynamic radius can be measured using dynamic light scattering techniques known within the art. In addition, particle size can be measured via other techniques, such as AFM and transmission electron microscopy (TEM) image analysis. In some embodiments, the nanoparticle has an average hydrodynamic radius of about 20 nm to about 125 nm, such as about 25 nm to about 100 nm, or about 20 nm to about 60 nm. In some embodiments, the nanoparticle has an average hydrodynamic radius of about 50 nm. The assembly and nanoparticle thereof can have a micellular structure. In some embodiments, the nanoparticle is a micelle.

The amphiphilic polynucleotide can provide an assembly that is advantageously stable. Stability, as used herein, refers to the assembly being able to maintain its structural (e.g., size) and/or functional features (e.g., binding capability of aptamer portion) for a specified amount of time in a particular environment (e.g., saline, serum, blood, etc.). For example, the assembly being able to maintain its average particle size within +25% of its initial average size for 1 day corresponds to the assembly being stable for greater than or equal to 1 day. In addition, stability can also include the assembly being able to maintain a functional effect (e.g., within 5% of its aptamer portion binding activity) over a period of time. In some embodiments, the assembly can be stable in serum and mixtures that include serum for extended periods of time compared to an individual amphiphilic polynucleotide not part of an assembly. This can be useful for in vivo applications by, e.g., affording the assembly an extended circulation time. In some embodiments, the assembly can be stable in a mixture of about 50% fetal bovine serum for about 30 minutes to about 1 day, such as about 1 hour to about 22 hours, about 30 minutes to about 20 hours, or about 2 hours to about 1 day.

A. Aptamer Portion

The aptamer portion of the amphiphilic polynucleotide can be used as an initiator for the synthesis of the amphiphilic polynucleotide, as well as can be used to localize the amphiphilic polynucleotide and assembly thereof to a specific target molecule, protein, cell, tissue, or the like. In some embodiments, the aptamer portion is capable of binding to a specific target protein. The target protein can be a cell surface protein or a protein present intracellularly. In addition, the target protein can be associated with a disease or disorder. For example, the target protein can be a protein that is overexpressed in a diseased cell, tissue, or the like. An overexpressed protein refers to a protein that is expressed by a diseased cell or tissue at greater than 100×, greater than 500×, or greater than 1000× the expression level of that protein in the non-diseased (e.g., healthy) cell or tissue. In some embodiments, the aptamer portion is capable of binding to a surface protein that is overexpressed in a cancer cell.

The aptamer portion can include an aptamer and a linker. The aptamer can instill the capability of the aptamer portion and amphiphilic polynucleotide (and assembly thereof) to bind to specific proteins and non-protein molecules. As used herein, "aptamer" refers to a nucleotide sequence that can bind to a target molecule. The aptamer can be DNA, RNA, or a combination thereof. The binding description in regards to the aptamer portion can also be applied to the aptamer. In some embodiments, the aptamer is selected from the group consisting of

```
AS1411
                                           (SEQ ID NO: 1)
(5'-GGTGGTGGTGGTTGTGGTGGTGGTGG-3'),

AIR-3
                                           (SEQ ID NO: 2)
(5'-GGAAGAAAGAGGUCUGAGACAUUCUCUUAUAGGGGAGGCUGUGGUG

AGGGAAUAUUAAGAGAAUUAACGGUCUAGUUCACCUCGACUUCUGGAGUU

GACGUUGCUU-3'),

A10
                                           (SEQ ID NO: 3)
(5'-GGGAGGACGAUGCGGAUCAGCCAUGUUUACGUCACUCCU-

3'),

Sgc8c
                                           (SEQ ID NO: 4)
(5'-ATCTAACTGCTGCGCCGCCGGGAAAATACTGTACGGTTAGA-3'),

MUC1-5TR-1
                                           (SEQ ID NO: 5)
(GGGAGACAAGAATAAACGCTCAAGAAGTGAAAATGACAGAACACAACAT

TCGACAGGAGGCTCACAACAGGC),
and

AP1153
                                           (SEQ ID NO: 6)
(5'-CAT GGT GCA GGT GTG GCT GGG ATT CAT TTG CCG

GTG CTG GTG CGT CCG CGG CCG CTA ATC CTG TTC-3').
```

The aptamer may also include non-natural nucleotides that can be useful for nuclease resistance. Modifications that can be useful for nuclease resistance include a phosphorothioate backbone and/or sugar modification: 2' fluoro and 2'-O-methyl.

The linker can be used to decrease intermolecular hinderance between, e.g., the aptamer portion and the first nucleotide portion. The linker can be coupled to the 5' end, the 3' end, or both of the aptamer. In some embodiments, the linker includes about 2 nucleotides to about 30 nucleotides, such as about 3 nucleotides to about 20 nucleotides, or about 4 nucleotides to about 15 nucleotides. The nucleotides of the linker can be a natural nucleotide or a non-natural nucleotide. In some embodiments, the linker includes dTTP.

The aptamer portion can include about 15 nucleotides to about 100 nucleotides, such as about 20 nucleotides to about 90 nucleotides or about 25 nucleotides to about 100 nucleotides. In some embodiments, the aptamer portion includes a nucleotide sequence of (SEQ ID NO:7). In some embodiments, the aptamer portion is (SEQ ID NO:7).

B. First Nucleotide Portion

The first nucleotide portion of the amphiphilic polynucleotide can be used to provide a therapeutic nucleotide, as well as can be used to provide a hydrophilic portion of the amphiphilic polynucleotide. The first nucleotide portion can include non-natural therapeutic nucleotides, such as non-natural cytostatic nucleotides. As used herein, "non-natural cytostatic nucleotide" refers to a non-natural nucleotide that can inhibit cell growth, cell division, cell metabolism, or a combination thereof. Examples of non-natural cytostatic nucleotides include, but are not limited to, 5-fluoro-2'-deoxyuridne-5'triphosphate (FdUTP), arabinofuranosylcytosine triphosphate, 8-chloro-adenosine triphosphate, 8-amino-adenosine triphosphate, 5-aza-2'-deoxycytidine triphosphate. In some embodiments, the non-natural cytostatic nucleotide is selected from the group consisting of FdUTP, arabinofuranosylcytosine triphosphate, 8-chloro-adenosine triphosphate, 8-amino-adenosine triphosphate, 5-aza-2'-deoxycytidine triphosphate, and a combination thereof. In some embodiments, the non-natural cytostatic nucleotide is selected from FdUTP, arabinofuranosylcytosine triphosphate, and a combination thereof. In some embodiments, the non-natural cytostatic nucleotide is FdUTP.

The first nucleotide portion can include a nucleotide sequence of $(X^1)_m$ (SEQ ID NO:8), wherein $X^1$ is a non-natural cytostatic nucleotide, and m is 100 to 2,000. In some embodiments, the first nucleotide portion includes a nucleotide sequence of $(FdUTP)_m$ (SEQ ID NO:9), wherein m is 100 to 2,000. In some embodiments of (SEQ ID NO:8) or (SEQ ID NO:9), m is 100 to 1,000. In some embodiments, the first nucleotide portion is (SEQ ID NO:8). In some embodiments, the first nucleotide portion is (SEQ ID NO:9).

The first nucleotide portion can also include other non-natural nucleotides and sequences thereof that can be used to alter properties of the amphiphilic polynucleotide and/or the assembly thereof. For example, other non-natural nucleotides and sequences thereof can be used to cross-link the assembly or can be used to add imaging agents to the assembly. These other non-natural nucleotides and sequences thereof can include a variety of different functional groups attached to the base of the non-natural nucleotide. In some embodiments, the base that is modified is uracil. Examples of functional groups include, but are not limited to:

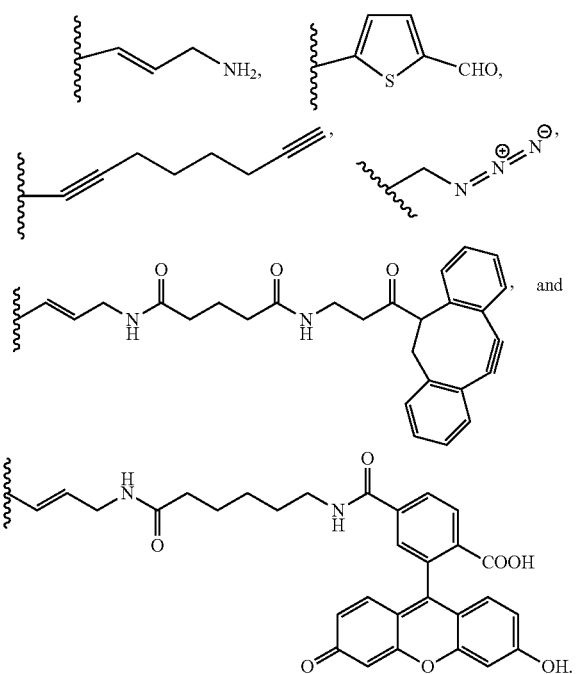

In some embodiments, the first nucleotide portion includes a nucleotide sequence of $(Z^1)_p$ (SEQ ID NO:10), wherein $Z^1$ is a non-natural nucleotide having an amino group, an alkynyl group, an azide group, or a combination thereof, and p is 5 to 80. In some embodiments, the non-natural nucleotide is a modified dUTP having an amino group, an alkynyl group, an azide group, or a combination thereof. In some embodiments, the non-natural nucleotide is a base-modified dUTP having an amino group, an alkynyl group, an azide group, or a combination thereof.

The first nucleotide portion can include (SEQ ID NO:8), (SEQ ID NO:9), and/or (SEQ ID NO:10) in different arrangements. For example, the first nucleotide portion can include (SEQ ID NO:9) and (SEQ ID NO:10) as blocks. In other embodiments, the first nucleotide portion can include (SEQ ID NO:9) and (SEQ ID NO:10) randomly. In some embodiments, the first nucleotide portion includes more than one occurrence of (SEQ ID NO:8), (SEQ ID NO:9), and/or (SEQ ID NO:10). For example, the first nucleotide portion can include (SEQ ID NO:9) at more than one occurrence and can include (SEQ ID NO:10) at more than one occurrence.

C. Second Nucleotide Portion

The second nucleotide portion of the amphiphilic polynucleotide can be used to provide a hydrophobic portion of the amphiphilic polynucleotide. The second nucleotide portion can include non-natural hydrophobic nucleotides. As used herein, "non-natural hydrophobic nucleotide" refers to a non-natural nucleotide that includes a base modified with a hydrophobic molecule or hydrophobic functional group. The hydrophobicity characteristic of the second nucleotide portion can be measured via the Log P of the modified base of the non-natural hydrophobic nucleotide. Log P is the log(concentration of a compound in octanol/concentration of the compound in water). Log P=0 implies equal affinity for organic and aqueous phase; Log P<1 implies affinity towards aqueous phase; and Log P>1 implies affinity towards organic phase. Log P can be estimated, e.g., using Crippen's fragmentation method in the software ChemDraw. The second nucleotide portion can include non-natural hydrophobic nucleotides, wherein each individual non-natural hydrophobic nucleotide includes a base having a Log P≥1.95. In some embodiments, the second nucleotide portion includes more than one type of non-natural hydrophobic nucleotide, wherein each individual non-natural hydrophobic nucleotide includes a base having a Log P≥1.95. In some embodiments, the modified base of the non-natural hydrophobic nucleotide is uracil. In some embodiments, the non-natural hydrophobic nucleotide is a dUTP having a hydrophobic molecule or hydrophobic functional group attached to its base.

The second nucleotide portion can include a nucleotide sequence of $(Y^1)_n$ (SEQ ID NO:11), wherein $Y^1$ is a non-natural hydrophobic nucleotide including a base having a Log P≥1.95, and n is 2 to 10. In some embodiments, the non-natural hydrophobic nucleotide includes a base having a Log P greater than or equal to 2, greater than or equal to 2.5, or greater than or equal to 3. In some embodiments, the non-natural hydrophobic nucleotide includes a base having a Log P less than or equal to 5, less than or equal to 4.5, less than or equal to 4.25, or less than or equal to 4.

In some embodiments, the non-natural hydrophobic nucleotide is selected from the group consisting of 5-(3-Aminoallyl)-2'-deoxyuridine-5'-triphosphate, labeled with ATTO 425 (ATTO-dUTP), 4,4-difluoro-4-bora-3a,4a-diaza-s-indacene (BODIPY)-dUTP, and a combination thereof.

In some embodiments, the second nucleotide portion is (SEQ ID NO:11).

3. Methods of Making the Amphiphilic Polynucleotides

The present disclosure also provides methods of making amphiphilic polynucleotides. The description of the compositions, amphiphilic polynucleotides, assemblies, and different portions of the amphiphilic polynucleotide can also be applied to the methods disclosed herein. The method can include combining a terminal deoxynucleotidyl transferase (TdT), an aptamer initiator having a secondary structure, and a non-natural cytostatic deoxynucleoside triphosphate (dNTP) monomer in a buffer to provide a first reaction mixture. In the method, the non-natural cytostatic dNTP monomer can be polymerized and coupled to the aptamer initiator by TdT. The aptamer initiator can also be referred to as the aptamer portion as described above. The non-natural cytostatic dNTP monomer can refer to individual non-natural cytostatic nucleotides as described above regarding the first nucleotide portion. Accordingly, the non-natural cytostatic dNTP monomer can be polymerized to provide at least a portion of the first nucleotide portion.

The different components can be added to provide the first reaction mixture at varying concentrations. The TdT can be added at a concentration of about 0.7 U/μL to about 2.4 U/μL. The aptamer initiator can be added at a concentration of about 0.3 μM to about 1 μM. The non-natural cytostatic dNTP monomer can be added at a concentration of about 90 μM to about 1 mM. The buffer can have a pH of about 7.2. In addition, the buffer can include potassium cacodylate, $CoCl_2$, and DTT. In some embodiments, the buffer includes about 100 mM potassium cacodylate, about 1 mM $CoCl_2$, and about 0.2 mM DTT at a pH of about 7.2. Further discussion on TdT catalyzed enzymatic polymerization (TcEP) can be found in Tang et al., "High-Molecular-Weight Polynucleotides by Transferase-Catalyzed Living Chain-Growth Polycondensation," Angew. Chem., 56 (24), 6778, 2017, which is incorporated by reference herein in its entirety.

The method can also include incubating the first reaction mixture. The first reaction mixture can be incubated for about 30 minutes to about 10 hours. In some embodiments, the first reaction mixture is incubated for about 1 hour to about 3 hours. In some embodiments, the first reaction mixture is incubated at about 37° C.

The method can further include adding a non-natural hydrophobic dNTP monomer to the first reaction mixture to provide a second reaction mixture. Similar to above, TdT can polymerize the non-natural hydrophobic dNTP monomer and couple it to the first nucleotide portion. The non-natural hydrophobic dNTP monomer refers to individual non-natural hydrophobic nucleotides as described above regarding the second nucleotide portion. Accordingly, the non-natural hydrophobic dNTP monomer can be polymerized to provide at least a portion of the second nucleotide portion. The non-natural hydrophobic dNTP monomer can be added at a concentration of about 3 µM to about 300 µM. The method can also include incubating the second reaction mixture to provide the amphiphilic polynucleotide as disclosed herein. The description of incubating the first reaction mixture can also be applied to incubating the second reaction mixture.

The method may include adding TdT to the first reaction mixture in multiple rounds (e.g., 2 rounds, 5 rounds, 10 rounds, etc.) before or after incubating. The amount of TdT added can depend on the type of dNTP monomer, the desired length of the amphiphilic polynucleotide, the length of the relevant portion, or a combination thereof. TdT can also be added in multiple rounds to the second reaction mixture for the reasons discussed for addition to the first reaction mixture. In some embodiments, the TdT is added to the first reaction mixture, the second reaction mixture, or both in multiple rounds. In some embodiments, the TdT is added to the first reaction mixture, the second reaction mixture, or both in 2 to 10 rounds.

The method may include refolding the aptamer portion of the provided amphiphilic polynucleotide. Refolding the aptamer portion can provide this portion with a secondary structure. Secondary structure, in reference to the aptamer and aptamer portion, refers to intrachain nucleobase hybridization that can provide stem structures, loop structures, and combinations thereof. Further discussion on aptamer secondary structure can be found in Sullivan et al., "Analyzing Secondary Structure Patterns in DNA Aptamers Identified via CompELS," Molecules, 2019 April; 24(8): 1572, which is incorporated by reference herein in its entirety. Providing an aptamer portion with secondary structure can aid self-assembly with decreased aggregates, as well as may aid in binding properties of the aptamer portion.

4. Uses of the Amphiphilic Polynucleotides

The present disclosure also provides methods of treating a disease or disorder in a subject in need thereof. The method may include administering to the subject a therapeutically effective amount of the disclosed compositions including the assembly of amphiphilic polynucleotides. The description of the compositions, amphiphilic polynucleotides, assemblies, and different portions of the amphiphilic polynucleotide can also be applied to the methods disclosed herein.

The disease or disorder may be cancer. Many different cancer types and subtypes may be treated by the disclosed compositions. For example, the cancer may be a carcinoma, sarcoma, lymphoma, leukemia, melanoma, mesothelioma, multiple myeloma, or seminoma. The cancer may be a cancer of the bladder, blood, bone, brain, breast, cervix, colon/rectum, endometrium, head and neck, kidney, liver, lung, muscle tissue, ovary, pancreas, prostate, skin, spleen, stomach, testicle, thyroid, or uterus. In some embodiments, the cancer is prostate cancer.

5. Administration

The disclosed compositions may be incorporated into pharmaceutical compositions suitable for administration to a subject (such as a patient, which may be a human or non-human) well known to those skilled in the pharmaceutical art. The pharmaceutical composition may be prepared for administration to a subject. Such pharmaceutical compositions can be administered in dosages and by techniques well known to those skilled in the medical arts taking into consideration such factors as the age, sex, weight, and condition of the particular subject, and the route of administration.

The pharmaceutical compositions may include pharmaceutically acceptable carriers. The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols, such as propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator. The route by which the composition is administered and the form of the composition will dictate the type of carrier to be used.

The composition can be administered prophylactically or therapeutically. The compositions can be administered by methods well known in the art as described in Donnelly et al. (*Ann. Rev. Immunol.* 1997, 15, 617-648); Felgner et al. (U.S. Pat. No. 5,580,859, issued Dec. 3, 1996); Felgner (U.S. Pat. No. 5,703,055, issued Dec. 30, 1997); and Carson et al. (U.S. Pat. No. 5,679,647, issued Oct. 21, 1997), which are all incorporated by reference herein in their entirety. One skilled in the art would know that the choice of a pharmaceutically acceptable carrier, including a physiologically acceptable compound, depends, for example, on the route of administration. The compositions can be delivered via a variety of routes. Typical delivery routes include parenteral administration, e.g., intradermal, intramuscular or subcutaneous delivery. Other routes include oral administration, intranasal, intravaginal, transdermal, intravenous, intraarterial, intratumoral, intraperitoneal, and epidermal routes. In some embodiments, the composition is administered intravenously to the subject.

6. Examples

Example 1

Aptamer AS1411

Aptamer AS1411 has a strong binding affinity to nucleolin (NCL)50 and binding results in internalization of both the aptamer and attached drugs. NCL is a multifunctional protein that is overexpressed in malignant cells, including prostate cancer cells, both in the nucleus and on the cell membrane. In addition to DNA aptamers, RNA aptamers which contain a 2'-OH, provide a more diverse set of secondary structures and; unlike DNA aptamers, RNA aptamers are expediently synthesized by in vitro transcription. For example, RNA aptamer A10 binds to prostate-specific membrane antigen (PSMA) with high affinity ($K_d$=2.1 nM) and can deliver small molecule drugs, therapeutic siRNAs, and nanoparticles to LNCaP prostate cancer cells. Thus, the aptamer AS1411 may be a useful initiator and targeting moiety for the disclosed amphiphilic polynucleotides.

Example 2

Synthesis, In Vitro, and In Vivo Evaluation of Therapeutic Polynucleotides

We hypothesize that in contrast to monomeric 5FU, the polymeric form poly(FdU) is more cytotoxic in the intracellular environment because poly(FdU) degrades directly into the active drug (FdUMP) by a one-step nuclease cleavage that circumvents the multiple steps needed to activate 5FU.

Figure 1:
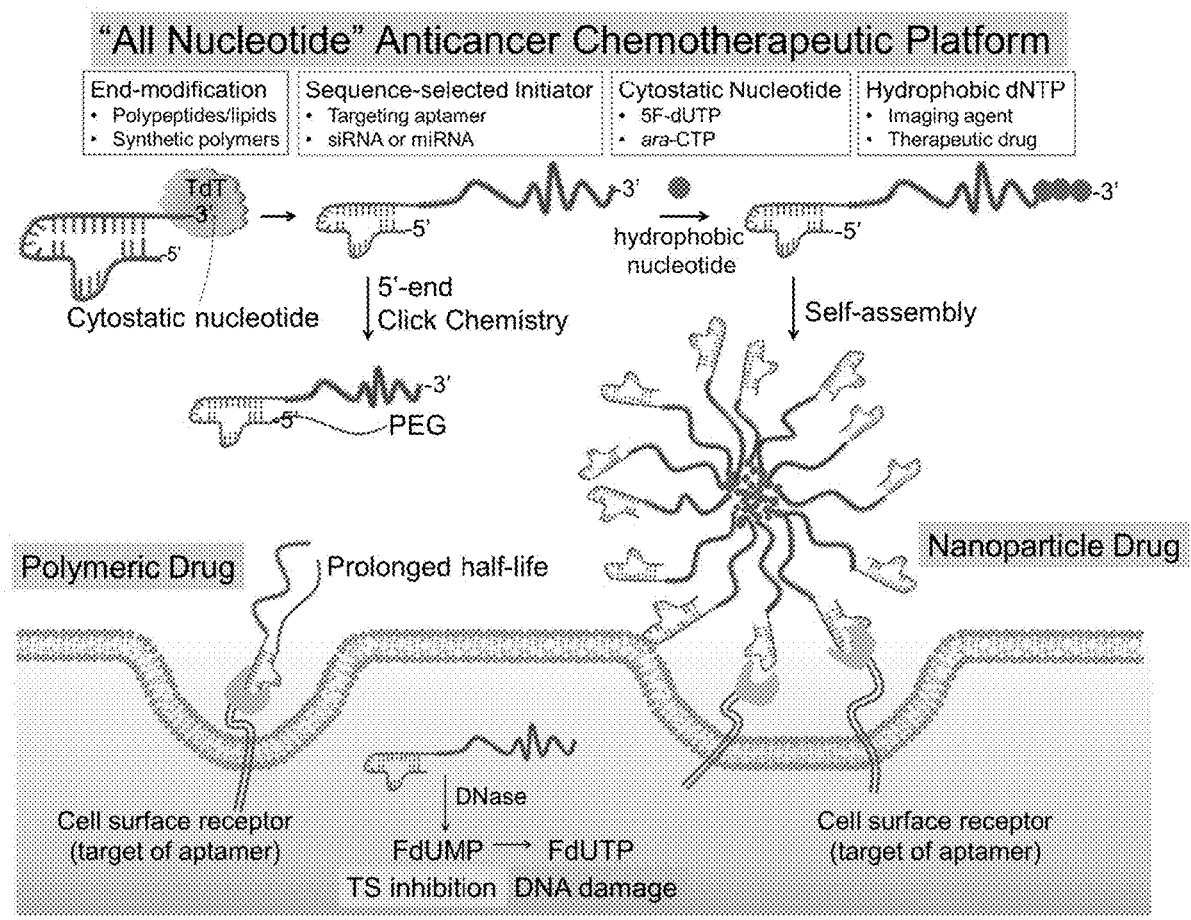
FIG. 1 shows a schematic of a synthesis of amphiphilic polynucleotides and their application in drug delivery applications.
Figure 2:
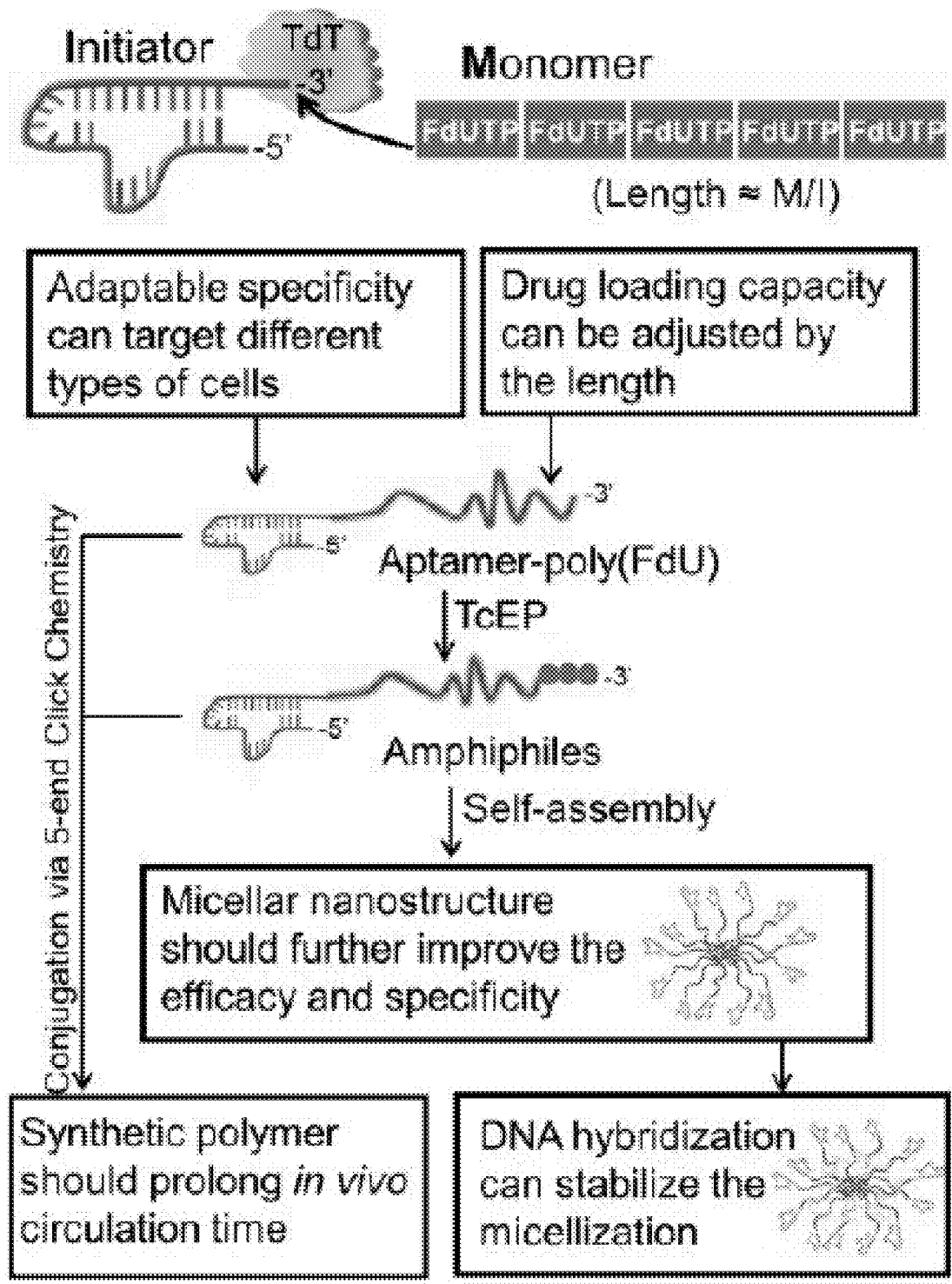
FIG. 2 shows a schematic workflow of a polydeoxyfluorouracil (which is referred to herein as polyFdU, polyFU, or polyFdUTP) amphiphilic polynucleotide.
Figure 3A:
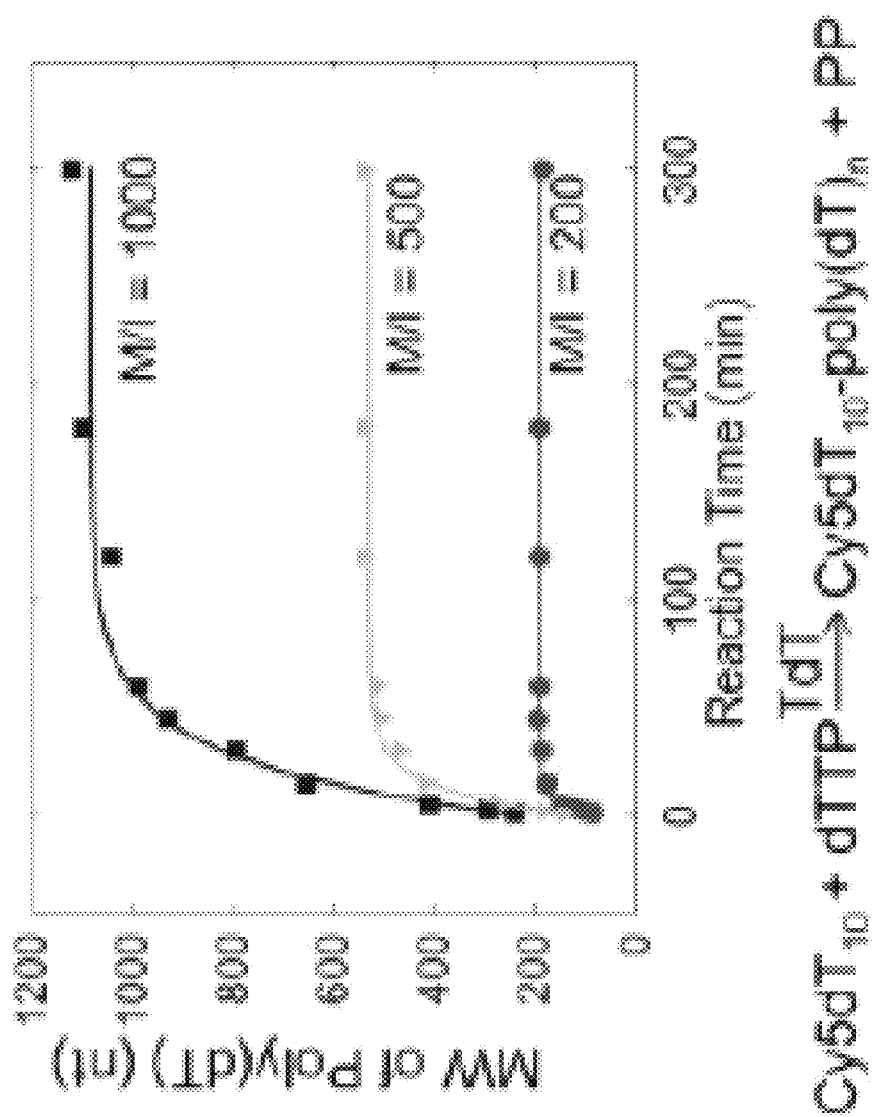
FIGS. 3A-3C show (A) the molecular weight (MW) vs. reaction time for different initial monomer/initiator (M/I) ratios; (B) chemical structures of deoxythymidine triphosphate (dTTP), deoxycytidine triphosphate (dCTP) and their analogs FdUTP, ara-CTP, respectively; and (C) polyacrylamide gel electrophoresis (PAGE) images showing that different MWs are generated by different M/I ratios of FdUTP to Cy5T10, ranging from 200 to 1000 at a constant [TdT] of 1 unit/µl.

Synthesis and Characterization of Therapeutic Polynucleotides with 5'-Terminal Aptamer Motif (i) TdT can polymerize FdUTP into a polymer prodrug (poly(FdU), (ii) TdT can initiate the polymerization from a nucleic acid aptamer which targets an overexpressed protein receptor in malignant cells, (iii) the MW of poly(FdU) is a function of the concentrations of FdUTP (monomer), aptamer (initiator) and TdT (biocatalyst), and (iv) the MW of poly(FdU) is nearly monodisperse, which is an important parameter affecting the in vivo pharmacokinetic (PK) and biodistribution profile (FIG. 1 and FIG. 2). This is supported by our findings that TdT can polymerize dTTP from a Cy5-labeled dT10 oligo (Cy5dT10) initiator by a living chain growth polycondensation mechanism. As a result, the MWs of the reaction products (Cy5dT10-poly(dT)n) are nearly monodisperse, and can be adjusted by the initial molar concentrations of monomer (dTTP) to initiator (Cy5dT10), as typically observed for living polymerization reactions. By increasing the molar ratio of monomer to initiator from 200 to 1000, the polynucleotide MW grows from 185 nt to 1120 nt (FIG. 3A).

Figure 3B:
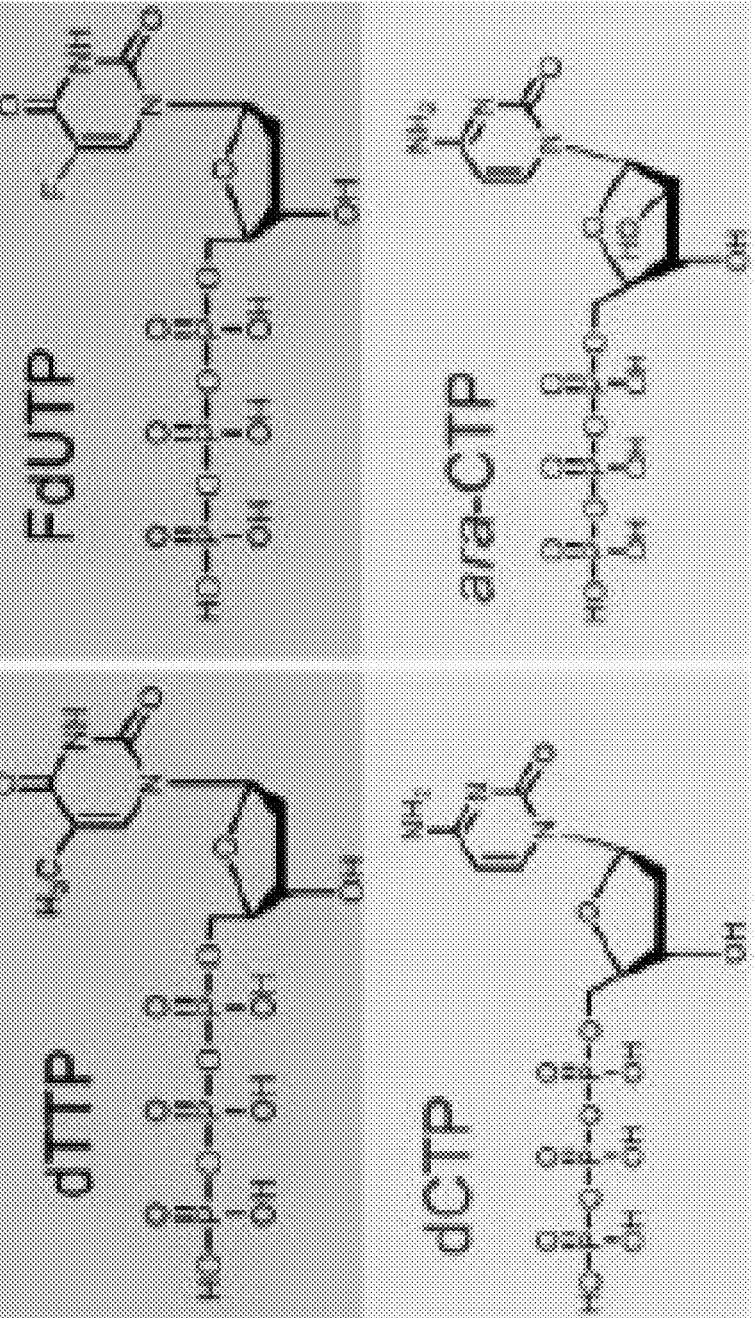
Figure 3C:
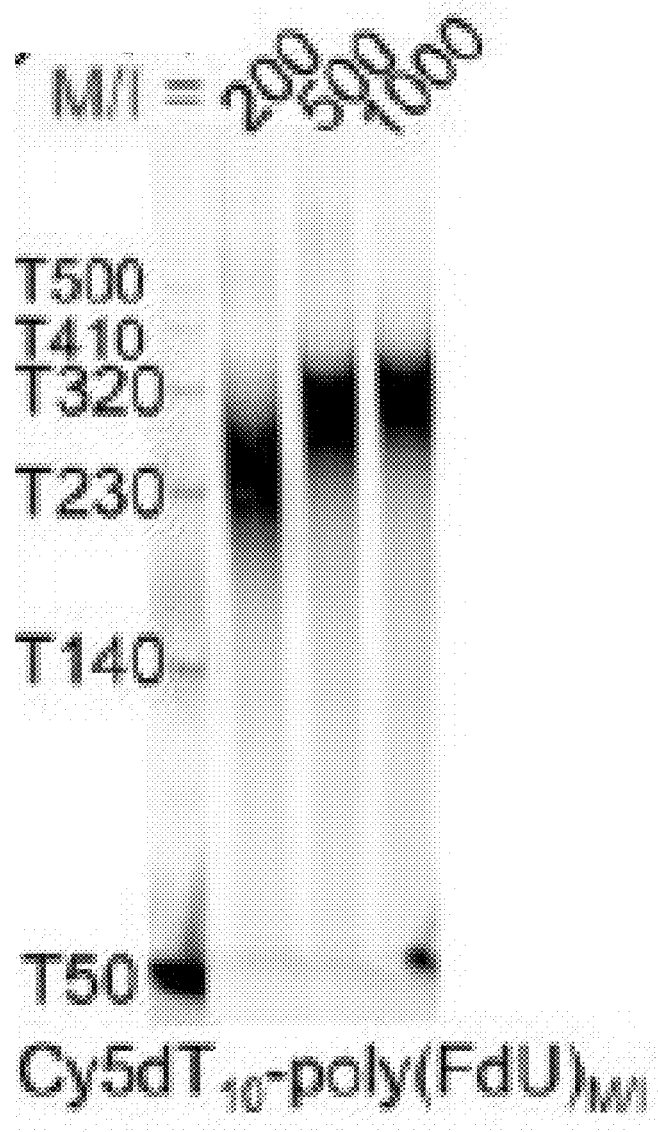

Since FdUTP possesses a minor nucleobase modification (i.e., the $CH_3$ group at the C-5 of dTTP is substituted by F, FIG. 3B) it should not substantially affect the TcEP reaction. TdT can indeed polymerize FdUTP from a Cy5T10 initiator to generate Cy5T10-poly(FdU)n (FIG. 3C).

Synthesis of poly(FdU) by TcEP. We use TdT to polymerize FdUTP from three different initiators: (i) DNA aptamer AS1411, (ii) RNA aptamer A10, and (iii) clickable dibenzocyclooctyne (DBCO) modified oligonucleotide. To avoid intramolecular hindrance, we will a dT12 extension at both the 5'- and 3'-end of AS1411 aptamer, and a dT4 extension at the 3'-end of A10 to aid reaction initiation.

Synthesis of poly(ara-C) by TcEP. To demonstrate the therapeutic adaptability of our integrated delivery platform, we will also polymerize ara-CTP to generate poly(ara-C). The rationale to choose this nucleotide analog stems from the fact that (i) ara-C (the prodrug of ara-CTP) is widely used for acute myeloid leukemia treatment, and (ii) ara-CTP contains a cytosine base with an arabinose sugar (FIG. 3B) that is similar to cytosine deoxyribose that can be polymerized by TdT.

In Vitro Evaluation of Aptamer-Poly(FdU)

Compared to the monomeric free drug (5FU), the aptamer functionalized poly(FdU) can improve the efficacy and the specificity of poly(FdU) towards selected cancer cell lines.

Evaluate specific internalization and cytotoxicity of aptamer-poly(FdU). We will use AS1411-poly(FdU) and A10-poly(FdU) to confirm the targeting specificity to DU145 (NCL+) and LNCaP cells (PSMA+), respectively. We will use aptamers functionalized at the 5'-end with Cy5, to visualize cellular internalization on both positive and negative cell lines (i.e., MCF-10A, female non-cancerous cell line) by confocal microscopy. While we expect the presence of a poly(FdU) chain to not significantly affect aptamer targeting, its presence, particularly at large MW, may hinder effective poly(FdU) internalization due to charge repulsion between ssDNA and the cell surface. To establish the relationship between poly(FdU) MW and cellular internalization, we will synthesize aptamer-poly(FdU) drugs with different lengths and evaluate their internalization by confocal microscopy and flow cytometry. Once aptamer-poly(FdU)$_n$ candidates that maximize cellular uptake have been identified, we will evaluate their cytotoxicity using a MTT assay.

Evaluate stability of aptamer-poly(FdU). The degradation kinetics of poly(FdU) will determine the release of active drug (5FdUMP) in serum and within cells. We will use HPLC to monitor the degradation of the aptamer-poly(FdU) in fetal bovine serum (FBS) and in the presence of DNAses.

Example 3

Figure 4:
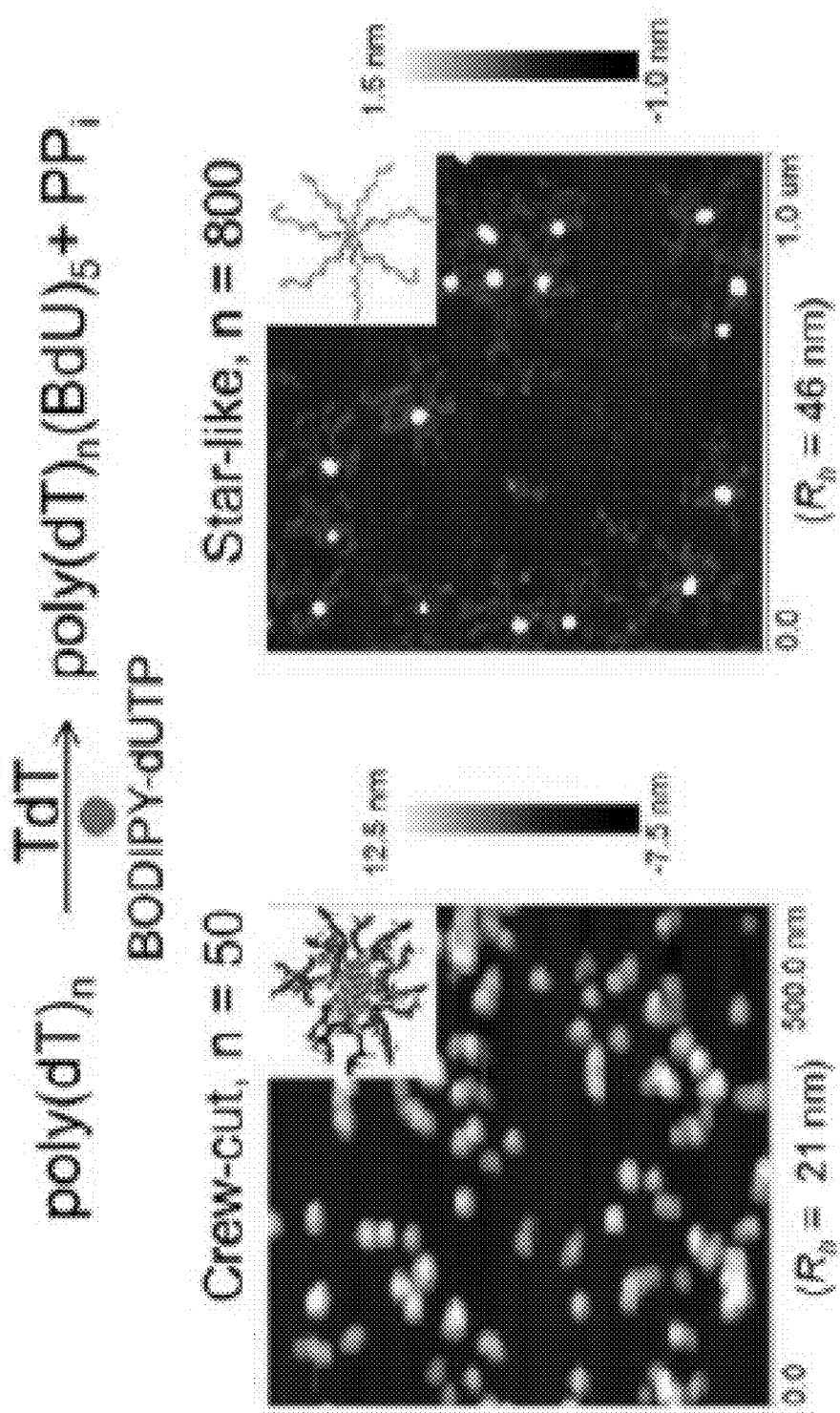
FIG. 4 shows (A) a schematic of a TdT catalyzed enzymatic polymerization (TcEP) reaction for the synthesis of amphiphilic polynucleotides; and (B) atomic force microscopy (AFM) images showing self-assemblies of amphiphilic polynucleotides with different hydrophobic block lengths (n=50 and n=800).

Synthesis, In Vitro, and In Vivo Evaluation of Micellar Therapeutic Micellar DNA NPs TdT can also polymerize nucleotides that contain a hydrophobic modification on the nucleobase, such as BODIPY-dUTP. This allows the sequential synthesis of amphiphilic block copolynucleotides that self-assemble into micellar structures. By changing the hydrophilic block length we were able to tune the micellar morphologies from star-like to crew-cut micelles (FIG. 4).

The goal of this Example is to transform the polymeric drugs developed above into micellar DNA NPs by appending hydrophobic, unnatural dNTP to the 3'-terminus of poly(FdU). This formulation may provide (i) the increased drug loading capacity of the micelles, (ii) the presence of multiple aptamers on the micellar surface, and (iii) the micellar size (~20-80 nm) may improve the drug efficacy, specificity, and in vivo circulation lifetime of the micellar DNA NPs.

Synthesis and Characterization of Micellar DNA NPs

The reaction mechanism of TcEP is similar to that of a living polymerization and thus allows for the seamless polymerization of a second block, simply by adding a new type of monomer (dNTP). This "one-pot" reaction obviates the need for challenging and yield limiting purifications steps, that are required in the synthesis of traditional biohybrid drug conjugates.

Synthesis of amphiphilic poly(FdU) copolynucleotides by TcEP. We synthesized amphiphilic DNA block co-polynucleotides by sequential polymerization of first, FdUTP from an aptamer initiator (see above), followed by the polymerization of hydrophobic, unnatural nucleotides (e.g., BODIPY-dUTP). Specifically, we will synthesize a range of amphiphilic block co-polynucleotides with different hydrophilic and hydrophobic block lengths. We will then establish the relationship between block lengths and micellar morphology and size. We will characterize the micelle size and their stability in the presence of DNases by static and dynamic light scattering techniques, and visualize the micellar morphology by atomic force microscopy.

In Vitro Evaluation of Micellar DNA NPs

Micelle formation may (i) significantly improve the cytotoxicity by delivering a concentrated dose of FdUMP, (ii) enhance specificity via display of multiple aptamer moieties on the micelle surface, and (iii) increase the in vivo circulation half-life time.

Evaluate specific internalization and cytotoxicity of micellar DNA NPs. We will evaluate the specific internalization and cytotoxicity of micellar DNA NPs with the matched aptamer/cell line pairs, used above. The fluorescent BODIPY-dUTP (BdUTP)) will allow us to monitor the cellular internalization by confocal microscopy. We will test the cytotoxicity of different micellar candidates (synthesized above) and compare their potency to that of polymeric aptamer-poly(5FdU) and monomeric 5FU drugs in the aptamer targeting cancer cells.

In Vivo Evaluation of DNA-Drug Nanocarriers

Here we will evaluate the most effective nanocarrier designs in a series of murine in vivo experiments to assess their toxicity, pharmacokinetics, pharmacodynamics, and anti-cancer efficacy. We will evaluate three drug formulations: free 5FU, aptamer-poly(FdU), and micellar aptamer-poly(FdU)B(dU), all injected intravenously. The preclinical model will include xenografts of human prostate cancer cell lines in male, athymic nude mice. AS1411-based nanocarriers will be evaluated in the DU145 model, while A10 nanocarriers will utilize LNCaP tumors. Tumor cells will be inoculated subcutaneously and grown to a target size of 75-125 mm$^3$ in all experiments.

Evaluate toxicity of drug formulations and establish maximum tolerable dose (MTD). Prior to any other experiments, a 4-dose escalation study will be used to determine the MTD for each drug formulation. Using the reported MTD for free 5FU of 15-20 mg/kg, groups of mice (n=5) will receive 10 mg/kg incremental doses of each formulation. Mice will be monitored daily for weight loss and behavioral changes. Any weight loss >15% will be classified as an adverse event. As myelosuppression is a major side effect of 5FU, 25 μL of blood will also be collected daily to monitor changes in absolute neutrophil count using flow cytometry. Counts below 10 neutrophil per L will be classified as severe neutropenia, an adverse event. The MTD will be defined as the highest dose that causes no adverse events.

Assess pharmacokinetic and pharmacodynamic profile of DNA-drug nanocarriers. Next, improvement of the pharmacokinetic behavior of the polymer and NPs drug in circulation will be assessed. Each nanocarrier drug will be assigned to a group (n=5) and injected at the lowest common MTD identified.

10 μL blood samples will be collected and processed into serum at time points of 15 min, 30 min, 1 h, 2 h, 4 h, 8 h, 12 h, 24 h, 48 h, 72 h, 96 h, and 120 h. We will use LC-ESI-MS mass spectroscopy to quantify the 5FU in each sample using a standard curve. The data will be fit to a 2-compartment model to determine the distribution phase and elimination phase half-life ($t_{1/2}$) values for each construct. A subsequent biodistribution study will then examine tumor-specific accumulation compared to non-targeted tissues. Mice will be similarly injected at the lowest common MTD, sacrificed at specified time points, and dissected. Each construct will be evaluated at 4 time points (n=6) corresponding to the pharmacokinetic timeline. The first time point will occur at the end of the distribution phase, with subsequent measurements at the elimination phase $t_{1/2}$, $2t_{1/2}$, and $4t_{1/2}$. Tissues will be homogenized and analyzed using LC-ESI-MS/MS.

Evaluate efficacy of DNA-drug nanocarriers against prostate tumor models. To evaluate the antitumor potency of our DNA-drug nanocarriers, a longitudinal regression study will be carried out. Each nanocarrier drug will be administered as a single dose, both at its own MTD and dose-matched to the MTD of free 5FU. Mice will be tracked for up to 90 days following initial treatment. Tumors will be measured using calipers and volume determined by the formula L*W2/2. Any mouse whose tumor exceeds 1650 mm$^3$ or whose weight loss exceeds 15% will be humanely euthanized. Tumor response and overall survival will be analyzed to determine efficacy of the new nanodrug formulations.

In Vivo Animal Testing

All in vivo procedures included in this proposal involve studying targeted drug delivery to xenografted prostate tumors in a mouse model. As prostate cancer is a gender-specific disease, male athymic nu/nu mice will be purchased at 5-6 weeks of age with an approximate body weight of 22 grams. This immunocompromised mouse model was selected as it allows investigators to directly investigate the therapeutic response of human cancers to the aptamer-poly (FdU) drugs. Tumor inoculations will occur before mice reach 10 weeks of age. We have designed a sequential set of in vivo experiments to examine toxicity, pharmacokinetics, targeting specificity, and efficacy. As devised, the results of each experiment will inform the next to minimize the experimental groups required in each experiment. 198 total mice are required to complete all experiments, with an additional 48 required if pharmacokinetic performance necessitates redesigning the carriers to include a PEG. Experimental break-downs are included in the descriptions as follows:

MTD of 5-FU Nanodrugs. An in vivo experiment will include determining the maximum tolerable dose (MTD) of each different formulation of 5 FU in a 4-dose scaled escalation study in nude mice. First, a baseline MTD of free 5-FU will be verified using the reported value of 20 mg/kg. Free 5-FU will be by administered via intravenous injection at doses of 10, 20, 30, and 40 mg/kg. Mice will be monitored daily for behavioral changes and weight loss. 25 μL blood samples will likewise be collected daily from the tail to assess absolute neutrophil count. The MTD will be defined as the highest dose at which no adverse events are observed in any mice at a given dose. An adverse events will include weight loss >15% of initial body weight, the onset of severe neutropenia (neutrophil count <10/μL), or the development of debilitating physiological behaviors and conditions. We have calculated that 5 mice, aged 5-6 weeks old, will be necessary to assess tolerable toxicity effects at each dose level. Once a baseline MTD reference for free 5-FU is established (MTD5FU), we will then evaluate the MTD of an aptamer-poly(FdU) (e.g., AS1411-poly(FdU)) in both polymer and micelle form. A similar 4-dose scaled escalation will be conducted for each, in healthy nude mice using a 10 mg/kg dose increment starting at the MTD5FU. The same adverse event criteria will be applied to determine the MTD of each individual construct. When combined, 60 mice will be required for evaluating all MTDs (3 formulations*4=doses*n=5). In the potential situation that the pharmacokinetic performance of the polynucleotides needs to be improved, a second toxicity study will be replicated to affirm the MTD of the PEGylated versions of the aptamer-poly(FdU). As the MTD of the poly(FdU) already known, only 3-dose escalation is expected to be necessary, requiring a further 30 mice.

Pharmacokinetic and Pharmacodynamic analysis of Aptamer-poly(FdU) Nanocarriers. An advantage of formulating 5-FU as a polymeric nanocarrier is to improve upon the 8-14 minute half-life of the small molecule drug. Nanoparticle formulations have been widely shown to vastly extend the pharmacokinetic half-life of drugs, reduce the frequency of drug injection regimens, and thus temper the associated toxicity profile of a drug. As such, we will measure the pharmacokinetic elimination profile of each nanocarrier against free 5-FU in the same athymic nu/nu mouse model. To eliminate dose-dependence complications in comparing the pharmacokinetics of each formulation, all will be injected intravenously at the MTD of free 5-FU. 10 µL of blood will be collected from mouse tail veins using a lancet at time points of 15 min, 30 min, 1 h, 2 h, 4 h, 8 h, 12 h, 24 h, 48 h, 72 h, 96 h, and 120 h. Pressure will be applied to collection site to stanch the blood flow once complete. Upon collection, blood will be stored on ice, centrifuged to separate into serum, and then quantified using LC-ESI-MS mass spectroscopy. Mass of 5-FU over time will be fitted to a 2-compartmental model to determine the duration of the distribution phase and half-life of the elimination phase. Based on our experience, a sample size of 6 mice per drug formulation is sufficient for robust pharmacokinetic characterization. This necessitates the use of 18 mice for this experiment (3 formulations*n=6). If the initial pharmacokinetic profiles of the poly(FdU) carriers are poor, alternative formulations that use PEG can be developed to enhance the circulating half-life further. In this case, an additional 18 mice will be required to repeat the pharmacokinetic evaluation after the MTD is verified. Only the best option (aptamer-poly(FdU) vs. PEGylated nanocarriers) will be used in the remaining experiments. Subsequently, a biodistribution study will be conducted to quantify the targeted accumulation of 5-FU. Unlike previous studies, athymic nu/nu mice will be inoculated with tumor cell lines. Based on our in vitro studies, either DU145 (a nucleolin expressing prostate cell line) or LNCaP (a PSMA expressing cell line), will be used for assessing AS1411 and A10 targeting, respectively. 3 groups will be tested in the identified model: free 5-FU, aptamer-poly(FdU), and micelle nanocarrier. Accumulation of the drugs, both at the tumor site and in off-target tissues, will be quantified at 4 different time points. Each time point, with an n=6, will correspond to the pharmacokinetic profile of each drug: end of the distribution phase, and at $t_{1/2}$, $2t_{1/2}$, and $4t_{1/2}$ of the elimination phase. Mice will be sacrificed and the following tissues collected: tumor, kidneys, liver, heart, lungs, stomach, pancreas, spleen, intestines, and rectum. Tissues will be homogenized and analyzed using LC-ESI-MS/MS.

Anti-Tumor Regression Studies. In the final set of experiments of this Example, the aptamer nanocarrier formulation will be used to intravenously treat its corresponding tumor model. Tumors will be grown subcutaneously to a volume of 100 mm³ before being treated. An untreated group and free 5-FU group will be included as controls for comparison of results. The polymer and micelle formulations will be administered at 2 different doses. One dose will be matched to the MTD of free 5-FU for direct comparison. The second dose will be at the unique MTD of the polymer and micelle to illustrate the efficacious advantages of improved PK/PD characteristics. Thus, the aptamer/tumor model will require 6 groups with an n=8. This group size was determined using a 90% power calculation for achieving statistical significance between the different formulations and doses. Once treated, mice will be monitored for up to 90 days. Tumor size will be measured using calipers and body weight will be tracked. Mice whose tumors exceed 1650 mm³ or who lose more than 15% of initial body weight will be euthanized. 48 mice will be required for both aptamer tumor regression studies. Efficacy will be assessed by tumor response and overall survival.

Example 4

Enzymatic Synthesis of Nucleobase-Modified Single-Stranded DNA Offers Tunable Resistance of Nuclease Degradation Materials & Methods Materials. All oligonucleotides were purchased from Integrated DNA Technologies (Coralville, IA, U.S.A.). Recombinant terminal deoxynucleotidyl transferase was purchased from Promega (Madison, WI, U.S.A.). Aminoallyl-dUTP (NH$_2$-dUTP), fluorescein-12-dUTP (FITC-dUTP), dTTP, agarose, and 2% SYBR Green II were purchased from Thermo Fisher Scientific (Waltham, MA, U.S.A.). 5-Dibenzylcyclooctyne-dUTP (DBCO-dUTP) and alkyne-dUTP were purchased from Jena Bioscience (Jena, Germany). AldehydedUTP (CHO-dUTP) was synthesized by Duke University's small molecule synthesis facility. Cyanine 3-dUTP (Cy3-dUTP) was purchased from Enzo Life Science, Inc. (Farmingdale, NY, U.S.A.). Sulfo-Cyanine3 N-hydroxysuccinimide (NHS) ester and dimethylformamide (labeling grade) were purchased from Lumiprobe (Hallandale Beach, FL, U.S.A.). Exonuclease I (*E. coli*) and DNase I (RNasefree) were purchased from New England BioLabs Inc., (Ipswich, MA, U.S.A.). Human serum (male AB clotted whole blood) was purchased from Sigma-Aldrich (St. Louis, MO, U.S.A.). Illustra ProbeQuant G-50 microcolumns were purchased from GE Healthcare Life Sciences (Pittsburgh, PA, U.S.A.). Microcon-10 kDa centrifugal filter unit was purchased from EMD Millipore (Billerica, MA, U.S.A.). 10% Mini-PROTEAN TBE Gels, 15 well, 15 µL were purchased from Bio-Rad (Hercules, CA, U.S.A.). NANOpure water (18.2 QM) was used for all aqueous solution reactions.

Synthesis of ssDNA (polyT) Using TdT. The reaction mixture included 1 µM Cy5-labeled oligonucleotide initiator 5'-Cy5-dT10-3', 1 mM dTTP, and 1 U/µL TdT in TdT buffer (1×, 100 mM potassium cacodylate, 1 mM CoCl$_2$, and 0.2 mM DTT, pH 7.2). The reaction mixture was incubated at 37° C. for 2 h and terminated by heating at 90° C. for 3 min, followed with purification using a Microcon-10 kDa centrifugal filter unit. Product of this reaction: Cy5dT10-poly(dT)$_n$.

End-Functionalization of ssDNA Using TdT. The reaction mixture included 1 µM synthesized 5'-Cy5-polyT-3', 20 µMNH$_2$-dUTP (aldehyde-dUTP, alkyne-dUTP, DBCO-dUTP, FITC-dUTP, or Cy3-dUTP), and 1 U/µL TdT in TdT buffer. The reaction mixture was incubated at 37° C. for 2 h and terminated by heating at 90° C. for 3 min, followed with purification using a Microcon-10 kDa centrifugal filter unit. The product of this reaction: Cy5poly(dT)$_n$-(unnatural nucleotide). According to the type of nucleotide used, the sequence of the third block will vary. For example, if $NH_2$-dUTP is used, the product will be: Cy5poly(dT)$_n$-poly($NH_2$dU).

Synthesis of ssDNA with Various Densities of Unnatural Nucleotides ($NH_2$-dUTP, CHO-dUTP, alkyne-dUTP, DBCO-dUTP, FITC-dUTP, and Cy3-dUTP). The reaction mixture included 1 μM 5'-Cy5-dT10-3', 1 mM nucleotides (dTTP+unnatural nucleotides) with a range of ratios of unnatural nucleotides to dTTP (0.1, 0.2, 0.5, 1.0, and 2.0 (only for $NH_2$-dUTP)) and 1 U/μL TdT in TdT buffer. The reaction mixture was incubated at 37° C. for 2 h and terminated by heating at 90° C. for 3 min, followed by purification using a Microcon-10 kDa centrifugal filter unit. The product of this reaction: Cy5dT10-poly(dT-co-unnatural nucleotide).

Sulfo-Cy3 NHS Ester and 3-Sulfo-N-succinimidyl Benzoate Coupling on Synthesized Poly(T-co-$NH_2$). The reaction mixture included of 1.25 μM poly(T-co-$NH_2$) (feeding ratio of $NH_2$-dUTP/dTTP=0.1, 0.2, 0.5, 1.0 and 2.0) and sulfo-Cy3 NHS ester or 3-sulfo-N-succinimidyl benzoate (300 μM, 600 μM, 1.125 mM, 1.67 mM, and 2.2 mM) in a 9/10 reaction volume of 100 mM sodium bicarbonate buffer (pH=8.5) and 1/10 reaction volume of DMF. The reaction mixture was incubated at room temperature in a shaker overnight, followed by purification using illustra ProbeQuant G-50 microcolumns and a Microcon-10 kDa centrifugal filter unit.

Copper-Catalyzed Click Reaction on Synthesized Poly(T-co-alkyne). The reaction mixture included 0.25 μM poly(T-co-alkyne), 0.1 M triethylammonium acetate buffer, pH 7.0, 0.1 mM azide-Cy3, 0.5 mM ascorbic acid, and 0.5 mM copper(II)-TBTA in water and DMSO (1:1 in volume). The reaction mixture was degassed by bubbling $N_2$ gas for 2 min and then incubated at room temperature in a shaker overnight, followed by purification using illustra ProbeQuant G-50 micro columns and a Microcon-10 kDa centrifugal filter unit.

Copper-Free Click Reaction on Synthesized Poly(T-co-DBCO). The reaction mixture included 0.35 μM poly(T-co-DBCO) and 62.5 μM azide-Cy3 in H2O and t-BuOH (1:1 in volume). The reaction mixture was incubated at room temperature in a shaker overnight, followed with purification using illustra ProbeQuant G-50 micro columns and a Microcon-10 kDa centrifugal filter unit.

Degradation of ssDNA in the Presence of Exo- and Endonucleases. The degradation reaction mixture included 64 ng/μL (or 100 ng/μL) synthesized ssDNA, 0.02 U/μL exonuclease I (or 0.02 U/μL DNase I) in exonuclease I reaction buffer (1×, 67 mM Glycine-KOH, 6.7 mM $MgCl_2$, 10 mM 3-ME, pH 9.5 @ 25° C.) or DNase I reaction buffer (1×, 10 mM Tris-HCl, 2.5 mM $MgCl_2$, 0.5 mM $CaCl_2$), pH 7.6 @ 25° C.). The mixture was incubated at 37° C. At each time point, 4 μL was taken and added into 2 μL of 100 mM EDTA followed by heating at 90° C. for 3 min. All samples were analyzed by polyacrylamide gel electrophoresis.

Stability of ssDNA in human serum. The degradation reaction mixture included 30 ng/μL synthesized polyT (poly(T-co-$NH_2$) 0.5 or poly(T-co-Cy3) 0.5 in 85% human serum. The mixture was incubated at 37° C. for up to 3 days. At each time point, 1 μL was taken and added to 4 μL of 1×TBE and 5 μL of 2× urea sample loading buffer (1×, 89 mM Tris-HCl, 89 mM boric acid, 2 mM EDTA, 7 M urea, 12% Ficoll, pH 8.0). All samples were analyzed by agarose gel electrophoresis.

Characterization. Gel electrophoresis was conducted on a mini-PROTEAN tetra vertical electrophoresis cell by loading a 2 μL sample (~0.2 μM) and 2×RNA loading buffer (loading dyes were removed) into a 10% Mini-PROTEAN TBE gel purchased from Bio-Rad Laboratories, and then applying 130 V for 45 min. The gels were imaged with a Typhoon 9410 scanner (GE Healthcare Life Science, Piscataway, NJ) at 633 nm (Cy5) or 532 nm (Cy3) laser excitation. The fluorescence intensities of CHO, FITC, Cy5, and Cy3 were measured on a Nanodrop 3300 fluorescence spectrometer (Thermo Scientific). The concentration of ssDNA was measured on a Nanodrop 1000 UV-vis spectrophotometer (Thermo Scientific).

All-Atom Molecular Dynamics (MD) Simulations. Nucleic Acid Builder (NAB) software was used to generate a 40-mer of the Bform adenine-thymine double helix. The complementary adenine strand was subsequently deleted using BIOVIA Discover Studio, to create a 40-mer single-stranded thymine DNA molecule (polyT). Using the same software, poly(T-co-$NH_2$) and poly(T-co-Cy3) were created by replacing the methyl group of the thymine with —$NH_2$ and -Cy3, respectively. Poly(T-co-$NH_2$) and poly(T-co-Cy3) were formed with unnatural nucleotide densities of 5%, 7.5%, 20%, 35%, and 45% to stay consistent with experiment. The unnatural nucleotide placement was chosen randomly but kept consistent between poly(T-co-$NH_2$) and poly(T-co-Cy3). The partial charges for poly(T-co-$NH_2$) and poly(T-co-Cy3) were calculated using GAMESS-US and the RESP charge method (Red Server).

PolyT, poly(T-co-$NH_2$), and poly(T-co-Cy3) were simulated with the AMBER99 force field and the Generalized Born (GB) implicit solvent model at a 50 mM salt concentration. While there has not been a systemic evaluation of DNA in implicit solvent, improvements in the GB model have been shown to accurately predict the energetics and structures of nucleic acids. The generalized amber force field (GAFF) was used for the unnatural nucleotides. All starting structures for implicit simulations were subjected to minimization for 10000 steps, followed by an unconstrained heating to 300 K, and an MD equilibration using a Berendsen thermostat. The production MD runs were performed at 300 K for 300 ns using a 1 fs time step. Our simulation setup was validated via the agreement between the simulations and Forster Resonance Energy Transfer (FRET) measurements of the polyT end-to-end distance as well as the agreement between the simulations and Small Angle X-ray Scattering (SAXS) measurements of radius of gyration ($R_g$).

Analysis of All-Atom MD Simulations. The mass-weighted root-mean-square fluctuations (RMSF) was calculated per residue for each ssDNA strand's backbone with the CPPTRAJ 15 module in the AMBER 16 package. RMSF represents the positional standard deviation with reference to the average coordinates over the last 100 ns of the simulation trajectory. The per-residue, backbone RMSF values were summed for all modified nucleotides and their adjacent nucleotides in each ssDNA strand. A ΔRMSF value is reported based on equation (1):

$$\Delta RMSF = \sum_{R_N} RMSF_{PolyT_M(R_N)} + \\ RMSF_{PolyT_M(R_N-1)} + RMSF_{PolyT_M(R_N+1)} - \\ \sum_{R_N} RMSF_{PolyT(R_N)} + RMSF_{PolyT(R_N-1)} + RMSE_{PolyT(R_N+1)}$$

Equation (1)

where RN represents the set of modified nucleobases, polyTM represents the modified ssDNA strands (i.e., poly (T-co-NH$_2$) and poly(T-co-Cy3)), and polyT represents unmodified ssDNA strands. Each summation counted each residue a maximum of one time, thus, RN≠RN−1≠RN+1 across each set of modified nucleotides. Solvent accessible surface area (SASA) was calculated via an in-house TCL script and VMD 1.9.2.77 The SASA was calculated for the ssDNA backbones with a commonly used probe radius of 1.4 Å to elucidate the steric hindrance associated with ssDNA's conformation and incorporation of unnatural nucleotides.

Further details of this Example can be found in Gu et al., "Enzymatic synthesis of nucleobase-modified single-stranded DNA offers tunable resistance to nuclease degradation," Biomacromolecules 2018, 19, 3525-3535 (including the supplemental/supporting information), which is incorporated by reference herein in its entirety.

Results & Discussion

3' End-Functionalized ssDNA in the Presence of Exonuclease I. To investigate the effects of unnatural nucleobase size on ssDNA stability upon exposure to exonuclease, we separately modified the 3'-end of polyT with six different types of unnatural nucleotides: NH$_2$-dUTP, CHO-dUTP, alkyne-dUTP, DBCO-dUTP, FITC-dUTP, and Cy3-dUTP using TdT enzymatic polymerization. The polyTs were successfully tail-functionalized with these base-modified nucleotides at the 3'-end. These 3'-end functionalized ssDNAs were treated with exonuclease I. Unmodified polyT was degraded fastest while ssDNA with bulky nucleobases at their 3'-end (DBCO, FITC, and Cy3 modified polyT) were degraded significantly slower. These results suggest that bulky nucleobases increase the resistance of 3' end-functionalized ssDNA to exonuclease I degradation.

Exonuclease I is 3'-5' exonuclease and, thus, has to interact with the 3'-terminal nucleotide first before sequentially cleaving subsequent nucleotides in a ssDNA chain. During the hydrolytic degradation, Exonuclease I interacts with both the ssDNA backbone and the nucleobases; more specifically, the terminal nucleobase binds to a hydrophobic pocket formed by the side chains of exonuclease I. Therefore, certain unnatural nucleobases present at the 3'-end may not fit the hydrophobic pocket of exonuclease I well. This disrupts enzyme binding with the ssDNA backbone and thus prevents the effective hydrolysis of the phosphodiester bond. Compared to the relatively small, alkyne-, CHO-, and NH$_2$-functionalized nucleobases, the bulky, DBCO-, FITC-, and Cy3-functionalized nucleobases fit more poorly into the enzyme's hydrophobic pocket, this interferes with nuclease binding even more significantly, which is manifest in an enhanced stability of ssDNA upon exposure to exonuclease I. Although exonuclease I is not a sequence-specific nuclease, the size of the nucleobase modification still plays a significant role for the DNA cleavage by exonuclease. We note that DBCO and FITC are both hydrophobic, which may induce ssDNA self-assembly. If that were the case, the 3'-end of the ssDNA is buried in the hydrophobic core of the resulting DNA micelles, and the observed enhanced resistance to nuclease degradation could thus largely arise from the micellar self-assembly rather than from the poor fit between an unnatural nucleobase and the exonuclease. To rule out this possibility, we decreased the concentration of polyT-(DBCO)$_n$ and polyT-(FITC)$_n$ in the degradation system to prevent self-assembly (no assemblies were detected using dynamic light scattering). Compared to polyT control, both functionalized ssDNAs at low concentration, where the ssDNA would exist as free polymer chains, still showed significant resistance to degradation by exonuclease I. Hence, it is likely that the unnatural nucleobases present at the 3'-end disrupt DNA-exonuclease binding and retard DNA degradation rather than the lack of access of nuclease to the 3'-end of the ssDNA.

Internally Functionalized ssDNA in the Presence of Exonuclease I and DNase I. To investigate the effects of unnatural nucleobase density and size on ssDNA stability upon exposure to both exo- and endonuclease, we synthesized ssDNA with a controlled density of unnatural nucleobases along the polynucleotide chain. We refer to this type of ssDNA as "internally-functionalized ssDNA". We first studied the incorporation efficiency of six different, unnatural nucleotides. In these experiments, we kept the nucleotide (monomer)/oligonucleotide (initiator) ratio constant at 1000/1 and systematically varied the feed ratio of unnatural nucleotides/dTTP from 0.1 to 2.0. As the feed ratio of unnatural nucleotides/dTTP increases (as shown in Table 1), the MW of the synthesized ssDNA decreases dramatically, except for the incorporation of NH$_2$-dUTP. Some bulky, unnatural nucleotides (DBCO-dUTP and FITC-dUTP) nearly prohibited enzymatic polymerization when the unnatural nucleotide/dTTP ratio reached 0.5.

TABLE 1

Average degree of polymerization of ssDNA with different types of unnatural nucleotides.

| | feed ratio of unnatural nucleotide/dTTP | | | | |
|---|---|---|---|---|---|
| | 0.1 | 0.2 | 0.5 | 1.0 | 2.0 |
| unnatural nucleotides | avg number of nucleotides per chain (degree of polymerization) | | | | |
| NH$_2$-dUTP | ~730 | ~740 | ~750 | ~690 | ~640 |
| CHO-dUTP | ~350 | ~260 | ~150 | ~100 | |
| alkyne-dUTP | ~640 | ~480 | ~200 | ~130 | |
| DBCO-dUTP | ~260 | ~110 | | | |
| FITC-dUTP | ~180 | ~130 | | | |
| Cy3-dUTP | ~490 | ~260 | ~180 | ~140 | |
| no unnatural nucleotides (PolyT) | ~800 | | | | |

In addition, we calculated the density of incorporated unnatural nucleotides (Table 2). Compared to the other unnatural nucleotides, NH$_2$-dUTP had the highest incorporation density, especially when the ratio of unnatural nucleotide/dTTP was equal or larger than 0.5. Differences in the incorporation efficiency between natural and unnatural nucleotides may occur. For other DNA polymerases it has been demonstrated that the modification of the nucleobase structure impacts the incorporation efficiency of such modified nucleotides into the DNA strand. In many cases, the structural change of the enzyme-substrate complex renders nucleobase-modified nucleotides a worse substrate for DNA polymerases. However, other nucleobase-modified nucleotides were tolerated or even more efficiently processed, because the interactions between modified nucleobase and amino acids near the active site stabilize the enzyme-substrate complex. A similar argument may be invoked for TdT to explain why one nucleobase-modified nucleotide is better accepted than another. However, to gain structural insights into the processing of nucleobase-modified nucleotides by TdT requires further crystal structure analysis of the TdT-substrate complex.

TABLE 2

Incorporation density of different types of unnatural nucleotides in ssDNA.

| | feed ratio of unnatural nucleotide/dTTP | | | | |
|---|---|---|---|---|---|
| | 0.1 | 0.2 | 0.5 | 1.0 | 2.0 |
| unnatural nucleotides | density of incorporated unnatural nucleotides (per 100 nucleotides) | | | | |
| $NH_2$-dUTP | 4.4 ± 0.2 | 7.3 ± 1.3 | 20.8 ± 3.9 | 36.2 ± 0.9 | 46.3 ± 2.0 |
| CHO-dUTP | 6.3 | 4.2 | 2.7 | 1.9 | |
| alkyne-dUTP | 2.2 | 2.2 | | | |
| DBCO-dUTP | 2.7 | | | | |
| FITC-dUTP | 10.2 | 7.2 | | | |
| Cy3-dUTP | 4.3 | 7.2 | 4.1 | 2.6 | |

Because $NH_2$-dUTP exhibited the highest incorporation efficiency and because it can be readily functionalized to tune the size of unnatural nucleobase, we used it for the degradation study of internally functionalized ssDNA.

To investigate the effects of $NH_2$-functionalization density on ssDNA resistance to nuclease degradation, we treated the $NH_2$-internally functionalized ssDNA with two types of nucleases: Exonuclease I and DNase I. As shown in Tables 3 and 4, after treatment with the two nucleases, the rate and extent of degradation correlates inversely with the incorporation density of $NH_2$-dUTP. Although more complex models for exonuclease degradation are available, we chose a simple exponential decay function fit as we are interested in comparing the half-life of different synthesized ssDNA. This simple model fits the data well and yields an estimate of the half-life which thus provides a single, useful parameter that enables the quantitative comparison across different polynucleotides.

The data for $NH_2$-internally functionalized ssDNA in Table 3 show that the half-life increases with increasing incorporation density of $NH_2$-dUTP, which indicates the increased resistance of ssDNA to exonuclease degradation with increasing $NH_2$-dUTP incorporation density. This is because that for internally functionalized ssDNA, as the degradation proceeds, each incorporated $NH_2$-dUTP along the ssDNA chain can interfere with enzyme binding and will lead to a stepwise, retarded degradation. Therefore, when the density of incorporated $NH_2$-dUTP increases, the degradation rate of modified ssDNA will decrease.

TABLE 3

Half-life of polynucleotides upon exposure to Exonuclease I.

| | $t$ half $^{(min)}$ | | $t$ half $^{(min)}$ |
|---|---|---|---|
| polyT | 3.2 ± 0.2 | polyT | 3.2 ± 0.2 |
| poly(T-co-$NH_2$) 0.1 | 23.1 ± 5.6 | poly(T-co-Cy3) 0.1 | 76.4 ± 4.1 |
| poly(T-co-$NH_2$) 0.2 | 38.4 ± 11.7 | poly(T-co-Cy3) 0.2 | 126.6 ± 55.2 |
| poly(T-co-$NH_2$) 0.5 | 104.9 ± 31.0 | poly(T-co-Cy3) 0.5 | 265.3 ± 36.1 |
| poly(T-co-$NH_2$) 1.0 | 273.2 ± 37.5 | poly(T-co-Cy3) 1.0 | >360 |
| poly(T-co-$NH_2$) 2.0 | >360 | poly(T-co-Cy3) 2.0 | >360 |

$^a$Poly(T-co-$NH_2$) X refers to ssDNA synthesized with a feed radio of $NH_2$-dUTP/dTTP = X. Poly(T-co-Cy3) X refers to ssDNA after Cy3 NHS-ester conjugation to poly(T-co-$NH_2$) X (assuming a conjugation efficiency of 100%).

In contrast, in the endonuclease treatment, significant resistance to degradation was achieved only at high $NH_2$-dUTP incorporation density. DNase I indiscriminately cleaves the phosphate bonds within a ssDNA chain. Previous research showed that when DNase I binds the DNA backbone, the nucleobases typically point away from the DNase I without specific interactions.

Although the nucleobases seem not to interact with DNase I directly, our DNase I degradation results show that increasing the incorporation density of $NH_2$-dUTP enhances ssDNA resistance to endonuclease degradation significantly, especially at high incorporation density. In addition, ssDNA degradation by DNase I is likely correlated with local DNA flexibility, and several studies showed that increased conformational constraint of ssDNA can lead to enhanced resistance to DNase I degradation. Therefore, the mechanism underlying the enhanced resistance to DNase I degradation in our study likely arises from the local, conformational constraint caused by the incorporated $NH_2$-dUTP. To elucidate the local chain flexibility of ssDNA as a function of unnatural nucleobase (—$NH_2$) density, MD simulations were used to determine the local, mass-weighted root-mean-square fluctuations (RMSF), associated with the unnatural nucleotides in the ssDNA backbone. The ΔRMSF of poly(T-co-NH2), compared to polyT, decreases with increasing unnatural nucleobase density, which means more local regions of poly(T-co-NH2) become inflexible. Therefore, when the incorporation density of NH2-dUTP is low (4.4±0.2% and 7.3±1.3%, as shown in Table 4), DNase I has a high probability of binding to a conformationally unconstrained ssDNA chain segment and, thus, readily cleaves the ssDNA strand into smaller ssDNA fragments. As the $NH_2$-dUTP incorporation density increases, the increasing local conformational constraints in ssDNA make effective DNase I binding less likely and thus prevent ssDNA cleavage.

TABLE 4

Half-life of polynucleotides upon exposure to DNase I.

| | $t$ half $^{(min)}$ | | $t$ half $^{(min)}$ |
|---|---|---|---|
| polyT | 9.3 ± 0.2 | polyT | 9.3 ± 0.2 |
| poly(T-co-$NH_2$) 0.1 | 9.4 ± 0.7 | poly(T-co-Cy3) 0.1 | |
| poly(T-co-$NH_2$) 0.2 | 10.6 ± 0.5 | poly(T-co-Cy3) 0.2 | 17.0 ± 3.5 |
| poly(T-co-$NH_2$) 0.5 | 17.0 ± 0.2 | poly(T-co-Cy3) 0.5 | 25.4 ± 3.2 |
| poly(T-co-$NH_2$) 1.0 | 34.2 ± 9.2 | poly(T-co-Cy3) 1.0 | 30.4 ± 1.6 |
| poly(T-co-$NH_2$) 2.0 | 73.2 ± 13.2 | poly(T-co-Cy3) 2.0 | 63.2 ± 12.9 |

Furthermore, to investigate the size effect of unnatural nucleobase on resistance of internally functionalized ssDNA to nuclease degradation, we conjugated Cy3 groups onto the poly(T-co-$NH_2$) via NHS ester coupling chemistry to increase the unnatural nucleobase size. After this modification, the ssDNA resistance to both exo- and endonuclease degradation were further enhanced (Tables 3 and 4). Specifically, in exonuclease degradation, the change in the degradation rate for poly(T-co-$NH_2$) is larger than that for poly(T-co-Cy3), which suggests that exonuclease faces additional difficulties in binding to an unnatural nucleotide with large nucleobase modification. In contrast, for endonuclease degradation, the change in the degradation rate for poly(T-co-$NH_2$) is only slightly greater than that for poly(T-co-Cy3). This suggests that the size of the unnatural nucleobase may not play a significant role in determining the resistance of ssDNA to endonuclease degradation. This is also supported by our simulation results that show that the substantial size difference between the Cy3 moiety and $NH_2$ moiety on the nucleobase does not affect the local chain flexibility (ΔRMSF) significantly.

However, we also noticed that, unlike exonuclease I, which degrades ssDNA into single nucleotides, DNase I degrades ssDNA into small fragments. During the degradation process, DNase I not only cleaves intact ssDNA, but also further cleaves degraded ssDNA fragments. Therefore, besides the fraction of residual, intact ssDNA, the fraction and size of the degraded ssDNA fragments are also an important parameter to assess the resistance of ssDNA to DNase I degradation. However, our synthesized polyT and poly(T-co-NH$_2$) are only labeled with a Cy5 molecule at the 5' end, and thus the degraded fragments, without the Cy5 label, do not show up in the gel chromatogram. To visualize these degraded fragments by gel electrophoresis, we replaced a fraction of dTTP with other natural nucleotides (dATP, dCTP, and dGTP) in the enzymatic polymerization reaction, so that the resulting ssDNA and also the degraded fragments now have secondary structure which can trap SYBR Green staining dye. We first tested different combinations of the natural nucleotides for efficient ssDNA synthesis. We found that all ssDNA reaction products could be stained, and that the combination of dTTP, dATP, and dCTP and NH$_2$-dUTP, dATP, and dCTP resulted in the narrowest MW distributions. These latter ssDNAs were chosen for Cy3 NHS-ester conjugation and subsequent DNase I degradation analysis.

Although, after incorporating NH$_2$- or Cy3-unnatural nucleobases, the amount of intact ssDNA remaining after degradation with DNase I is about the same for all three types of copolynucleotides, the degradation patterns are very different. While degraded poly(Cy3-co-Aco incorporation density of Cy3 unnatural nucleobases, the SASA of the ssDNA backbone decreases significantly. This is in contrast to ssDNA that contains NH$_2$-dUTP. Therefore, the incorporation of Cy3 moieties makes the ssDNA backbone less accessible to endonuclease binding. Thus, both density and size of the unnatural nucleobases appear to be important factors determining the internally functionalized ssDNA resistance to endonuclease degradation.

Stability of Internally Functionalized ssDNA in Human Serum. At last, we evaluated the stability of the synthesized ssDNA in human serum mimicking the in vivo environment that contains both exonuclease and endonuclease. We chose one set of internally functionalized ssDNA (poly(T-co-NH$_2$) 0.5 and poly(T-co-Cy3) 0.5) and incubated them in 85% human serum for up to 3 days. The half-life of polyT is ~4 h (control), while the half-life of poly(T-co-NH$_2$) 0.5 increases to ~9 h. After Cy3 conjugation, the half-life of poly(T-co-Cy3) further increases to ~15 h. Thus, the NH$_2$- and Cy3-internally functionalized ssDNA are significantly more stable than unfunctionalized polyT toward degradation by human serum. This result is consistent with our stability investigations of the synthesized ssDNA in the presence of Exonuclease I or DNaseI.

In this Example, different nucleotides with modified nucleobase structure were shown to be easily and effectively incorporated into growing ssDNA using TdT enzymatic polymerization. Although the nuclease degradation of ssDNA is due to the hydrolysis of the phosphate backbone, we demonstrated that the presence of unnatural nucleobases can also impede the degradation, and does not entail modification of the sugar-phosphate backbone structure. We discovered that both the size and density of unnatural nucleobases are factors that determine the half-life of ssDNA in nuclease degradation. MD simulations show that the incorporated unnatural nucleobases induce a decrease in local ssDNA chain flexibility and accessibility of nucleases to the ssDNA backbone with increasing size and incorporation density of unnatural nucleobases. Finally, unnatural nucleobase functionalized ssDNA also showed improved resistance to nuclease degradation in human serum, which contains both exonuclease and endonuclease. Therefore, the enzymatic incorporation of unnatural nucleotides with modified nucleobase structures into ssDNA can be an effective strategy to tune and prolong the lifetime of DNA-based materials for in vivo applications.

Example 5

In Situ Enzymatic Synthesis of Aptamer Targeted Polynucleotide Drug Nanoparticles for Cancer Therapy Synthesis of Cy5-T50-poly(FU) by TdT-catalyzed enzymatic polymerization (TcEP). Upon increasing the M/I ratio to 1000, the MW remained constant at ~300 nucleotides (nts). This MW plateau is likely caused by the deactivation of TdT when only unnatural nucleotides are present in the reaction mixture. By adding multiple rounds of TdT, we can generate polyFU with length longer than 300 nts.

Synthesis and Characterization of Micellar DNA Nanoparticles (NPs). We found that FITC-dUTP is insufficiently hydrophobic to drive self-assembly. This motivated the search for another unnatural dUTP that has the proper hydrophobicity. Although Atto 425 dUTP is a fairly bulky hydrophobe, we confirmed that TdT can successfully add multiple copies to the 3' end of ssDNA chains. The polynucleotide used was Cy5-T50-poly(FU)$_n$-poly(AttodU).

Figure 5A:
FIGS. 5A-5C show (A): agarose gel electrophoresis. From left to right: Cy5T50-polyFU, Cy5T50-polyFU-AttodU (M/I=20), Cy5T50-polyFU-AttodU (M/I=50), 100 bp ladder. (B) and (C): AFM images for Cy5T50-polyFU-AttodU (M/I=10) in water, sample concentration is 0.1 µM. The monomer to initiator ratio (M/I) is the feed ratio of Atto-dUTP to the single-stranded (ss)DNA initiator (polyFU).
Figure 5B:
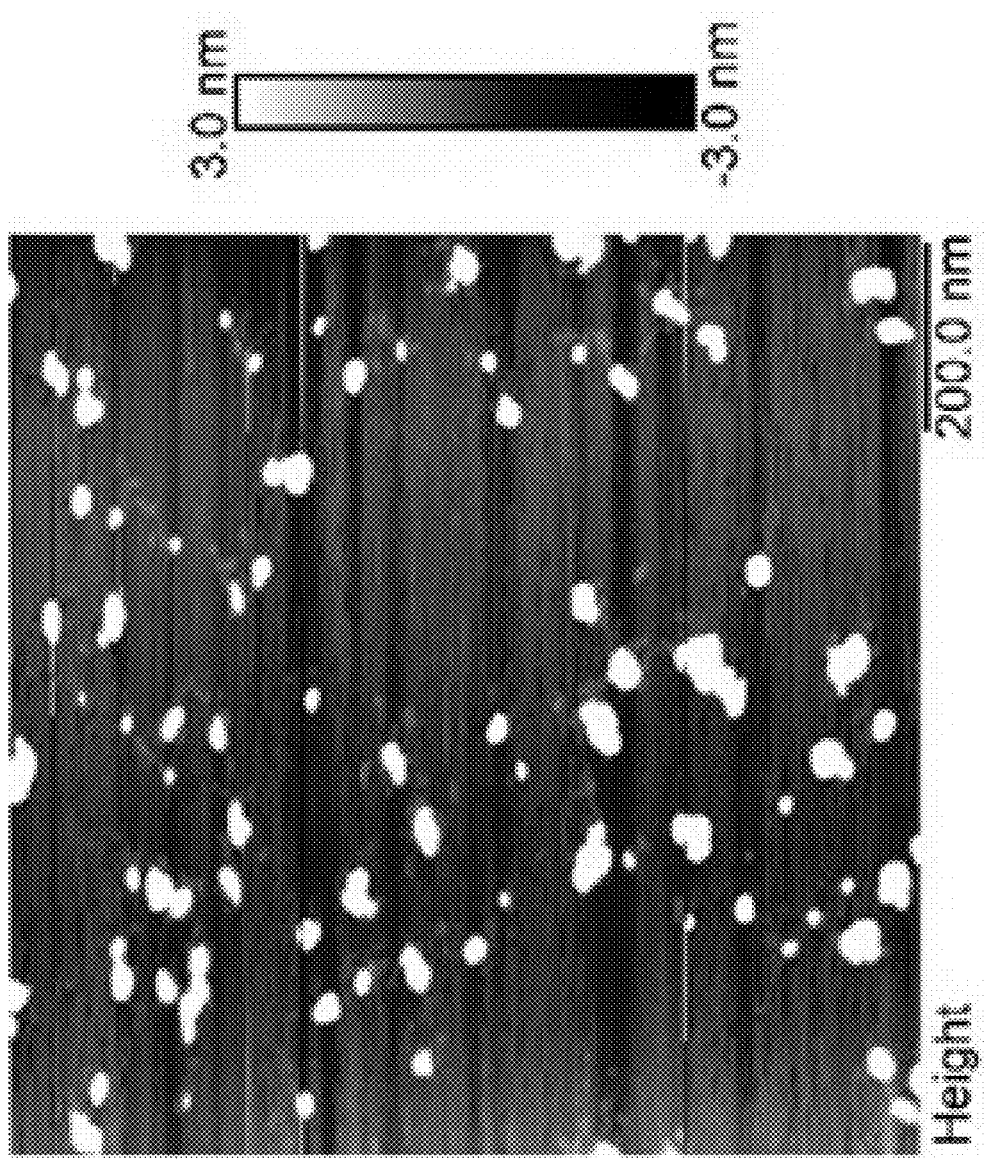
Figure 5C:
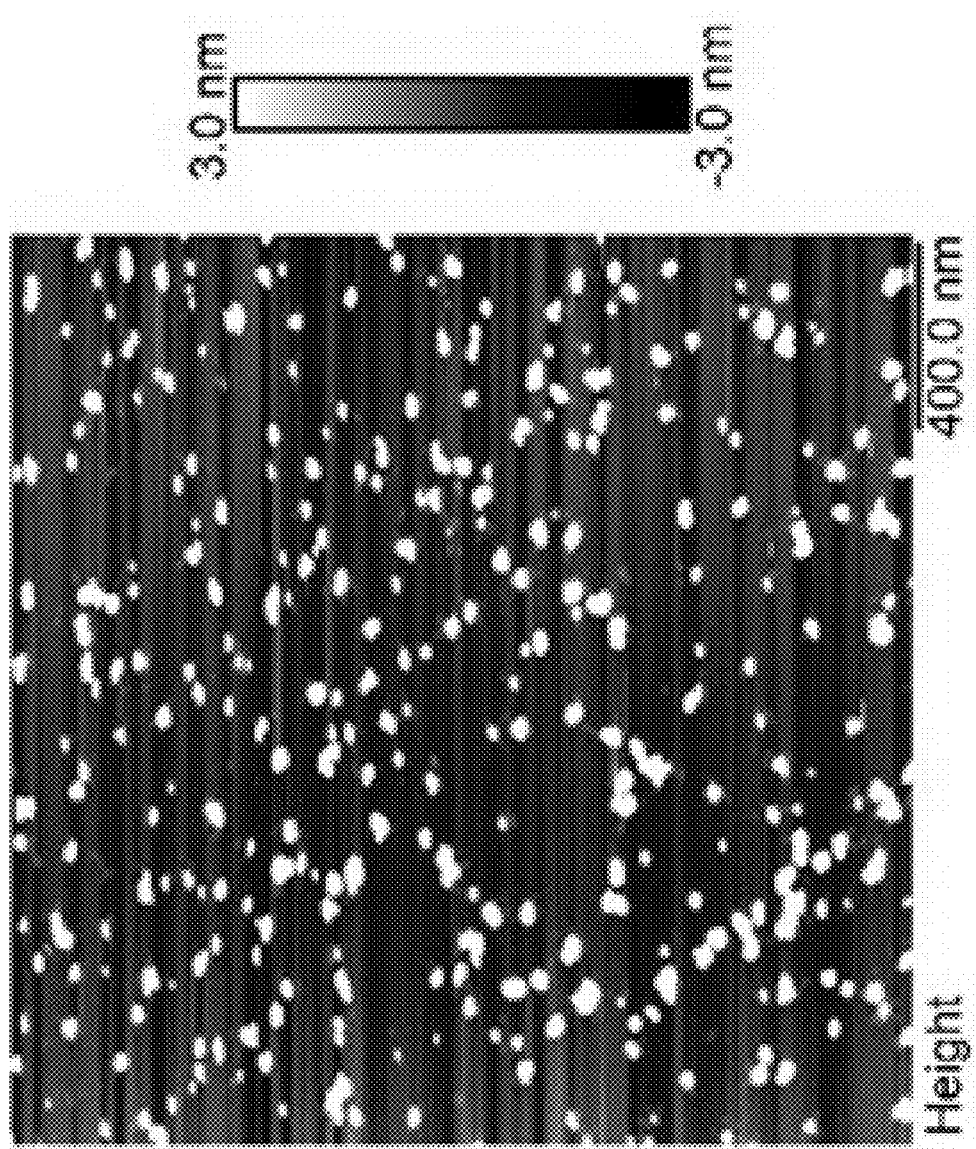

When running an agarose gel we observed that in addition to a band at the same position as Cy5T50-polyFU (e.g., disassembled strands due to electrophoresis), Cy5T50-poly(FU)-poly(AttodU) products contain smears and ladder-like bands as well as a strong signal in the wells, which both likely stem from DNA micelles (FIG. 5A). In addition, AFM images confirm the existence of micellar structures (FIG. 5B and FIG. 5C).

Figure 6A:
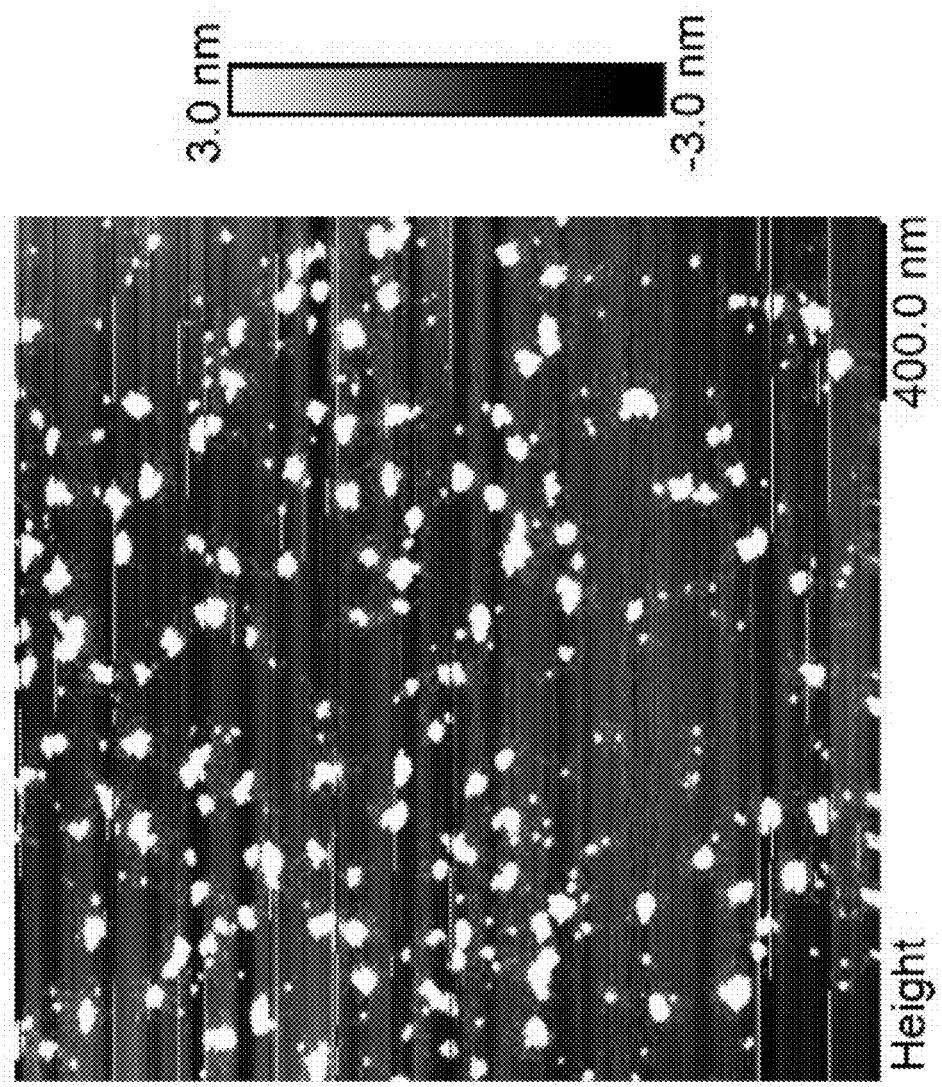
FIGS. 6A-6B are a set of AFM images for Cy5T50-polyFdU-AttodU with (A) M/I=50, and (B) M/I=300. Sample concentration is 0.1 µM, solvent is water.
Figure 6B:
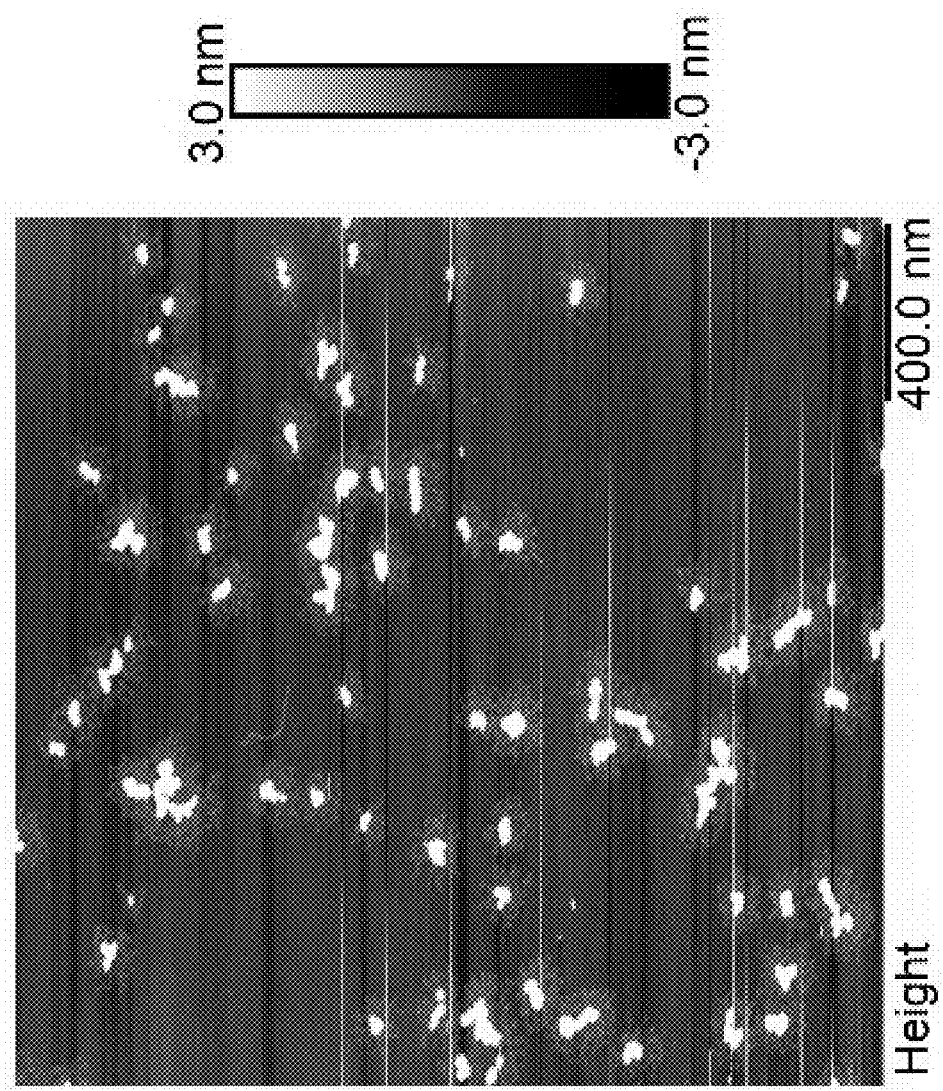
Figure 7A:
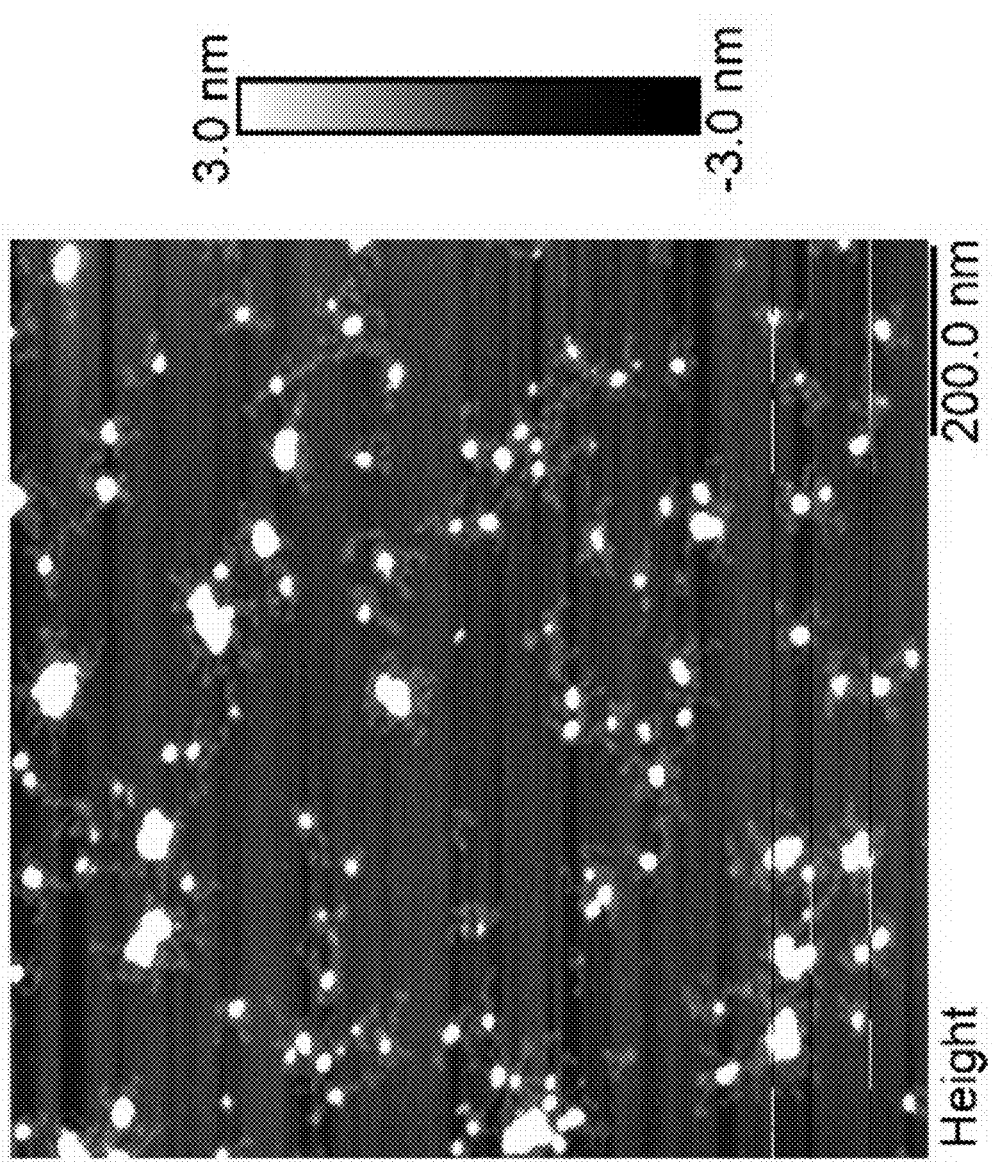
FIGS. 7A-7B are a set of AFM images for Cy5T50-polyFU-AttodU (M/I=20). Sample concentrations are (A) 0.05 µM and (B) 0.01 µM in water.
Figure 7B:
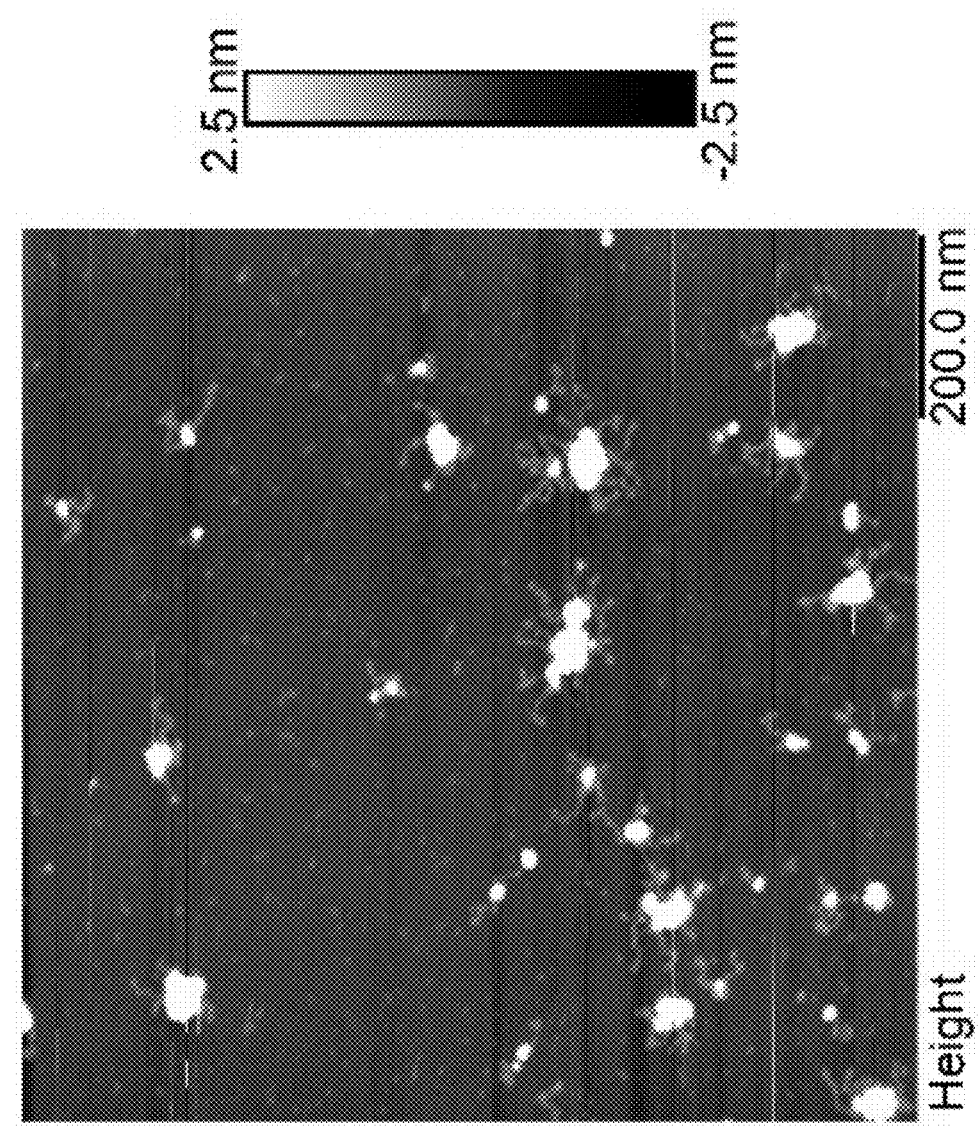

After confirming the ability of Atto 425 dUTP to drive self-assembly into micellar structures, we investigated the effect of changing the M/I ratios on micelle formation. With increased M/I ratio, the aggregation number increased. Furthermore, rod-like nanoparticles formed at a high M/I=300 (FIG. 6). We tried to estimate the CMC of the micelles by changing the sample concentration and imaging with AFM. From FIG. 7A, micellar structure appear to be still stable at 0.05 μM (50 nM), and no free chains are visible. However, at 0.01 μM (10 nM), although some micelles still form, there are free chains visible, which means that some micelles are not stable or did not form in the first place (FIG. 7B).

Figure 8A:
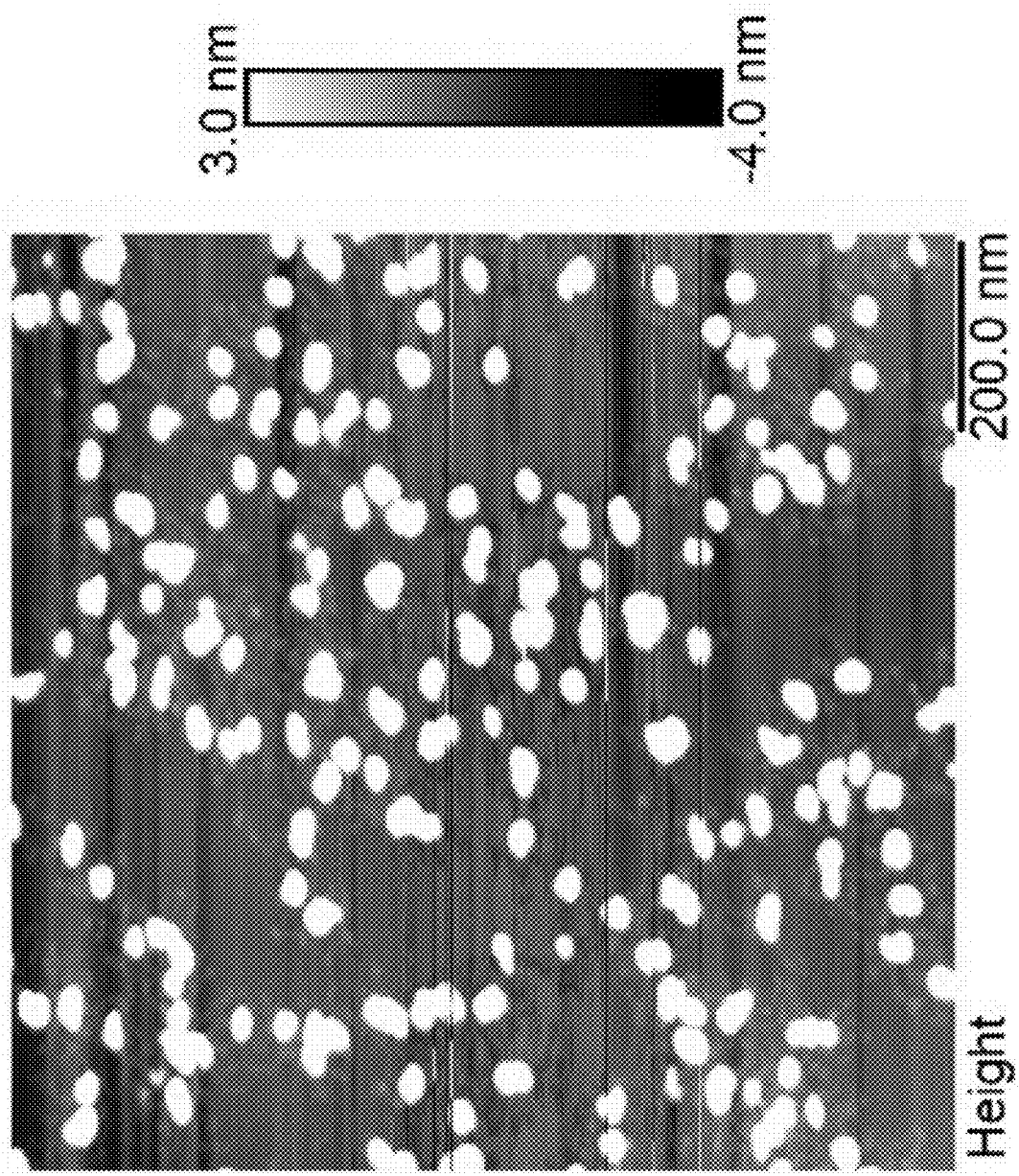
FIGS. 8A-8B are an (A) AFM image for A10-polyFU-AttodU (M/I=20). Sample concentration is 0.1 µM in water; and (B) measured height of micelles from AFM images.
Figure 8B:
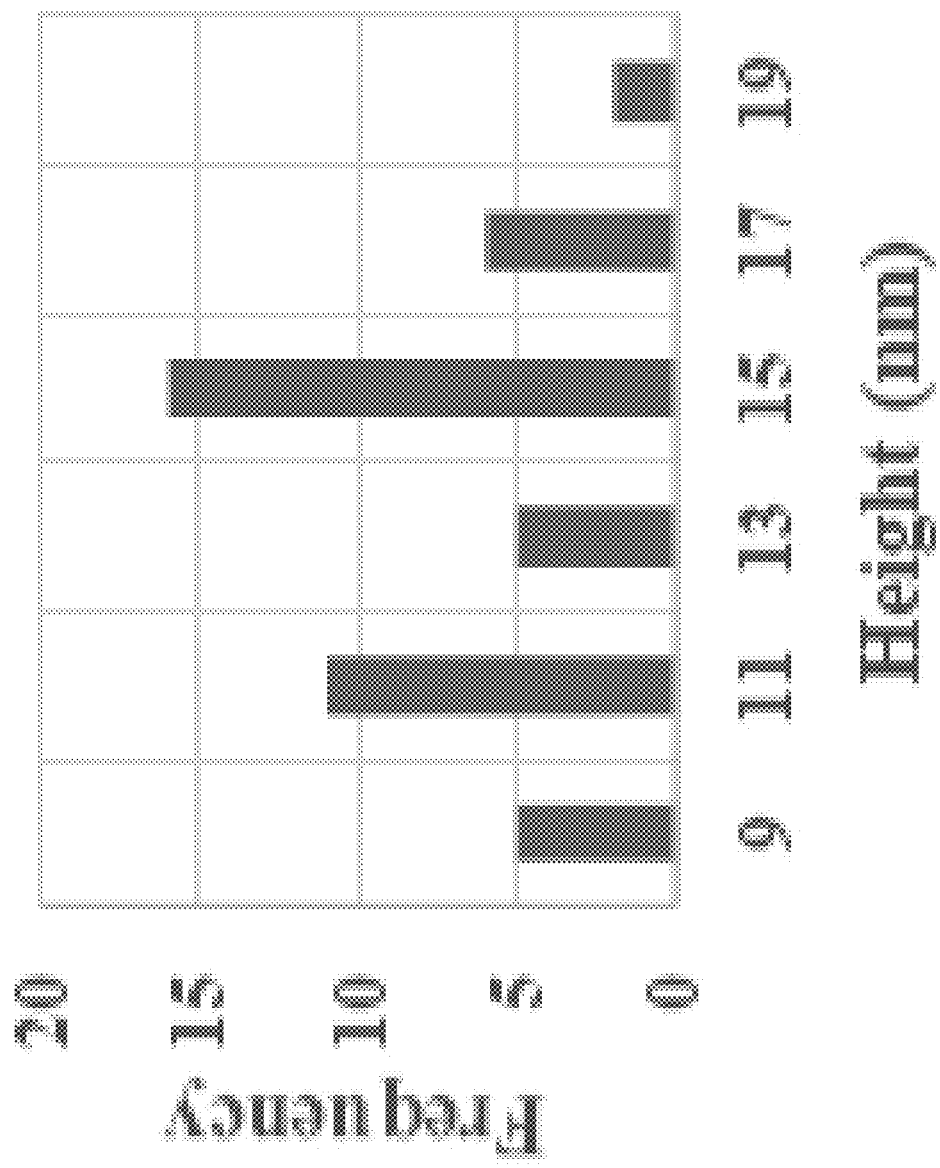

In addition, we synthesized A10-poly(FU)$_n$-poly(AttodU) (where Atto dUTP/A10-polyFU: M/I=20) and imaged with AFM. A10 had a dT4 extension at the 3'-end. Results show successful formation of micelles similar to those generated with the Cy5 initiator (FIG. 8). We measured an average dry-height of 13.5±2.8 nm from AFM images.

Figure 9A:
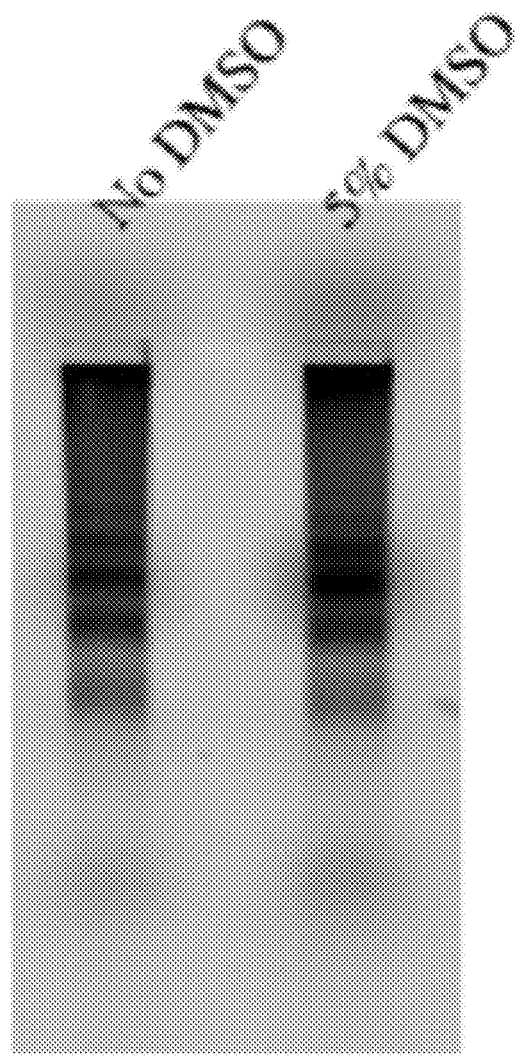
FIGS. 9A-9B are a set of agarose gel electrophoresis images showing: (A) Exonuclease I degradation of Cy5T50-polyFU-AttodU (M/I=20) micelles at 0.05 µM for 24 h. 5% DMSO was added to disassemble micelles. (B) FBS degradation of Cy5T50-polyFU-AttodU (M/I=20) micelles at 0.2 µM concentration as a function of incubation time.
Figure 9B:
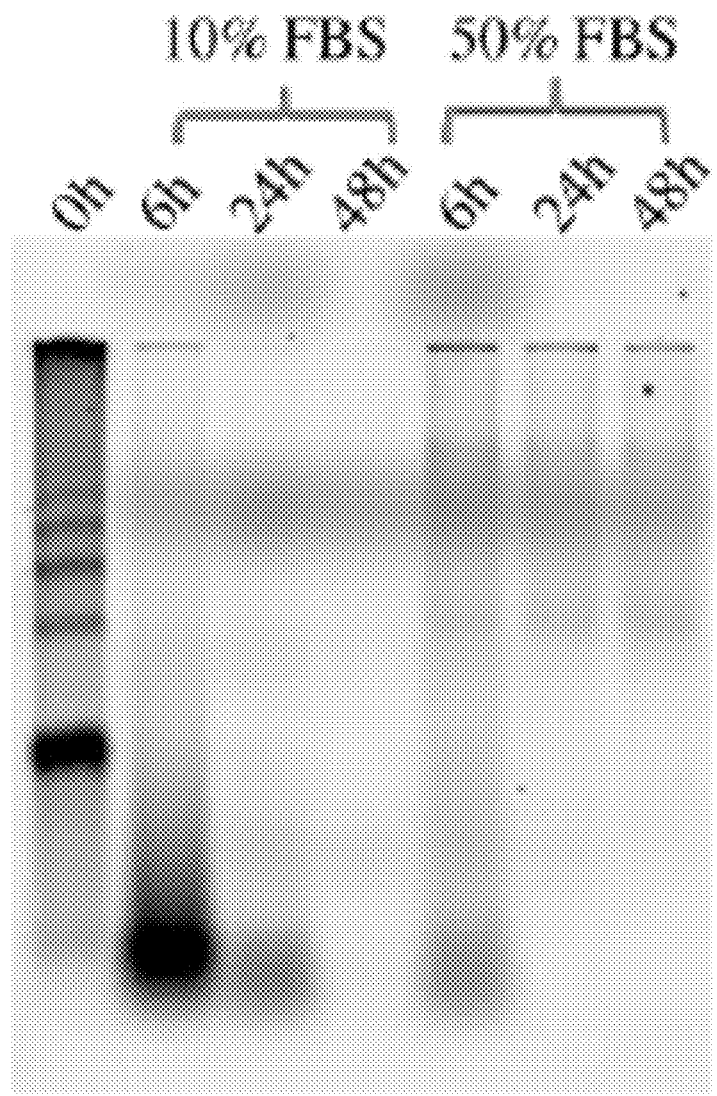

To estimate the number of Atto-dUTP on each polynucleotide chain, we tried to degrade the sample with Exonuclease I, which depolymerizes a polynucleotide chain from the 3' end. Unexpectedly, we found that our products are largely resistant to Exonuclease I even at a polynucleotide concentration as low as 0.05 μM (FIG. 9A). In addition, 5% DMSO is not effective in disassembling micelles. Next we tested the FBS resistance of the micelles at a concentration of 0.2 μM. We found, however, that the micelles are sufficiently stable to survive in 10% FBS over a duration of 6 h (FIG. 9B).

Figure 10A:
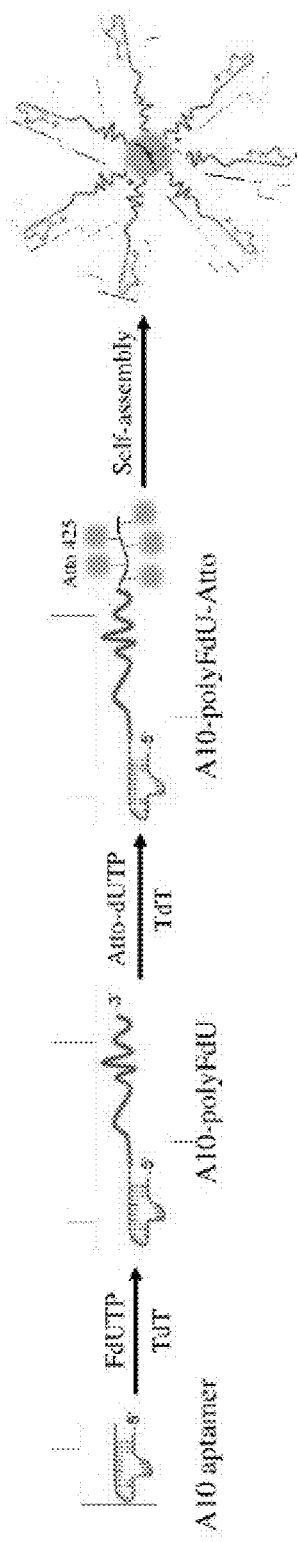
FIGS. 10A-10D are (A) a schematic illustration of the formation of an A10-PolyFU-AttodU amphiphilic block polynucleotide; and a series of AFM images for (B) A10-polyFU500-AttodU10, (C) A10-polyFU800-AttodU10, and (D) A10-polyFU1000-AttodU10. All sample concentrations are 0.1 µM in 1×PBS.
Figure 10B:
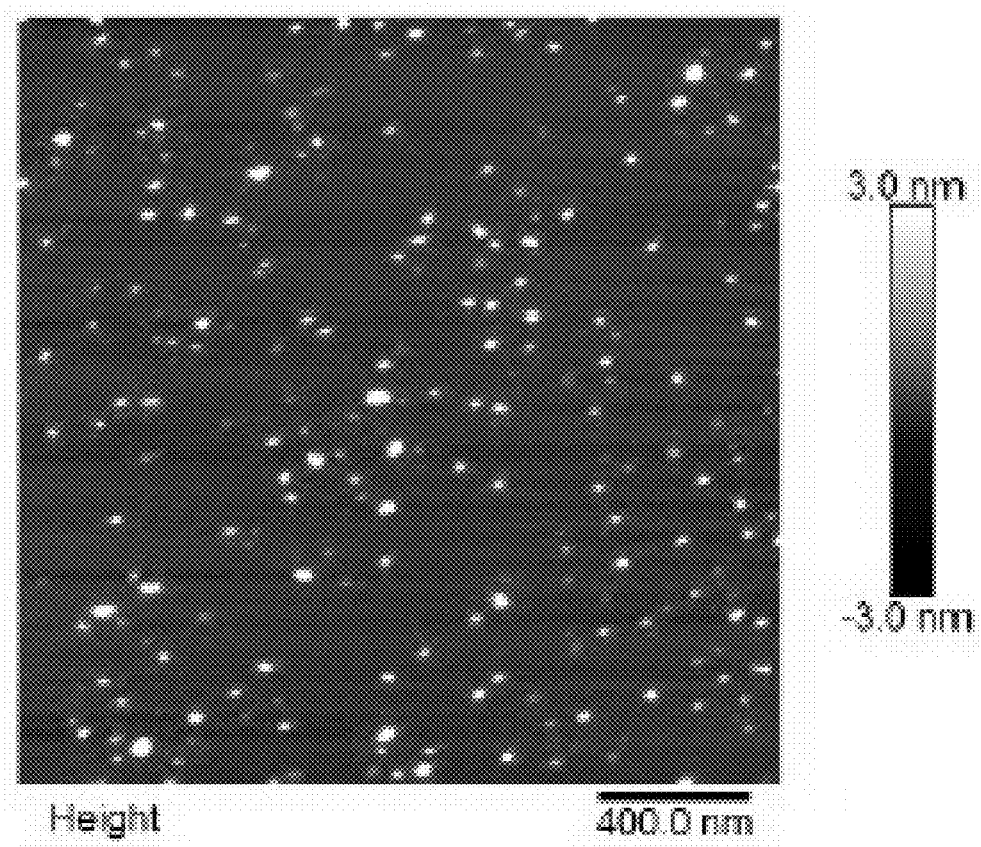
Figure 10C:
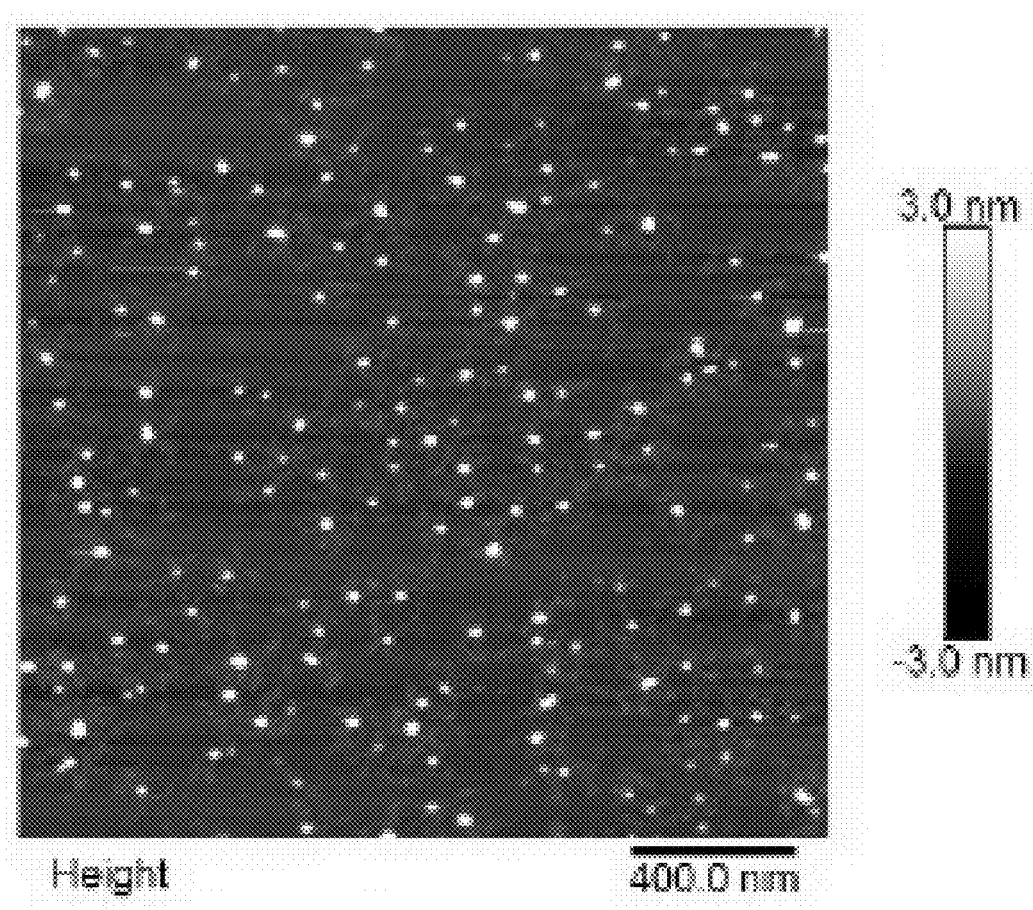
Figure 10D:
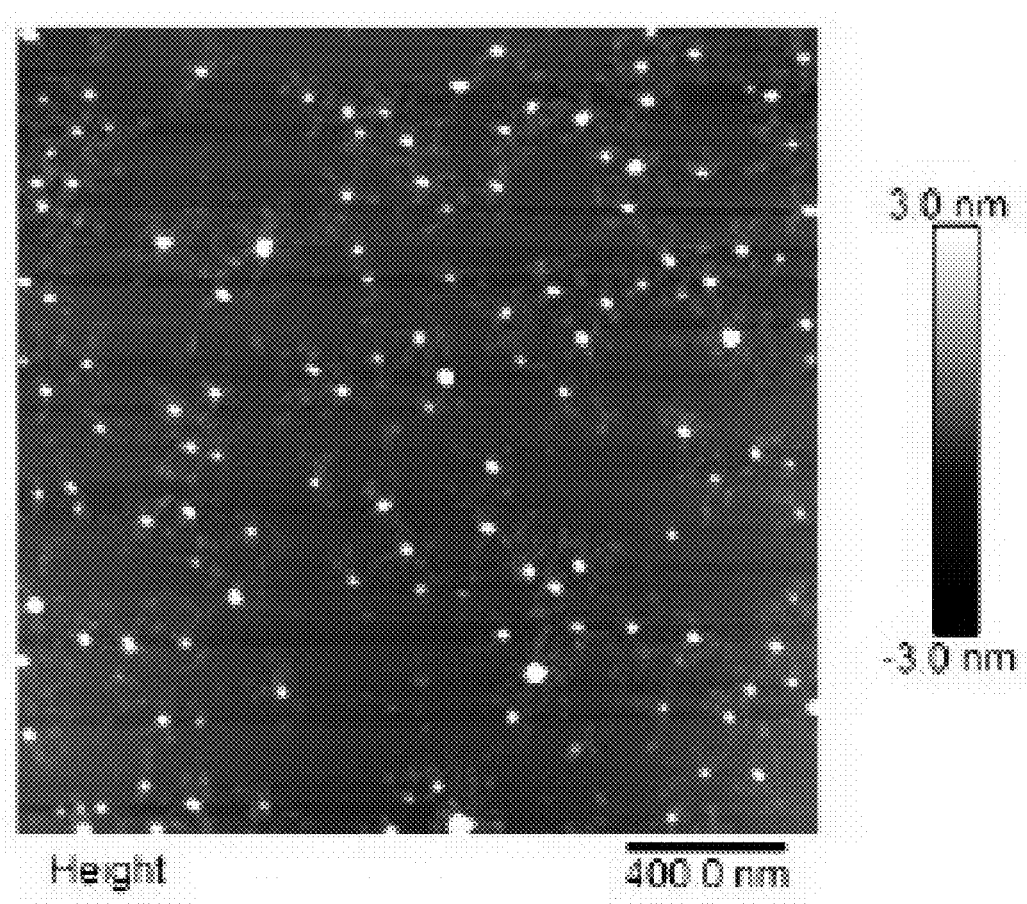
Figure 11A:
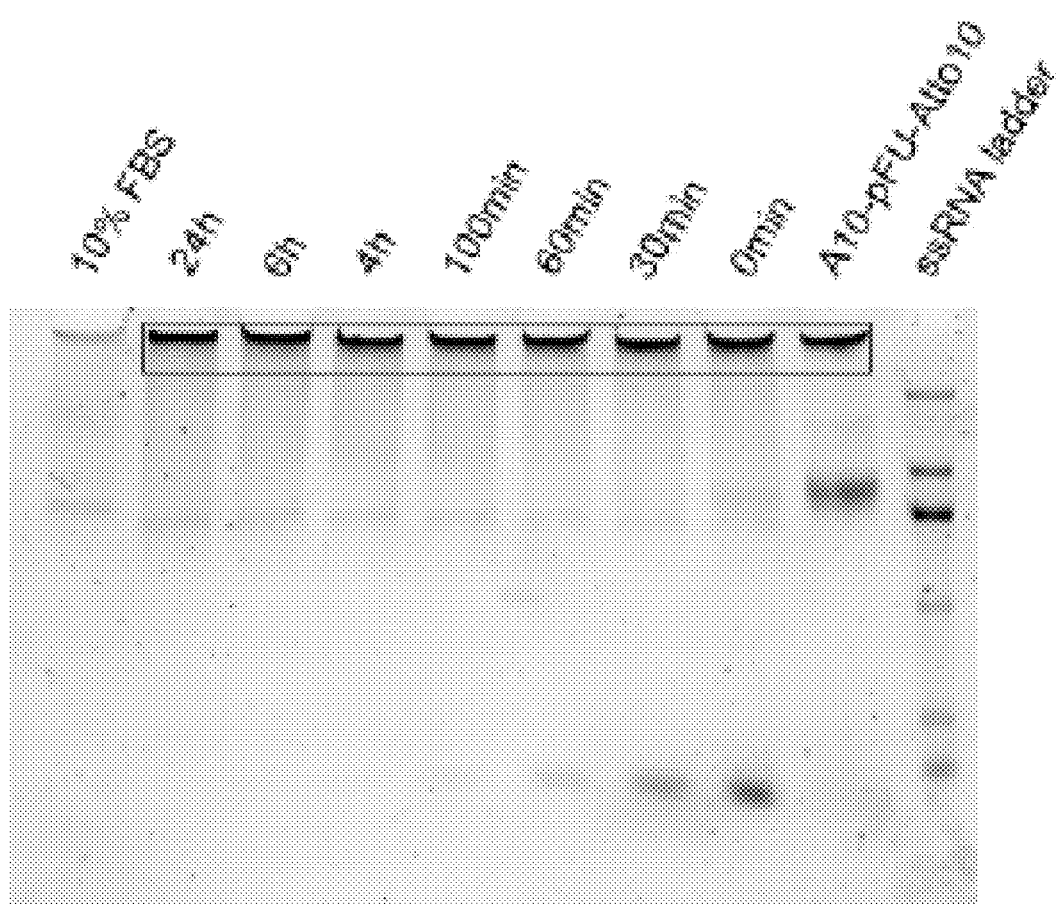
FIGS. 11A-11B are a set of 5% (Tris-borate-ethylenediaminetetraacetic acid (EDTA)) (TBE)-PAGE images for 10% fetal bovine serum (FBS) degradation of (A) A10-polyFU-AttodU10, and (B) A10-polyFU at different time points. Final concentrations of samples are both 1 µM.
Figure 11B:
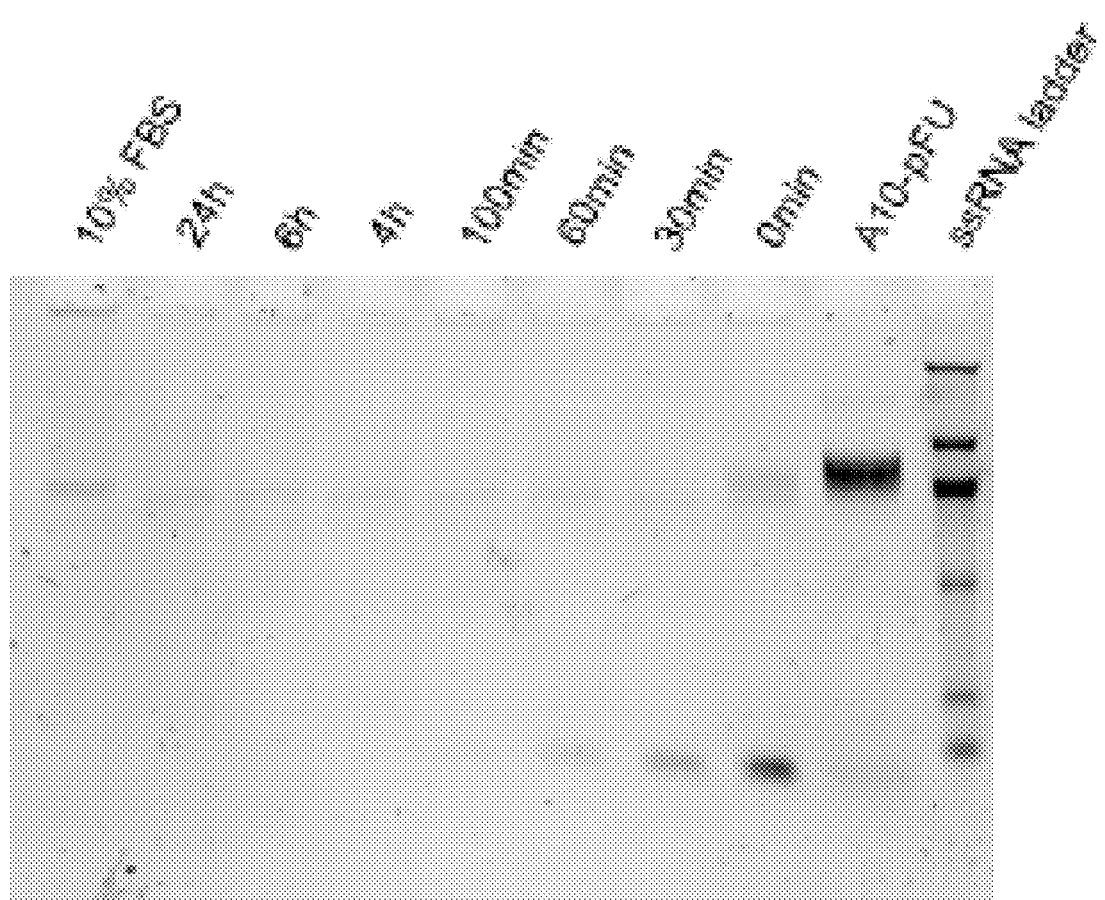
Figure 12A:
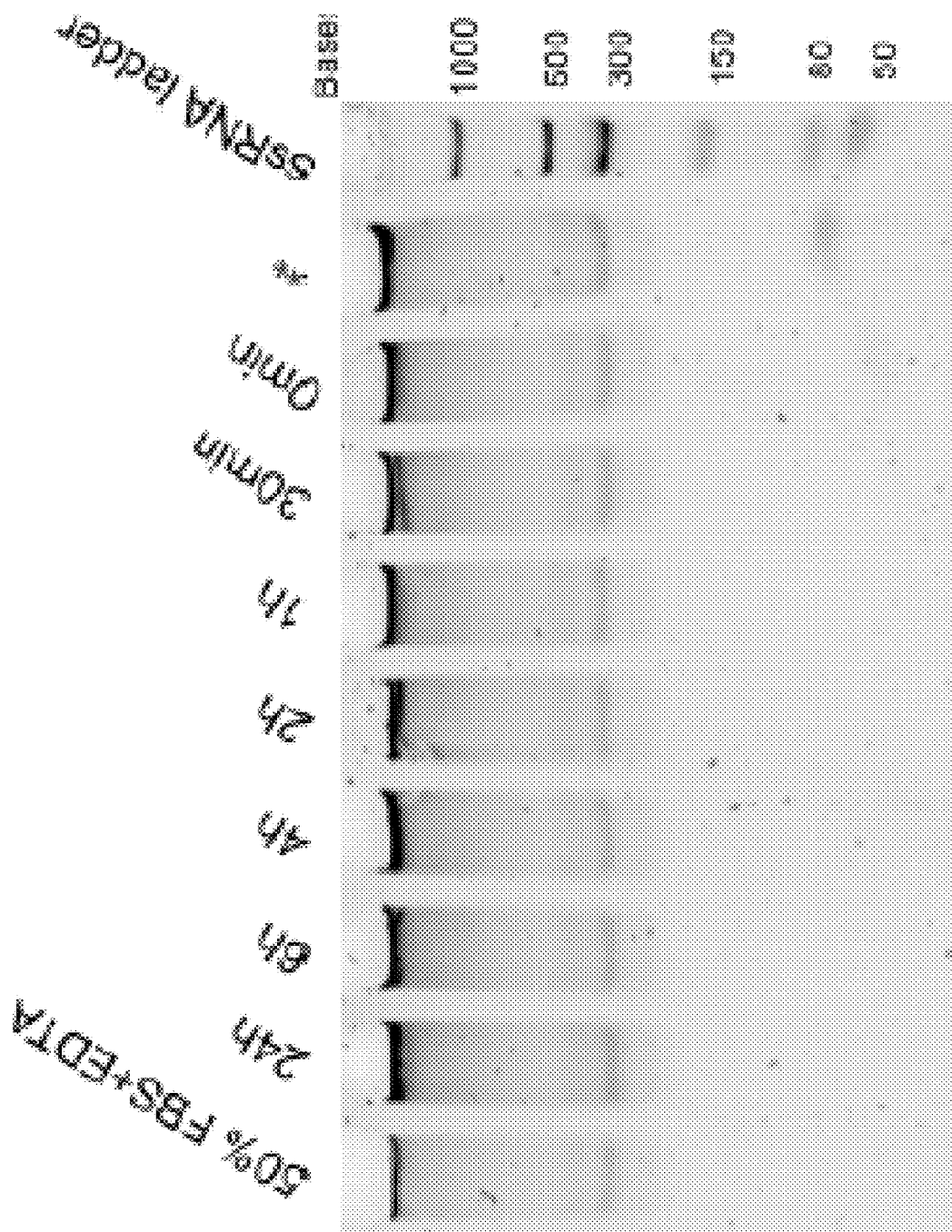
FIGS. 12A-12B are a set of 5% TBE-PAGE images for 50% FBS degradation of (A) A10-polyFU-AttodU10, and (B) A10-polyFU at different time points. Lanes with red asterisks stand for samples in EDTA inactivated FBS. Final concentrations of samples are both 0.7 µM.
Figure 12B:
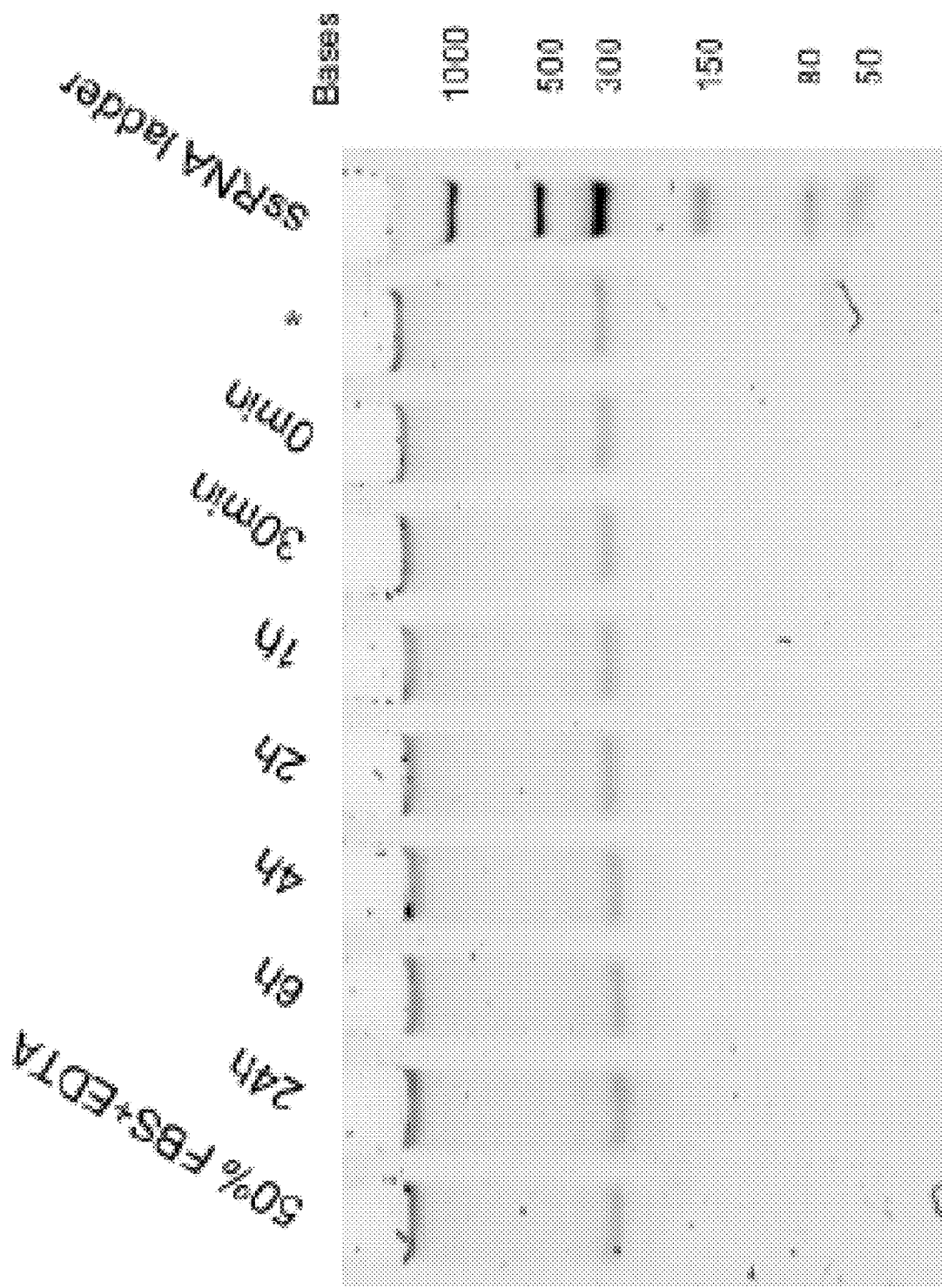
Figure 13:
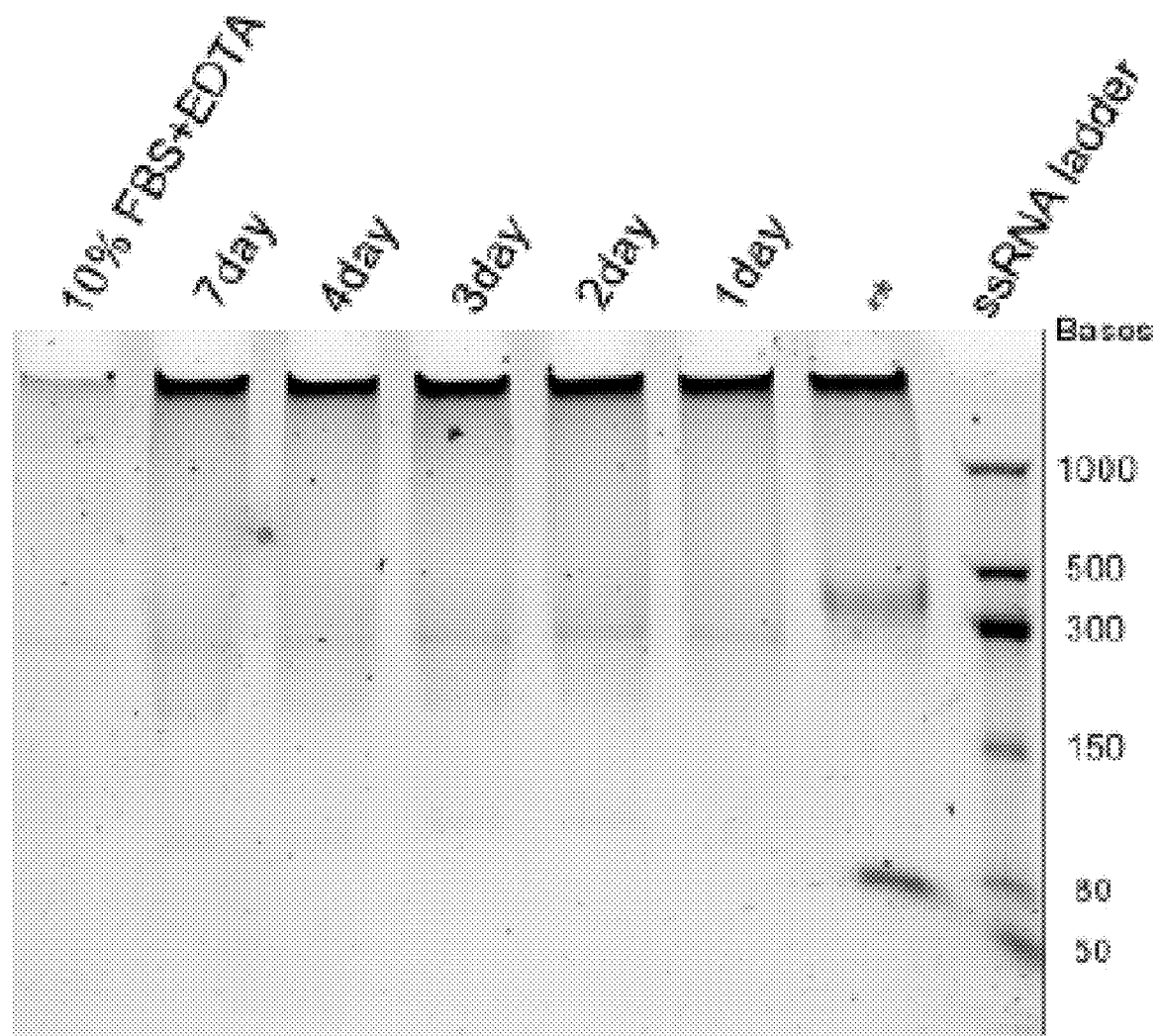
FIG. 13 is a 5% TBE-PAGE image for 10% FBS degradation of A10-polyFU-AttodU10 at different time points within a week. Red asterisk stands for sample in EDTA inactivated FBS. Final concentration of sample is 1 µM.

Stability of Micelles. Since we realized that the Cy5 fluorophore interferes with the dynamic light scattering (DLS) characterization of micelles, we shifted to an A10 aptamer initiator at this stage (FIG. 10A) to synthesize A10-poly(FU)$_n$-poly(AttodU). The resulting micelles were imaged with AFM (FIG. 10B, FIG. 10C, and FIG. 10D). Once we realized that for degradation studies we should use a concentration that is much higher than the CMC of the micelles, we again investigated the nuclease resistance of our micellar structures. Briefly, immediately after adding FBS to the reaction mixture, 3 μL of the solution was removed, and added to 2 μL 0.5 M EDTA, the mixture was kept at −20° C. The remaining solution was kept at 37° C. At different time points, we removed 3 μL of the reaction mixture and added it to 2 μL 0.5 M EDTA, again storing the mixture at −20° C. At the end of the experiments, we ran a TBE-PAGE gel for all the aliquots. Due to the lower intensity of A10-Syber Safe and the smaller pore size of the PAGE gel, the A10-polyFU-AttodU products on 5% TBE-PAGE gels appear to mostly stay in wells, producing strong signals in wells compared with A10-polyFU products (FIG. 11A and FIG. 11B). We concluded that the micellar structures are stable in 50% FBS for at least 24 hours (FIG. 12), and mostly stable in 10% FBS for at least a week (FIG. 13).

By including multiple controls, we confirmed that the strong signals in the wells arise not from FBS, but from micelles. This is further supported by a band, visible in all the lanes, at the 300-base position that is associated with FBS.

Figure 14A:
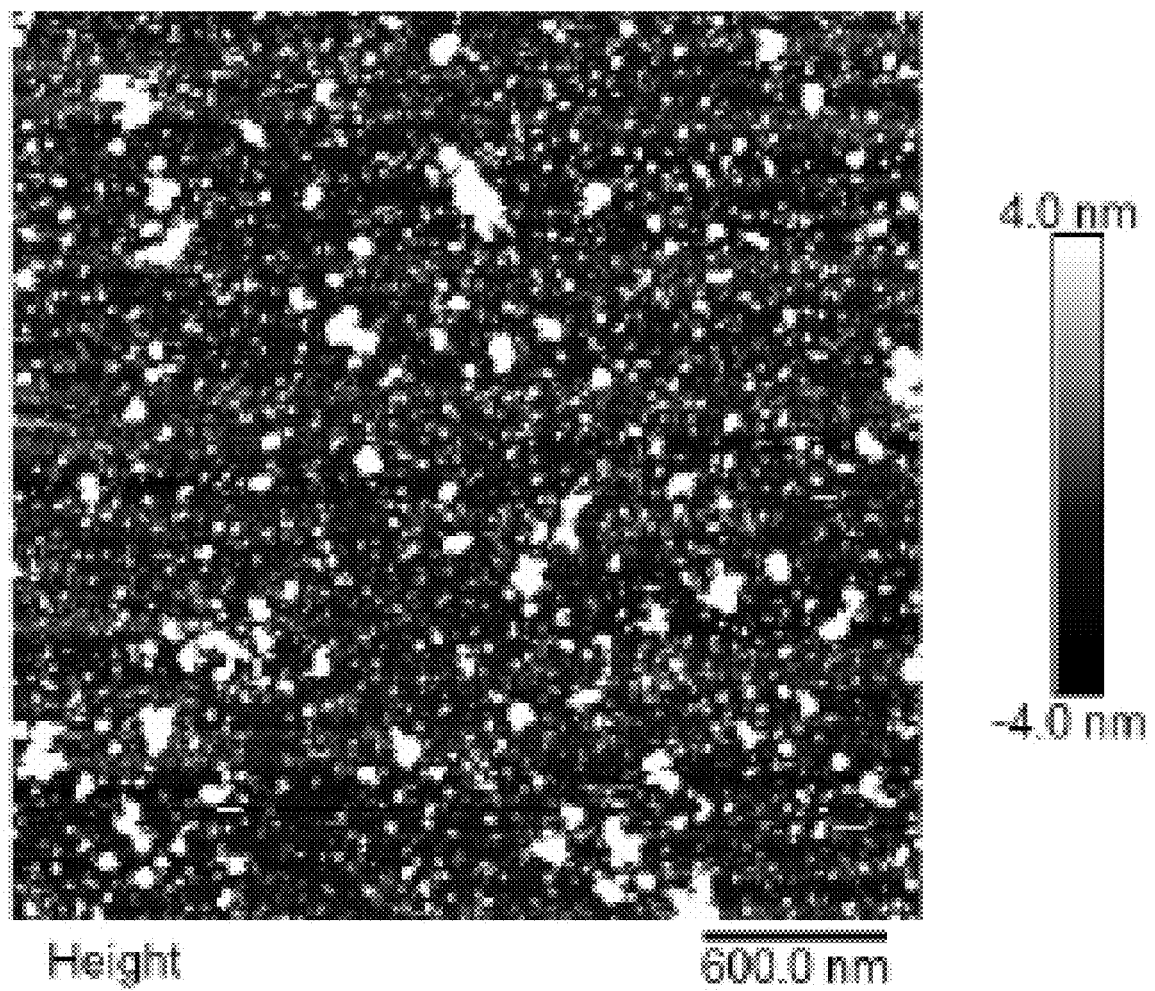
FIGS. 14A-14B are a set of AFM images for (A) 1 day degradation of A10-polyFU-AttodU10 micelle in 10% FBS and (B) 10% FBS as control.
Figure 14B:
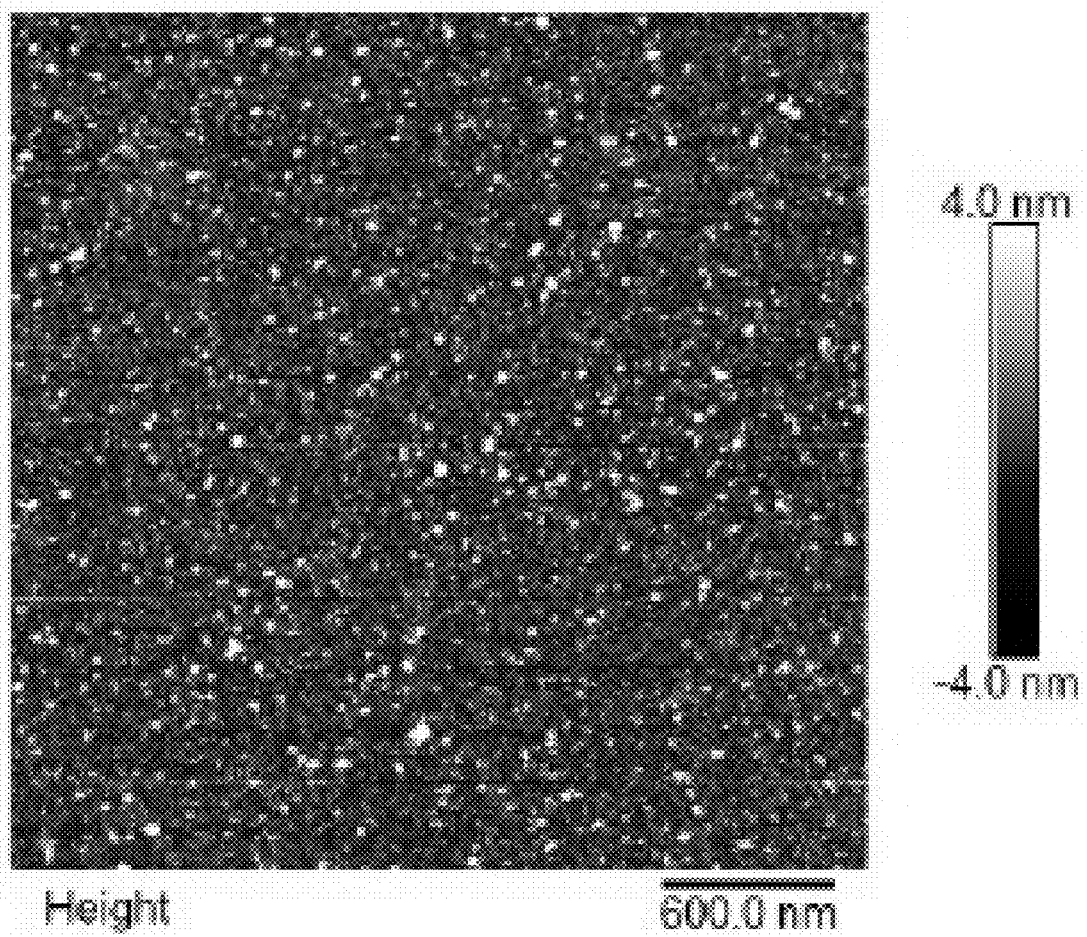
Figure 15A:
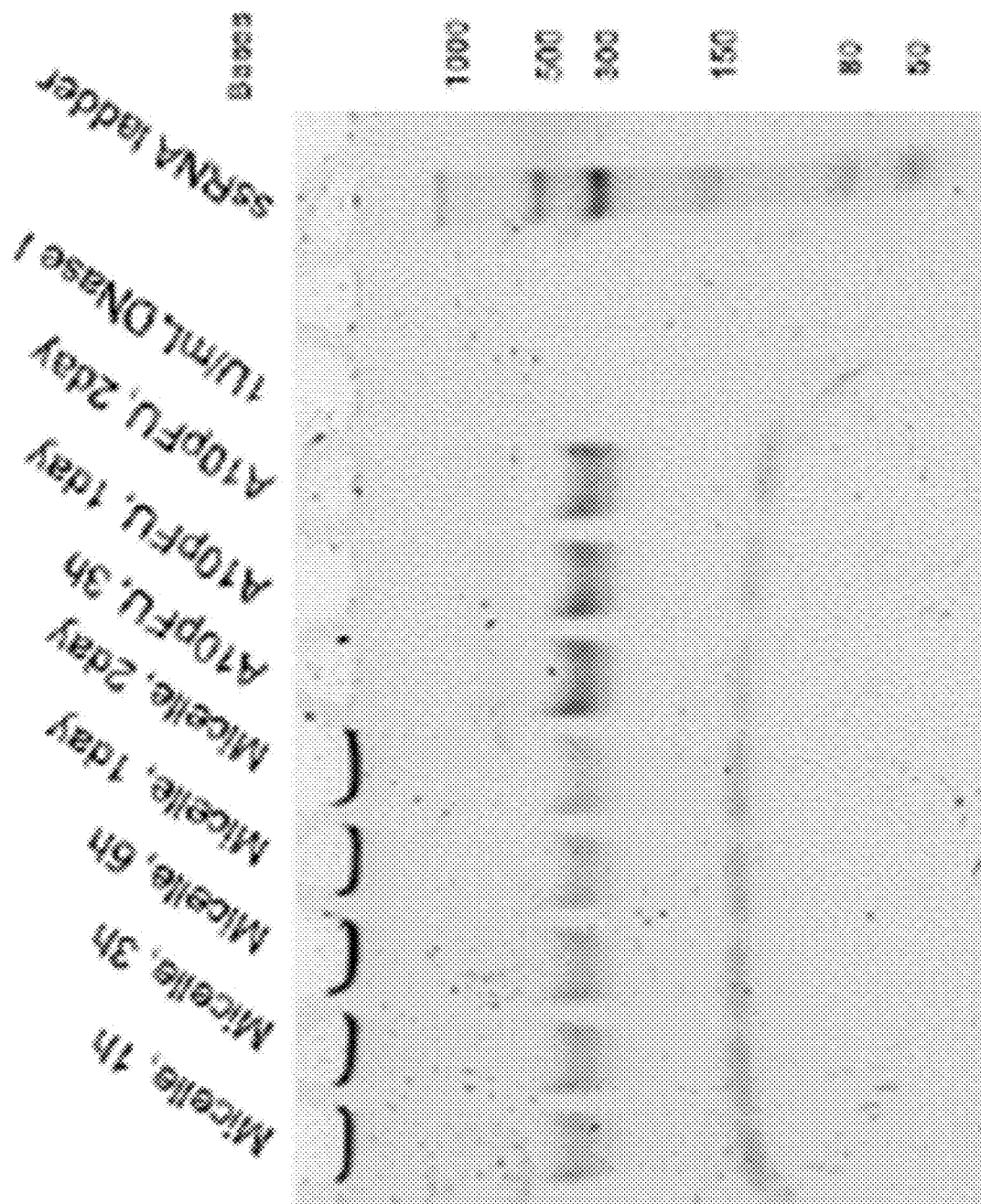
FIGS. 15A-15F are a series of 5% TBE-PAGE images for DNase I degradation at different time points for: (A) A10-polyFU-AttodU10 micelle and A10polyFU, 1 U/mL DNase I; (B) A10-polyFU-AttodU10 micelle, 200 U/mL DNase I; (C) A10polyFU, 200 U/mL DNase I; (D) A10-polyFU-AttodU10 micelle and A10polyFU, 100 U/mL DNase I; (E)
Figure 15B:
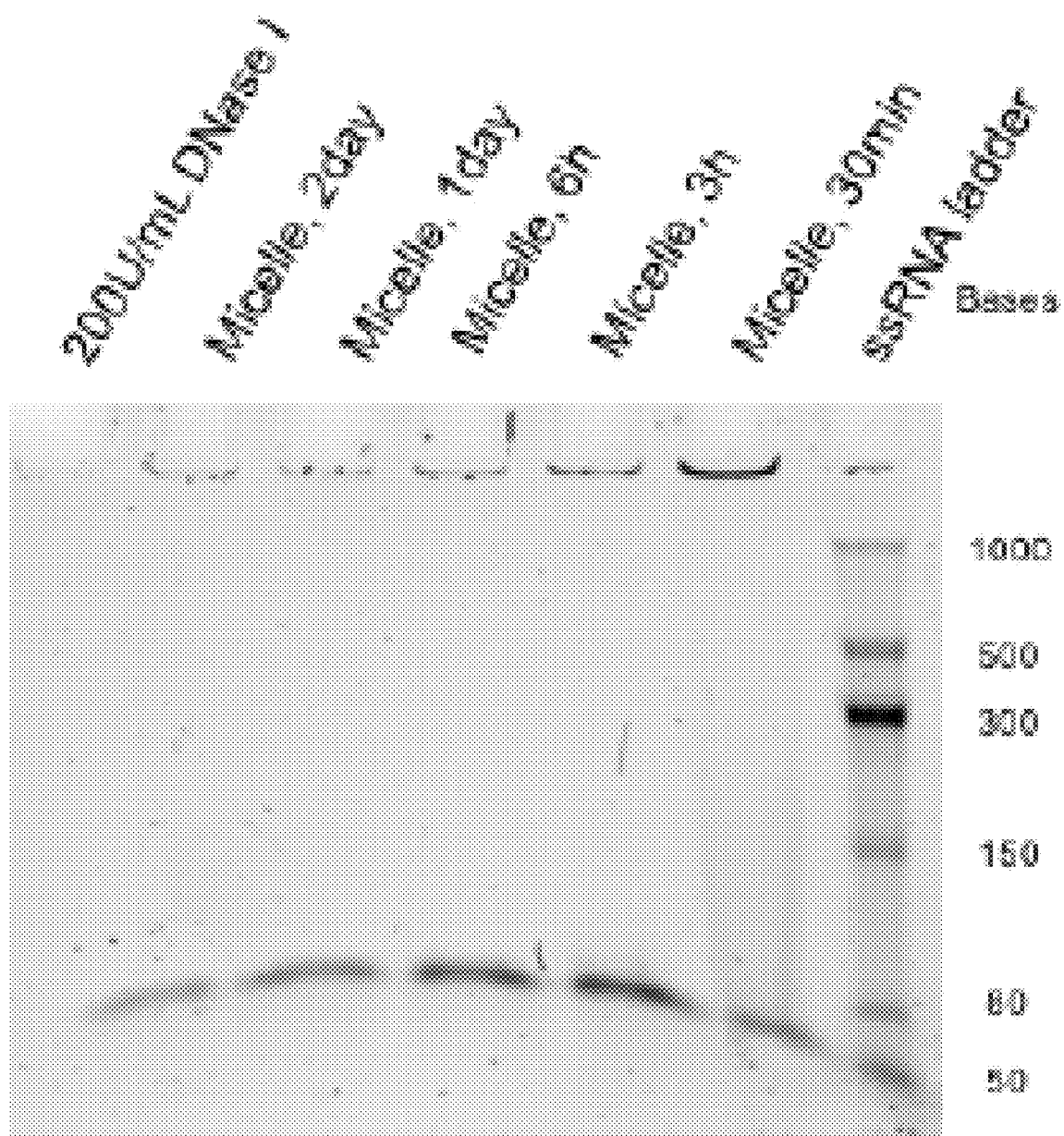
Figure 15C:
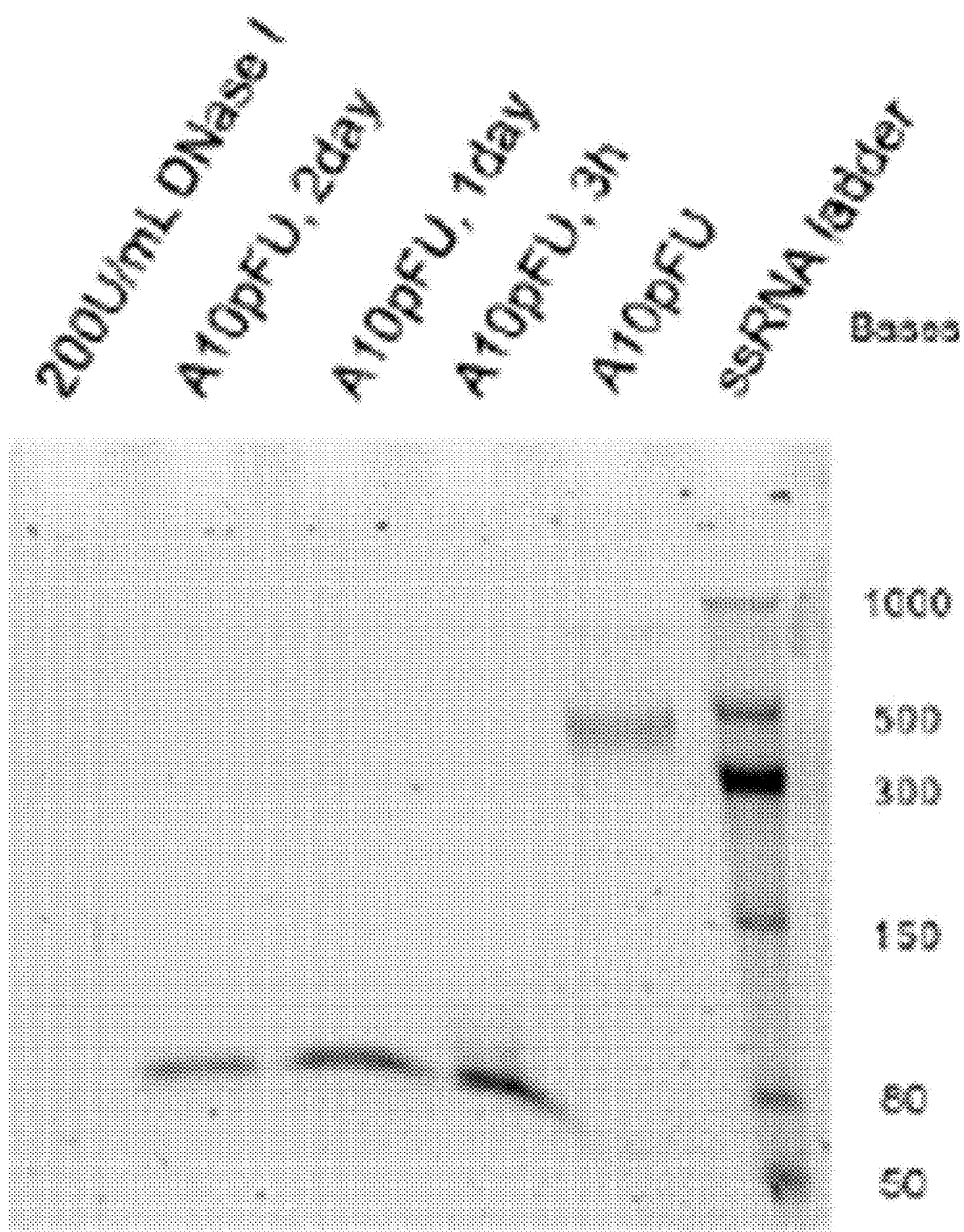
Figure 15D:
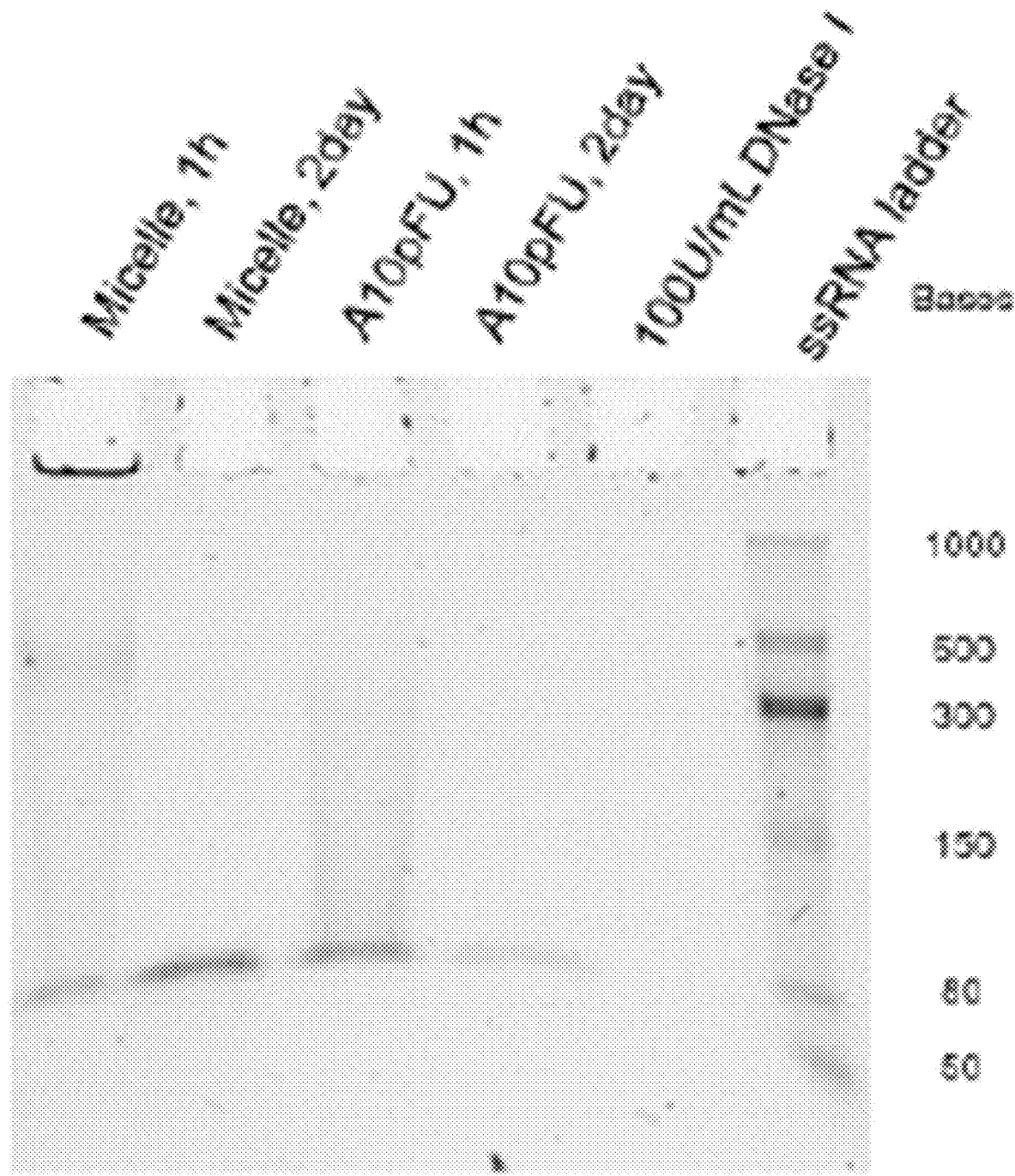
Figure 15E:
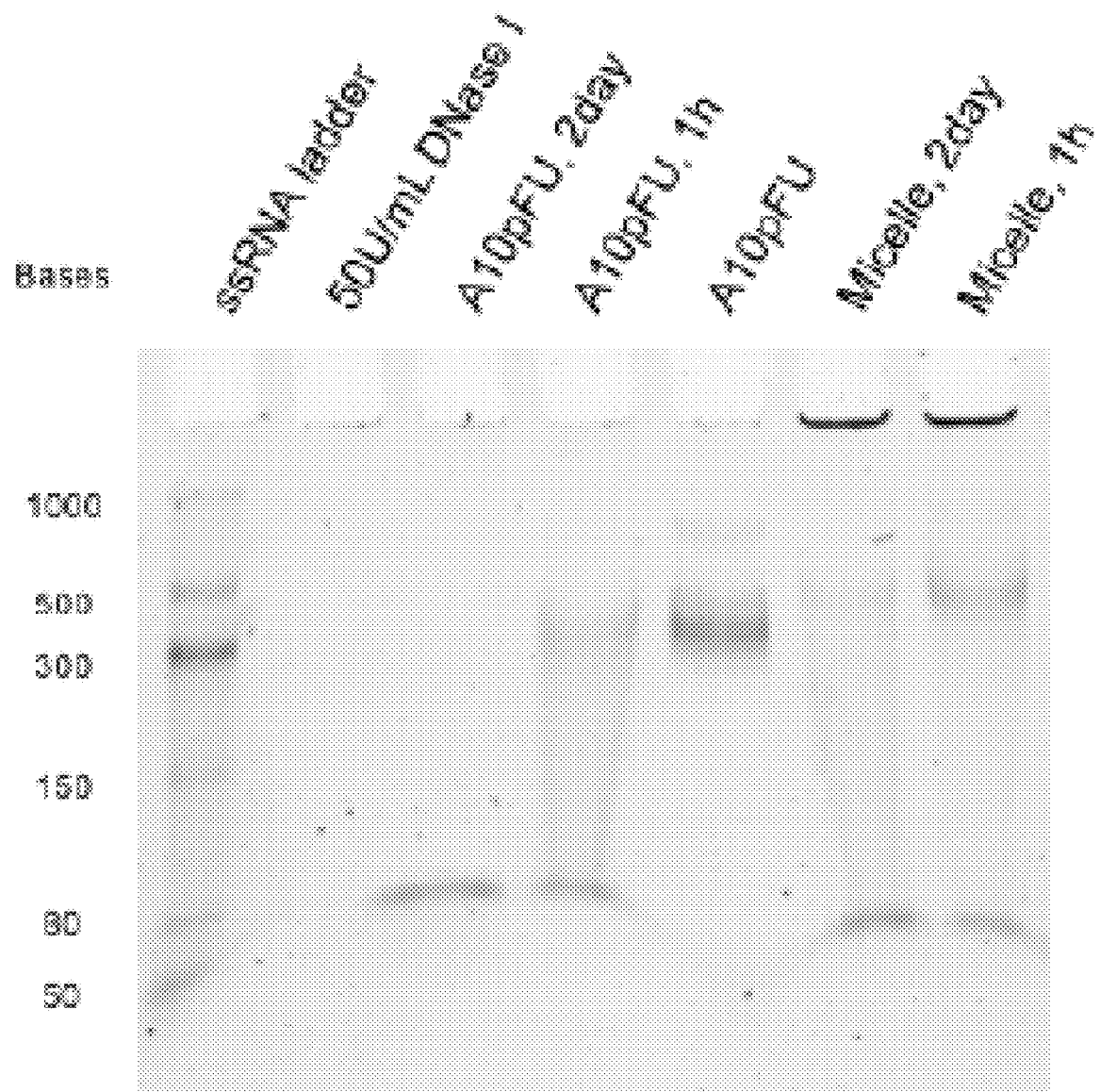
Figure 15F:
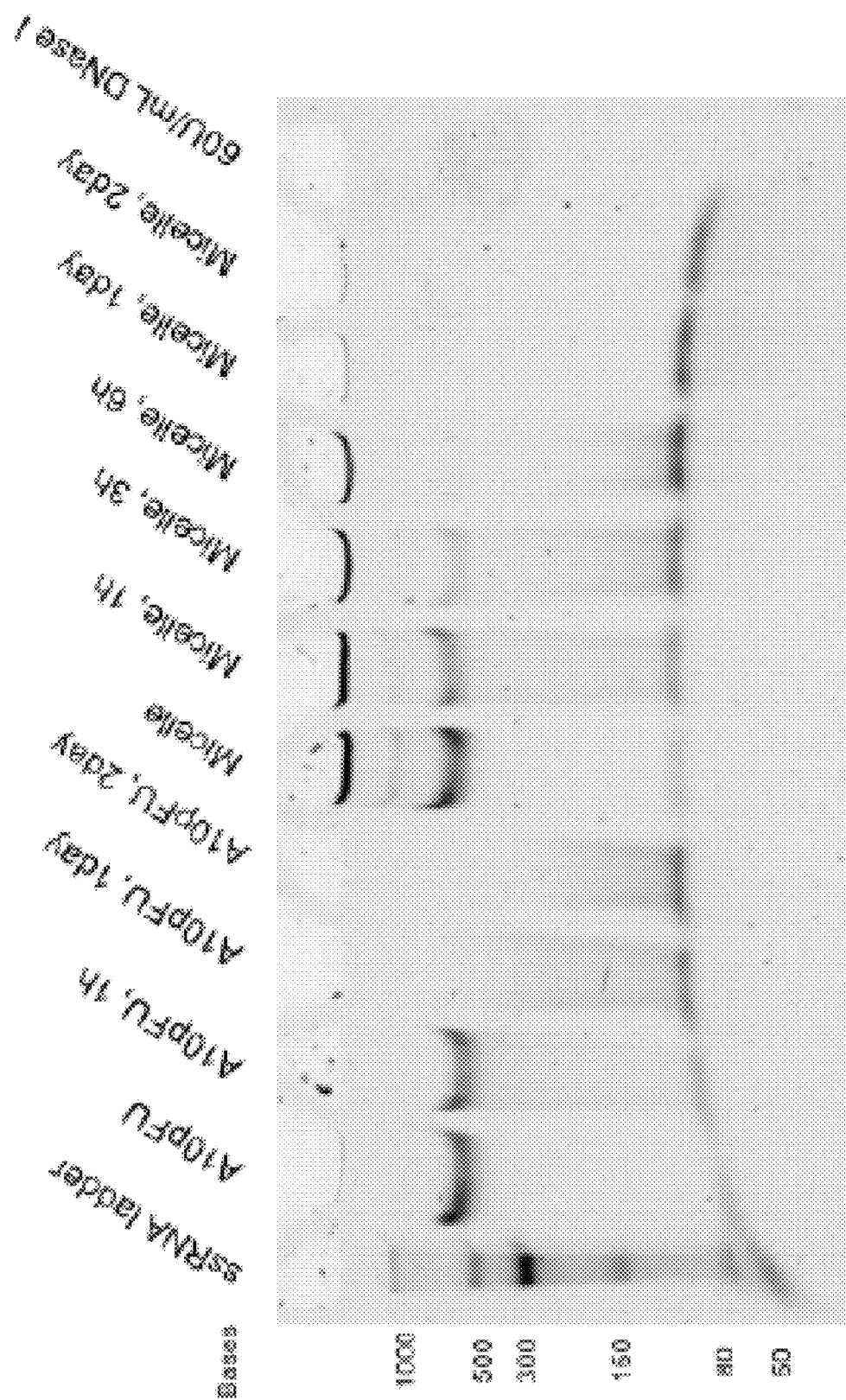

We have tried to characterize the morphology of micelles in FBS using AFM (FIG. 14) and with DLS. But both techniques could not clearly show the integrity of micelles due to the high concentration of proteins in FBS. Going forward, we studied the DNase I (DNA specific endonuclease) degradation of the micelles. The first trial experiment was done by adding 1 U/mL DNase I. However, the results show that even A10pFU could not be degraded (FIG. 15A). We then increased the DNase I concentration to as high as 200 U/mL, and our results show that micelles were degraded under this condition (FIG. 15 B and FIG. 15C). We thus investigated DNase I concentrations between the range of 1 U/mL and 200 U/mL. Under 100 U/mL DNase I, both A10pFU and micelles were degraded (FIG. 15D); under 50 U/mL DNase I, A10pFU were degraded, while micelles were stable up to 2 days (FIG. 15E). When slightly increasing the DNase I concentration to 60 U/mL, we found that micelles were largely stable for about 6 hours, and were finally degraded within 24 h (FIG. 15F).

The different abilities of serum (FBS) and DNase I to degrade A10-polyFU ssDNA and A10-polyFU-Atto10 micelles may arise from the fact that FBS not only contains endonucleases, but also exonucleases, which can degrade ssDNA but not our micellar structures. Thus, for only the DNase I system, a higher concentration of DNase I is needed to degrade ssDNA, but in turn that may also entail the degradation of a higher fraction of micelles.

Size Characterization of NPs. To measure the size of our micellar DNA NPs, we used a Zetasizer from Malvern, with a 1730 backward scatter detection. We found that the z-average size for ssDNA is much larger than the root-mean-square (RMS) length of ssDNA with ~400 bases (FIG. 16): $\langle rr2 \rangle 1/2 \approx \sqrt{400 \times 0.3} = 11$ nm. AFM imaging for different batches of samples showed star-like aggregates and larger aggregates for all the batches (FIG. 17).

However, for the samples for which the A10 aptamer has been refolded by PCR (FIG. 18A), the AFM images showed a random distribution of small ssDNA chains, and much more reasonable concentrations (FIG. 18B). DLS measurements for A10pFU with refolded aptamers showed ~20 nm radius, consistent with the calculated RMS radius (FIG. 19). Therefore, we conclude that aptamers which are not properly refolded have random interactions with each other and lead to unexpected aggregations.

In this Experiment, we successfully synthesized amphiphilic block polynucleotides that self-assemble into micellar nanoparticles by Atto-dUTP extension. The micelles have a CMC as low as 50 nM, and are stable in 50% FBS for 24 hours without chemical crosslinking. The radius of the A10-polyFU-Atto micelles with 250-450 FdU and M/I=10 of Atto-dUTP is in the range of 60-100 nm in water, and 30-60 nm in 1×DPBS. We also showed that longer polyFU can be produced by adding multiple rounds of TdT, and corresponding micelles with larger size can be formed.

Cross-linking of Micelles. To increase the resistance of the micelles in serum, we decided to crosslink the micelles with bis(succinimidyl) nona(ethylene glycol) (BS(PEG)$_9$), which could also help to reduce their disassembly when diluted.

By increasing the feed ratio (2%, 5%, and 10% of total monomer) of aadUTP (aminoallyl-dUTP), we obtained copolynucleotides that contain increasing amounts of amine groups (FIG. 20A). The change of band positions likely arises from the positive charges on the amine groups. By reacting with Cy3-NHS, we could confirm the existence of amino groups on the chains from the Cy3 signal on the gel (FIG. 20B).

Example 6

Aptamer-Based Polynucleotide Synthesis Via TcEP

Different aptamers were used as initiators for polynucleotide synthesis. Each of the different aptamers of A10 (with a dT4 extension at the 3'-end), Ap1153 and sgc8c were extended with FdUTP using TcEP. In FIG. 21A sgc8c was extended with (FdUTP)$_{30}$. In FIG. 21B, A10 was extended with (FdUTP)$_{\sim257}$; Ap1153 was extended with (FdUTP)$_{\sim84}$; and sgc8c was extended with (FdUTP)$_{\sim80}$.

```
                        Sequences

AS1411 (5'-GGTGGTGGTGGTTGTGGTGGTGTGG-3') (SEQ ID
NO: 1)

AIR-3 (5'-GGAAGAAAGAGGUCUGAGACAUUCUCUUAUAGGGGAGGCU
GUGGUGAGGGAAUAUUAAGAGAAUUAACGGUCUAGUUCACCUCGACUUCU
GGAGUUGACGUUGCUU-3') (SEQ ID NO: 2)

A10 (5'-GGGAGGACGAUGCGGAUCAGCCAUGUUUACGUCACUCCU-
3') (SEQ ID NO: 3)

Sgc8c (5'-ATCTAACTGCTGCGCCGCCGGGAAAATACTGTACGGTTAG
A-3') (SEQ ID NO: 4)

MUC1-5TR-1 (GGGAGACAAGAATAAACGCTCAAGAAGTGAAAATGACA
GAACACAACATTCGACAGGAGGCTCACAACAGGC) (SEQ ID NO: 5)

AP1153 (5'-CAT GGT GCA GGT GTG GCT GGG ATT CAT TTG
CCG GTG CTG GTG CGT CCG CGG CCG CTA ATC CTG TTC-
3') (SEQ ID NO: 6)

A10 + Linker (5'-GGGAGGACGAUGCGGAUCAGCCAUGUUUACGUC
ACUCCUdTd TdTdT-3', (SEQ ID NO: 7)
where dT = deoxythymidine (X$^1$)$_m$ (SEQ ID NO: 8)

(FdUTP)$_m$ (SEQ ID NO: 9)

(Z$^1$)$_p$ (SEQ ID NO: 10)

(Y$^1$)$_n$ (SEQ ID NO: 11)
```

What is claimed is:

1. A method of making an amphiphilic polynucleotide that can self-assemble into a nanoparticle, the method comprising combining a terminal deoxynucleotidyl transferase (TdT), an aptamer initiator having a secondary structure, and a non-natural cytostatic deoxynucleoside triphosphate (dNTP) monomer in a buffer to provide a first reaction mixture;

incubating the first reaction mixture;

adding a non-natural hydrophobic dNTP monomer to the first reaction mixture to provide a second reaction mixture; and incubating the second reaction mixture to provide a single-stranded amphiphilic polynucleotide comprising, in a 5' to 3' direction:

an aptamer portion;

a first nucleotide portion comprising a nucleotide sequence of $(FdUTP)_m$ (SEQ ID NO:9), wherein m is 100 to 2,000; and a second nucleotide portion comprising a nucleotide sequence of $(Y^1)_n$ (SEQ ID NO:11), wherein $Y^1$ is a non-natural hydrophobic nucleotide including a base having a Log P≥1.95, and n is 2 to 10.

2. The method of claim 1, wherein the aptamer portion of the amphiphilic polynucleotide is refolded to provide a secondary structure.

3. The method of claim 1, wherein TdT is added to the first reaction mixture, the second reaction mixture, or both in multiple rounds.

4. A method of treating a disease or disorder in a subject in need thereof, the method comprising administering to the subject a therapeutically effective amount of the composition comprising an assembly of amphiphilic polynucleotides, each amphiphilic polynucleotide being single-stranded and comprising, in a 5' to 3' direction, an aptamer portion;

a first nucleotide portion comprising a nucleotide sequence of $(FdUTP)_m$ (SEQ ID NO:9), wherein m is 100 to 2,000; and a second nucleotide portion comprising a nucleotide sequence of $(Y^1)_n$ (SEQ ID NO:11), wherein $Y^1$ is a non-natural hydrophobic nucleotide including a base having a Log P≥1.95, and n is 2 to 10.

5. The method of claim 4, wherein the disease or disorder is cancer.

* * * * *

```
                              SEQUENCE LISTING

Sequence total quantity: 11
SEQ ID NO: 1                  moltype = DNA   length = 26
FEATURE                       Location/Qualifiers
misc_feature                  1..26
                              note = Synthetic
source                        1..26
                              mol_type = other DNA
                              organism = synthetic construct
SEQUENCE: 1
ggtggtggtg gttgtggtgg tggtgg                                          26

SEQ ID NO: 2                  moltype = RNA   length = 106
FEATURE                       Location/Qualifiers
misc_feature                  1..106
                              note = Synthetic
source                        1..106
                              mol_type = other RNA
                              organism = synthetic construct
SEQUENCE: 2
ggaagaaaga ggtctgagac attctcttat aggggaggct gtggtgaggg aatattaaga     60
gaattaacgg tctagttcac ctcgacttct ggagttgacg ttgctt                   106

SEQ ID NO: 3                  moltype = RNA   length = 39
FEATURE                       Location/Qualifiers
misc_feature                  1..39
                              note = Synthetic
source                        1..39
                              mol_type = other RNA
                              organism = synthetic construct
SEQUENCE: 3
gggaggacga tgcggatcag ccatgtttac gtcactcct                            39

SEQ ID NO: 4                  moltype = DNA   length = 41
FEATURE                       Location/Qualifiers
misc_feature                  1..41
                              note = Synthetic
source                        1..41
                              mol_type = other DNA
                              organism = synthetic construct
SEQUENCE: 4
atctaactgc tgcgccgccg ggaaaatact gtacggttag a                         41

SEQ ID NO: 5                  moltype = DNA   length = 72
FEATURE                       Location/Qualifiers
misc_feature                  1..72
                              note = Synthetic
source                        1..72
                              mol_type = other DNA
                              organism = synthetic construct
SEQUENCE: 5
gggagacaag aataaacgct caagaagtga aaatgacaga acacaacatt cgacaggagg     60
ctcacaacag gc                                                         72

SEQ ID NO: 6                  moltype = DNA   length = 66
FEATURE                       Location/Qualifiers
misc_feature                  1..66
                              note = Synthetic
source                        1..66
                              mol_type = other DNA
                              organism = synthetic construct
SEQUENCE: 6
catggtgcag gtgtggctgg gattcatttg ccggtgctgg tgcgtccgcg gccgctaatc     60
ctgttc                                                                66

SEQ ID NO: 7                  moltype = RNA   length = 47
FEATURE                       Location/Qualifiers
source                        1..47
                              mol_type = other RNA
                              organism = synthetic construct
SEQUENCE: 7
gggaggacga tgcggatcag ccatgtttac gtcactcctd tdtdtdt                   47

SEQ ID NO: 8                  moltype =       length =
SEQUENCE: 8
000
```

| | | | |
|---|---|---|---|
| SEQ ID NO: 9<br>SEQUENCE: 9<br>000 | moltype = | length = | |
| SEQ ID NO: 10<br>SEQUENCE: 10<br>000 | moltype = | length = | |
| SEQ ID NO: 11<br>SEQUENCE: 11<br>000 | moltype = | length = | |